United States Patent
Levin

(10) Patent No.: US 11,547,681 B2
(45) Date of Patent: *Jan. 10, 2023

(54) N-ACYLETHANOLAMIDE DERIVATIVES AND USES THEREOF

(71) Applicant: ELIEM THERAPEUTICS, INC., Boston, MA (US)

(72) Inventor: Andrew D. Levin, Newton, MA (US)

(73) Assignee: ELIEM THERAPEUTICS, INC., Boston, MA (US)

( * ) Notice: Subject to any disclaimer, the term of this patent is extended or adjusted under 35 U.S.C. 154(b) by 63 days.

This patent is subject to a terminal disclaimer.

(21) Appl. No.: 17/116,414

(22) Filed: Dec. 9, 2020

(65) Prior Publication Data

US 2021/0093589 A1    Apr. 1, 2021

Related U.S. Application Data

(63) Continuation of application No. 16/349,548, filed as application No. PCT/US2017/056353 on Oct. 12, 2017, now Pat. No. 10,933,037.

(60) Provisional application No. 62/517,344, filed on Jun. 9, 2017, provisional application No. 62/407,796, filed on Oct. 13, 2016.

(51) Int. Cl.
| | |
|---|---|
| *A61K 31/164* | (2006.01) |
| *A61K 47/54* | (2017.01) |
| *A61P 1/14* | (2006.01) |
| *A61P 29/02* | (2006.01) |
| *C07C 233/18* | (2006.01) |
| *C07C 235/00* | (2006.01) |
| *C07H 13/04* | (2006.01) |
| *C07F 9/09* | (2006.01) |
| *C07C 233/20* | (2006.01) |

(52) U.S. Cl.
CPC .......... *A61K 31/164* (2013.01); *A61K 47/542* (2017.08); *A61P 1/14* (2018.01); *A61P 29/02* (2018.01); *C07C 233/18* (2013.01); *C07C 233/20* (2013.01); *C07C 235/00* (2013.01); *C07F 9/091* (2013.01); *C07H 13/04* (2013.01)

(58) Field of Classification Search
CPC .......................... C07C 233/18; A61K 31/164
See application file for complete search history.

(56) References Cited

U.S. PATENT DOCUMENTS

| | | |
|---|---|---|
| 2,440,361 A | 4/1948 | Behrens |
| 5,925,678 A | 7/1999 | Della Valle et al. |
| 5,990,170 A | 11/1999 | Della Valle .......... A61K 31/164 514/613 |
| 7,090,903 B2 | 8/2006 | Katoh et al. |
| 9,107,931 B2 | 8/2015 | Zelphati ................ C07C 237/08 |
| 10,933,037 B2 * | 3/2021 | Levin .................... C07C 235/00 |
| 2015/0157733 A1 | 6/2015 | Calignano et al. |
| 2019/0262288 A1 | 8/2019 | Levin |

OTHER PUBLICATIONS

Database Pubchem, CID 10309854, Oct. 25, 2006, 7 pages.
Database Pubchem, CID 24808239, Jun. 9, 2008. 6 pages.
Extended European Search Report issued in European Application No. 17860455.9, dated Apr. 24, 2020, 6 pages.
Gizzi et al., 2009, Molecular Tailored Histidine-Based Complexing Surfactants: From Micelles to Hydrogels, European Journal of Organic Chemistry, vol. 2009, No. 23, pp. 3953-3963.
International Search Report issued in International Application No. PCT/US2017/56353, dated Jan. 8, 2018, 3 pages.

* cited by examiner

*Primary Examiner* — Golam M Shameem
(74) *Attorney, Agent, or Firm* — Heslin Rothenberg Farley & Mesiti P C.

(57) ABSTRACT

The present disclosure provides certain N-Acylethanolamide derivatives, and uses relating thereto.

15 Claims, 40 Drawing Sheets

ENDOSCOPIC SCORE

N-ACYLETHANOLAMIDE DERIVATIVES AND USES THEREOF

CROSS REFERENCE TO RELATED APPLICATIONS

This application is a continuation of U.S. application Ser. No. 16/349,548, which is a U.S. national phase entry under Section 371 of International Application No. PCT/US2017/056353, filed on Oct. 12, 2017, which published as WO/2018/071679 on Apr. 19, 2018, which claims priority to U.S. provisional application No. 62/517,344, filed Jun. 9, 2017, and U.S. provisional application No. 62/407,796, filed Oct. 13, 2016. The entire contents of each of the prior applications are hereby incorporated by reference herein.

BACKGROUND

N-acylethanolamides are uniquely useful and valuable compounds. Studies have shown that N-acylethanolamides can be effective in the treatment of a variety of diseases, disorders, and conditions.

SUMMARY

N-acylethanolamides are widely recognized as potentially useful therapeutic compounds, and have been extensively studied in particular for their analgesic and/or anti-inflammatory effects.

However, the present disclosure appreciates that N-acylethanolamide compounds often suffer from one or more poor pharmacological properties, for example resulting in limited bioavailability when administered by a particular route (e.g., oral) and/or low exposure to a particular target site of interest (e.g., bowel or, more specifically, lower bowel). In many cases, these poor properties can limit dosage, limit exposure or delivery to a particular site of interest, limit susceptibility to effective delivery by a particular route, etc and/or may therefore or otherwise necessitate alternative modes of administration.

The present disclosure further appreciates that some or all of the poor pharmacological properties encountered with many N-acylethanolamide compounds may be relieved or obviated by provision of an appropriate prodrug. As is known in the art, a prodrug is in most cases a pharmacologically inactive derivative of a parent drug molecule that requires spontaneous or enzymatic transformation within the body in order to release the active drug. The present disclosure encompasses the insight that one source of pharmacological problems with certain N-acylethanolamide compounds may be failure of the compound to reach a relevant target site in sufficient level to achieve its desired biological effect. Alternatively or additionally, an N-acylethanolamide compound may interact with non-target sites, and/or may display undesirable side effects. The present disclosure provides certain derivative (e.g., prodrug) forms of N-acylethanolamide compounds that may relieve or obviate such problem(s) and/or source(s).

In some embodiments, the present disclosure provides derivatives of N-acylethanolamides that exhibit improved pharmacological properties and/or display biological activity that is reasonably comparable to (or, in some cases may be better than) that of its parent N-acylethanolamide (or another appropriate reference N-acylethanolamide). In some embodiments, a provided N-acylethanolamide derivative compound may exhibit one or more properties such as, for example, increased oral bioavailability, increased cell permeability, increased water solubility, reduced first-pass effect, increased stability, active transport by intestinal transporters, avoidance of efflux transporters, and/or combinations thereof when compared to a reference N-acylethanolamide such as, for example, its parent N-acylethanolamide.

In some embodiments, a compound for use in accordance with the present disclosure is one wherein an N-acylethanolamide is conjugated to a moiety selected from the group consisting of phosphate, butyric acid, glycerol, succinate, caprylic acid, gluconoic acid, eicosapentaeonoic acid, linoleic acid, succinate, and sucrose moieties, and combinations thereof. In some embodiments, an N-acylethanolamide is conjugated to one or more such moieties through use of a linker moiety. In some embodiments, an N-acylethanolamide is conjugated to two or more such moieties. In some embodiments, an N-acylethanolamide is conjugated to one, two, or three such moieties.

In some embodiments, a provided compound has a chemical structure represented by formula I-a:

or a pharmaceutically acceptable salt thereof; wherein
$X_1$ is an N-acylethanolamide; and
$X_2$ is a moiety conjugated to the N-acylethanolamide.
In some embodiments, $X_1$ is selected from the group consisting of N-palmitoylethanolamide, N-oleoylethanolamide, and N-arachidonoylethanolamide; in some particular embodiments, $X_1$ is N-palmitoylethanolamide. In some embodiments, $X_2$ comprises a moiety selected from the group consisting of phosphate, butyric acid, glycerol, succinate, caprylic acid, gluconoic acid, eicosapentaeonoic acid, linoleic acid, succinate, and sucrose moieties.

In some embodiments, a provided compound has a chemical structure represented by formula I:

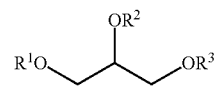

or a pharmaceutically acceptable salt thereof, wherein:
each $R^1$, $R^2$, or $R^3$ is independently hydrogen or -T-$R^4$, wherein at least one of $R^1$, $R^2$, or $R^3$ is -T-$R^4$;
-T- represents a bivalent moiety; and
$R^4$ is an optionally substituted group selected from the group consisting of $C_{1-40}$ aliphatic, —C(O)R, and $X_1$: wherein
R is selected from the group consisting of hydrogen and optionally substituted $C_{1-20}$ aliphatic; and
$X_1$ is as defined above.
In some embodiments, a provided compound has a chemical structure represented by formula I-b:

or a pharmaceutically acceptable salt thereof, wherein:
$X_1$ is as defined above;
$X_3$ is an optionally substituted group selected from the group consisting of —$(CH_2)_m$—P(O)(OR)$_2$, $C_{1-40}$ aliphatic -T-$X_4$; further wherein
m is an integer select from the group consisting of 0-10;
-T- is as defined above;
$X_4$ is a saccharide moiety, in some particular embodiments, $X_4$ is a disaccharide, for example, sucrose.
In some embodiments, the present disclosure provides compounds such as, for example:

I-1
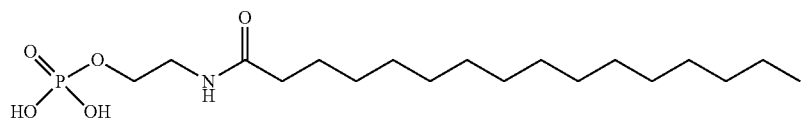
I-2
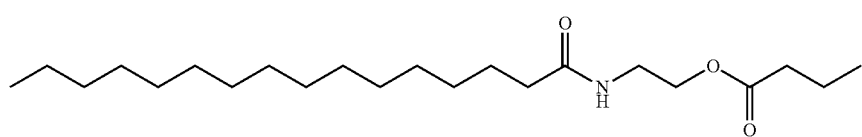
I-3
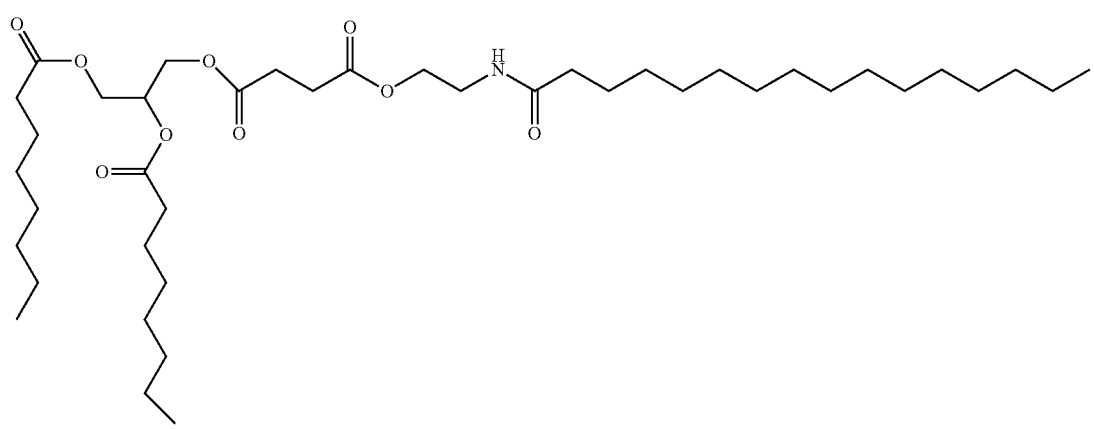
I-4
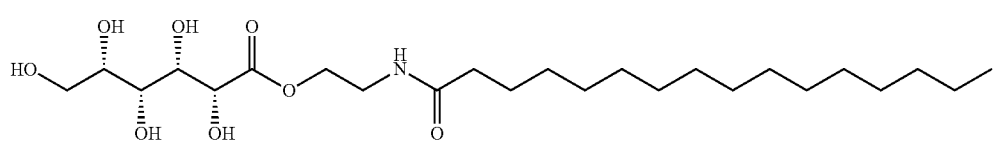
I-5
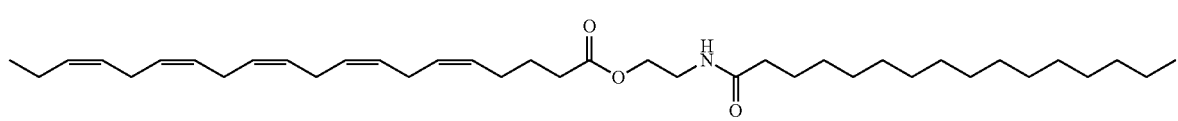
I-6
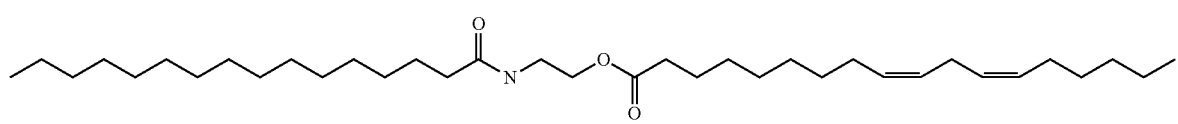
I-7
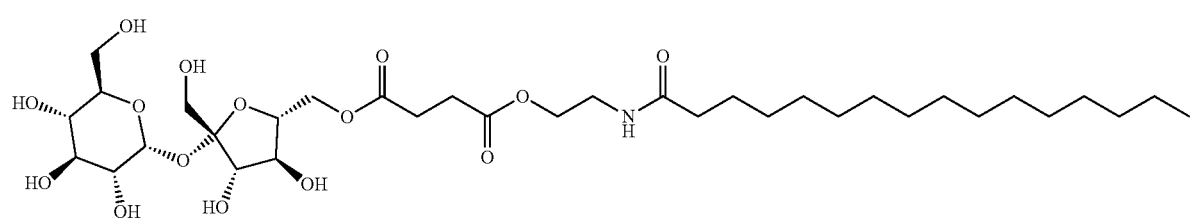

-continued

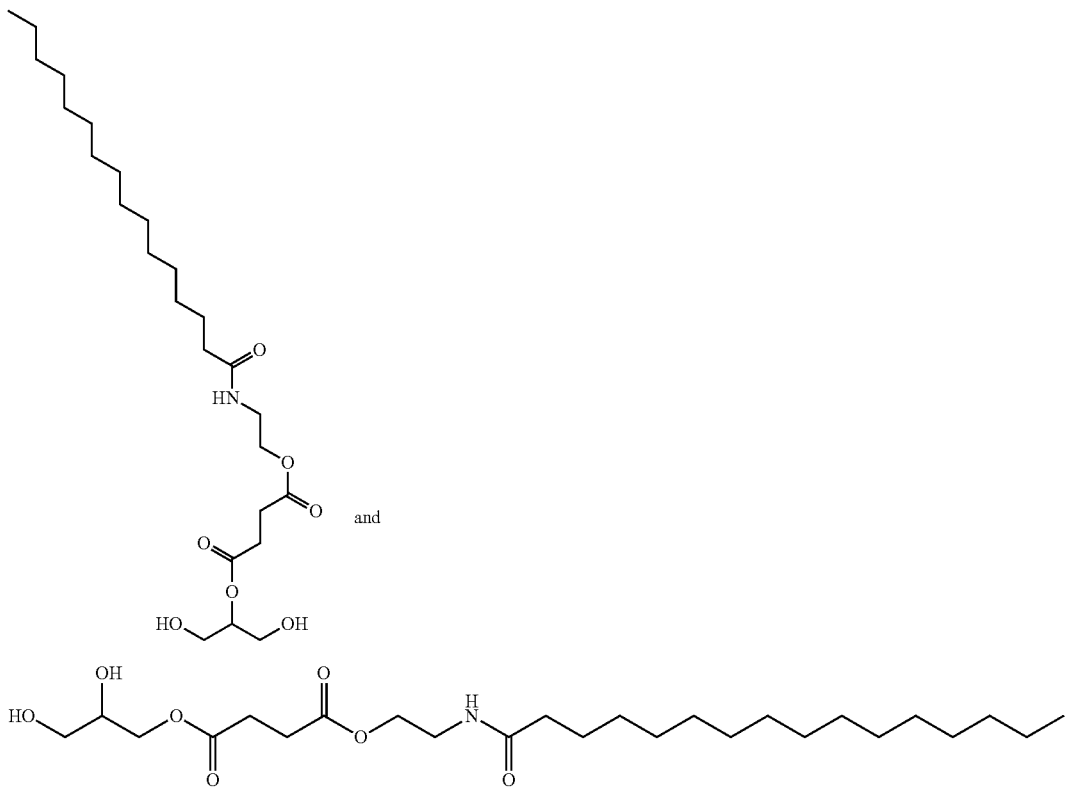

In some embodiments, the present disclosure provides N-acylethanolamide prodrugs. In some embodiments, a provided prodrug may be characterized by one or more desirable physical properties, which may, for example, be assessed relative to an appropriate reference N-acylethanolamide (e.g., to the parent N-acylethanolamide of the provided prodrug); in some embodiments, such desirable physical properties may be or include, for example, enhanced aqueous solubility (which may facilitate, for example, formulation into a pharmaceutical composition, particularly for oral or parenteral administration), enhanced absorption from the digestive tract, enhanced stability under relevant storage conditions, etc.

In some embodiments, a parent N-acylethanolamide compound is one that is characterized by limited aqueous solubility and/or limited oral bioavailability. For example, in some embodiments, a parent N-acylethanolamide compound is characterized by aqueous solubility below a relevant threshold and/or oral bioavailability below a relevant threshold.

In some embodiments, a parent N-acylethanolamide compound is characterized by one or more pharmacological properties that impact its amenability to pharmaceutical formulation, for example, so that challenges are encountered preparing pharmaceutical compositions containing a desirable unit dose amount and/or a desirable concentration of the compound. In some embodiments, the present disclosure provides derivatives of such parent N-acylethanolamide compounds; in some embodiments, derivatives provided by the present disclosure act as prodrugs of the relevant parent compounds in that, when administered to a subject (e.g., in the context of a pharmaceutical composition), the provided derivatives deliver the parent compound and/or an active metabolite thereof. In some embodiments, as described herein, provided N-acylethanolamide derivative compounds comprise one or more moieties modifying or otherwise linked to a parent N-acylethanolamide compound.

In some embodiments, provided N-acylethanolainide derivative compounds are amenable to pharmaceutical formulations at unit doses and/or concentrations that are higher than those achieved with the relevant parent N-acylethanolamide compounds under comparable conditions.

Among other things, the present disclosure provides compounds of formula I and pharmaceutically acceptable salts thereof, the preparation of the above-mentioned compounds, medicaments containing them and their manufacture, as well as technologies for identifying and/or characterizing useful such compounds, and use of provided compounds, for example in the treatment of one or more diseases, disorders, or conditions, for example as described herein.

Prevalence for selected chronic pain conditions in the United States is indicates. Sources: Centers for Disease Control and Prevention, National Center for Health Statistics, Arthritis Foundation, National Institutes of Diabetes and Digestive Kidney Diseases, American Pain Society, The American Pain Foundation.

Figure 2A:
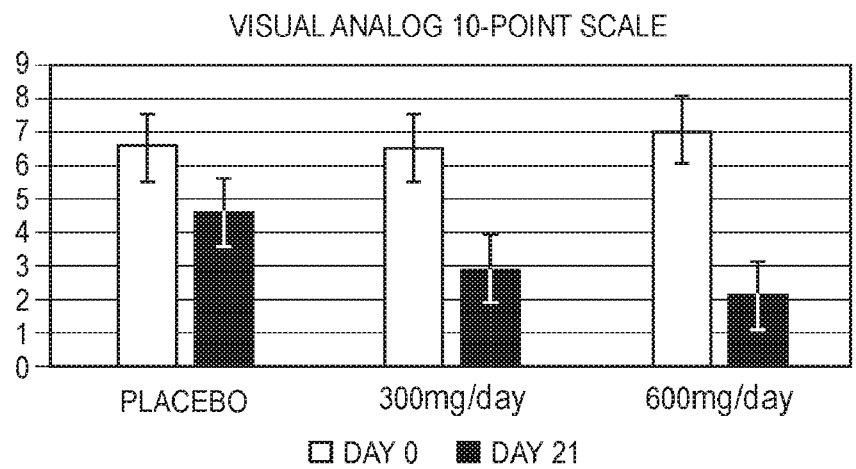

FIG. 2A is a bar graph illustrating visual analog 10-point scale measuring use of PEA to manage pain.

Figure 2B:
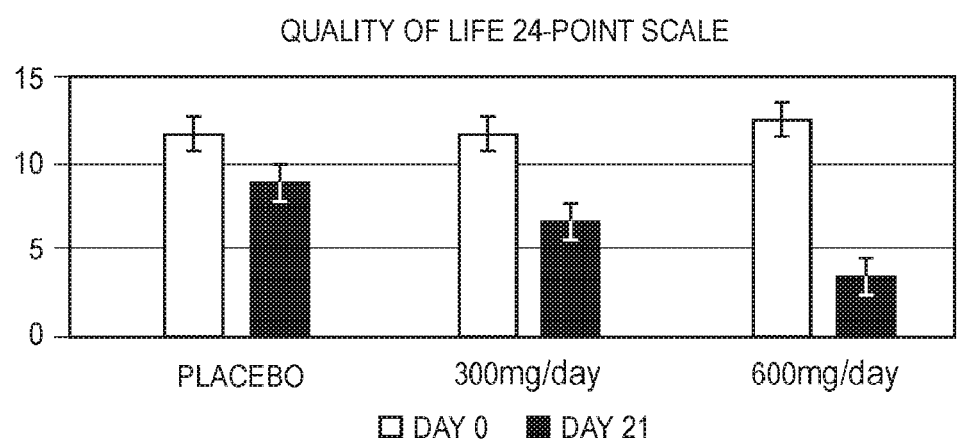

FIG. 2B is a bar graph illustrating quality of life over a 24-point scale for patients administered PEA to manage pain.

Figure 2C:
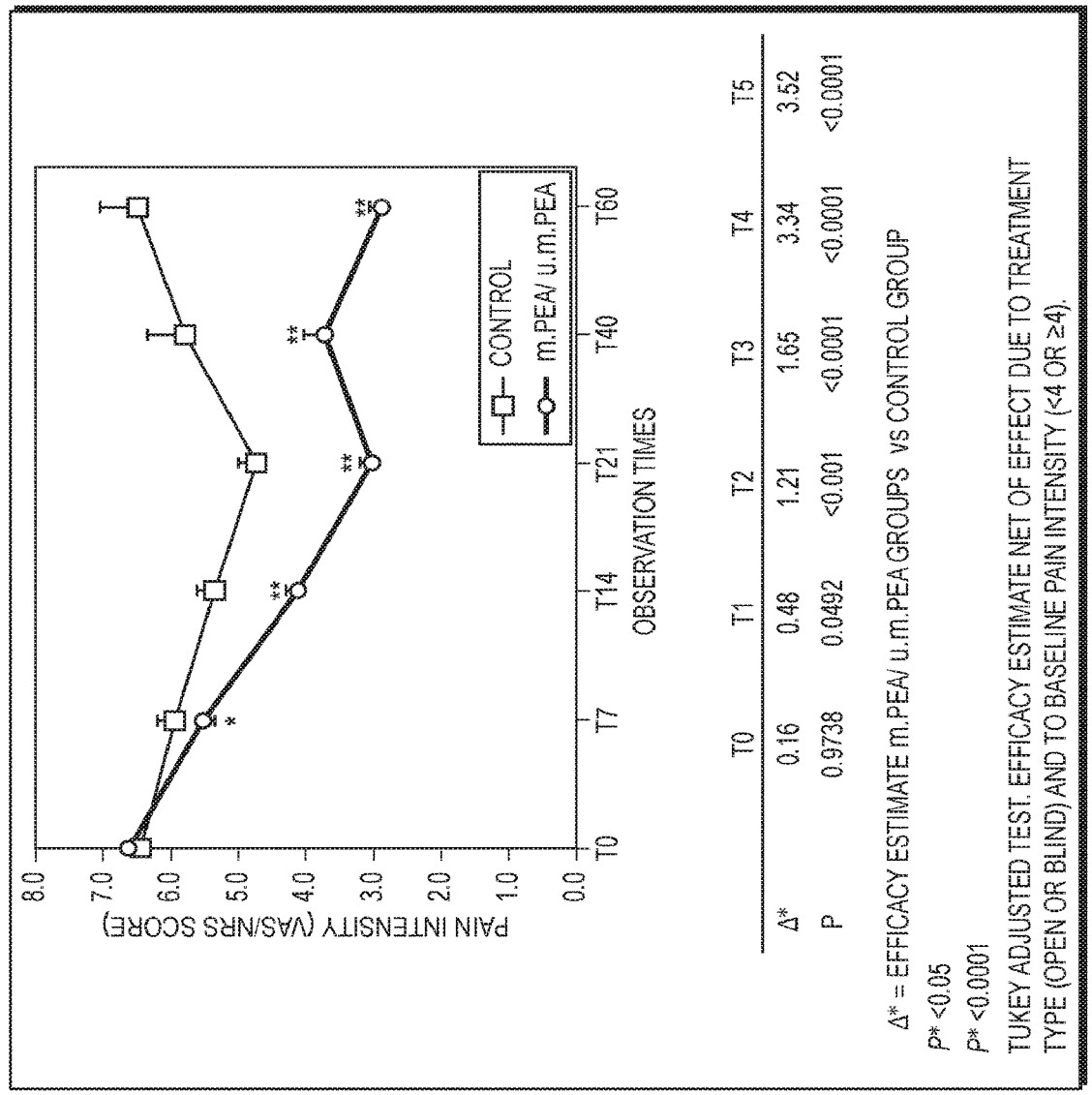

FIG. 2C is a scatter plot measuring changes in pain intensity in patients treated with PEA and control groups at different observation times. Values are expressed as mean±SEM.

Figure 2D:
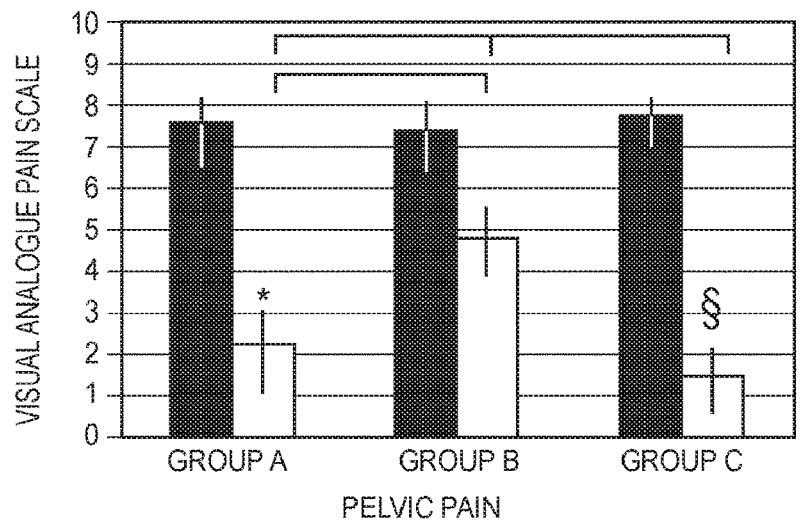

FIG. 2D is a bar graph measuring a visual analog of pelvic pain among Groups A, B, and C.

Figure 2E:
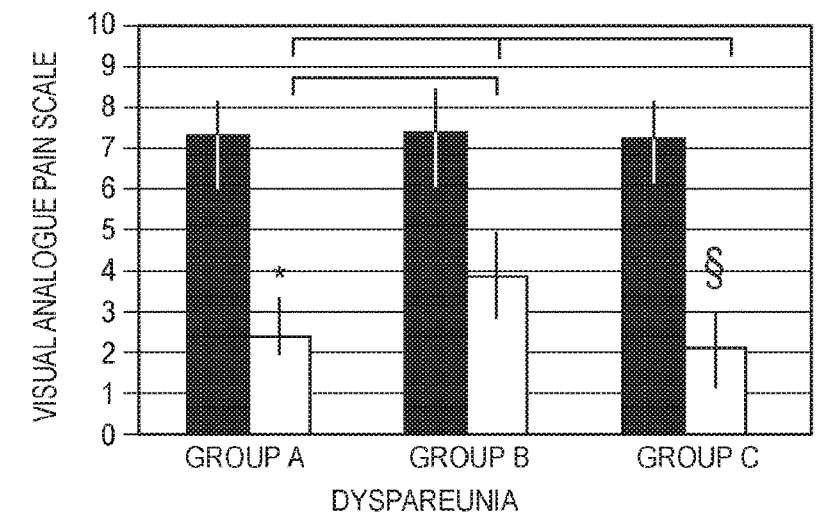

FIG. 2E is a bar graph measuring a visual analog of dyspareunia among Groups A, B, and C.

Figure 2F:
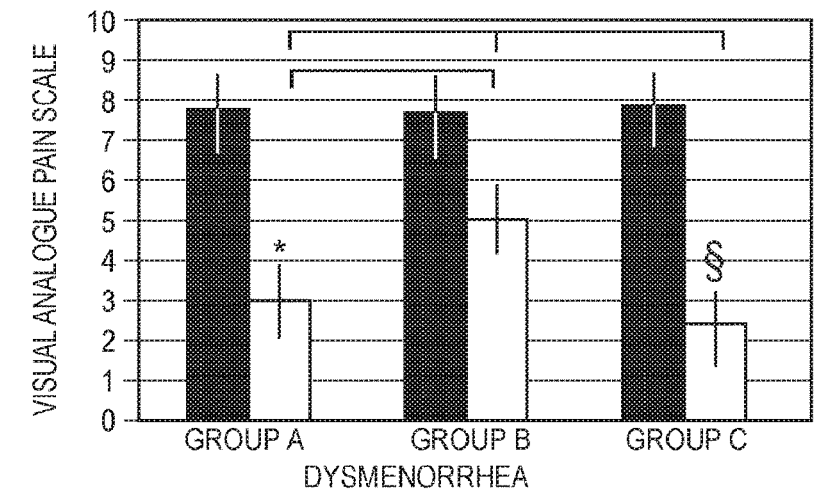

FIG. 2F is a bar graph measuring a visual analog of dysmenorrhea among Groups A, B. and C.

Figure 2G:
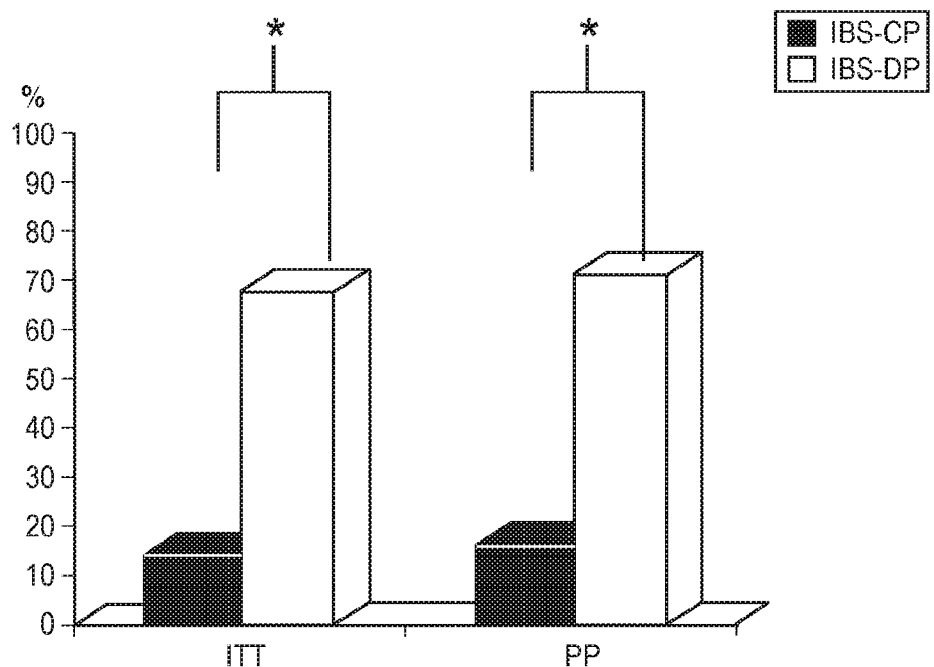

FIG. 2G is a bar graph illustrating percentage regularization of status following treatment with butyric acid and insulin. In particular, 15 IBS-DP patients vs. 4 IBS-CP patients: 68% vs 14% and 71% vs 16% respectively in the intent to treat (ITT) and per-protocol (PP) groups (p<0.005). *Statistically significant (p<0.005).

Figure 2H:
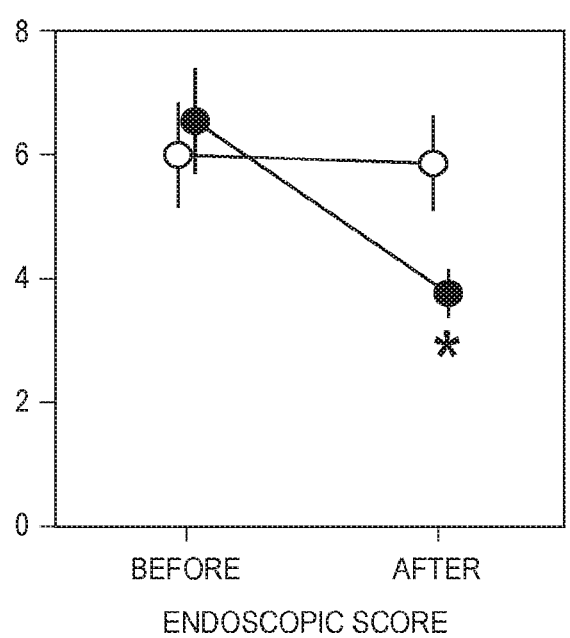

FIG. 2H is a scatter plot illustrating the endoscopic score (n=10) in patients with distal UC before and after treatment with sodium butyrate (black dot) or sodium chloride (white dot; control) enemas. Vertical bars indicate 1 SEM; *significant differences (endoscopic score, P<0.01; histological grading, P<0.02; upper-crypt labeling, P<0.03; Wilcoxon test).

Figure 2I:
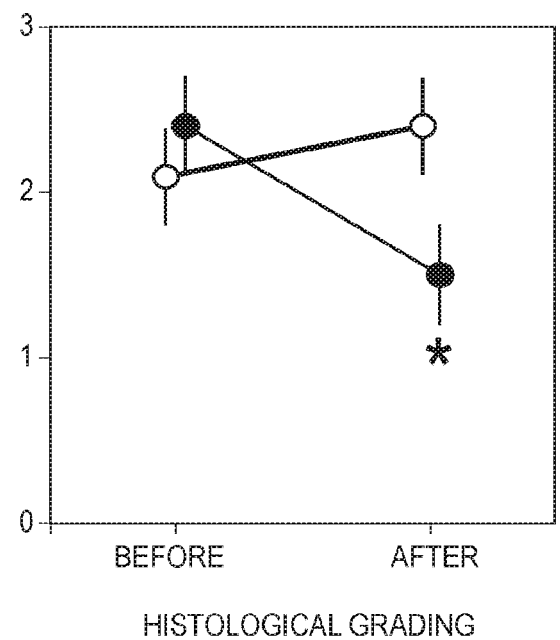

FIG. 2I is a scatter plot illustrating the histological grading (n=10) in patients with distal UC before and after treatment with sodium butyrate (black dot) or sodium chloride (white dot; control) enemas. Vertical bars indicate 1 SEM; *significant differences (endoscopic score, P<0.01; histological grading, P<0.02; upper-crypt labeling, P<0.03; Wilcoxon test).

Figure 2J:
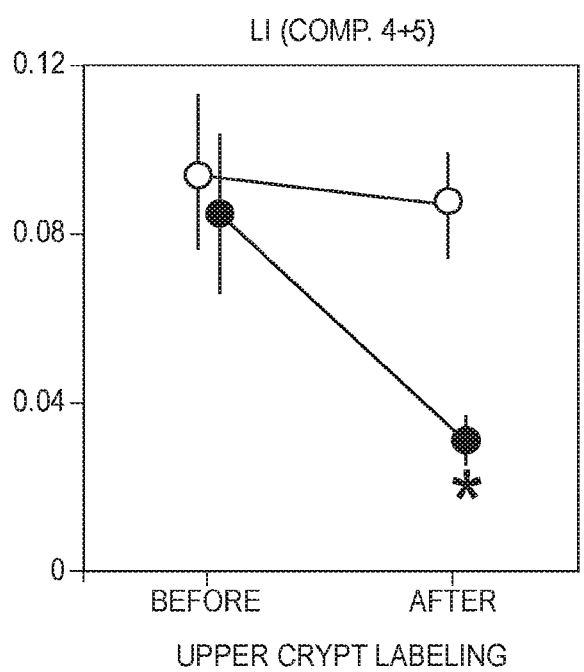

FIG. 2J is a scatter plot illustrating the upper-crypt labeling frequency (n=6) in patients with distal UC before and after treatment with sodium butyrate (black dot) or sodium chloride (white dot; control) enemas. Vertical bars indicate 1 SEM; *significant differences (endoscopic score, P<0.01; histological grading, P<0.02; upper-crypt labeling, P<0.03; Wilcoxon test).

Figure 2K:
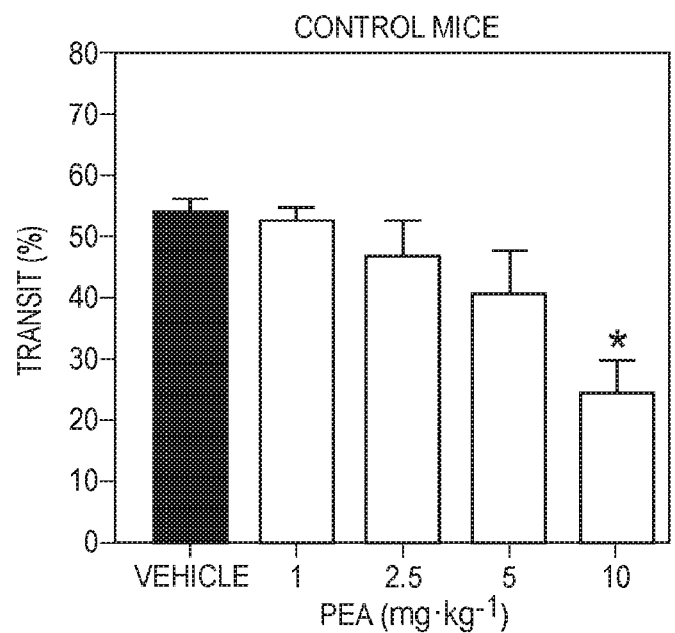

FIG. 2K is a bar graph illustrating inhibitory effect of PEA (1-10 mg·kg$^{-1}$, i.p.) on upper gastrointestinal transit in control mice. Transit was measured 28 days after OM or vehicle (30% ethanol) administration. Results (the means±SEM of 9-10 mice for each experimental group) are expressed as a percentage of upper gastrointestinal transit. *P<0.05, **P<0.01, significantly different from vehicle. The term "vehicle" refers to the vehicle used to dissolve PEA.

Figure 2L:
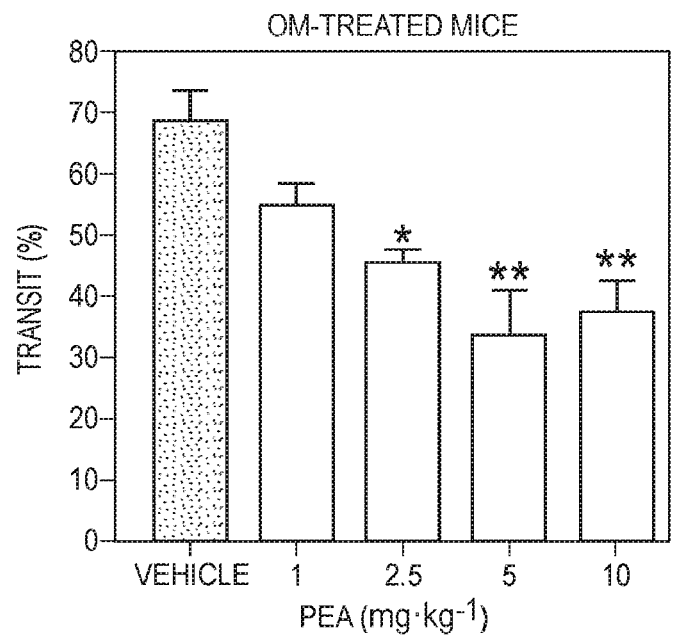

FIG. 2L is a bar graph illustrating inhibitory effect of PEA (1-10 mg·kg$^{-1}$, i.p.) on upper gastrointestinal transit in mice treated with OM (oil of mustard). Transit was measured 28 days after OM or vehicle (30% ethanol) administration. Results (the means±SEM of 9-10 mice for each experimental group) are expressed as a percentage of upper gastrointestinal transit. *P<0.05, **P<0.01, significantly different from vehicle. Note that in (B) the term "vehicle" refers to the vehicle used to dissolve OM. the % transit of a vehicle or PEA in OM-treated mice.

Figure 2M:
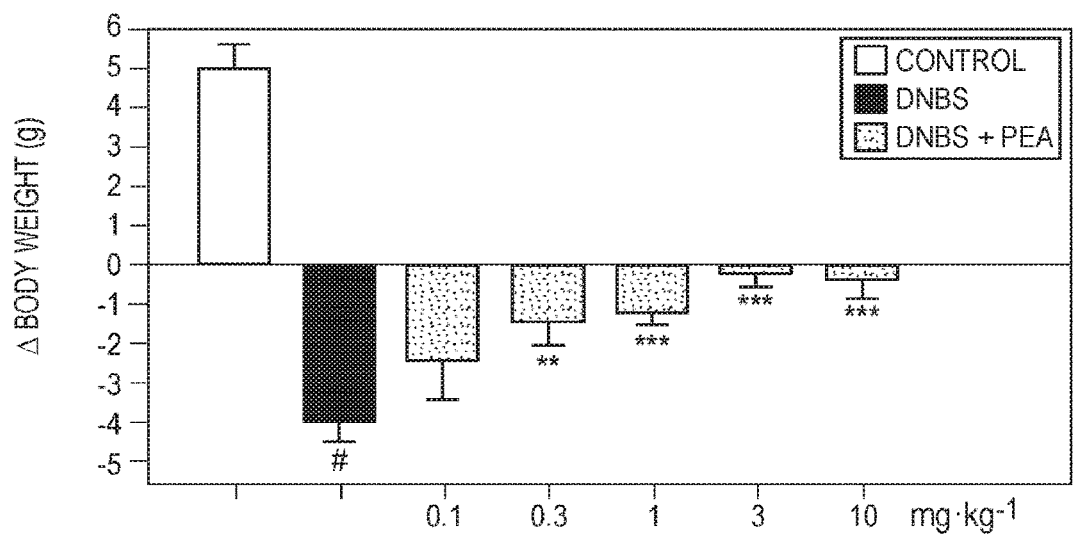

FIG. 2M is a bar graph illustrating 2,4,6-dinitrobenzenesulfonic acid-induced ("DNBS-induced") colitis in mice. Changes in body weight from control and DNBS-treated mice in the presence or absence of intraperitoneal (i.p.) PEA. Mice were weighed before DNBS (or vehicle) administration and immediately before killing. Tissues were analysed 3 days after vehicle or DNBS administration. PEA (0.1-10 mg·kg$^{-1}$) was administered once a day for three consecutive days starting 24 h after the inflammatory insult (therapeutic protocol). Bars are mean±SEM of 12-15 mice for each experimental group. #P<0.001 versus control (i.e. mice without intestinal inflammation). *P<0.05, P<0.01 and *P<0.001 versus DNBS alone.

Figure 2N:
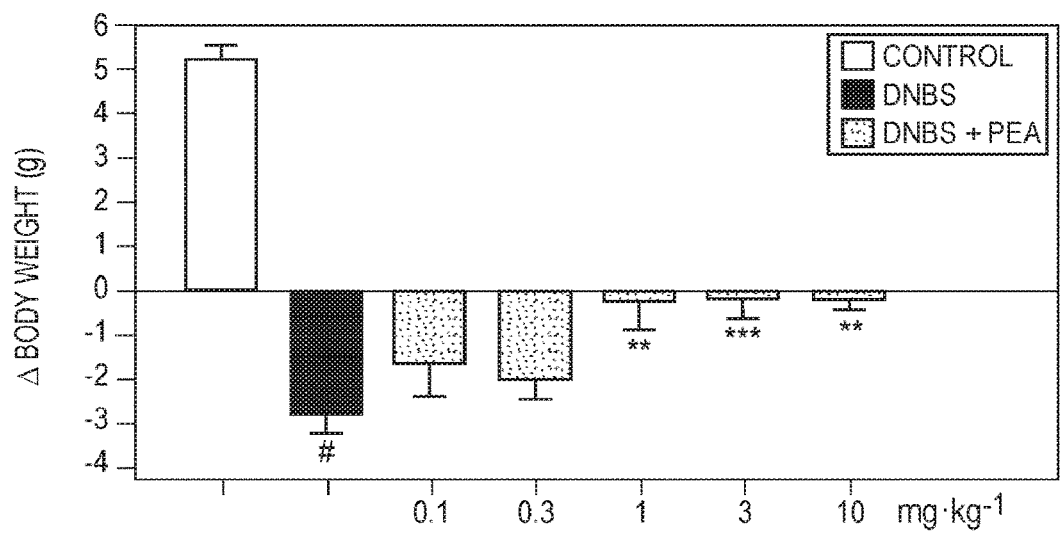

FIG. 2N is a bar graph illustrating DNBS-induced colitis in mice. Changes in body weight from control and DNBS-treated mice in the presence or absence of orally administered (p.o.) PEA. Mice were weighed before DNBS (or vehicle) administration and immediately before killing. Tissues were analysed 3 days after vehicle or DNBS administration. PEA (0.1-10 mg·kg$^{-1}$) was administered once a day for three consecutive days starting 24 h after the inflammatory insult (therapeutic protocol). Bars are mean±SEM of 12-15 mice for each experimental group. #P<0.001 versus control (i.e. mice without intestinal inflammation). *P<0.05, P<0.01 and *P<0.001 versus DNBS alone.

Figure 2O:
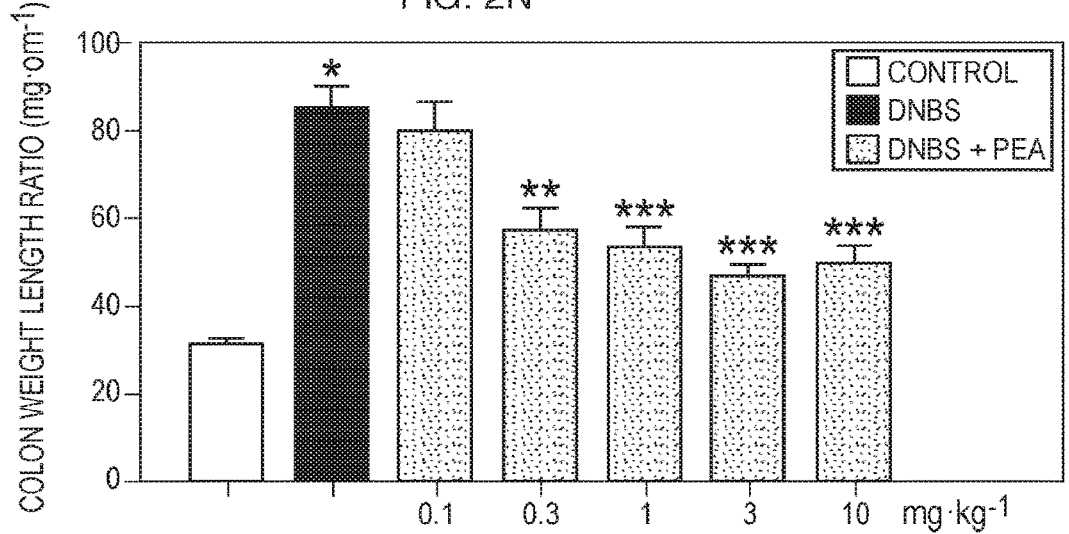

FIG. 2O is a bar graph illustrating DNBS-induced colitis in mice. Changes in colon weight/colon length ratio from control and DNBS-treated mice in the presence or absence of i.p. PEA. Mice were weighed before DNBS (or vehicle) administration and immediately before killing. Tissues were analysed 3 days after vehicle or DNBS administration. PEA (0.1-10 mg·kg$^{-1}$) was administered once a day for three consecutive days starting 24 h after the inflammatory insult (therapeutic protocol). Bars are mean±SEM of 12-15 mice for each experimental group. #P<0.001 versus control (i.e. mice without intestinal inflammation). *P<0.05, P<0.01 and *P<0.001 versus DNBS alone.

Figure 2P:
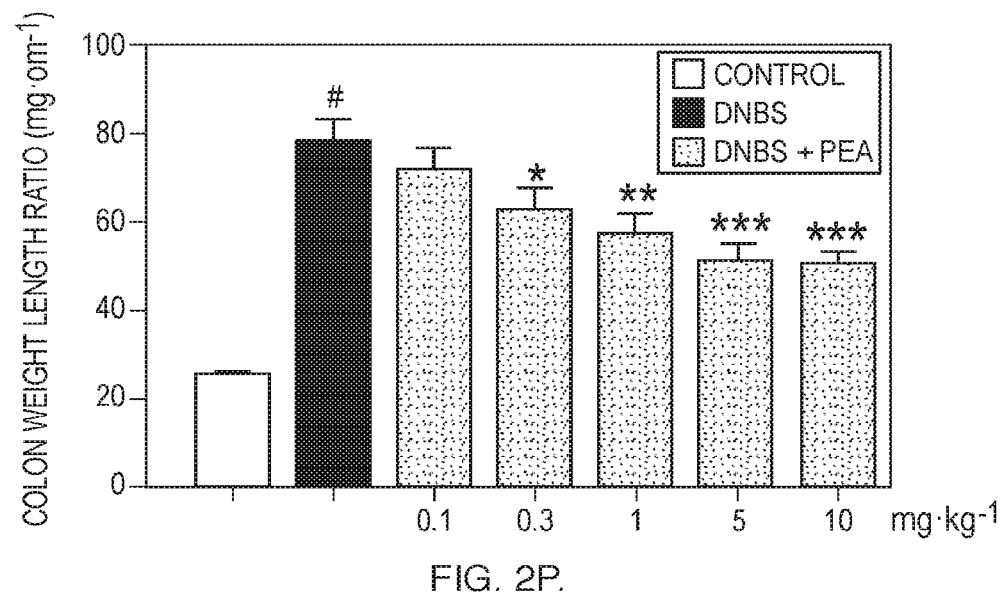

FIG. 2P is a bar graph illustrating DNBS-induced colitis in mice. Changes in colon weight/colon length ratio from control and DNBS-treated mice in the presence or absence of p.o. PEA. Mice were weighed before DNBS (or vehicle) administration and immediately before killing. Tissues were analysed 3 days after vehicle or DNBS administration. PEA (0.1-10 mg·kg$^{-1}$) was administered once a day for three consecutive days starting 24 h after the inflammatory insult (therapeutic protocol). Bars are mean±SEM of 12-15 mice for each experimental group. #P<0.001 versus control (i.e. mice without intestinal inflammation). *P<0.05, P<0.01 and *P<0.001 versus DNBS alone.

Figure 2Q:
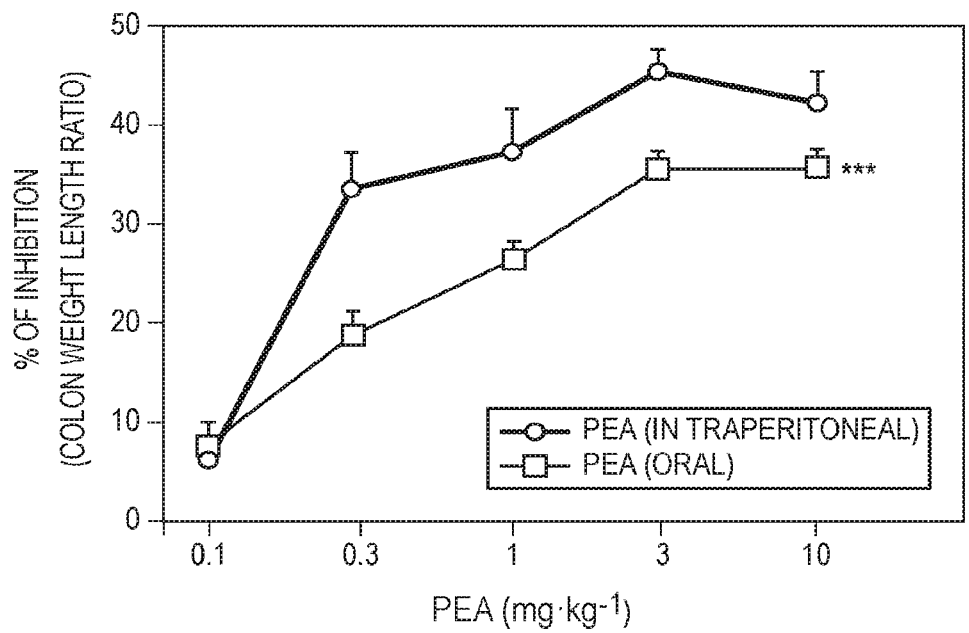

FIG. 2Q is a scatter plot measuring the % inhibition (as measured by colon weight: length ratio) versus the amount of PEA administered for two populations (one via oral administration, the other intraperitoneal).

Figure 3A:
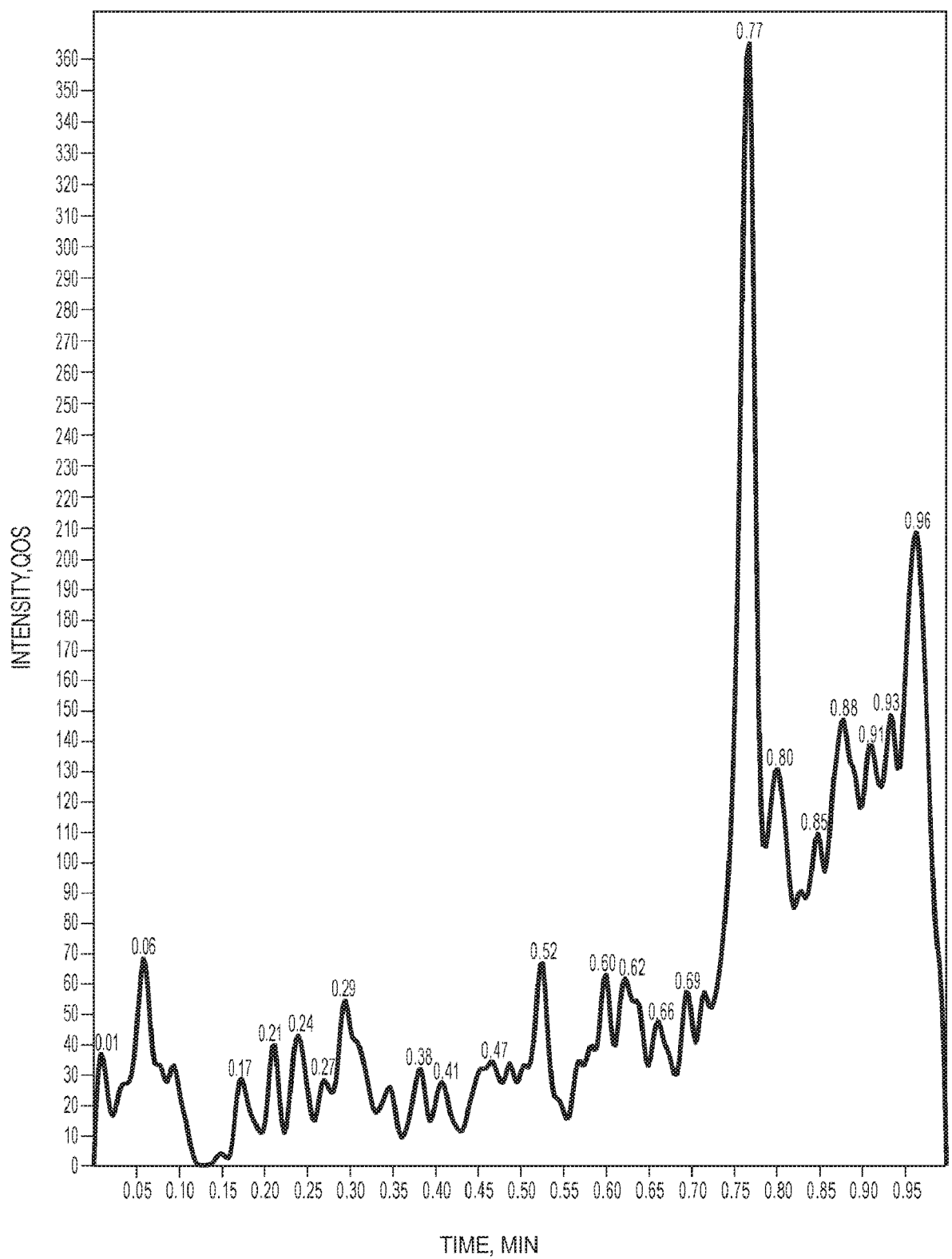

FIG. 3A is a blank plasma chromatogram of PEA. The Y-axis measures intensity (cps) on a scale from 0 to 365; the X-axs measured time (min) on a scale from 0 to 1.0.

Figure 3B:
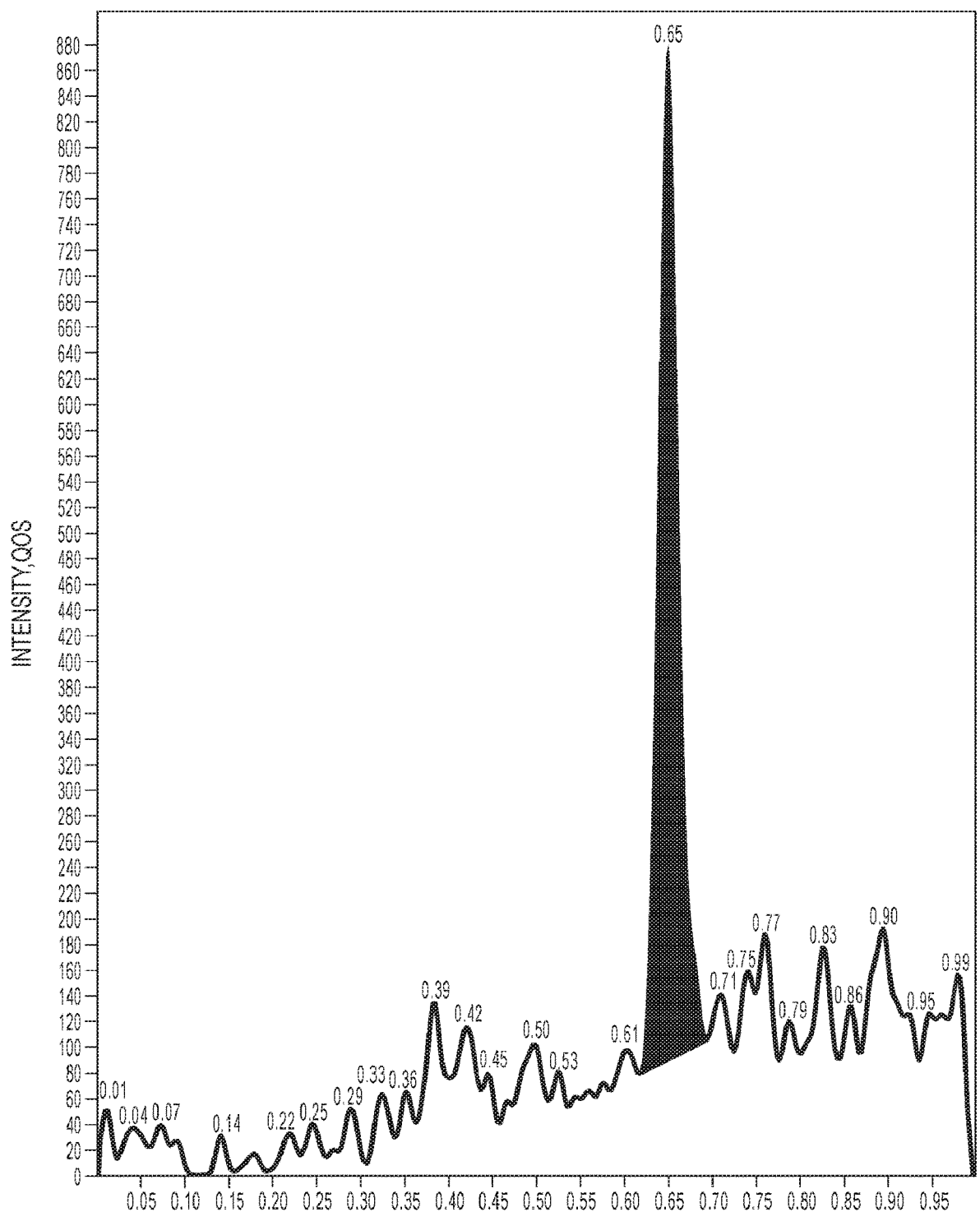

FIG. 3B is a representative chromatogram of LLOQ for PEA, 2.5 ng/mL. The Y-axis measures intensity (cps) on a scale from 0 to 870; the X-axs measures time (min) on a scale from 0 to 1.0.

Figure 3C:
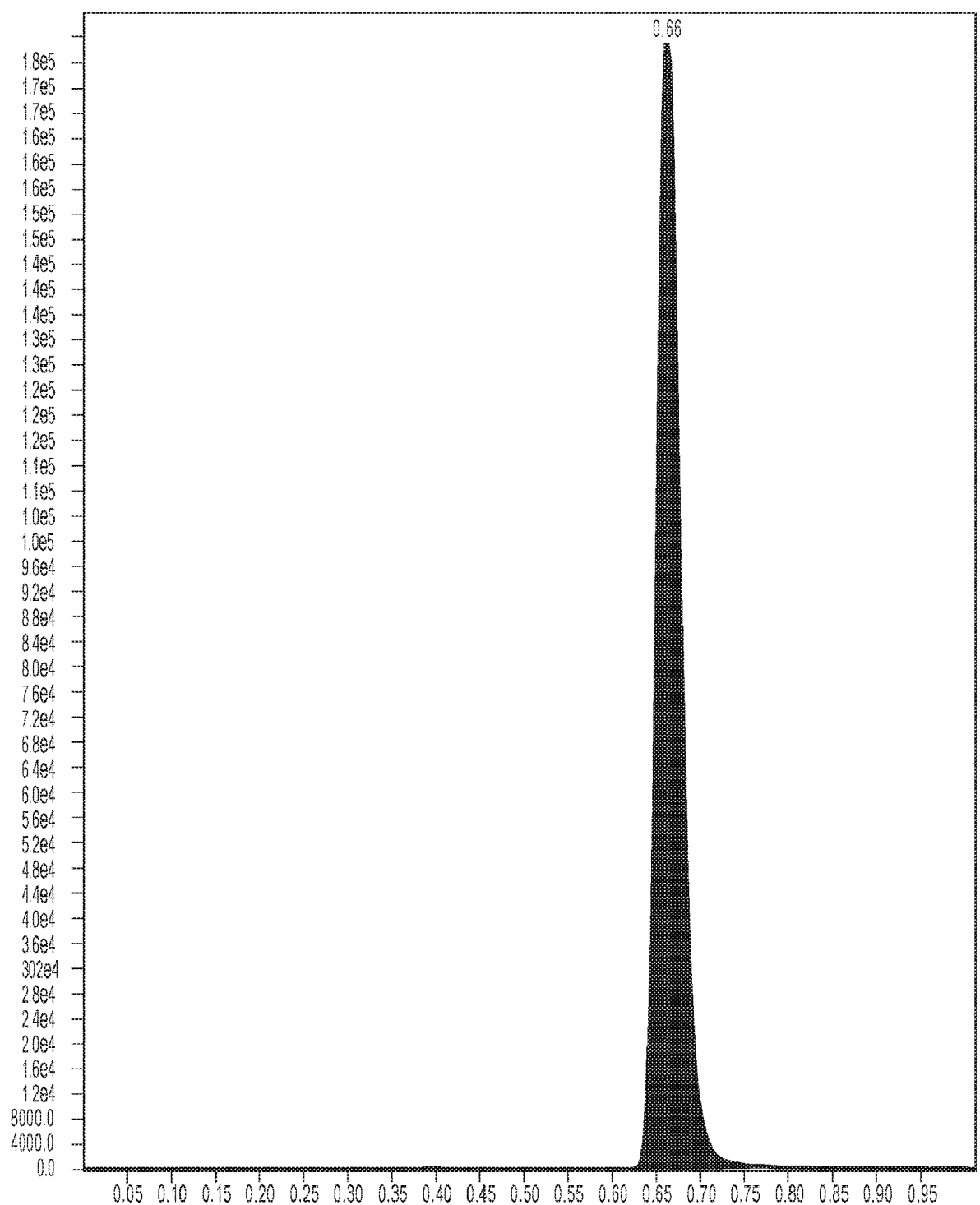

FIG. 3C is a representative chromatogram of the ULOQ for PEA, 1000 ng/mL. The Y-axis measures intensity (cps) on a scale from 0 to $1.8\times10^5$; the X-axs measures time (min) on a scale from 0 to 1.0.

Figure 3D:
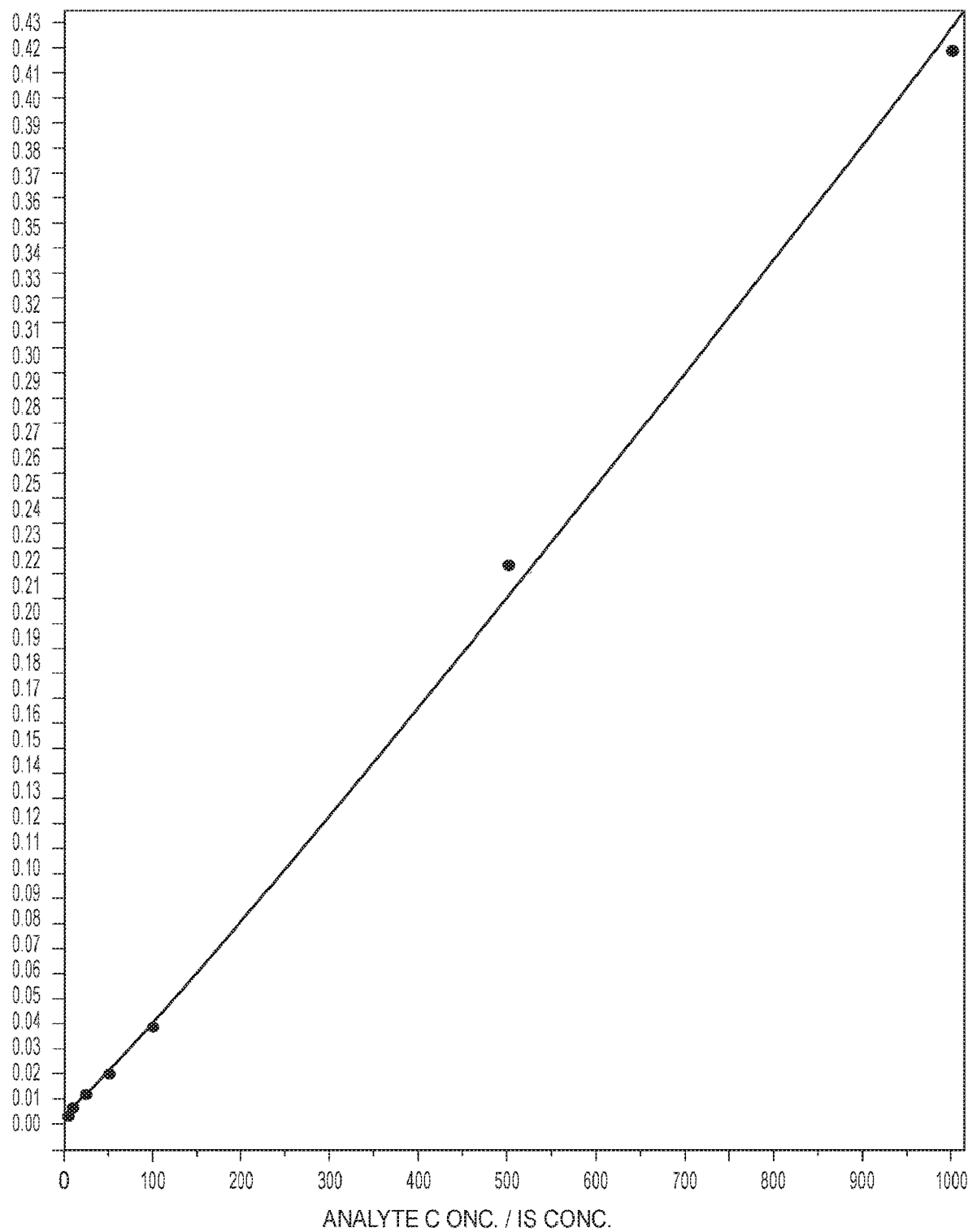

FIG. 3D is a representative calibration curve for PEA.

Figure 3E:
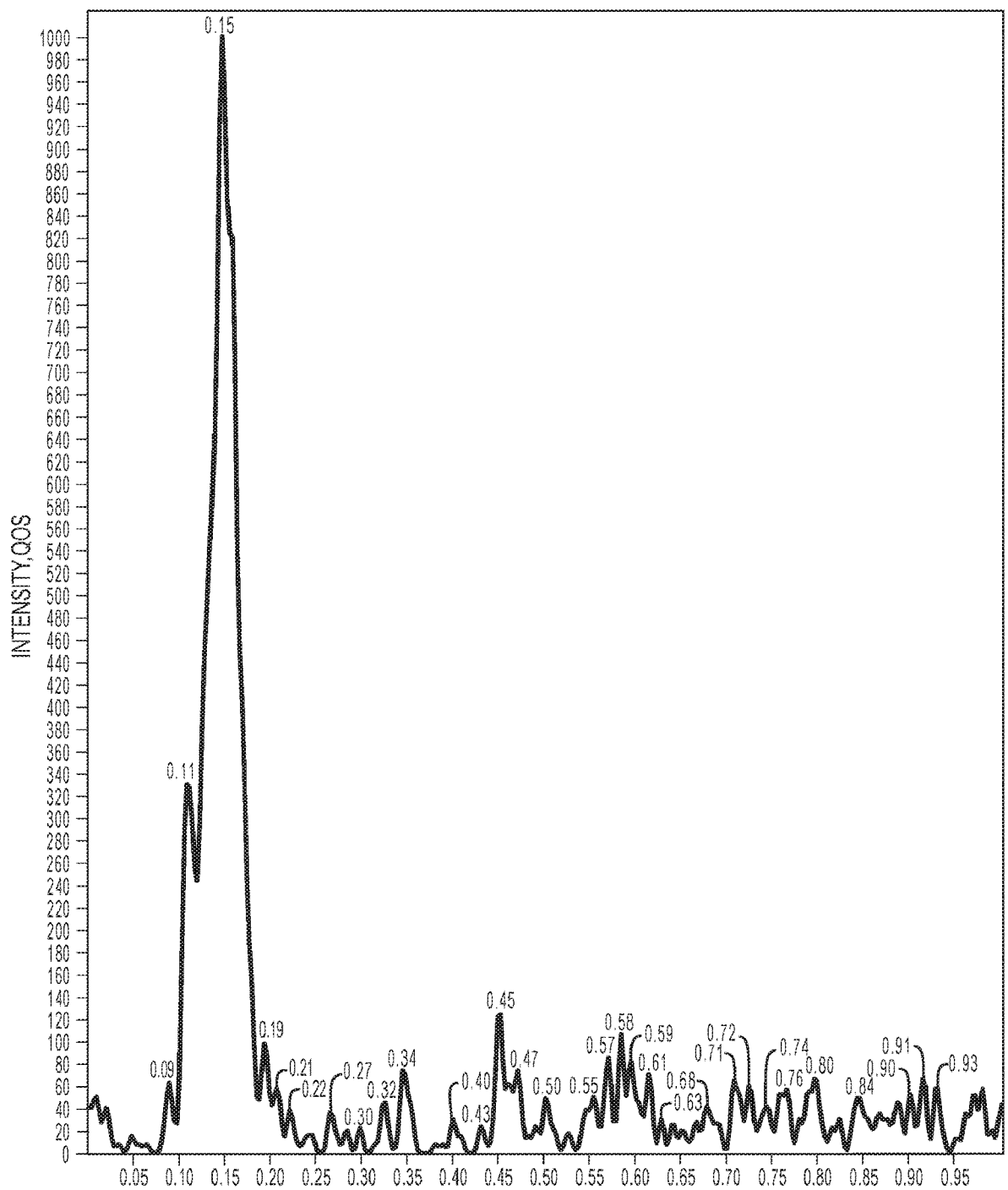

FIG. 3E is a blank plasma chromatogram of PEA-prodrug I-9. The Y-axis measures intensity (cps) on a scale from 0 to 1000; the X-axs measures time (min) on a scale from 0 to 1.0.

Figure 3F:
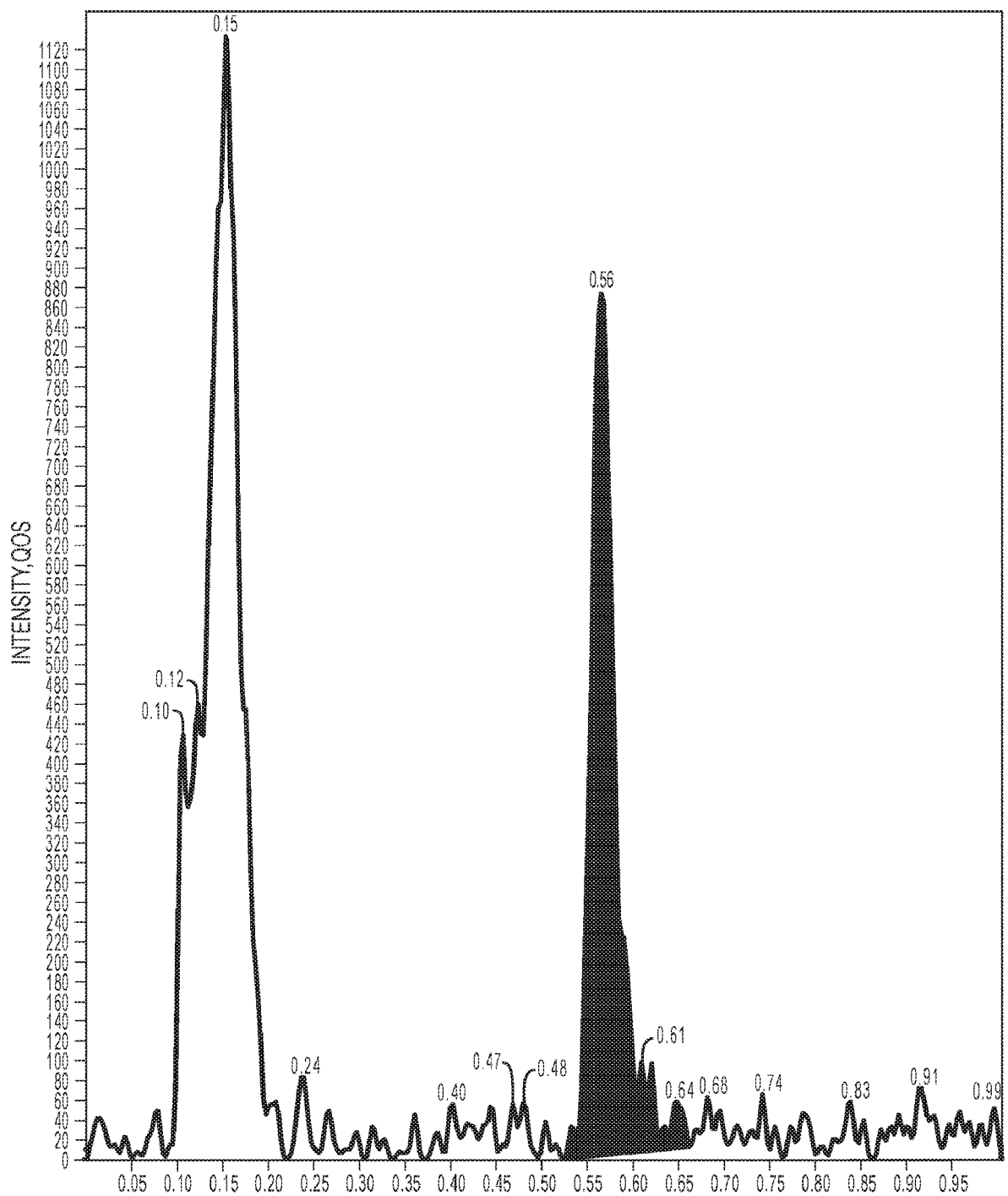

FIG. 3F is a representative chromatogram of LLOQ for PEA-prodrug I-9, 0.5 ng/mL. The Y-axis measures intensity (cps) on a scale from 0 to 1120; the X-axs measures time (min) on a scale from 0 to 1.0.

Figure 3G:
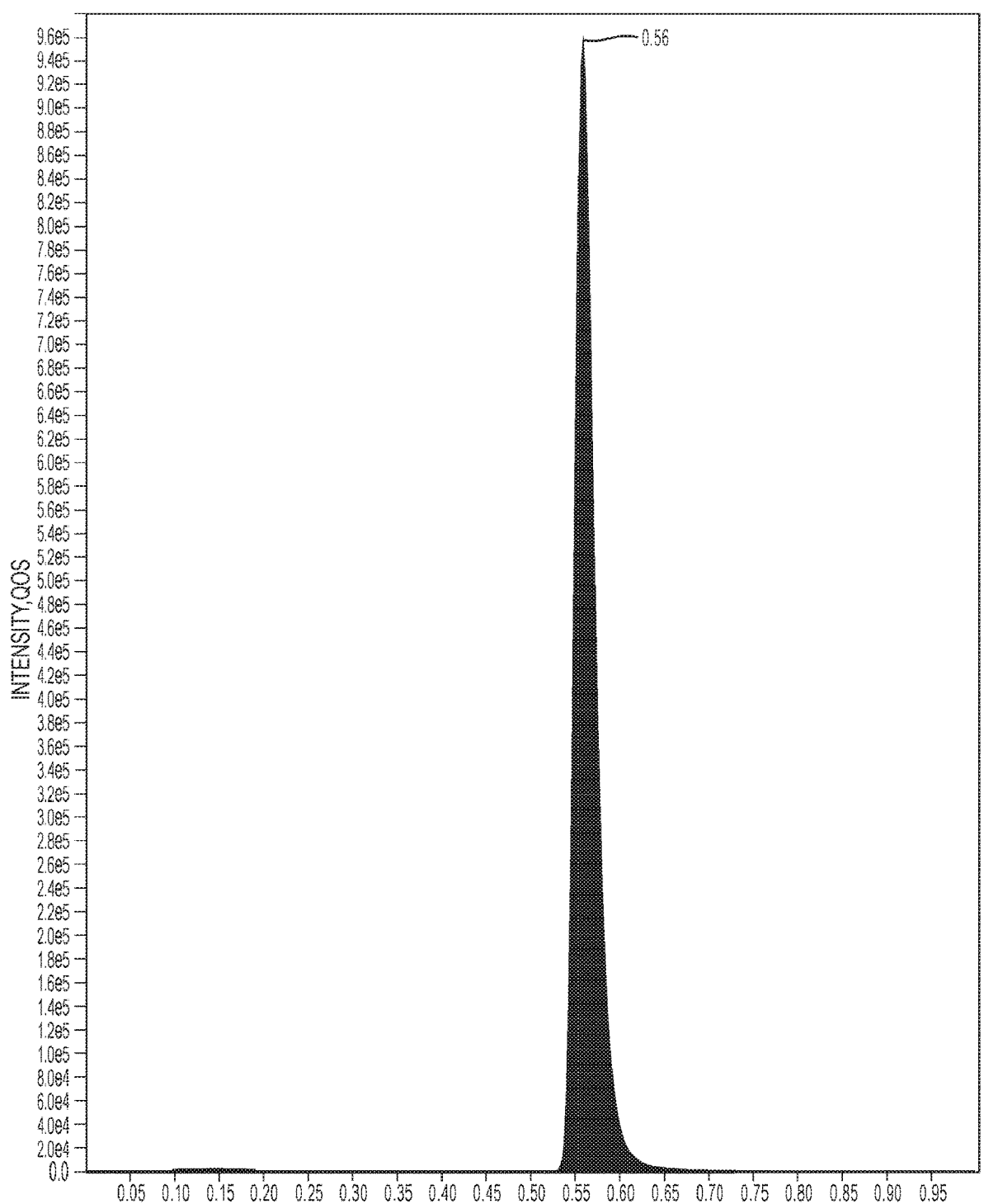

FIG. 3G is a representative chromatogram for ULOQ for PEA prodrug I-9, 1000 ng/mL. The Y-axis measures intensity (cps) on a scale from 0 to $9 \times 10^6$; the X-axs measures time (min) on a scale from 0 to 1.0.

Figure 3H:
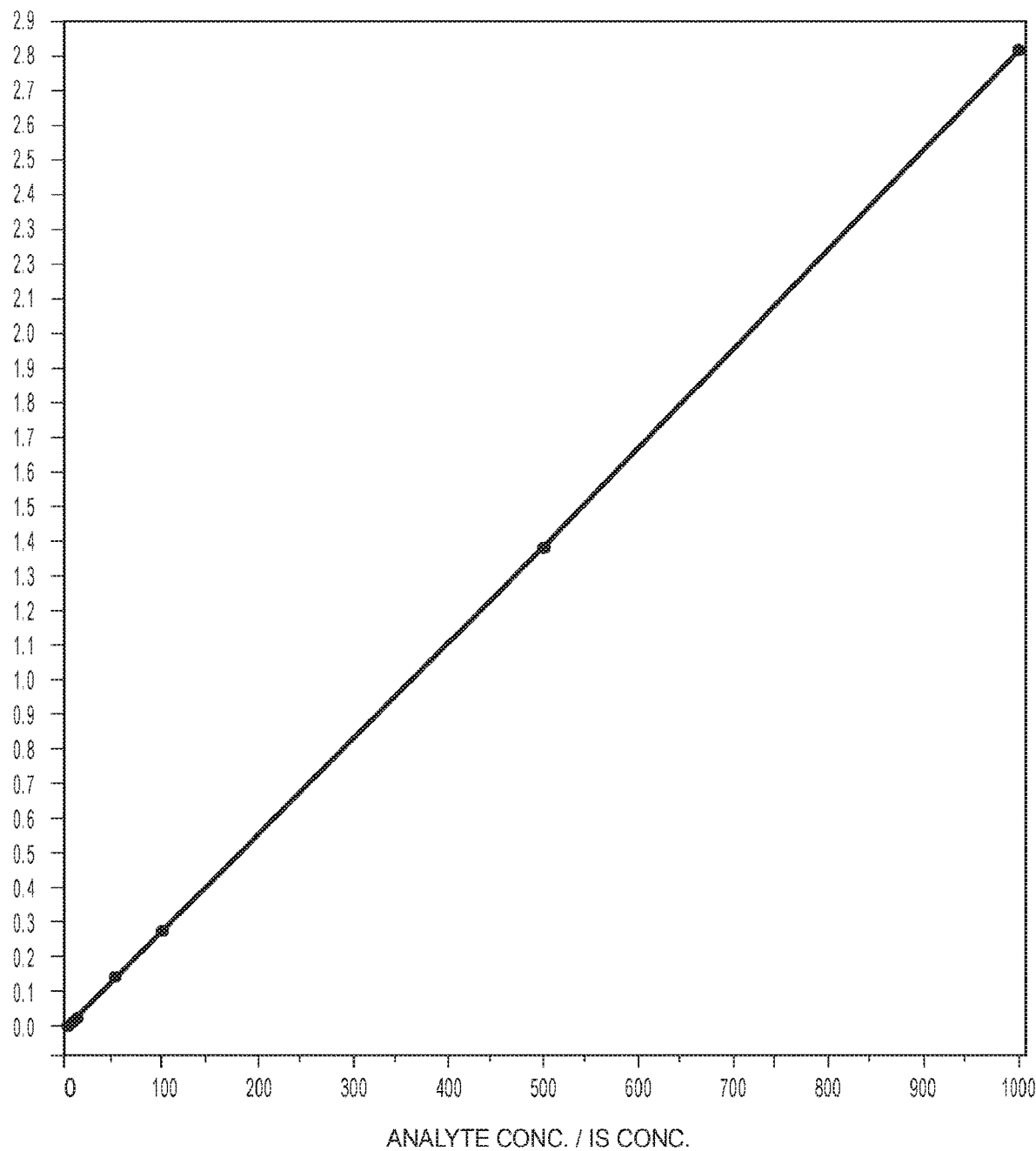

FIG. 3H is a representative calibration curve for PEA-prodrug I-9.

Figure 4A:
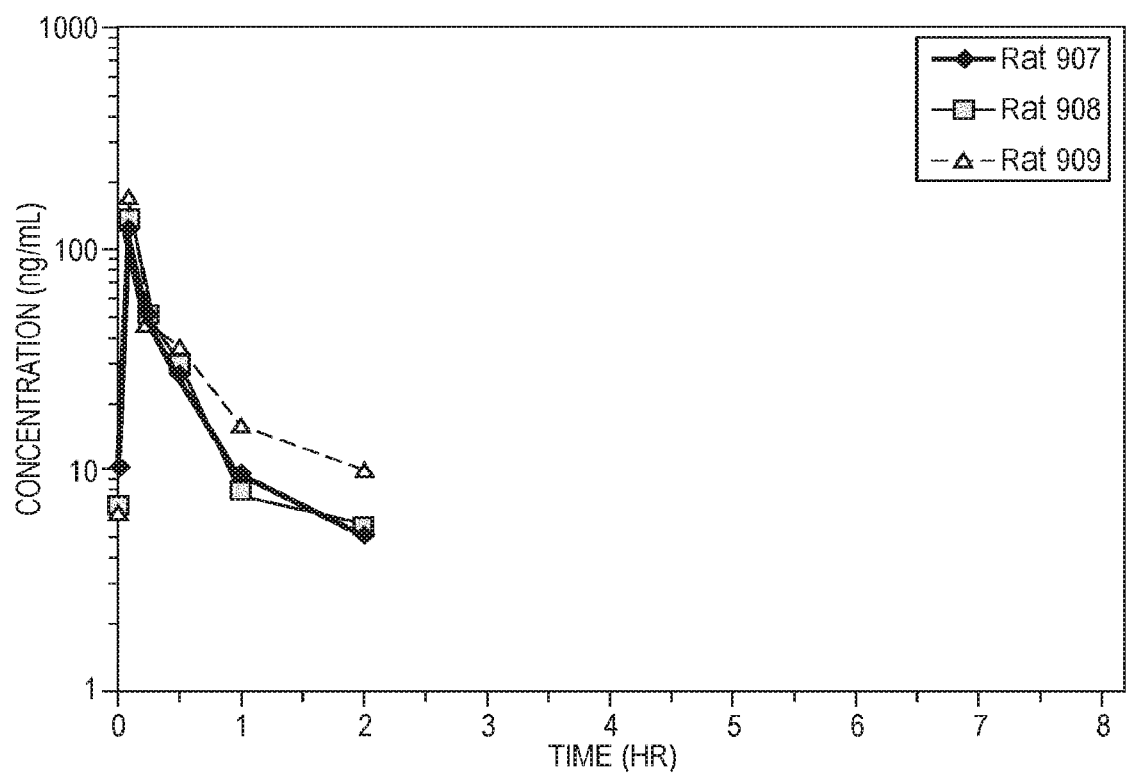

FIG. 4A is a scatter plot of individual plasma concentrations of PEA after intravenous administration of PEA in male Sprague-Dawley rats at 1 mg/kg (Group 1).

Figure 4B:
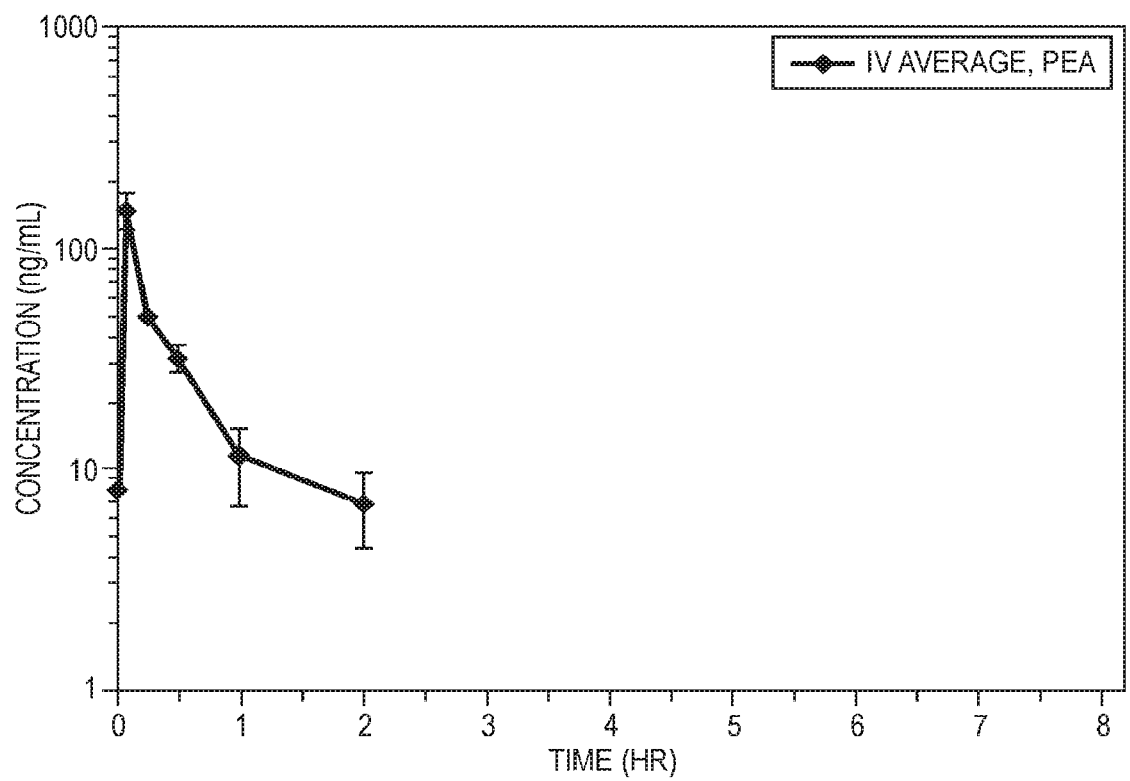

FIG. 4B is a scatter plot of average plasma concentrations of PEA after intravenous administration of PEA in male Sprague-Dawley rats at 1 mg/kg (Group 1).

Figure 5A:
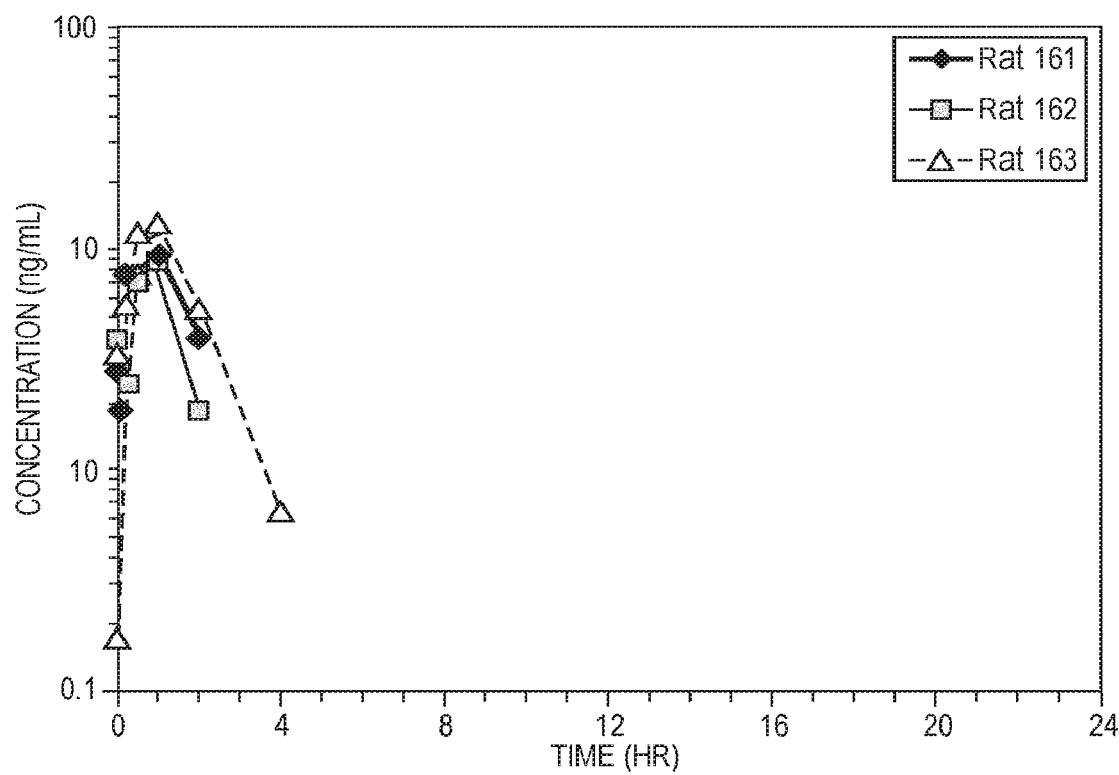

FIG. 5A is a scatter plot of individual plasma concentrations of PEA after oral administration of I-9 at 16 mg/kg in male Sprague Dawley rats.

Figure 5B:
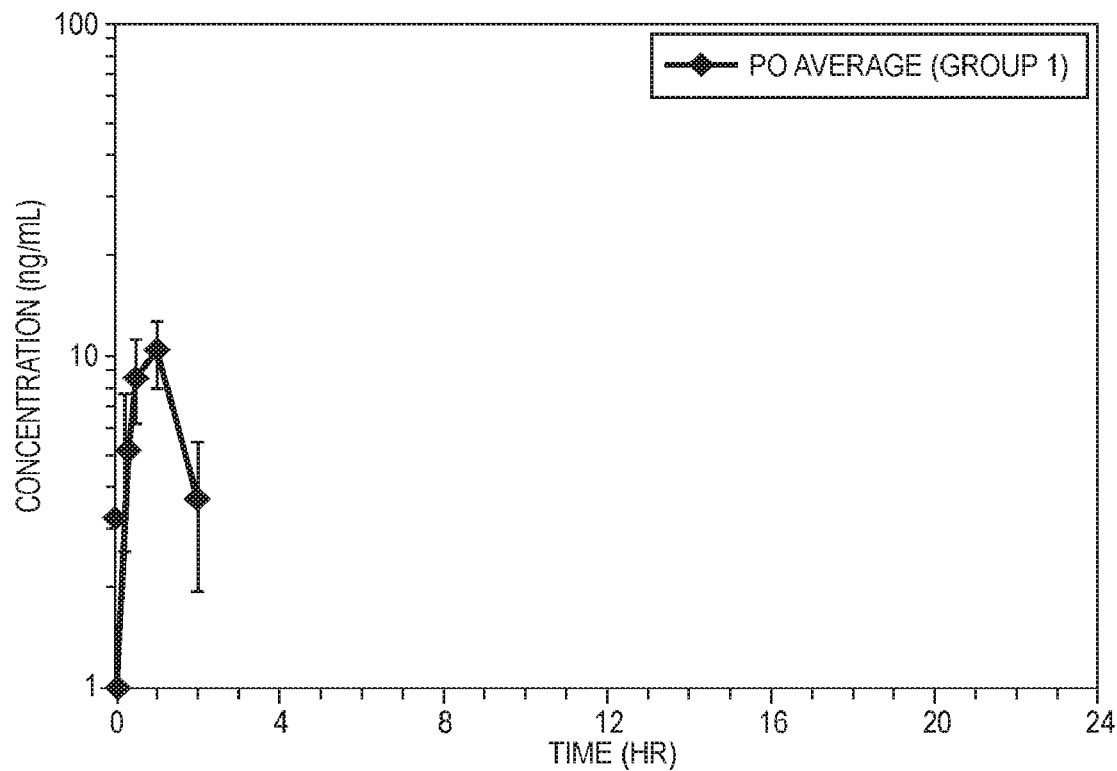

FIG. 5B is a scatter plot of average plasma concentrations of PEA after oral administration of I-9 at 16 mg/kg in male Sprague-Dawley rats.

Figure 5C:
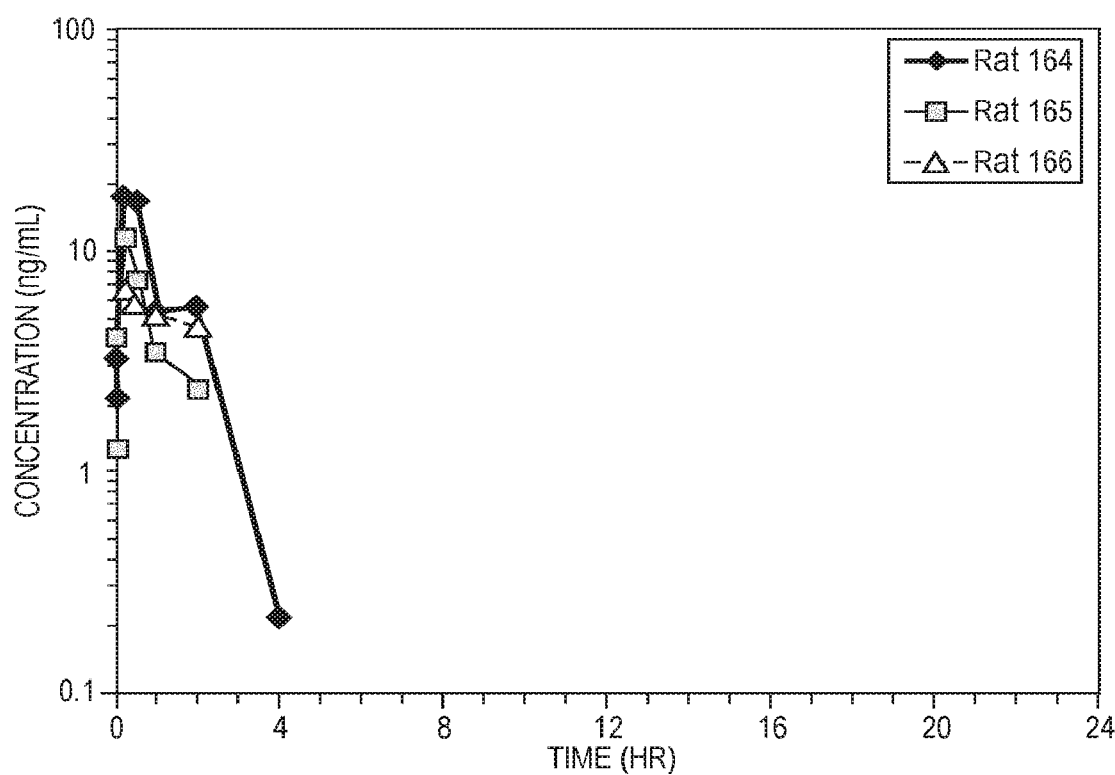

FIG. 5C is a scatter plot of individual plasma concentrations of PEA after oral administration of I-6 at 19 mg/kg in male Sprague-Dawley rats (Group 2).

Figure 5D:
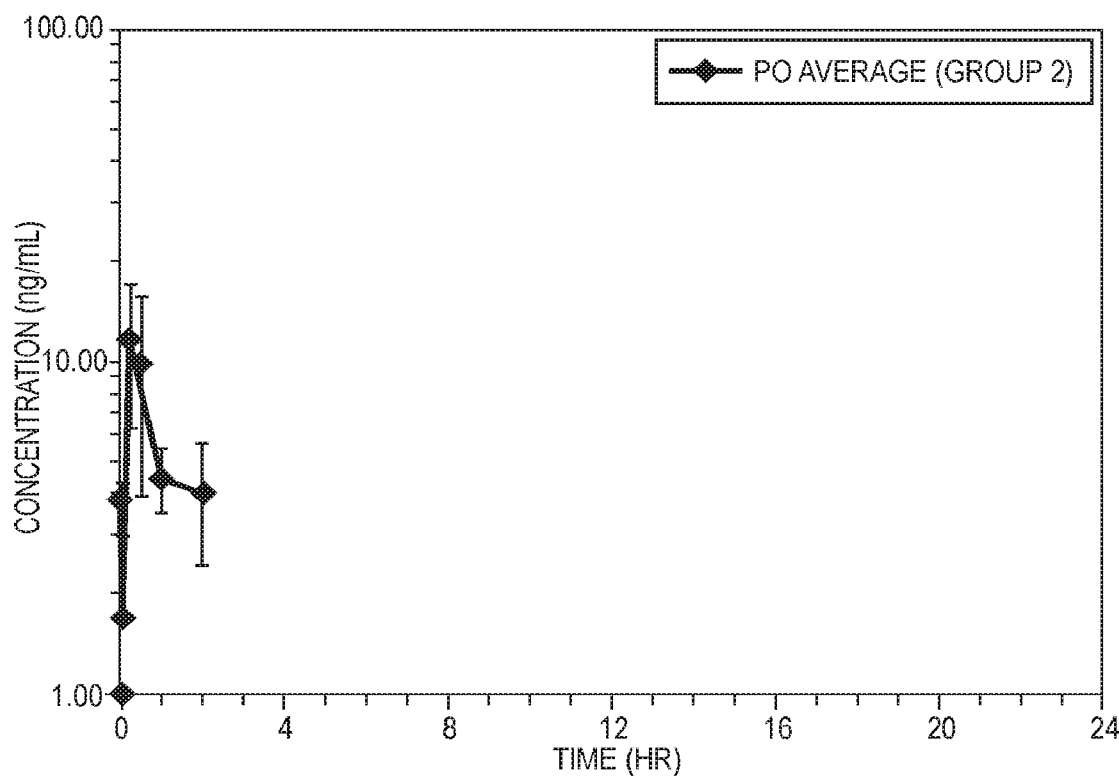

FIG. 5D is a scatter plot of average plasma concentrations of PEA after oral administration of I-6.

Figure 5E:
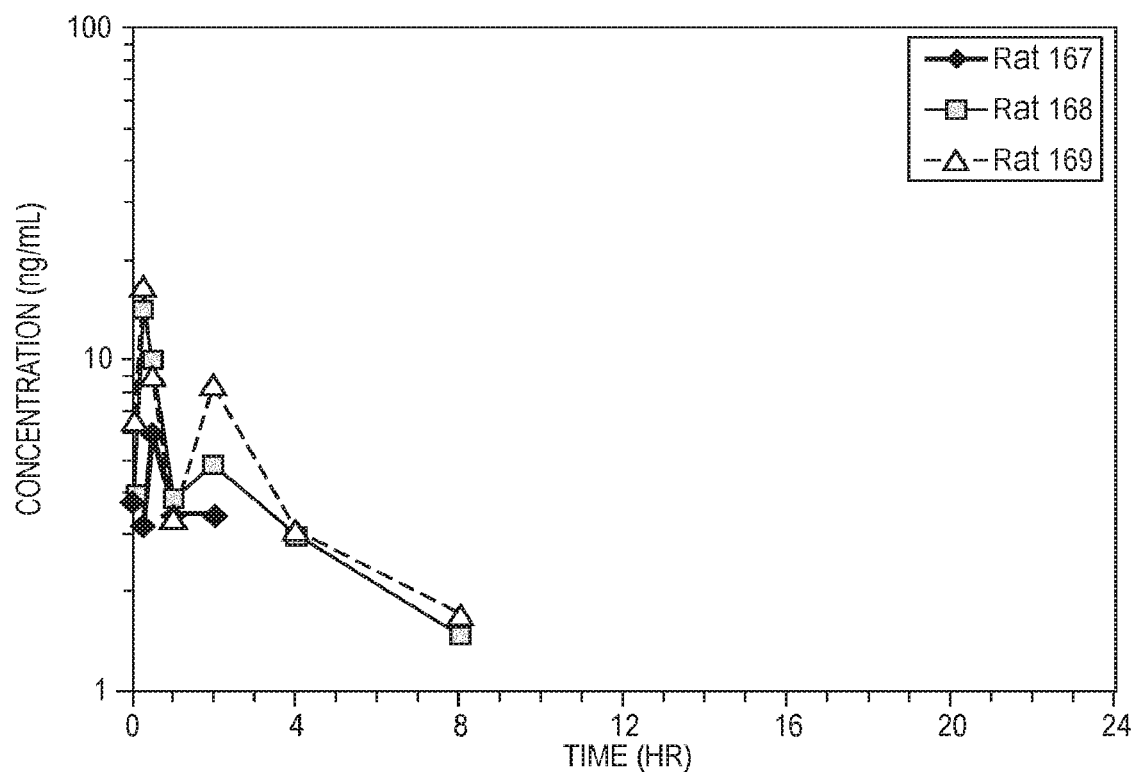

FIG. 5E is a scatter plot of individual plasma concentrations of PEA after oral administration of I-5 at 19.7 mg/kg in male Sprague-Dawley rats (Group 3).

Figure 5F:
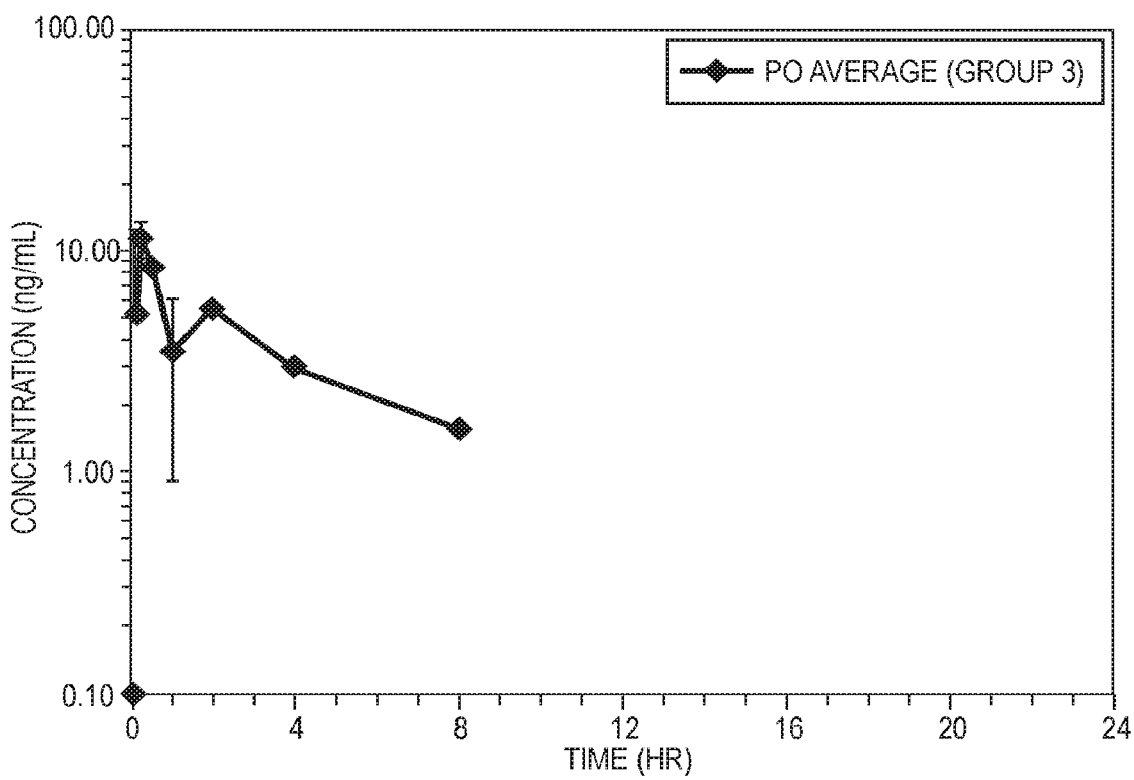

FIG. 5F is a scatter plot of average plasma concentrations of PEA after oral administration of I-5 at 19.7 mg/kg in male Sprague-Dawley rats (Group 3).

Figure 5G:
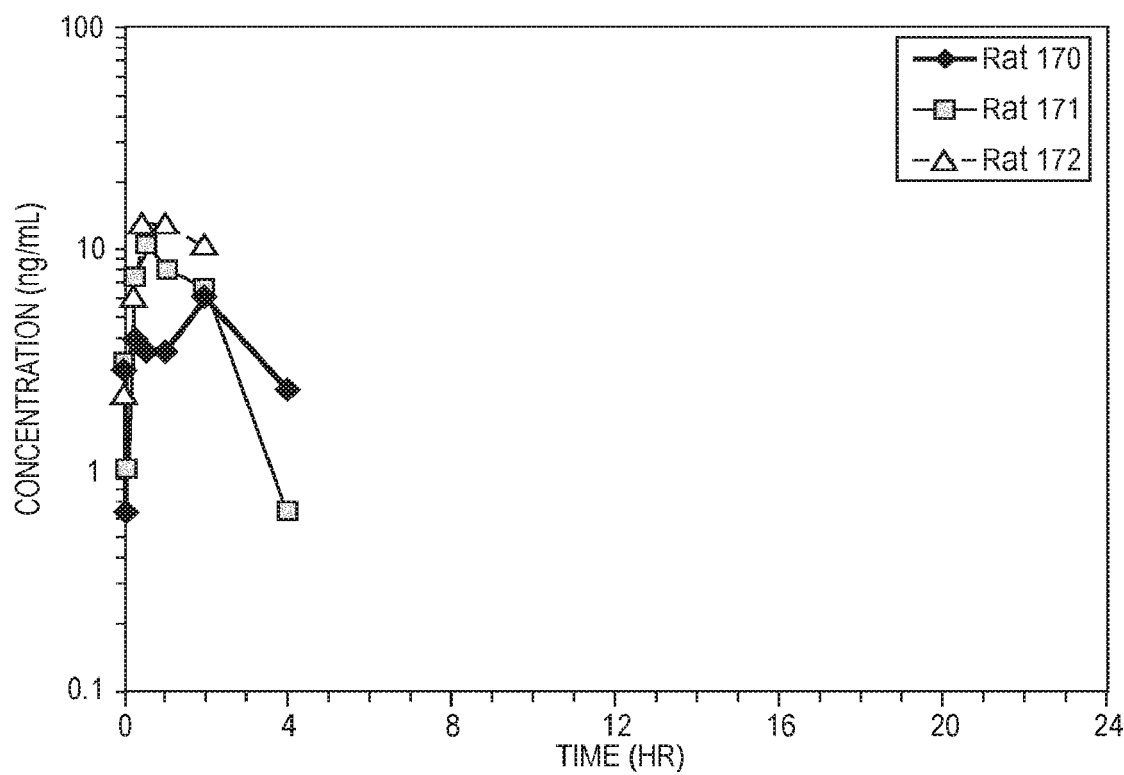

FIG. 5G is a scatter plot of individual plasma concentrations of PEA after oral administration of I-3 (PEA-Succinate-Glycerol-Di-Caprylic) at 24.5 mg/kg in male Sprague-Dawley rats (Group 4).

Figure 5H:
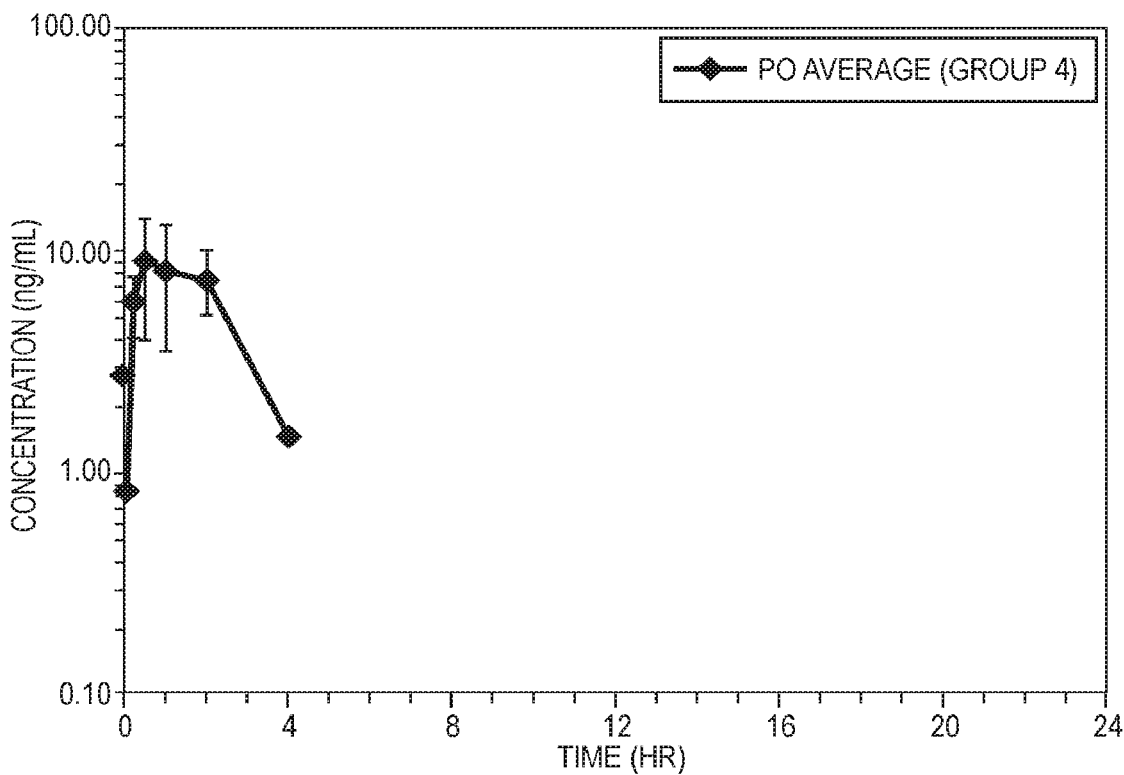

FIG. 5H is a scatter plot of average plasma concentrations of PEA after oral administration of I-3 (PEA-Succinate-Glycerol-Di-Caprylic) at 24.5 mg/kg in male Sprague-Dawley rats (Group 4).

Figure 5I:
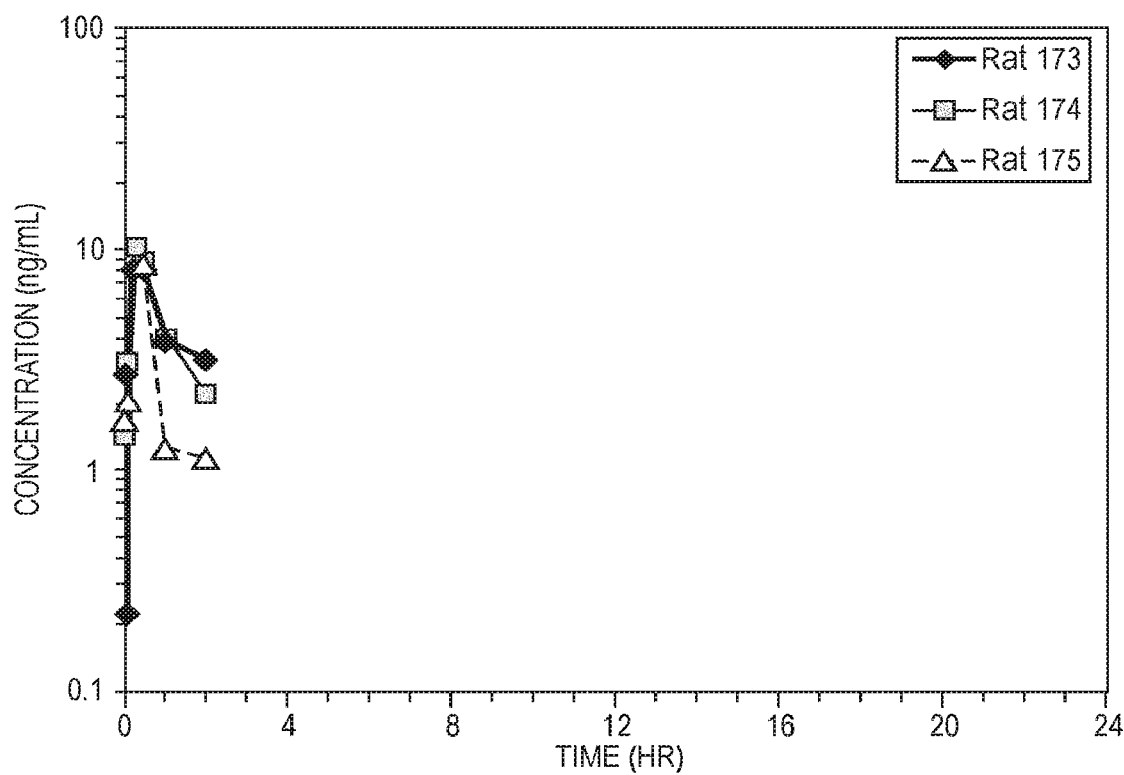

FIG. 5I is a scatter plot of individual plasma concentrations of PEA after oral administration of I-2 (PEA-BA) at 12/5 mg/kg in male Sprague-Dawley rats (Group 5).

Figure 5J:
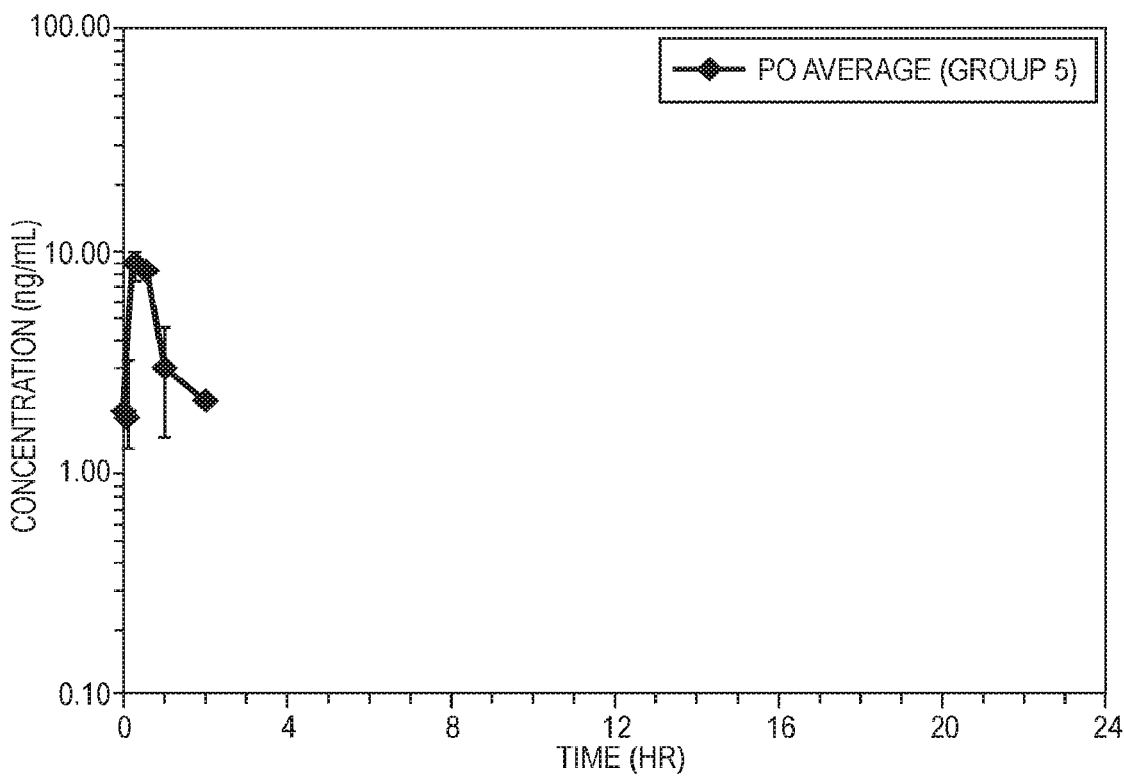

FIG. 5J is a scatter plot of average plasma concentrations of PEA after oral administration of I-2 (PEA-BA) at 12.5 mg/kg in male Sprague-Dawley rats (Group 5).

Figure 5K:
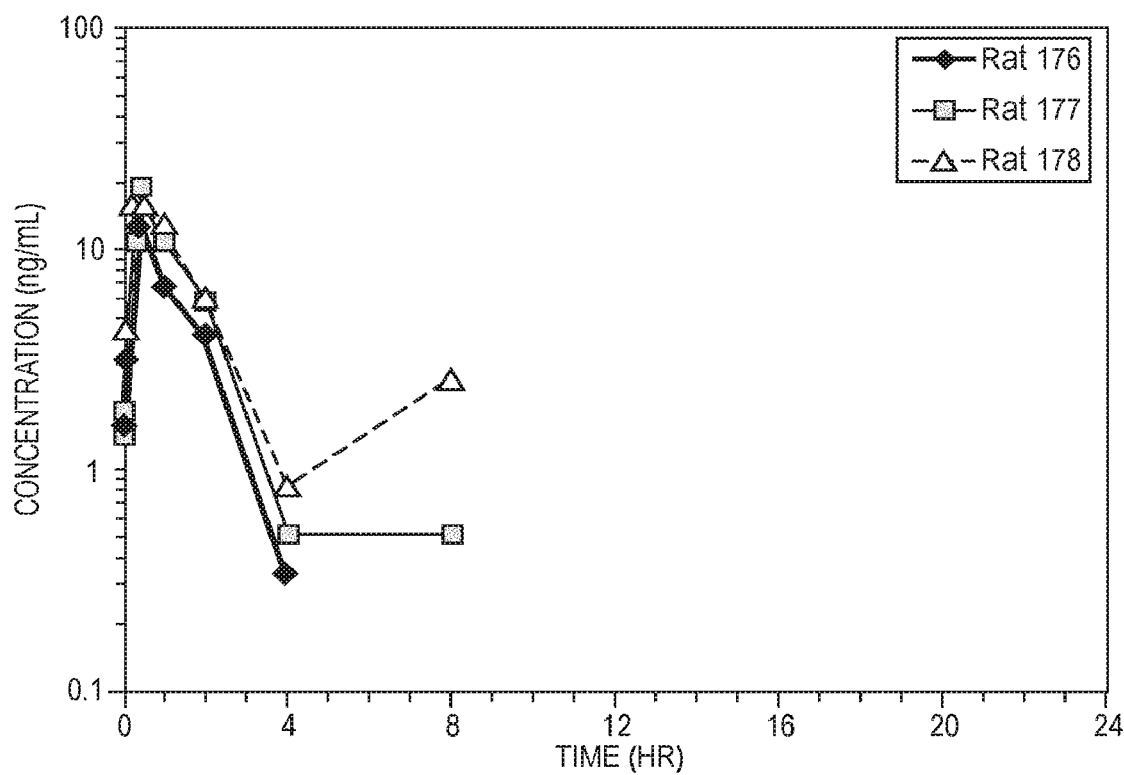

FIG. 5K is a scatter plot of individual plasma concentrations of PEA after oral administration of I-11 at 20.7 mg/kg in Male Sprague-Dawley Rats (Group 6).

Figure 5L:
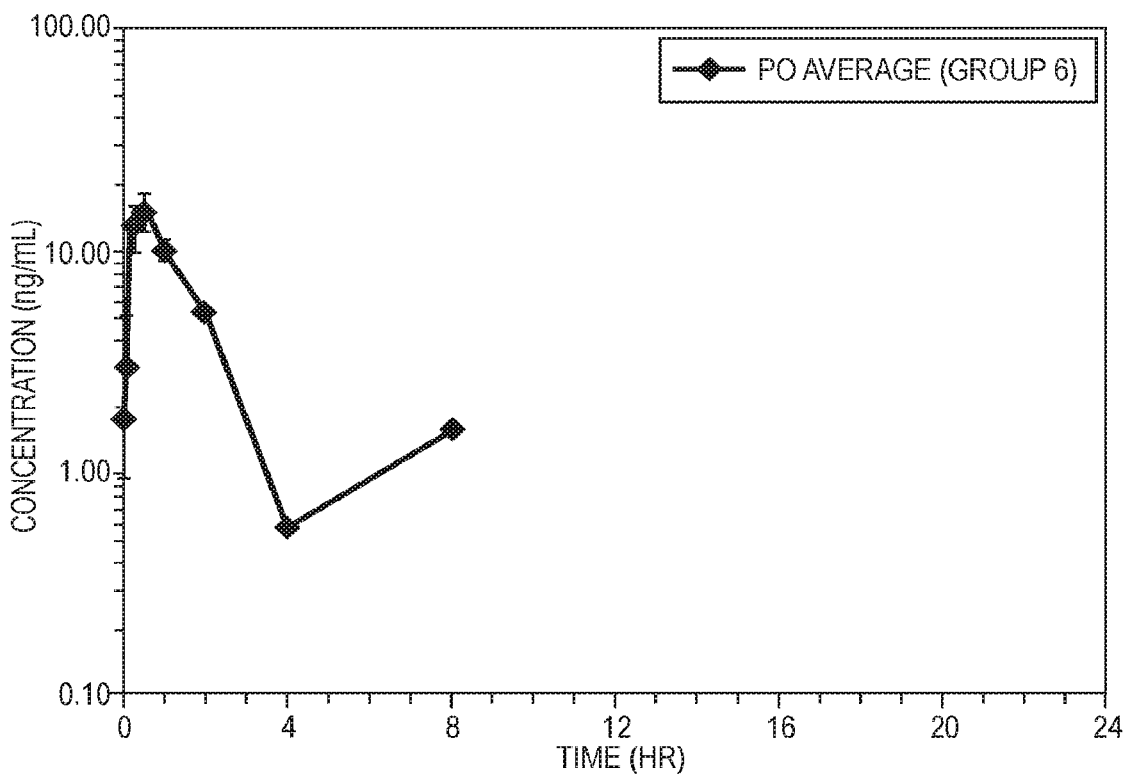

FIG. 5L is a scatter plot of average plasma concentrations of PEA after oral administration of I-11 at 20.7 mg/kg in Male Sprague-Dawley Rats (Group 6).

Figure 5M:
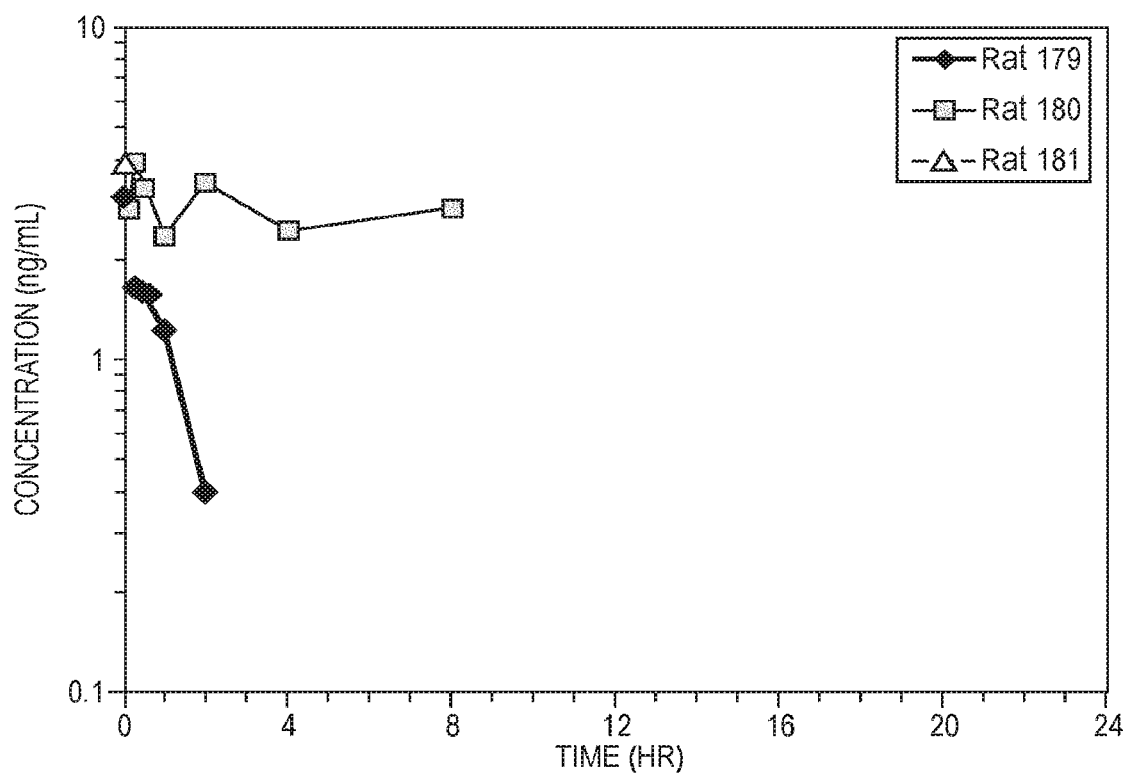

FIG. 5M is a scatter plot of individual plasma concentrations of PEA after oral administration of I-7 at 24.5 mg/kg in male Sprague-Dawley rats (Group 7).

Figure 5N:
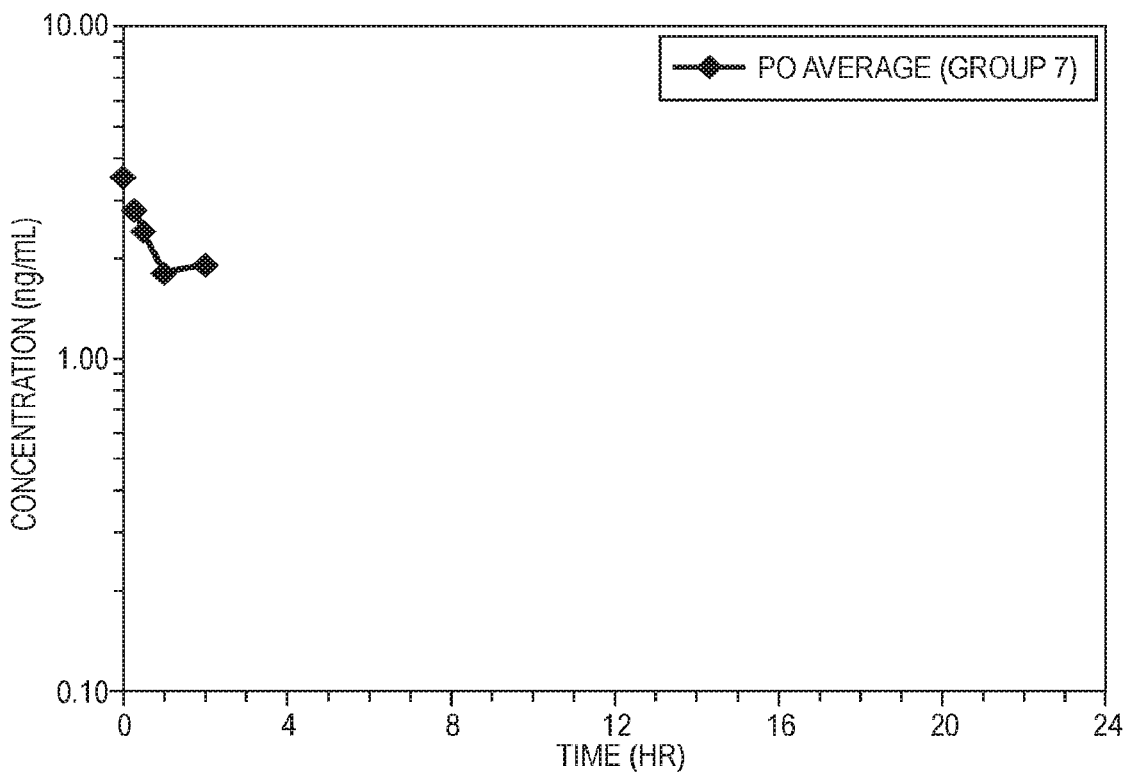

FIG. 5N is a scatter plot of average plasma concentrations of PEA after oral administration of I-7 at 24.5 mg/kg in male Sprague-Dawley rats (Group 7).

Figure 6:
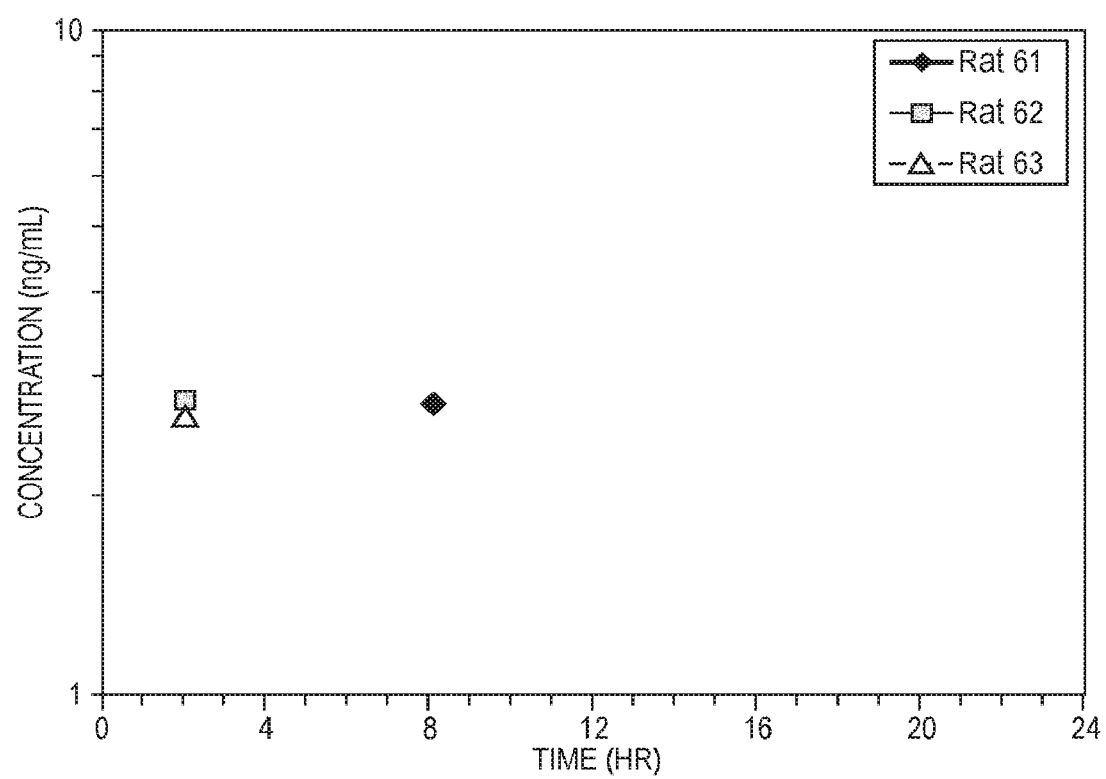

FIG. 6 is a scatter plot of individual plasma concentrations of PEA after oral administration of I-13 (in 20% (Solutol HS15:NMP 1:1) 10% PEG400, 70% $H_2O$) at 24.3 mg/kg in male Sprague-Dawley rats.

Figure 7A:
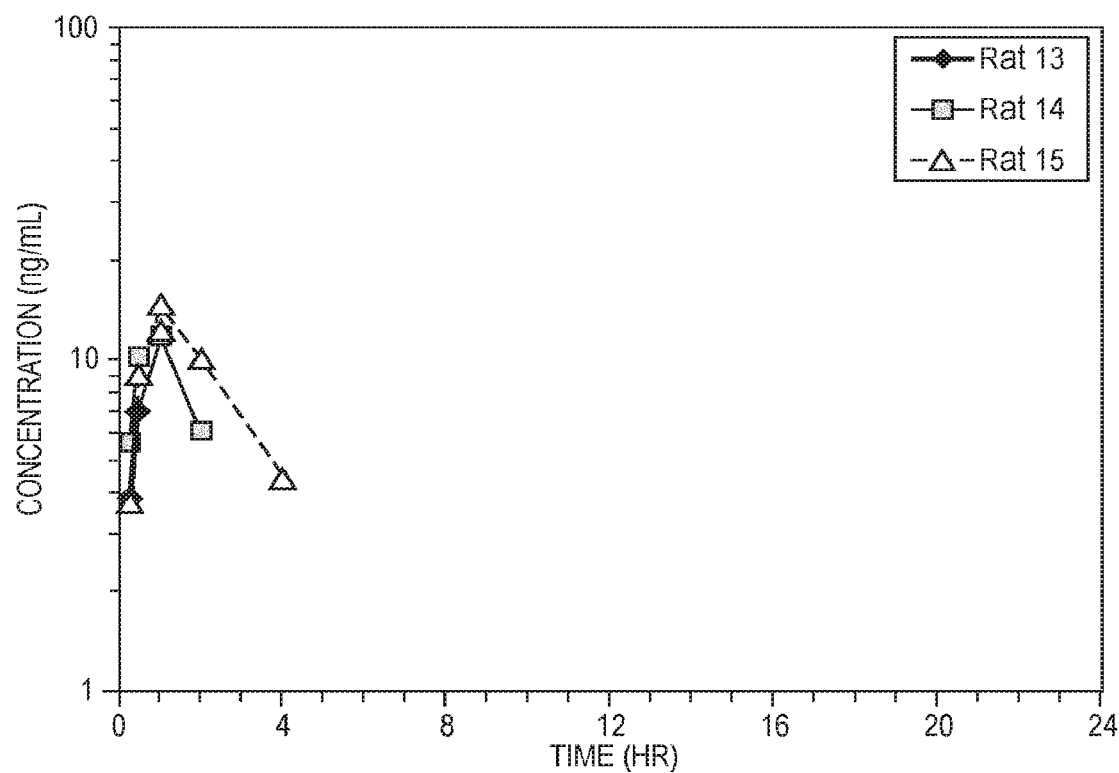

FIG. 7A is a scatter plot of individual plasma concentrations of PEA after oral administration of I-12 (in 20% Solutol HS15:NMP (1:1), 10% PEG400, 70% $H_2O$) at 35.2 mg/kg in male Sprague-Dawley rats (Group 1).

Figure 7B:
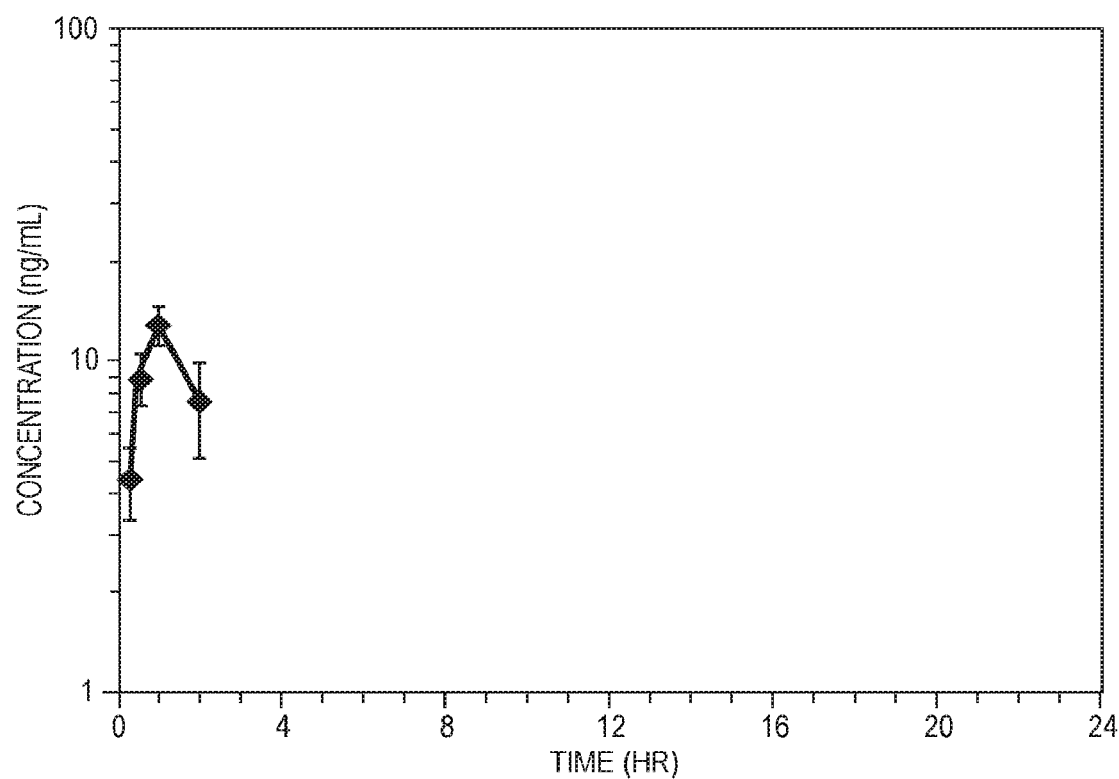

FIG. 7B is a scatter plot of average plasma concentrations of PEA after oral administration of I-12 (in 20% Solutol HS15:NMP (1:1), 10% PEG400, 70% $H_2O$) at 35.2 mg/kg in male Sprague-Dawley rats (Group 1).

Figure 7C:
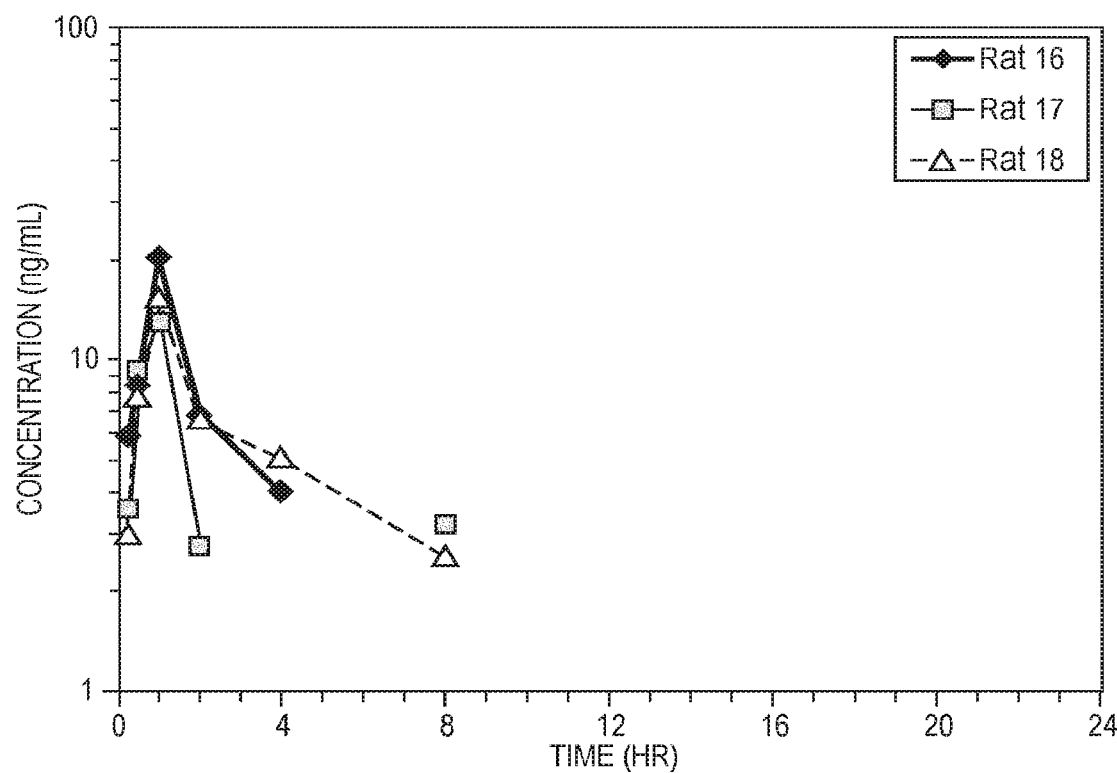

FIG. 7C is a scatter plot of individual plasma concentrations of PEA after oral administration of I-12 (in 0.5% Methyl Cellulose in 20% Solutol HS15:NMP (1:1), 10% PEG400, 70% $H_2O$) at 35.2 mg/kg in male Sprague-Dawley rats (Group 2).

Figure 7D:
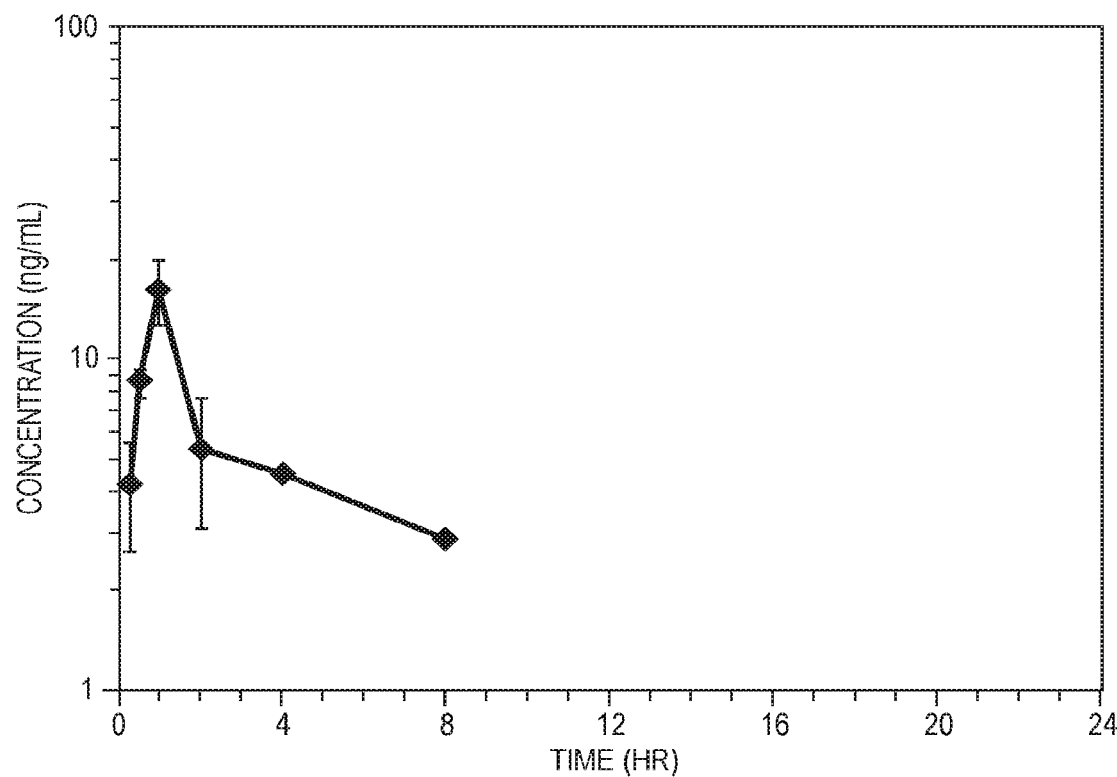

FIG. 7D is a scatter plot of average plasma concentrations of PEA after oral administration of I-12 (in 0.5% Methyl Cellulose in 20% Solutol HS15:NMP (1:1), 10% PEG400, 70% $H_2O$) at 35.2 mg/kg in male Sprague-Dawley rats (Group 2).

Figure 8A:
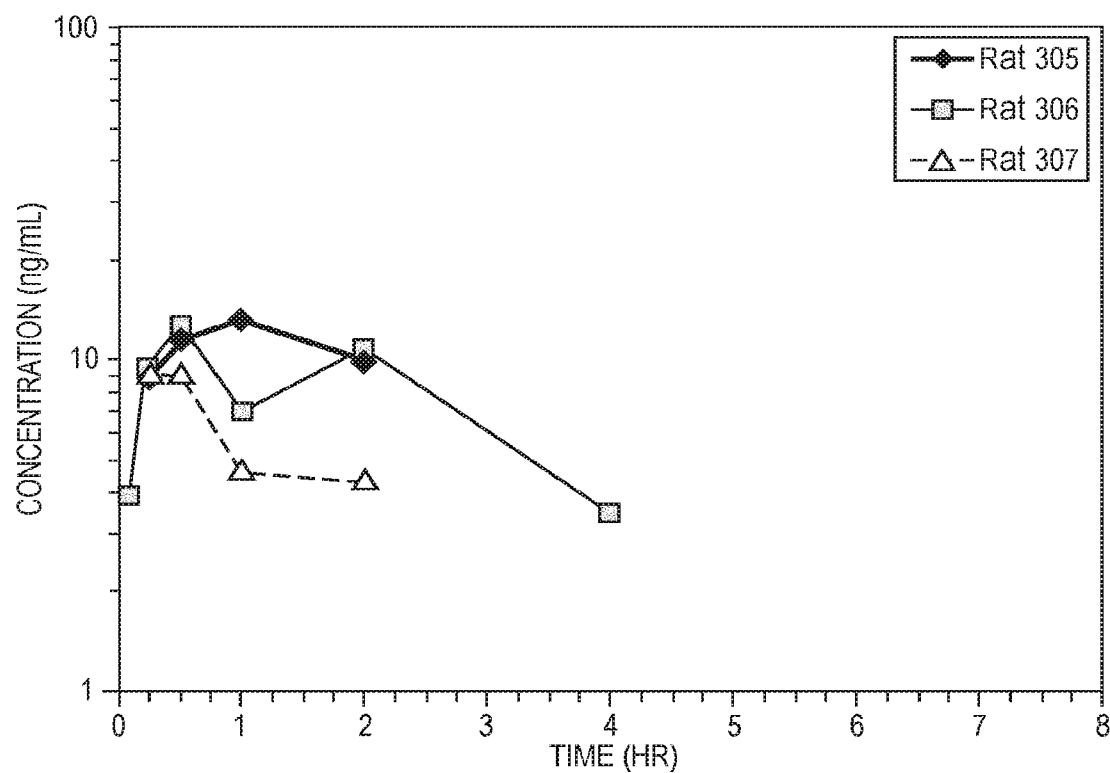

FIG. 8A is a scatter plot of individual plasma concentrations of PEA after oral administration of I-15 (in 20% Solutol HS15:NMP (1:1), 10% PEG400, 70% $H_2O$) at 20.7 mg/kg in male Sprague-Dawley rats (Group 1).

Figure 8B:
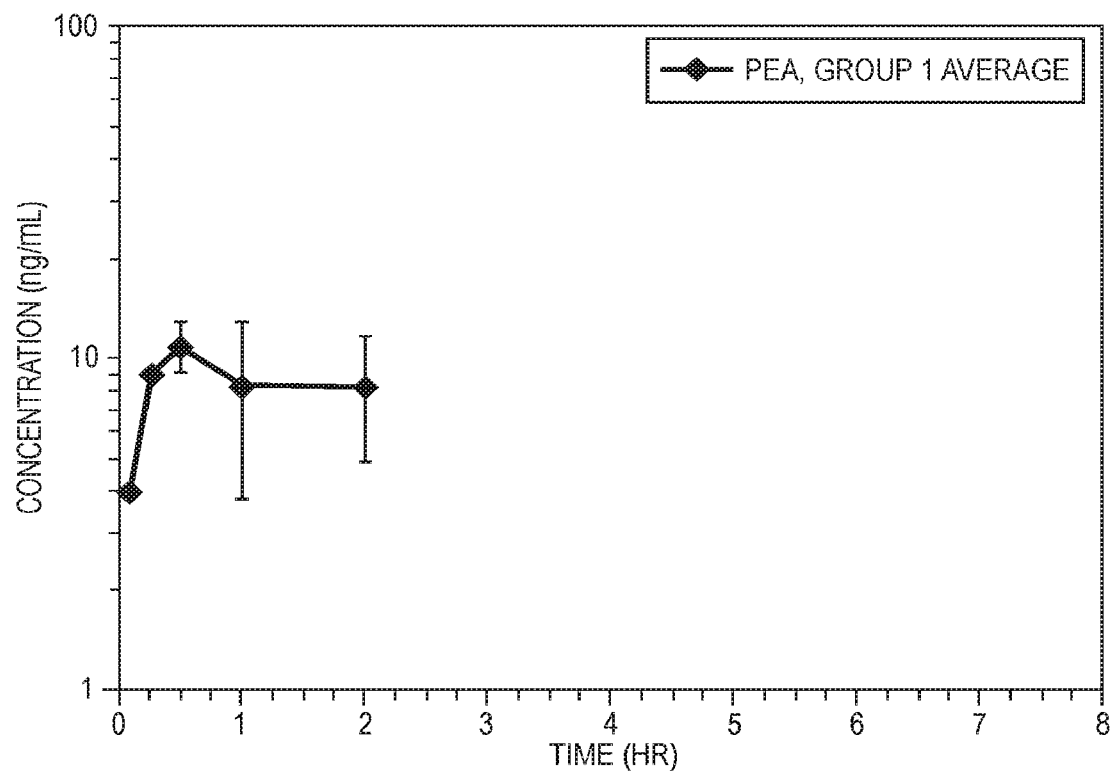

FIG. 8B is a scatter plot of average plasma concentrations of PEA after oral administration of I-15 (in 20% Solutol HS15:NMP (1:1), 10% PEG400, 70% $H_2O$) at 20.7 mg/kg in male Sprague-Dawley rats (Group 1).

Figure 8C:
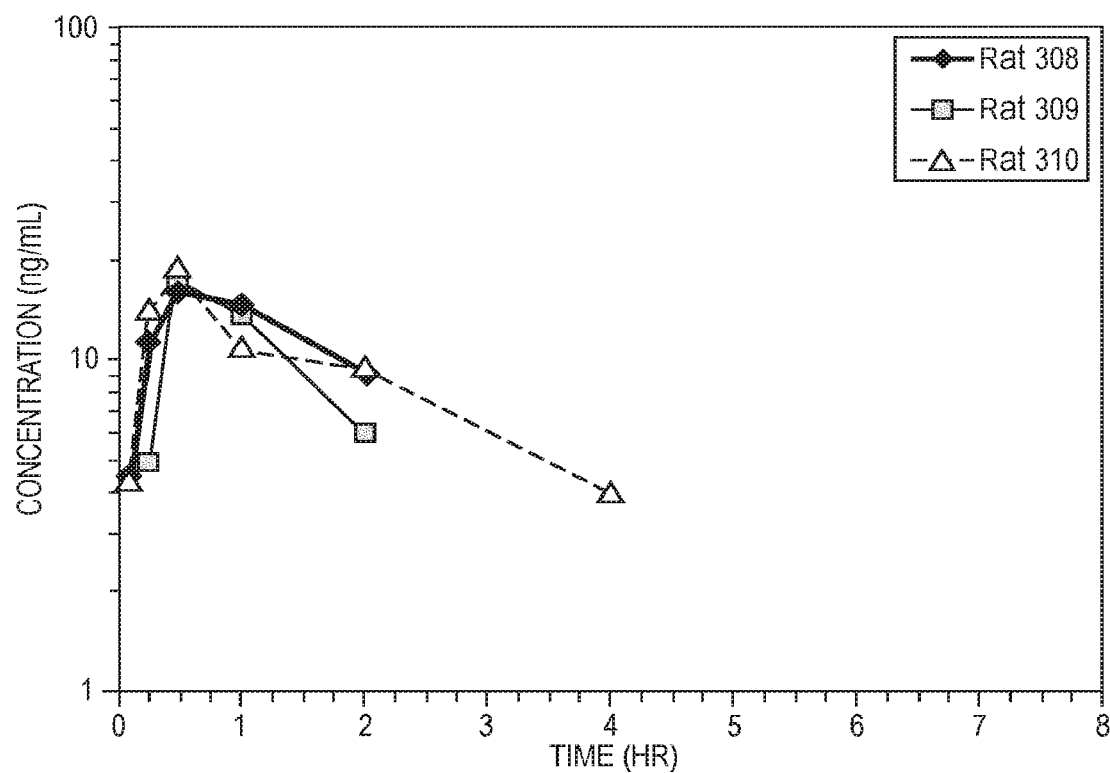

FIG. 8C is a scatter plot of individual plasma concentrations of PEA after oral administration of I-14 (in 20% Solutol HS15:NMP (1:1), 10% PEG400, 70% $H_2O$) at 20.7 mg/kg in male Sprague-Dawley rats (Group 1).

Figure 8D:
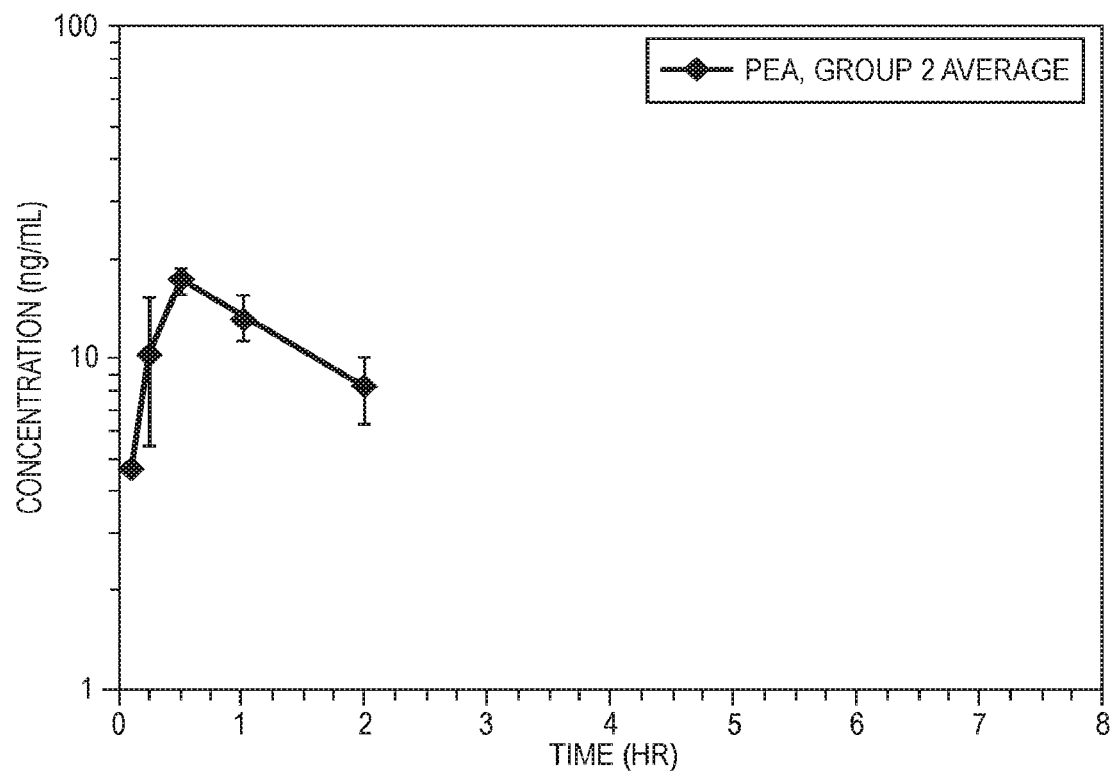

FIG. 8D is a scatter plot of average plasma concentrations of PEA after oral administration of I-14 (in 20% Solutol HS15:NMP (1:1), 10% PEG400, 70% $H_2O$) at 20.7 mg/kg in male Sprague-Dawley rats (Group 1).

Figure 9A:
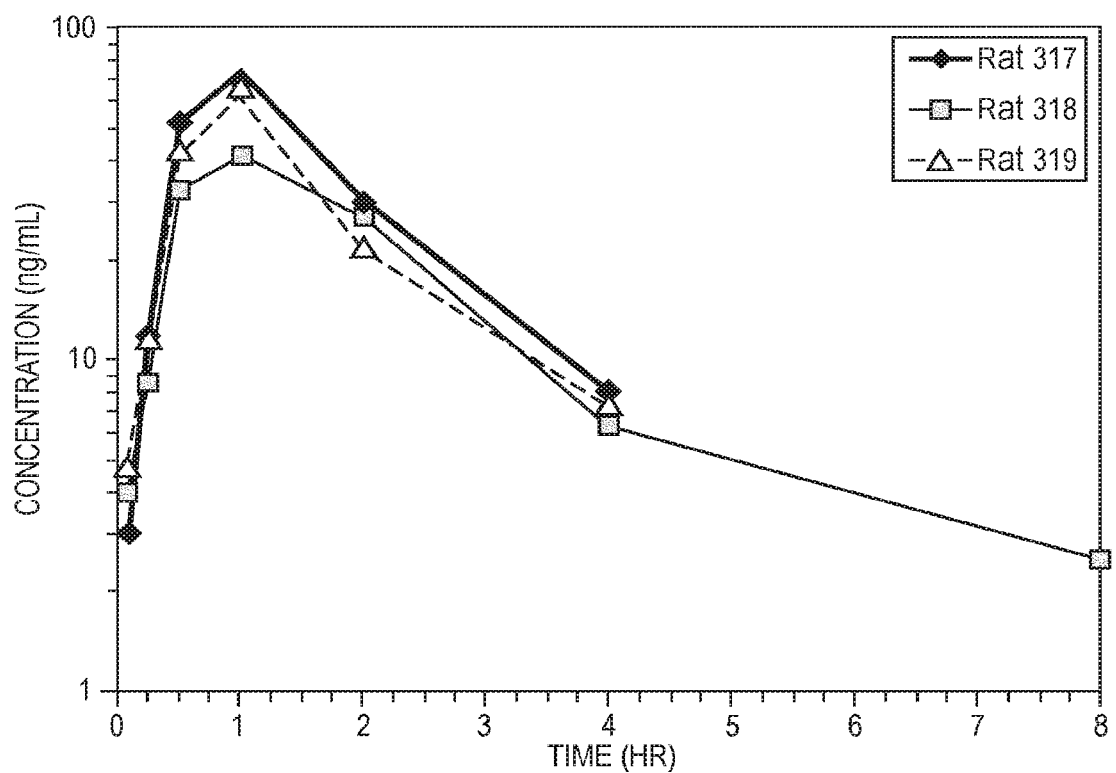

FIG. 9A is a scatter plot of individual plasma concentrations of PEA after oral administration of I-8.

Figure 9B:
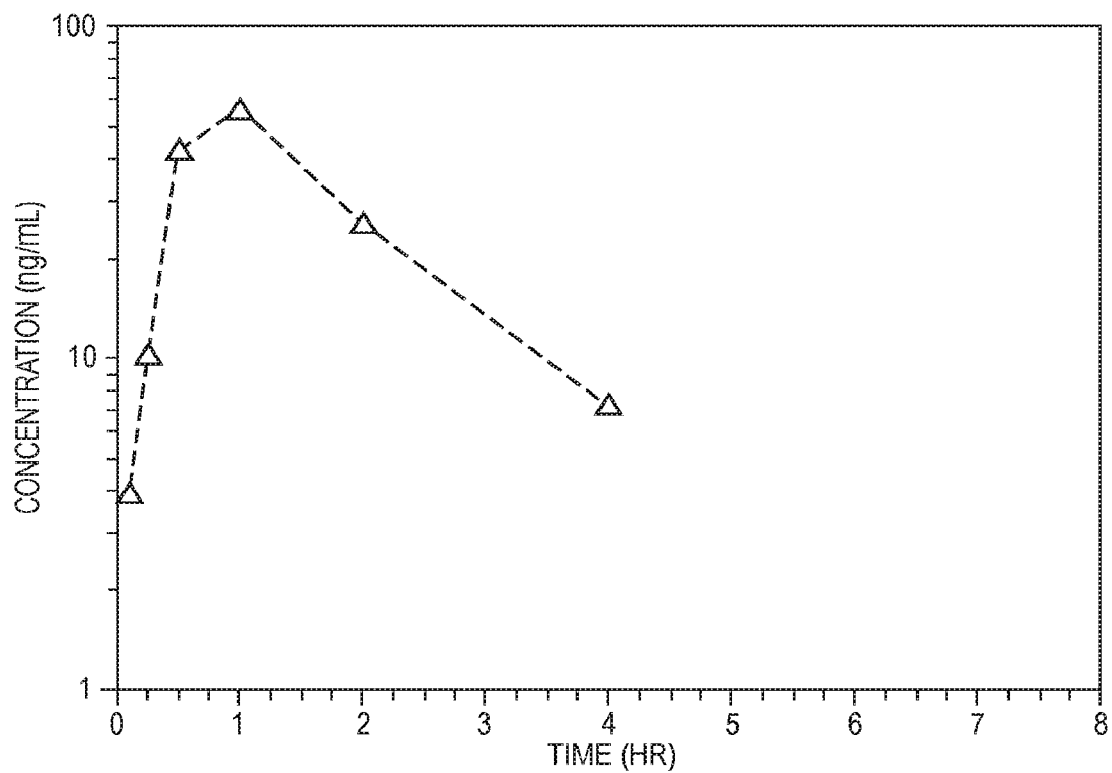

FIG. 9B is a scatter plot of average plasma concentrations of PEA after oral administration of I-8.

Figure 9C:
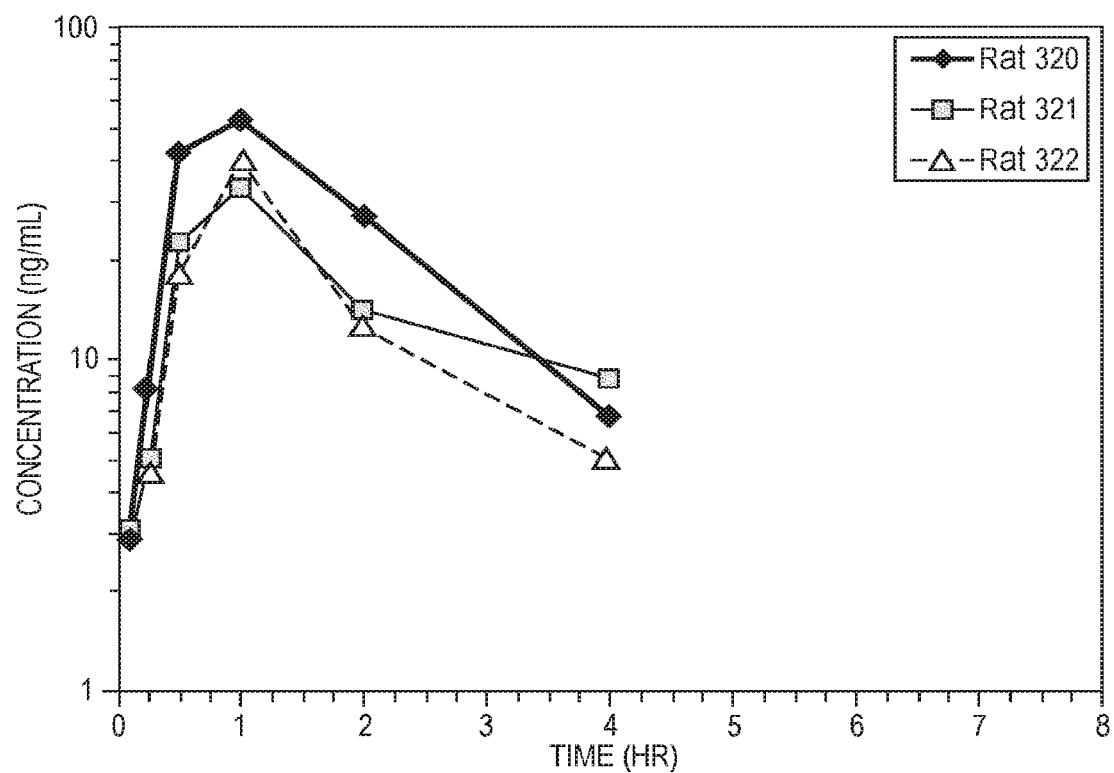

FIG. 9C is a scatter plot of individual plasma concentrations of PEA after oral administration of I-16.

Figure 9D:
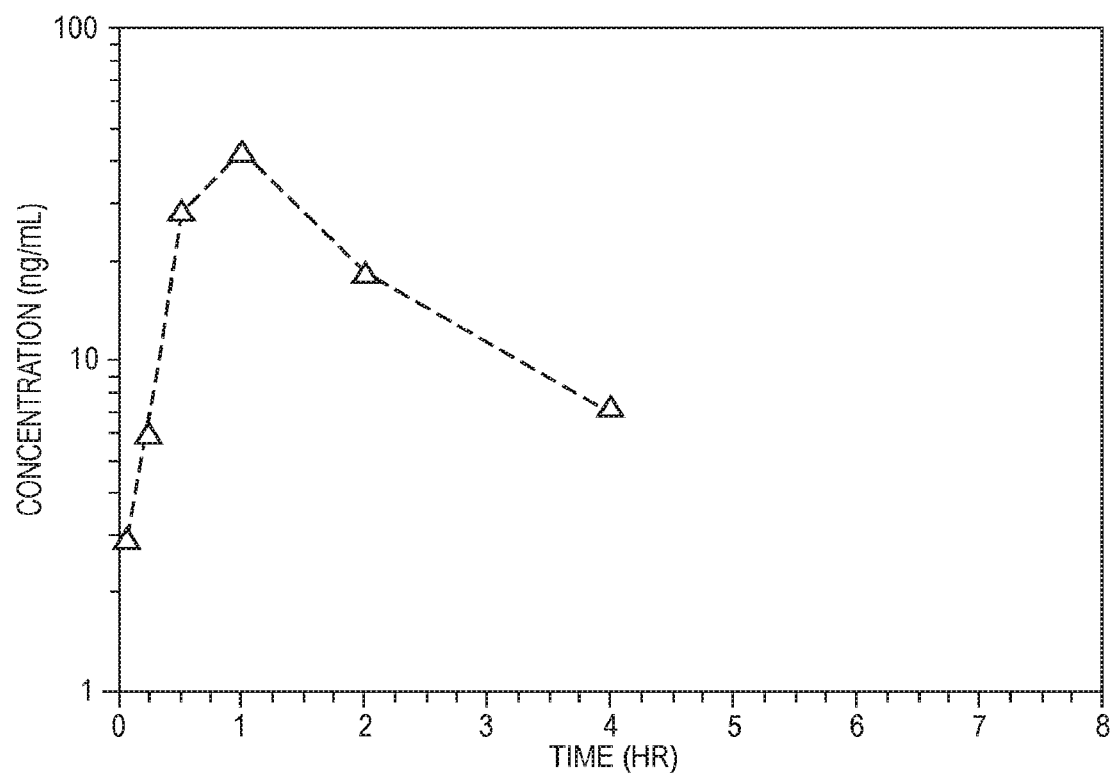

FIG. 9D is a scatter plot of average plasma concentrations of PEA after oral administration of I-16.

Figure 10A:
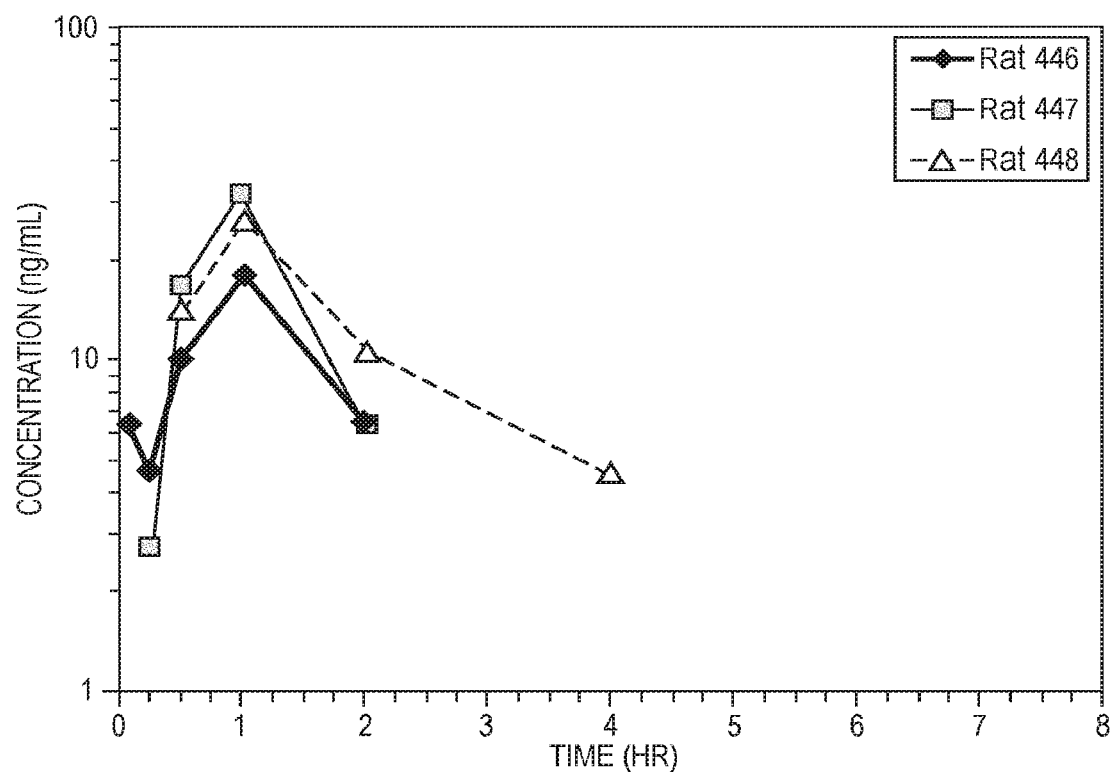

FIG. 10A is a scatter plot of individual plasma concentrations (ng/mL) and pharmacokinetic parameters for PEA after oral administration of I-8 in 20% Solutol HS15:NMP (1:1), 10% PEG400, 70% $H_2O$) at 4 mg/kg in male Sprague-Dawley rats.

Figure 10B:
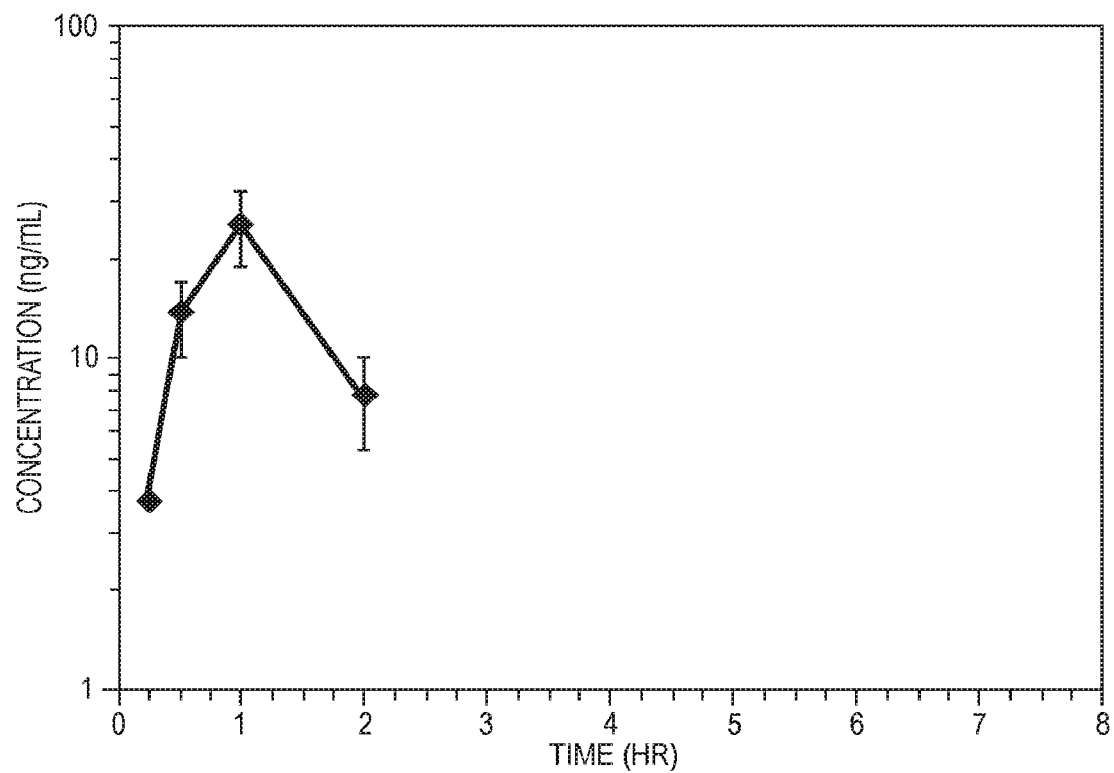

FIG. 10B is a scatter plot of average plasma concentrations (ng/mL) and phamiacokinetic parameters for PEA after oral administration of I-8 in 20% Solutol HS15:NMP (1:1), 10% PEG400, 70% $H_2O$) at 4 mg/kg in male Sprague-Dawley rats.

Figure 10C:
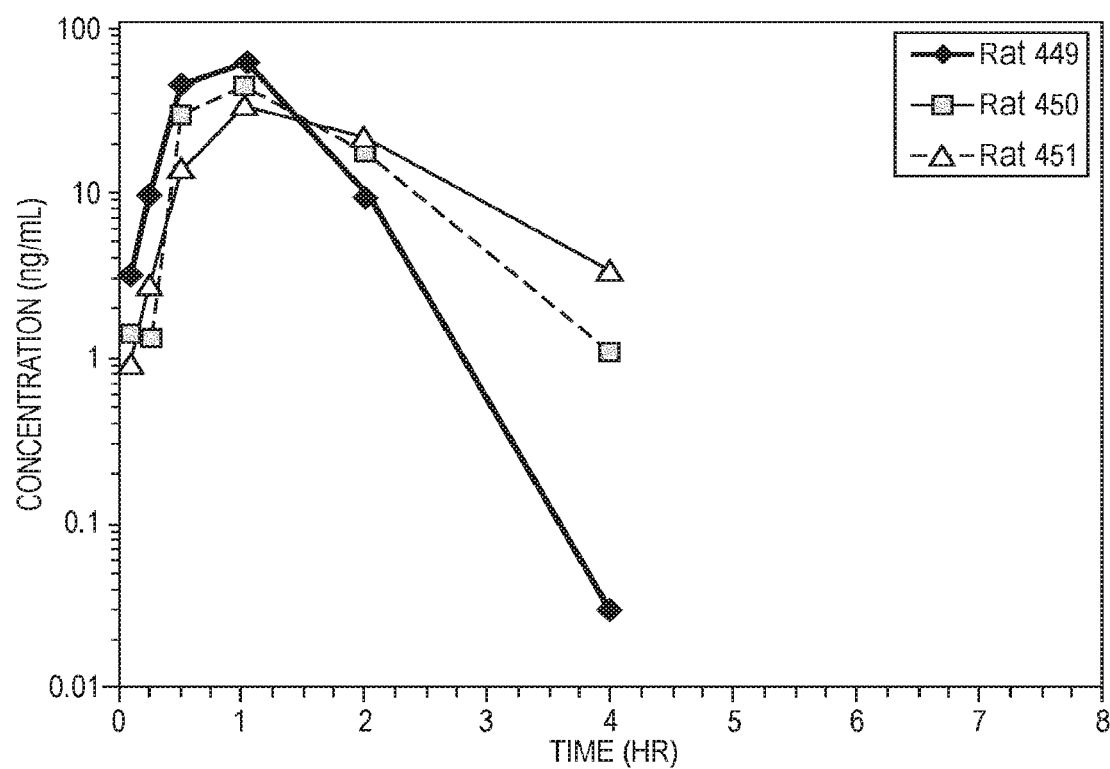

FIG. 10C is a scatter plot of individual plasma concentrations (ng/mL) and pharmacokinetic parameters for PEA after oral administration of I-8 in 20% Solutol HS15:NMP (1:1), 10% PEG400, 70% $H_2O$) at 8 mg/kg in male Sprague-Dawley rats.

Figure 10D:
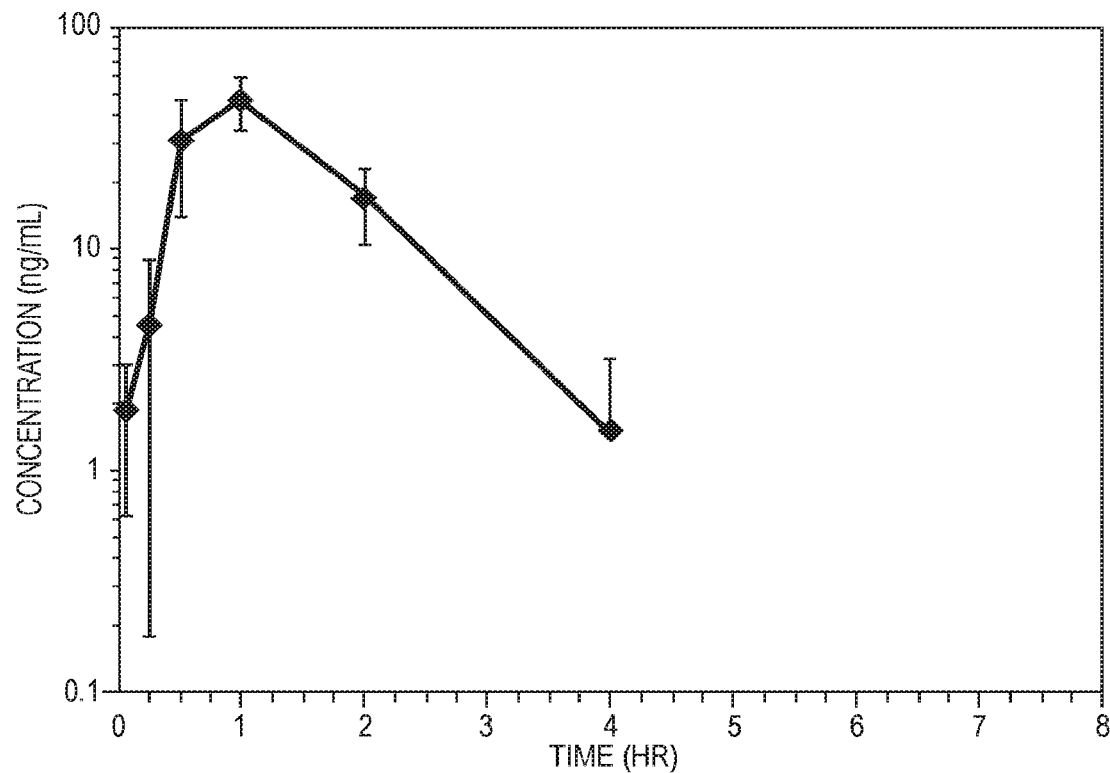

FIG. 10D is a scatter plot of average plasma concentrations (ng/mL) and pharmacokinetic parameters for PEA after oral administration of I-8 in 20% Solutol HS15:NMP (1:1), 10% PEG400, 70% $H_2O$) at 8 mg/kg in male Sprague-Dawley rats.

Figure 10E:
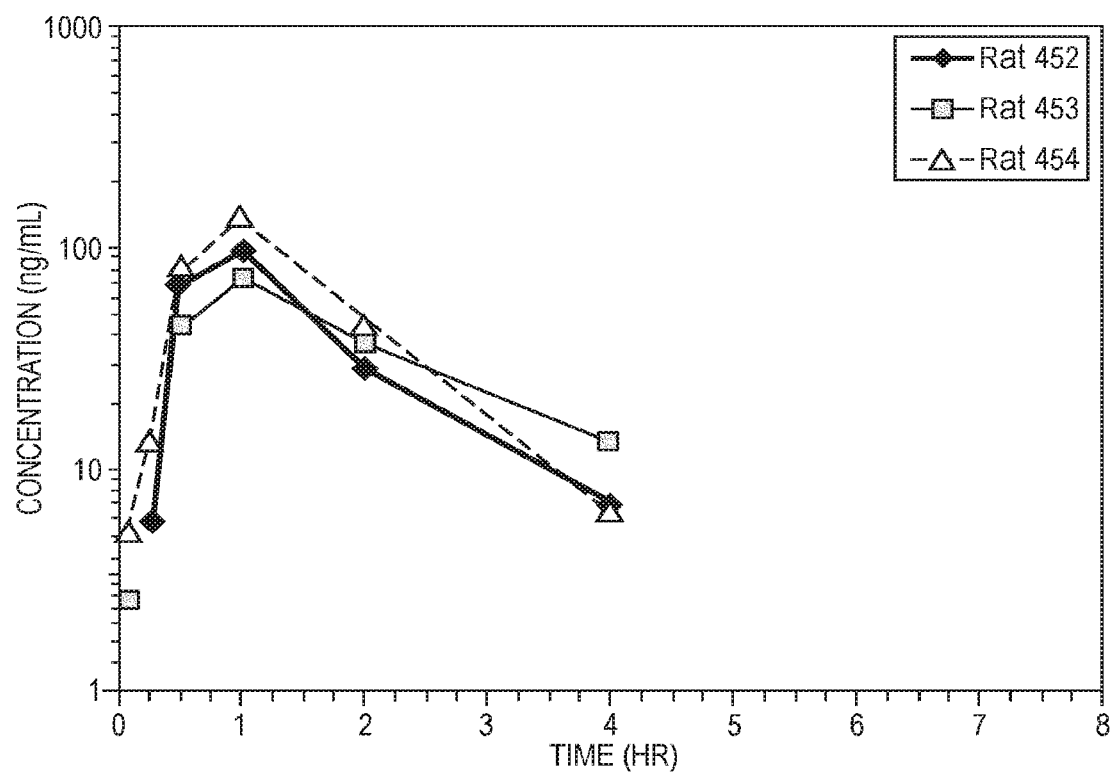

FIG. 10E is a scatter plot of individual plasma concentrations (ng/mL) and pharmacokinetic parameters for PEA after oral administration of I-8 in 20% Solutol HS15:NMP (1:1), 10% PEG400, 70% $H_2O$) at 16 mg/kg in male Sprague-Dawley rats.

Figure 10F:
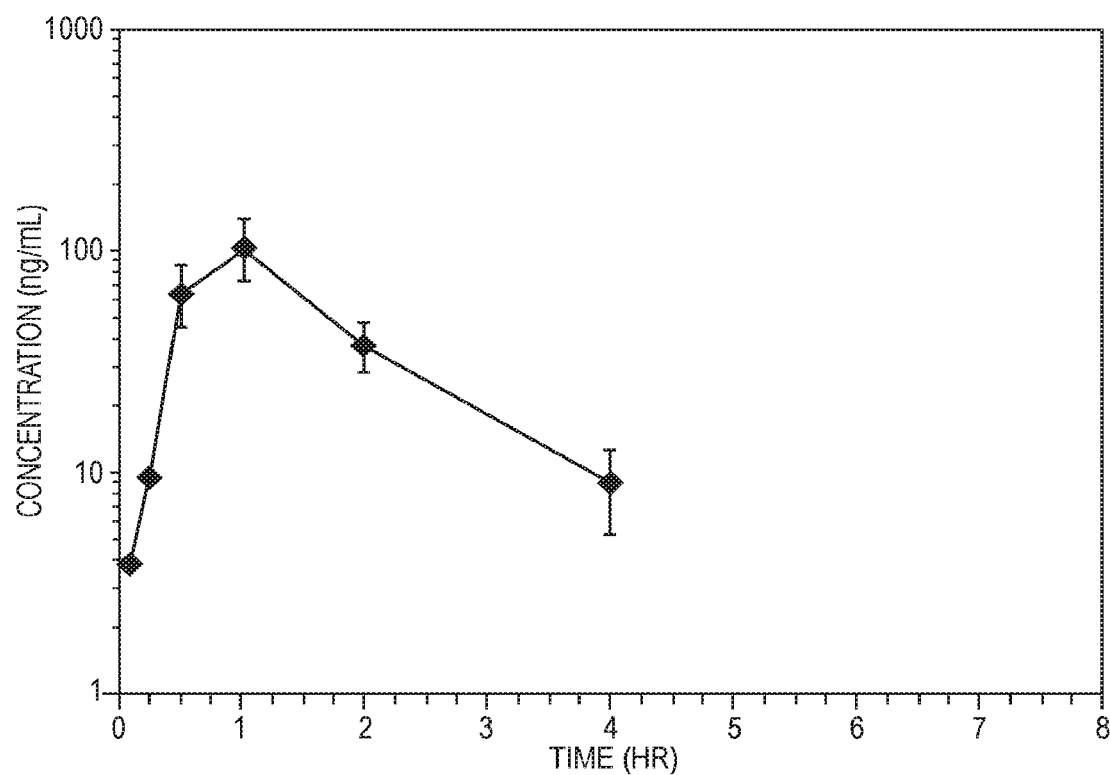

FIG. 10F is a scatter plot of average plasma concentrations (ng/mL) and pharmacokinetic parameters for PEA after oral administration of I-8 in 20% Solutol HS15:NMP (1:1), 10% PEG400, 70% $H_2O$) at 16 mg/kg in male Sprague-Dawley rats.

Figure 10G:
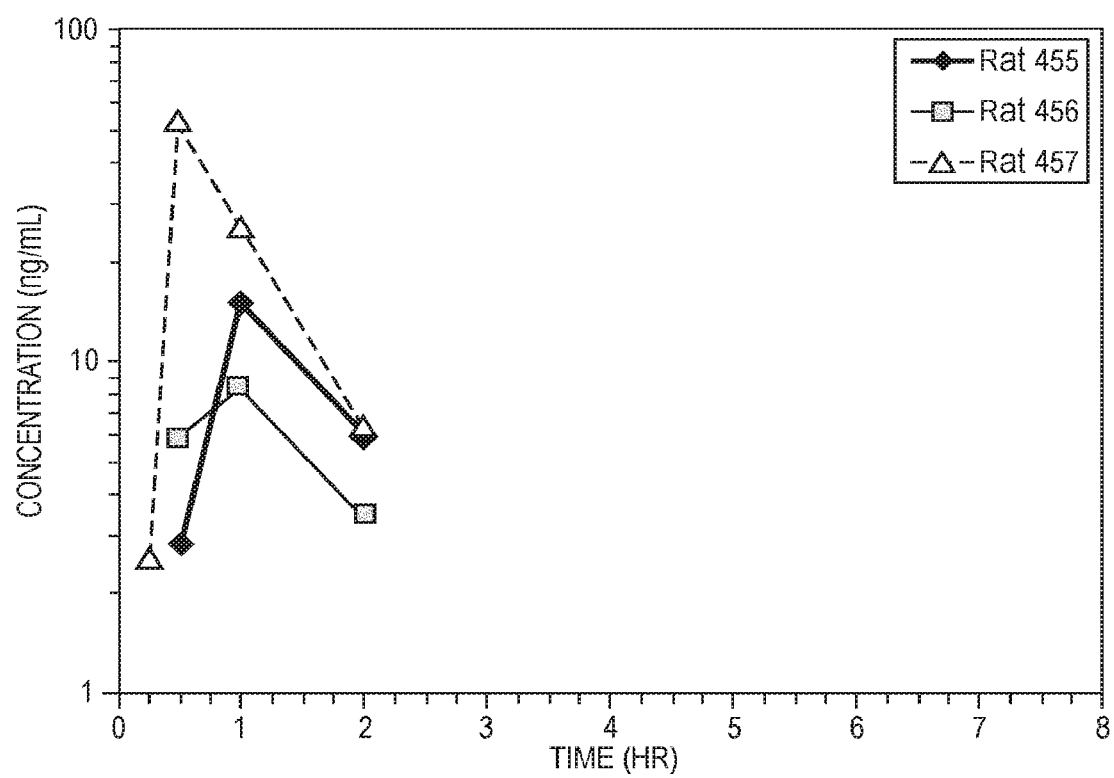

FIG. 10G is a scatter plot of individual plasma concentrations (ng/mL) and pharmacokinetic parameters for PEA after oral administration of I-16 in 20% Solutol HS15:NMP (1:1), 10% PEG400, 70% $H_2O$) at 5.2 mg/kg in male Sprague-Dawley rats.

Figure 10H:
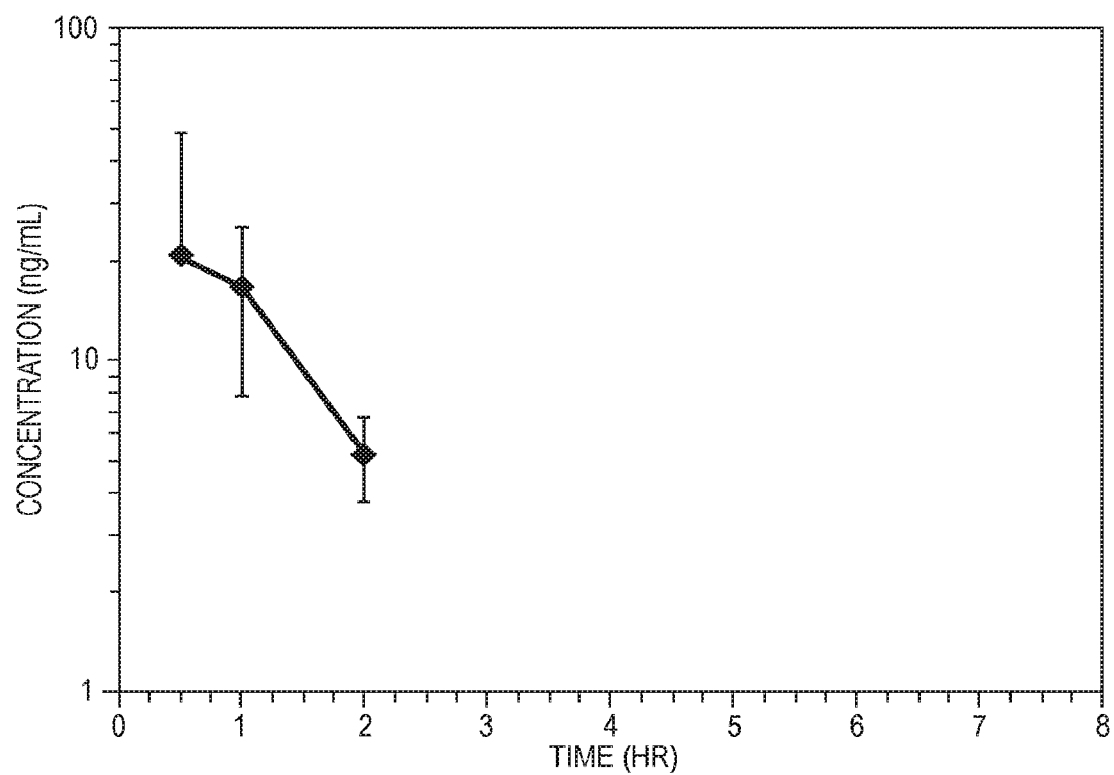

FIG. 10H is a scatter plot of average plasma concentrations (ng/mL) and pharmacokinetic parameters for PEA after oral administration of I-16 in 20% Solutol HS15:NMP (1:1), 10% PEG400, 70% $H_2O$) at 5.2 mg/kg in male Sprague-Dawley rats.

Figure 10I:
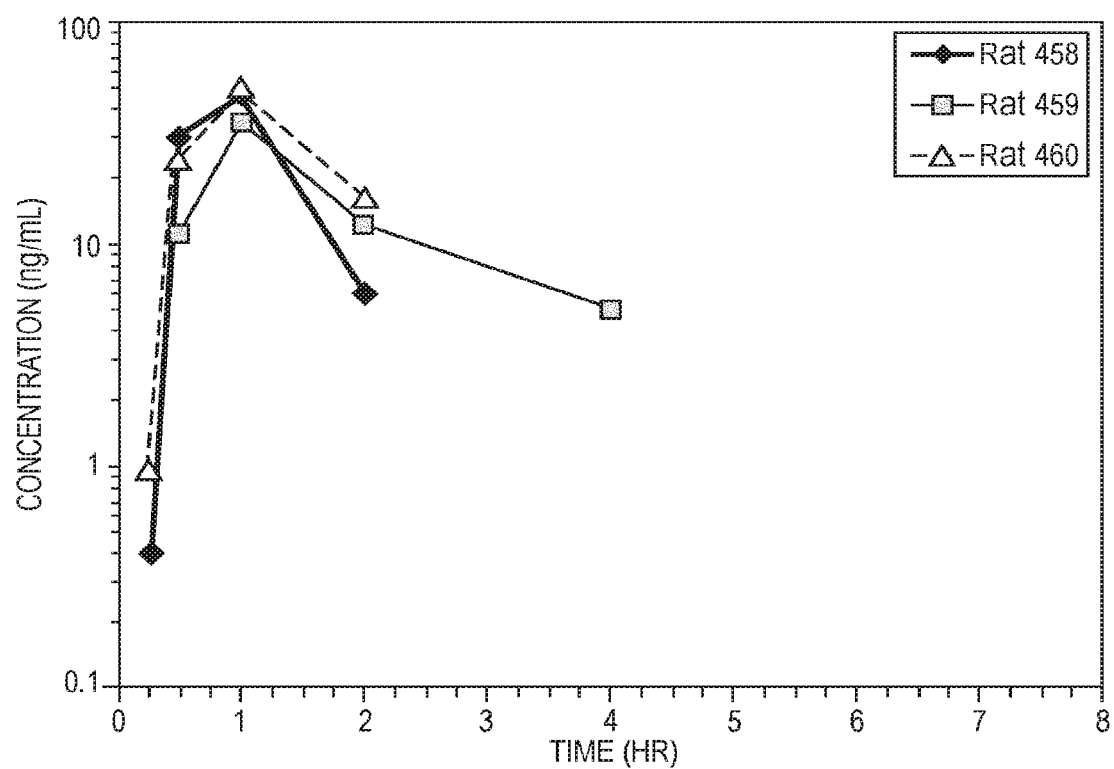

FIG. 10I is a scatter plot of individual plasma concentrations (ng/mL) and pharmacokinetic parameters for PEA after oral administration of I-16 in 20% Solutol HS15:NMP (1:1), 10% PEG400, 70% $H_2O$) at 10.35 mg/kg in male Sprague-Dawley rats.

Figure 10J:
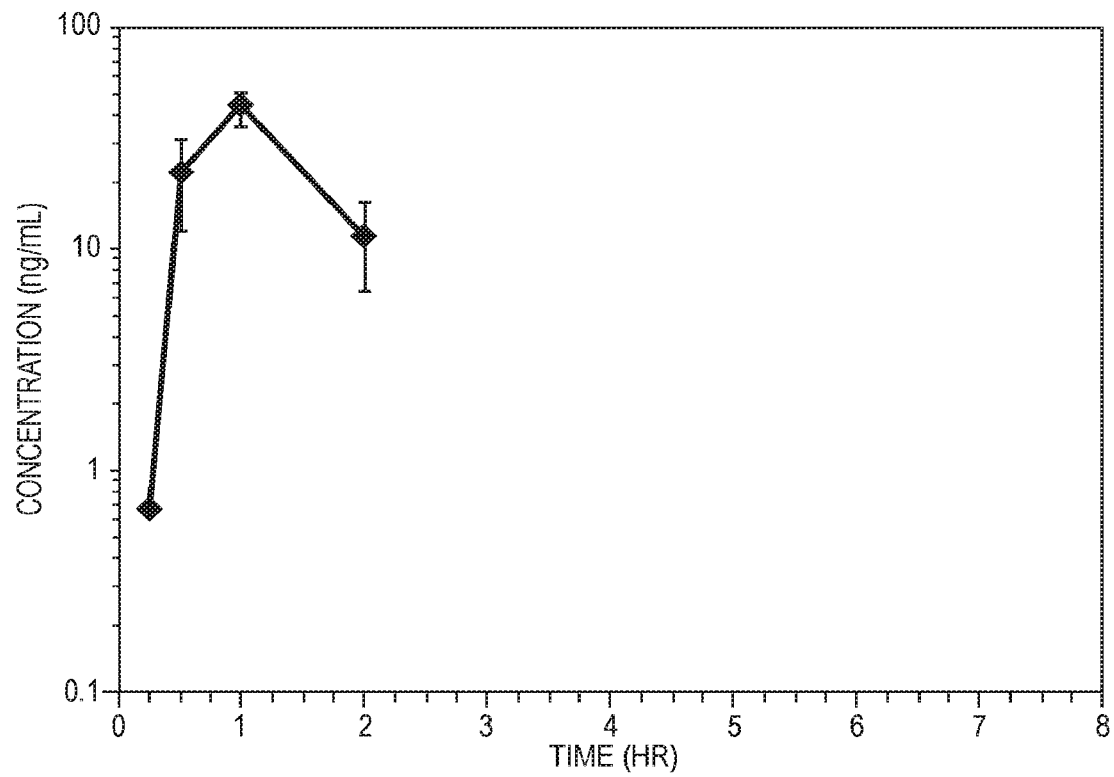

FIG. 10J is a scatter plot of average plasma concentrations (ng/mL) and pharmacokinetic parameters for PEA after oral administration of I-16 in 20% Solutol HS15:NMP (1:1), 10% PEG400, 70% $H_2O$) at 10.35 mg/kg in male Sprague-Dawley rats.

Figure 10K:
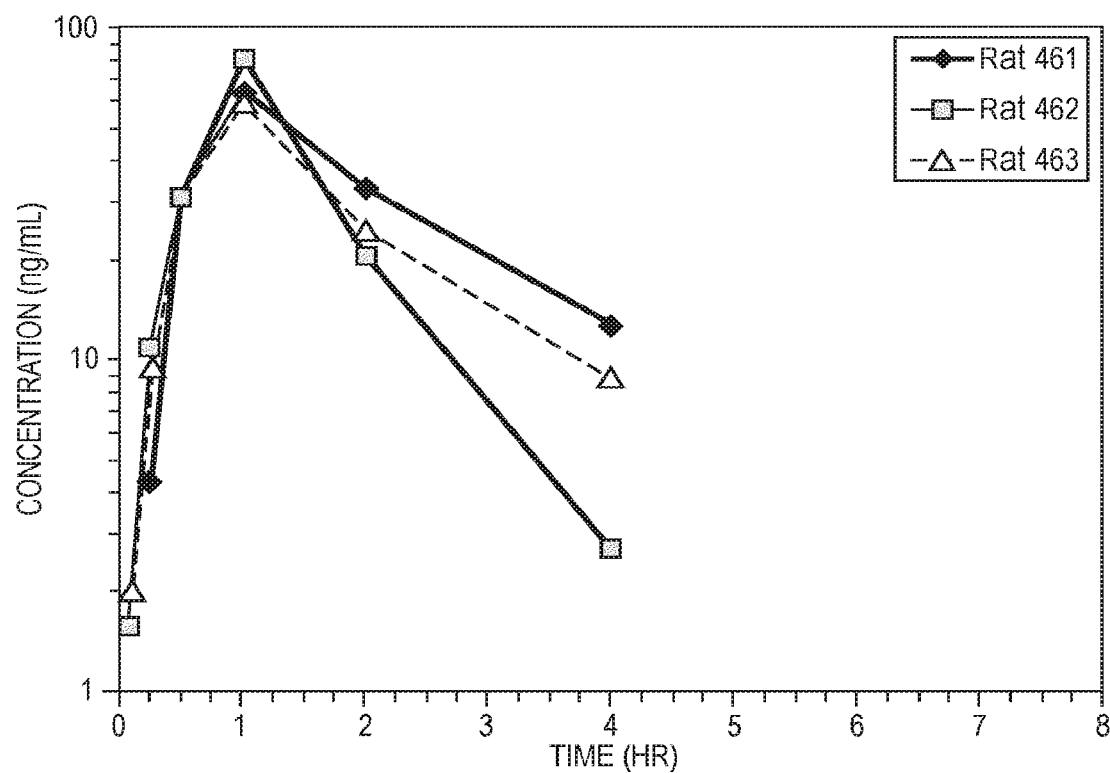

FIG. 10K is a scatter plot of individual plasma concentrations (ng/mL) and pharmacokinetic parameters for PEA after oral administration of I-16 in 20% Solutol HS15:NMP (1:1), 10% PEG400, 70% $H_2O$) at 20.7 mg/kg in male Sprague-Dawley rats.

Figure 10L:
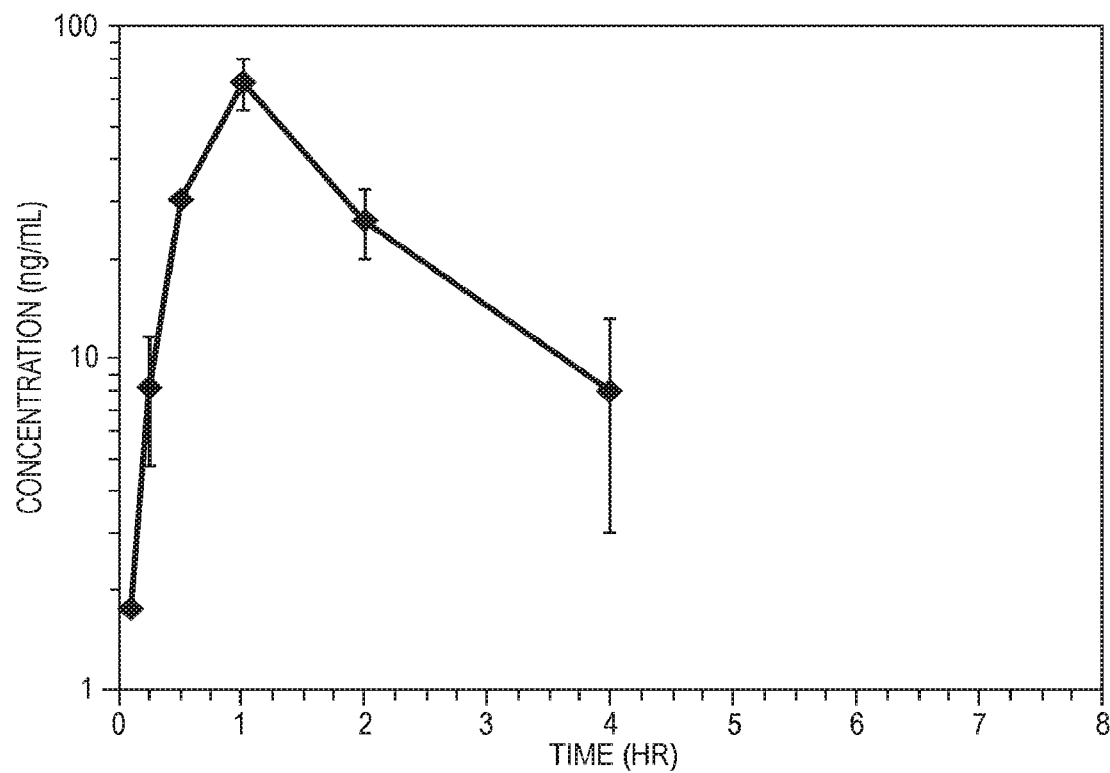

FIG. 10L is a scatter plot of average plasma concentrations (ng/mL) and pharmacokinetic parameters for PEA after oral administration of I-16 in 20% Solutol HS15:NMP (1:1), 10% PEG400, 70% $H_2O$) at 20.7 mg/kg in male Sprague-Dawley rats.

Figure 11:
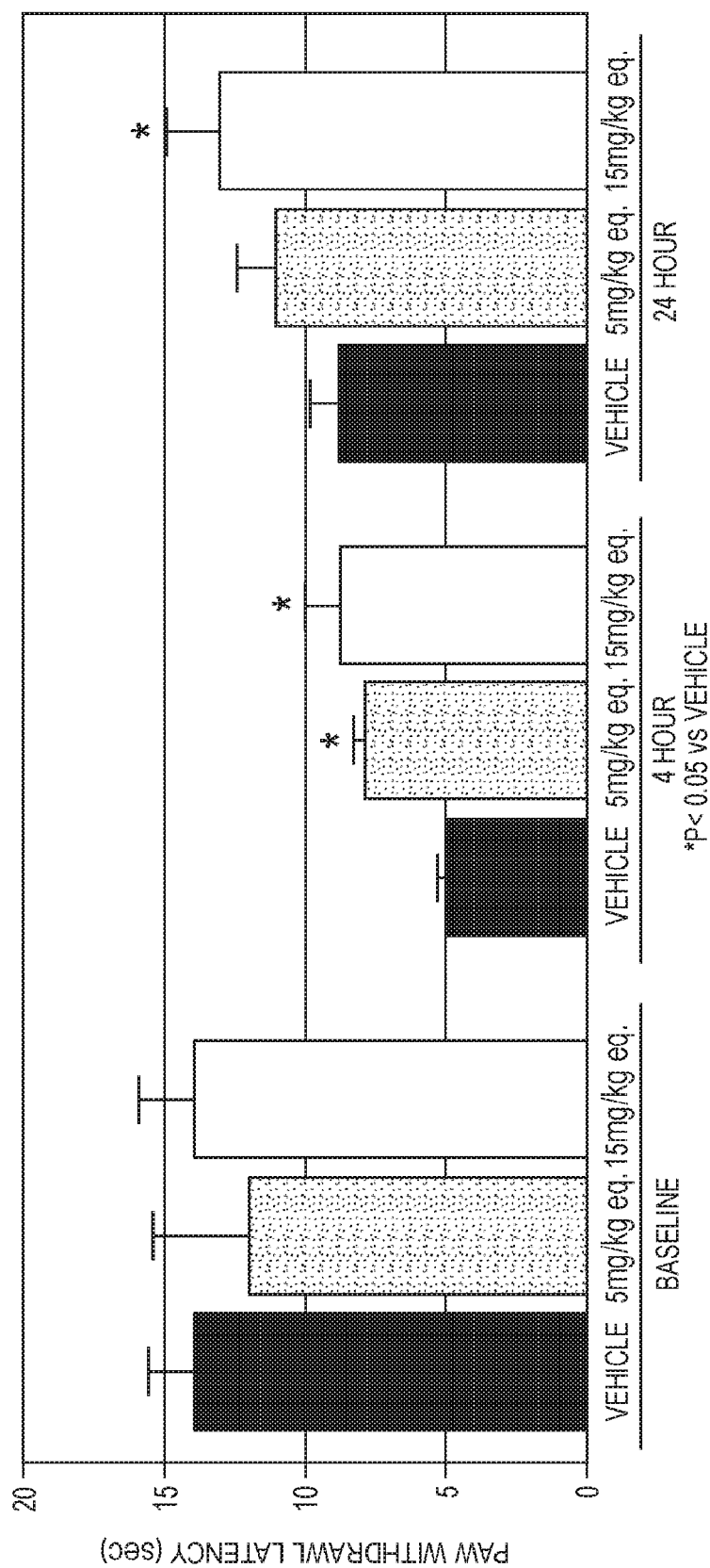

FIG. 11 is a bar graph illustrating the paw withdrawal latency (in seconds) as a function of amount of I-16 provided to an animal subject. The animal received either no I-16 (i.e., only the vehicle); 5 mg/kg equivalents of PEA (equivalent to 10.25 mg/kg of I-16); or 10 mg/kg equivalents of PEA (equivalent to 20.50 mg/kg of I-16).

Figure 12A:
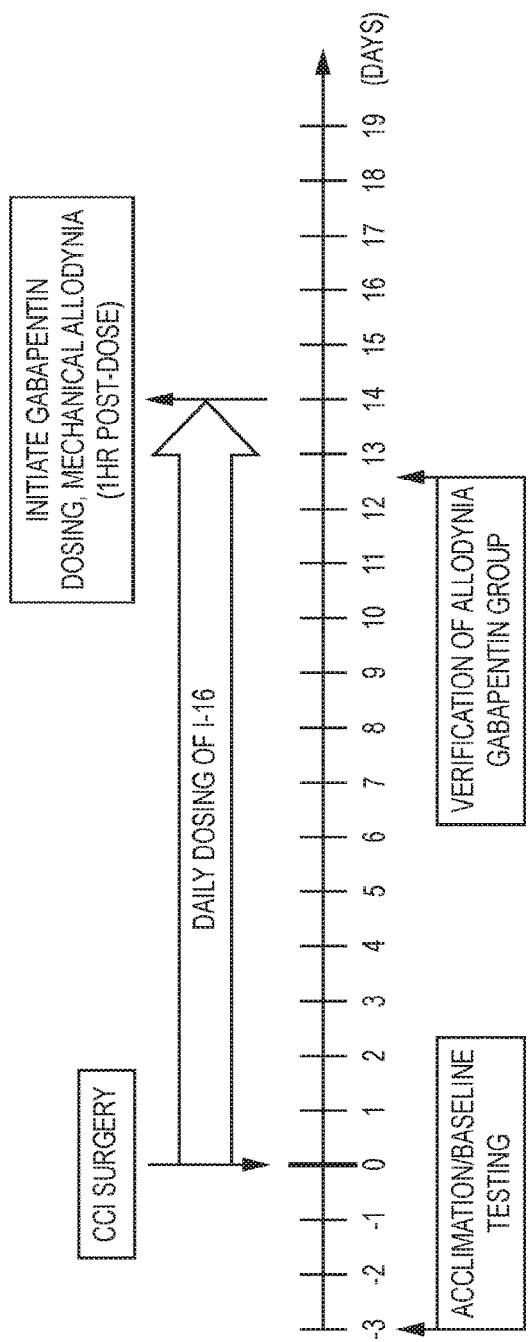

FIG. 12A is a timeline illustrating the dosing schedule of rats administered I-16 to evaluate analgesic effects in rat Chronic Constriction Injury (CCI) model.

Figure 12B:
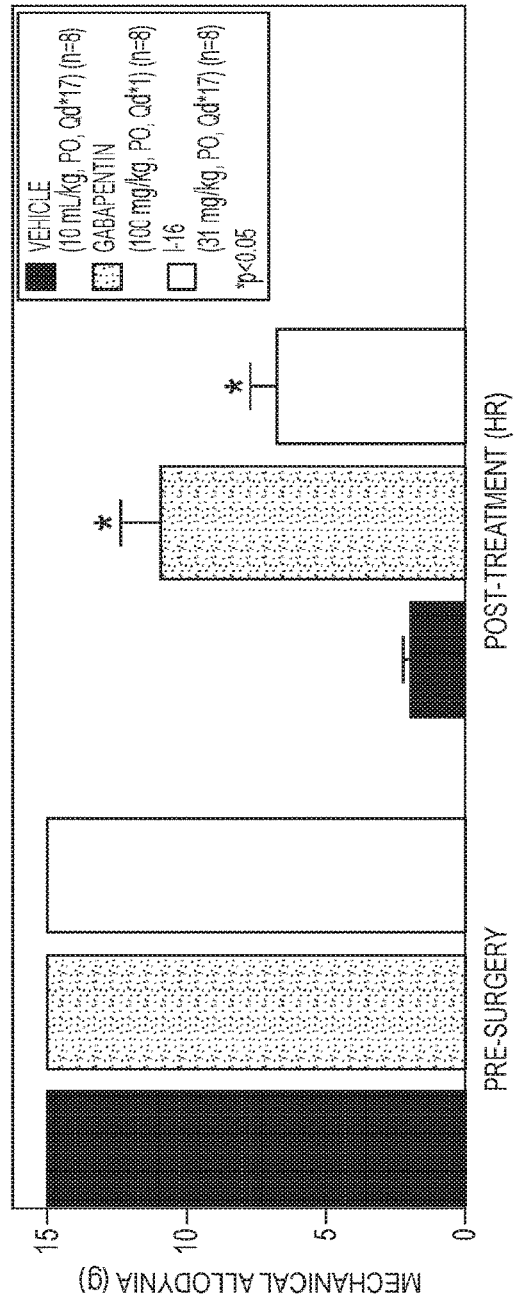

FIG. 12B is a bar graph illustrating mechanical allodynia in rats as a function of analgesic administered (vehicle: gabapentin; or I-16).

DEFINITIONS

A. Chemical Definitions

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry". Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Aliphatic: As used herein, "aliphatic" means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation that has a single point of attachment to the rest of the molecule. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, hut are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkenyl: As used herein, the term "alkenyl" refers to an alkyl group, as defined herein, having one or more double bonds.

Alkynyl: As used herein, the term "alkynyl" refers to an alkyl group, as defined herein, having one or more triple bonds.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxy acetate, p-chlorophenoxyacetate, 3-phenylpropionate, 4-oxopentanoate, 4,4-(ethylenedithio)

pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxy benzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents include halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}Ph$, which may be substituted with R°; —$(CH_2)_{0-4}(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; $N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$—, —$SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; —$SiR°_3$; —$OSiR°_3$; —$(C_{1-4}$ straight or branched)alkylene)O—$N(R°)_2$; or —$(C_{1-4}$ straight or branched)alkylene)C(O)O—$N(R°)_2$, wherein each R° may be substituted as defined below and is independently hydrogen, $C_{1-6}$, aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —$O(haloR^•)$, —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•2$, —$NO_2$, —$SiR^•_3$, —$C(O)SR^•$, —$(C_{1-4}$ straight or branched alkylene)C(O)OR$^•$, or —$SSR^•$ wherein each R$^•$ is unsubstituted or where preceded by "halo" is substituted only with one or more halogens, and is independently selected from $C_{1-4}$ aliphatic. —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents include the following: =O, =S, =NNR*$_2$, =NNHC(O)R*, =NNHC(O)OR*, =NNHS(O)$_2$R*, =NR*, =NOR. —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, R˙. -(haloR˙), —OH, —OR˙, —O(haloR˙), —CN, —C(O)OH, —C(O)OR˙, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In some embodiments, suitable substituents on a substitutable nitrogen include —R$^†$, —NR$^†_2$, —C(O)R$^†$, —C(O) OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S (O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$ taken together with their intervening atom(s) form an unsubstituted 3-12-membered saturated, partially unsaturated, or aryl mono- or bicyclic ring having 0-4 heteroatoms independently selected from nitrogen, oxygen, or sulfur. [105]

Suitable substituents on the aliphatic group of R$^†$ are independently halogen. —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6- membered saturated, partially unsaturated, or aryl ring having 0-4 heteroatoms independently selected from nitrogen, oxygen, or sulfur.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

B. Other Definitions

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, mtradermal, interdermal, transdermal, etc), enteral, intra-arterial, intradermal, mtragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected penod of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the tertn may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Agonist: Those skilled in the art will appreciate that the term "agonist" may be used to refer to an agent condition, or event whose presence, level, degree, type, or form correlates with increased level or activity of another agent (i.e., the agonized agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Animal: As used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity' of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Encapsulated: The term "encapsulated" is used herein to refer to substances that are completely surrounded by another material.

Excipient: as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Gel: As used herein, the term "gel" refers to viscoelastic materials whose rheological properties distinguish them from solutions, solids, etc. In some embodiments, a composition is considered to be a gel if its storage modulus (G') is larger than its modulus (G"). In some embodiments, a composition is considered to be a gel if there are chemical or physical cross-linked networks in solution, which is distinguished from entangled molecules in viscous solution.

"Improved," "increased" or "reduced": As used herein, these terms, or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Intraperitoneal: The phrases "intraperitoneal administration" and "administered intraperitoneally" as used herein have their art-understood meaning referring to administration of a compound or composition into the peritoneum of a subject.

Moiety: Those skilled in the art will appreciate that a "moiety" is a defined chemical group or entity with a particular structure and/or activity, as described herein.

Oral: The phrases "oral administration" and "administered orally" as used herein have their art-understood meaning referring to administration by mouth of a compound or composition.

Parent N-acylethanolamide compound: A "parent" N-acylethanolamide compound, for purposes of the present disclosure, is a compound relative to which the present disclosure provides derivatives (e.g., to provide a compound of described herein). Typically, a parent N-acylethanolamide compound has a structure as set forth below:

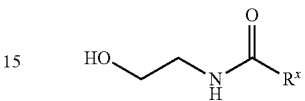

wherein $R^1$ is $C_{1-40}$ aliphatic.

In some embodiments, $R^x$ is $C_{1-40}$ aliphatic. In some embodiments, le is $C_{1-35}$ aliphatic. In some embodiments, $R^x$ is $C_{1-30}$ aliphatic. In some embodiments, $R^x$ is $C_{1-25}$ aliphatic. In some embodiments, $R^x$ is $C_{1-20}$ aliphatic. In some embodiments, $R^x$ is $C_{1-15}$ aliphatic. In some embodiments, $R^x$ is $C_{1-10}$ aliphatic. In some embodiments $R^x$ is $C_{1-5}$ aliphatic. In some embodiments, $R^x$ is $C_{5-30}$ aliphatic. In some embodiments, $R^x$ is $C_{10-15}$ aliphatic. In some embodiments, $R^x$ is $C_{10-20}$ aliphatic. In some embodiments, le is $C_{5-15}$ aliphatic. In some embodiments, $R^x$ is $C_{15-25}$ aliphatic. In some embodiments, a parent N-acylethanolamide compound is derived from a fatty acid selected from the group consisting of myristoleic acid, palmitoleic acid, sapienic acid, oleic acid, elaidic acid, vaccenic acid, linoleic acid, linoelaidic acid, a-linolenic acid, arachidonic acid, eicosapentaenoic acid, erucic acid, docosahexaenoic acid, caprylic acid, capric acid, lauric acid, myrishc acid, palmitic acid, stearic acid, arachidic acid, behemc acid, lignocenc acid, and cerotic acid. In some embodiments, a parent N-acylethanolamide compound is selected from the group consisting of N-palmitoylethanolamide, N-oleoylethanolamide, and N-arachidonoylethanolamide. In some embodiments, a parent N-acylethanolamide compound is N-palmitoylethanolamide. In some embodiments, a parent N-acylethanolamide compound is N-oleoylethanolamide. In some embodiments, a parent N-acylethanolamide compound is N-arachidonoylethanolamide.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, mtraspinal, and intrastemal injection and infusion.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonc acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Predetermined: By predetermined is meant deliberately selected, for example as opposed to randomly occurring or achieved.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

As used herein, the term "prodrug" refers to a compound that is a drug precursor which, following administration, released the drug in vivo via a chemical or physiological process (e.g., a prodrug released the drug upon reaching physiological pH or through enzyme action is converted to the desired drug form).

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the disclosure, chemical compositions may be provided that are or include pure preparations of a single tautomeric form of a compound. In some embodiments, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the disclosure, chemical compositions may contain all tautomeric forms of a compound. In some embodiments of the disclosure, chemical compositions may contain less than all tautomeric forms of a compound. In some embodiments of the disclosure, chemical compositions may contain one or more tautomeric forms of a compound in amounts that vary over time as a result of interconversion. In some embodiments of the disclosure, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an end derivative that may subsequently be isolated using one or more suitable techniques known in the art. Unless otherwise indicated, the present disclosure encompasses all tautomeric forms of relevant compounds, whether in pure form or in admixture with one another.

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Therapeutic regimen: A "therapeutic regimen", as that term is used herein, refers to a dosing regimen whose administration across a relevant population may be correlated with a desired or beneficial therapeutic outcome.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION OF CERTAIN EMBODIMENTS

N-acylethanolamides have shown promise in treatment of various diseases, disorders, and conditions. In some embodiments, one or more compounds provided herein may be useful in treatment of such diseases, disorders and conditions. In some embodiments, one or more provided compounds may be useful, for example, in treatment of one or more neurologic diseases, disorders or conditions. In some embodiments, one or more compounds provided herein may be useful, for example, in treatment of pain, anxiety, depression, schizophrenia, amyotrophic lateral sclerosis, multiple sclerosis, Parkinson's disease, Alzheimer's disease, Huntington's disease, neuropathic pain, cerebral ischemia, epilepsy, appetite loss, dental pain, osteoarthritis, reduced gastrointestinal motility, cancer, glaucoma, atopic dermatitis, respiratory infection, post-traumatic stress disorder, obesity, insomnia, sleepiness, and/or Irritable Bowel Syndrome with Diarrhea (IBS-D).

In some embodiments, one or more compounds provided herein may be useful in reducing gastrointestinal motility in a subject. In some embodiments, one or more compounds provided herein may be useful in reducing cancer cell proliferation in a subject or in a biological sample. In some embodiments, one or more compounds provided herein may be useful in inducing lipolysis in a patient or in a biological sample.

The success of N-acylethanolamides, as well as their sub-optimal pharmacological properties, has led to the development of derivatives, compositions, and prodrugs. Certain N-acylethanolamide derivatives display improved pharmacological properties. For example, polyethylene glycol derivatives of N-acylethanolamides result in improved physico-chemical properties for the treatment of inflammatory and itch- or pain-associated disorders. See, for example, US 2015/0157733 A1.

However, such derivatives, compositions, and prodrugs have failed to produce N-acylethanolamides with improved oral bioavailability suitable for oral administration at high dosages. As a result, current administration of N-acylethanolamides must be parenteral, often intravenous. See, for example, Vacondio, F. et al. "Amino Acid Derivatives as Palmitoylethanolamide Prodrugs: Synthesis, In Vitro Metabolism, and In Vivo Plasma Profile in Rats" *PLoS' One* 2015, 10(6), e0128699.

In some embodiments, the present invention provides derivatives of N-acylethanolamides with desirable pharmacological properties, for example, which may be or include one or more improved properties relative to appropriate N-acylethanolamide reference compounds (e.g., the parent compound of a particular derivative). In certain embodiments, the present disclosure provides derivatives of parent N-acylethanolamide compounds that are characterized by one or more suboptimal pharmacological properties.

In certain embodiments, provided N-acylethanolamide derivative compounds may be characterized by one or more of the properties of increased oral bioavailability, increased cell permeability, increased water solubility, reduced first-pass effect, increased stability, active transport by intestinal transporters, or avoidance of efflux transporters, when compared to N-acylethanolamide reference compounds (e.g., the parent N-acylethanolamide compound of a particular derivative). In some embodiments, provided N-acylethanolamide derivative compounds may be characterized by increased oral bioavailability when compared to N-acylethanolamide reference compounds (e.g., the parent N-acylethanolamide compound of a particular derivative). In some embodiments, the present invention provides N-acylethanolamide derivative compounds that are administered orally. In some embodiments, the present invention provides N-aclethanolamide derivative compounds that may be administered orally at high dosages.

Furthermore, administration of provided N-acylethanolamide derivative compounds may lead to its ability to function in the treatment of diseases, disorders, or conditions.

Provided N-Acylethanolamide Derivatives

In some embodiments, a compound for use in accordance with the present disclosure is one wherein an N-acyletha-nolamide is conjugated to a moiety selected from the group consisting of phosphate, butyric acid, glycerol, succinate, capryhc acid, gluconic acid, eicosapentaeonoic acid, linoleic acid, succinate, and sucrose moieties, and combinations thereof. In some embodiments, an N-acylethanolamide is conjugated to one or more such moieties through use of a linker moiety. In some embodiments, an N-acylethanolamide is conjugated to two or more such moieties. In some embodiments, an N-acylethanolamide is conjugated to one, two, or three such moieties.

In some embodiments, a provided compound has a chemical structure represented by formula I-a:

or a pharmaceutically acceptable salt thereof; wherein
$X_1$ is an N-acylethanolamide; and
$X_2$ is a moiety conjugated to the N-acylethanolamide.

In some embodiments, $X_1$ is selected from the group consisting of N-palmitoylethanolamide, N-oleoylethanolamide, and N-arachidonoylethanolamide; in some particular embodiments, $X_1$ is N-palmitoylethanolamide. In some embodiments, $X_2$ comprises a moiety selected from the group consisting of phosphate, butyric acid, glycerol, succinate, capryhc acid, gluconoic acid, eicosapentaeonoic acid, linoleic acid, succinate, and sucrose moieties.

In some embodiments, a provided compound has a chemical structure represented by formula I:

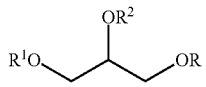

I or a pharmaceutically acceptable salt thereof, wherein:
each $R^1$, $R^2$, or $R^3$ is independently hydrogen or -T-$R^4$, wherein at least one of $R^1$, $R^2$, or $R^3$ is -T-$R^4$;
-T- represents a bivalent moiety; and
$R^4$ is an optionally substituted group selected from the group consisting of $C_{1-40}$ aliphatic, —C(O)R, and X1; wherein
R is selected from the group consisting of hydrogen and optionally substituted
$C_{1-20}$ aliphatic; and
$X_1$ is as defined above.

In some embodiments, a provided compound has a chemical structure represented by formula I-b:

$X_1$-$X_3$   I-b or a pharmaceutically acceptable salt thereof, wherein:
$X_1$ is as defined above;
$X_3$ is an optionally substituted group selected from the group consisting of —(CH$_2$)$_m$—P(O)(OR)$_2$, $C_{1-40}$ aliphatic, -T-$X_4$; further wherein
m is an integer select from the group consisting of 0-10;
-T- is as defined above;
$X_4$ is a saccharide moiety, in some particular embodiments, $X_4$ is a disaccharide, for example, sucrose.

In some embodiments, at least one of $R^1$, $R^2$, or $R^3$ is -T-$R^4$. In some embodiments, at least two of $R^1$, $R^2$, or $R^3$ is -T-$R^4$.

In some embodiments, one of $R^1$, $R^2$, or $R^3$ is -T-$R^4$. In some embodiments, two of $R^1$, $R^2$, $R^3$ are each independently -T-$R^4$. In some embodiments, $R^1$, $R^2$, and $R^3$ are each independently -T-$R^4$.

In some embodiments, $R^1$ is hydrogen. In some embodiments, $R^1$ is -T-$R^4$. In some embodiments, $R^2$ is hydrogen. In some embodiments, $R^2$ is -T-$R^4$. In some embodiments, $R^3$ is hydrogen. In some embodiments, $R^3$ is -T-$R^4$.

In some embodiments, $R^1$ and $R^2$ are hydrogen, and $R^3$ is -T-$R^4$. In some embodiments, $R^2$ and $R^3$ are hydrogen, and $R^1$ is -T-$R^4$. In some embodiments, $R^1$ and $R^3$ are hydrogen, and $R^2$ is -T-$R^4$. In some embodiments, $R^1$ is hydrogen, and $R^2$ and $R^3$ are each independently -T-$R^4$. In some embodiments, $R^2$ is hydrogen, and $R^1$ and $R^3$ are each independently -T-$R^4$. In some embodiments. $R^3$ is hydrogen, and $R^1$ and $R^2$ are each independently -T-$R^4$. In some embodiments, each of $R^1$, $R^2$, and $R^3$ are independently -T-$R^4$.

In some embodiments, -T- represents a bivalent moiety.

In some embodiments, -T- is a bivalent moiety derived from a dicarboxylic acid. In some embodiments, -T- is a bivalent moiety derived from an optionally substituted dicarboxylic acid selected from the group consisting of oxalic acid, malonic acid, succinic acid, glutaric acid, adipic acid, pimelic acid, suberic acid, azelaic acid, sebacic acid, maleic acid, fumaric acid, glutaconic acid, traumatic acid, muconic acid, glutinic acid, citraconic acid, mesaconic acid, malic acid, aspartic acid, glutamic acid, tartronic acid, tartaric acid, diaminopimelic acid, saccharic acid, mesoxalic acid, oxaloacetic acid, acetonedicarboxylic acid, arabinaric acid, phthalic acid, isophthalic acid, terephthalic acid, diphenic acid, and 2,6-napthalenedicarboxylic acid.

In some embodiments, -T- is a bivalent moiety derived from optionally substituted oxalic acid. In some embodiments, -T- is a bivalent moiety derived from optionally substituted malonic acid. In some embodiments, -T- is a bivalent moiety derived from optionally substituted succinic acid. In some embodiments, -T- is a bivalent moiety derived from optionally substituted glutaric acid. In some embodiments, -T- is a bivalent moiety derived from optionally substituted adipic acid. In some embodiments, -T- is a bivalent moiety derived from optionally substituted pimelic acid. In some embodiments, -T- is a bivalent moiety derived from optionally substituted suberic acid. In some embodiments, -T- is a bivalent moiety derived from optionally substituted azelaic acid. In some embodiments, -T- is a bivalent moiety derived from optionally substituted sebacic acid. In some embodiments, -T- is a bivalent moiety derived from optionally substituted maleic acid. In some embodiments, -T- is a bivalent moiety derived from optionally substituted fumaric acid. In some embodiments, -T- is a bivalent moiety derived from optionally substituted glutaconic acid. In some embodiments, -T- is a bivalent moiety derived from optionally substituted traumatic acid. In some embodiments, -T- is a bivalent moiety derived from optionally substituted muconic acid. In some embodiments, -T- is a bivalent moiety derived from optionally substituted glutinic acid. In some embodiments, -T- is a bivalent moiety derived from optionally substituted citraconic acid. In some embodiments, -T- is a bivalent moiety derived from optionally substituted mesaconic acid. In some embodiments, -T- is a bivalent moiety derived from optionally substituted malic acid. In some embodiments, -T- is a bivalent moiety derived from optionally substitutedaspartic acid. In some embodiments, -T- is a bivalent moiety derived from optionally substituted glutamic acid. In some embodiments, -T- is a bivalent moiety derived from optionally substituted tartromc acid. In some embodiments, -T- is a bivalent moiety derived from optionally substituted tartaric acid. In some embodiments, -T- is a bivalent moiety derived from optionally substituted diaminopimelic acid. In some embodiments, -T- is a bivalent moiety derived from optionally substituted saccharic acid. In some embodiments, -T- is a bivalent moiety derived from optionally substituted mesoxalic acid. In some embodiments, -T- is a bivalent moiety derived from optionally substituted oxaloacetic acid. In some embodiments, -T- is a bivalent moiety derived from optionally substituted acetonedicarboxylic acid. In some embodiments, -T- is a bivalent moiety derived from optionally substituted arabinaric acid. In some embodiments, -T- is a bivalent moiety derived from optionally substituted phthalic acid. In some embodiments, -T- is a bivalent moiety derived from optionally substituted isophthalic acid. In some embodiments, -T- is a bivalent moiety[7] derived from optionally substituted terephthalic acid. In some embodiments, -T- is a bivalent moiety derived from optionally substituted diphenic acid. In some embodiments, -T- is a bivalent moiety[7] derived from optionally substituted 2,6-naphthalenedicarboxylic acid.

In some embodiments, -T-R⁴ is:

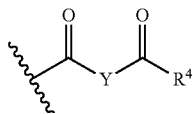

wherein R⁴ is as defined above; and
Y is a bivalent $C_{1-20}$ straight or branched hydrocarbon chain.

In some embodiments Y is a bivalent $C_{1-20}$ straight or branched hydrocarbon chain. In some embodiments Y is a bivalent $C_{1-15}$ straight or branched hydrocarbon chain. In some embodiments Y is a bivalent $C_{1-12}$ straight or branched hydrocarbon chain. In some embodiments Y is a bivalent $C_{1-10}$ straight or branched hydrocarbon chain. In some embodiments Y is a bivalent $C_{1-8}$ straight or branched hydrocarbon chain. In some embodiments Y is a bivalent $C_{1-6}$ straight or branched hydrocarbon chain. In some embodiments Y is a bivalent $C_{1-5}$ straight or branched hydrocarbon chain. In some embodiments Y is a bivalent $C_{1-4}$ straight or branched hydrocarbon chain. In some embodiments Y is a bivalent $C_{1-3}$ straight or branched hydrocarbon chain. In some embodiments Y is a bivalent $C_{1-2}$ straight or branched hydrocarbon chain.

In some embodiments Y is a bivalent $C_{1-20}$ straight hydrocarbon chain. In some embodiments Y is a bivalent $C_{1-15}$ straight hydrocarbon chain. In some embodiments Y is a bivalent $C_{1-12}$ straight hydrocarbon chain. In some embodiments Y is a bivalent $C_{1-4}$ straight hydrocarbon chain. In some embodiments Y is a bivalent $C_{1-8}$ straight hydrocarbon chain. In some embodiments Y is a bivalent $C_{1-6}$ straight hydrocarbon chain. In some embodiments Y is a bivalent $C_{1-5}$ straight hydrocarbon chain. In some embodiments Y is a bivalent $C_{1-4}$ straight hydrocarbon chain. In some embodiments Y is a bivalent $C_{1-3}$ straight hydrocarbon chain. In some embodiments Y is a bivalent $C_{1-2}$ straight hydrocarbon chain.

In some embodiments Y is a bivalent $C_1$ hydrocarbon chain. In some embodiments Y is a bivalent $C_2$ straight or branched hydrocarbon chain. In some embodiments Y is a bivalent $C_3$ straight or branched hydrocarbon chain. In some embodiments Y is a bivalent $C_4$ straight or branched hydrocarbon chain. In some embodiments Y is a bivalent $C_5$ straight or branched hydrocarbon chain. In some embodiments Y is a bivalent $C_6$, straight or branched hydrocarbon chain. In some embodiments Y is a bivalent $C_{10}$ straight or branched hydrocarbon chain.

In some embodiments, Y is propylene. In some embodiments, Y is ethylene. In some embodiments, Y is methylene.

In some embodiments, at least one of $R^1$, $R^2$, or $R^3$ is

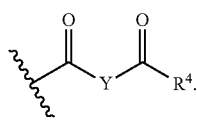

In some embodiments, at least two of $R^1$, $R^2$, or $R^3$ are each independently

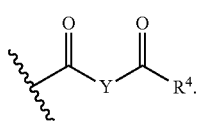

In some embodiments, one of $R^1$, $R^2$, or $R^3$ is

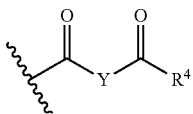

In some embodiments, $R^1$ is

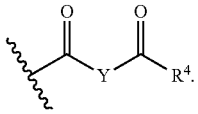

In some embodiments, $R^2$ is

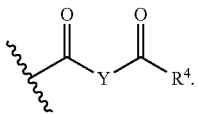

In some embodiments, two of $R^1$, $R^2$, or $R^3$ are each independently

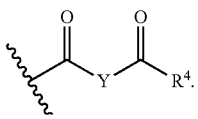

In some embodiments, $R^1$, $P^2$, and $R^3$ are each independently

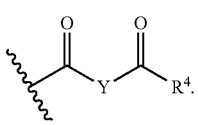

In some embodiments, $R^4$ is an optionally substituted group selected from the group consisting of $C_{1-40}$ aliphatic, —C(O)R, and $X_1$. In some embodiments, $R^4$ is optionally substituted $C_{1-40}$ aliphatic. In some embodiments, $R^4$ is optionally substituted $C_{1-35}$ aliphatic. In some embodiments, $R^4$ is optionally substituted $C_{1-30}$ aliphatic. In some embodiments, $R^4$ is optionally substituted $C_{1-25}$ aliphatic. In some embodiments, $R^4$ is optionally substituted $C_{1-20}$ aliphatic, some embodiments, $R^4$ is optionally substituted $C_{1-10}$ aliphatic. In some embodiments $R^4$ is optionally substituted $C_{1-6}$ aliphatic. In some embodiments, $R^4$ is optionally substituted —C(O)R. In some embodiments, $R^4$ is $X_1$.

In some embodiments, $X_1$ is selected from N-palmitoylethanolamide, N-oleoylethanolamide, or N-arachidonoylethanolamide. In some embodiments, $X_1$ is N-palmitoylethanolamide. In some embodiments, $X_1$ is N-oleoylethanolamide. In some embodiments, $X_1$ is N-arachidonoylethanolamide.

In some embodiments, R is selected from the group consisting of hydrogen and optionally substituted $C_{1-20}$ aliphatic. In some embodiments. R is hydrogen. In some embodiments, R is optionally substituted $C_{1-20}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-3}$ aliphatic.

In some embodiments, $X_3$ is an optionally substituted group selected from the group consisting of —$(CH_2)_m$—P(O)(OR)$_2$, $C_{1-40}$ aliphatic, and -T-$X_4$. In some embodiments, $X_3$ is optionally substituted —$(CH_2)_m$—P(O)(OR)$_2$. In some embodiments, $X_3$ is optionally substituted $C_{1-40}$ aliphatic. In some embodiments, $X_3$ is optionally substituted $C_{1-30}$ aliphatic. In some embodiments, $X_3$ is optionally substituted $C_{1-20}$ aliphatic. In some embodiments. $X_3$ is optionally substituted $C_{1-10}$ aliphatic. In some embodiments, $X_3$ is optionally substituted $C_{1-6}$ aliphatic. In some embodiments, $X_3$ is an optionally substituted -T-$X_4$.

In some embodiments, in is an integer select from the group consisting of 0-10. In some embodiments, m is an integer select from the group consisting of 0-5. In some embodiments, m is 0. In some embodiments, in is 1. In some embodiments, in is 2. In some embodiments, m is 3. In some embodiments, in is 4. In some embodiments, m is 5.

In some embodiments, $X_4$ is a saccharide moiety. In some embodiments, $X_4$ is a disaccharide. In some embodiments, $X_4$ is sucrose.

In some embodiments, a compound of formula I does not comprise a stereocenter within the glycerol backbone (e.g., when $R^1$ and $R^3$ are the same). In some embodiments, a compound of formula I comprises a stereocenter within the glycerol backbone (e.g., wherein $R^1$ and $R^3$ are different). In some embodiments, a compound of formula I is provided and/or utilized as a racemic mixture. In some embodiments, a compound of formula I is provided and/or utilized as a mixture of stereoforms that may or may not be a racemic mixture. In some embodiments, a compound of formula I is provided and/or utilized as a single enantiomer. In some embodiments, the present disclosure provides compounds of formula I' or I":

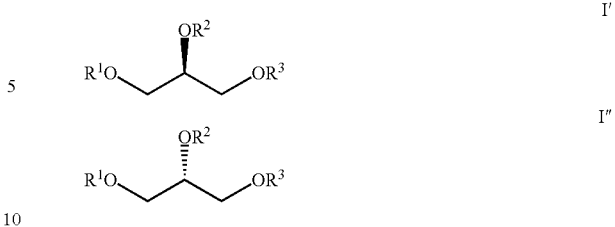

or a pharmaceutically acceptable salt thereof;
wherein $R^1$, $R^2$, and $R^3$ are as defined above.

The present disclosure also provides the insight that, in some embodiments, the position of the N-acylethanolamide, e.g., PEA, on the glycerol moiety may have an effect on its pharmacological properties. For example, a glycerol moiety with an N-acylethanolamide moiety conjugated to the 2 position (e.g., the position corresponding to *—$OR^2$ of formulae I, I', or I") may exhibit improved pharmacological properties over a glycerol moiety with an N-acylethanolamide moiety conjugated to the 1 or 3 position (e.g., the position corresponding to *—$OR^1$ or *—$OR^3$ of formulae I, I', or I"). Without wishing to be bound to a particular theory, the present disclosure proposes that, in some embodiments, the 1 and 3 positions of the glycerol backbone may be more susceptible to cellular lipases than the 2 position.

The present disclosure also provides the insight that, in some embodiments, a compound provided herein may isomerize, for example, undergoing positional isomerization. For example, the present disclosure proposes that, in some embodiments, when a glycerol moiety comprises a free alcohol (e.g., a free alcohol at a position corresponding to *—$OR^1$ or *—$OR^3$ of formulae I, I', or I"), a moiety conjugated to glycerol (e.g., a moiety comprising an N-acylethanolamide at a position corresponding to *—$OR^2$ of formulae I, I', or I"), may migrate to a free alcohol (e.g., migrate from a position corresponding to *—$OR^2$ of formulae I, I', or I" to a position corresponding to *—$OR^1$ or *—$OR^3$ of formulae I, I', or I"). For example, compounds I-8 and I-9 may interconvert among positional isomers.

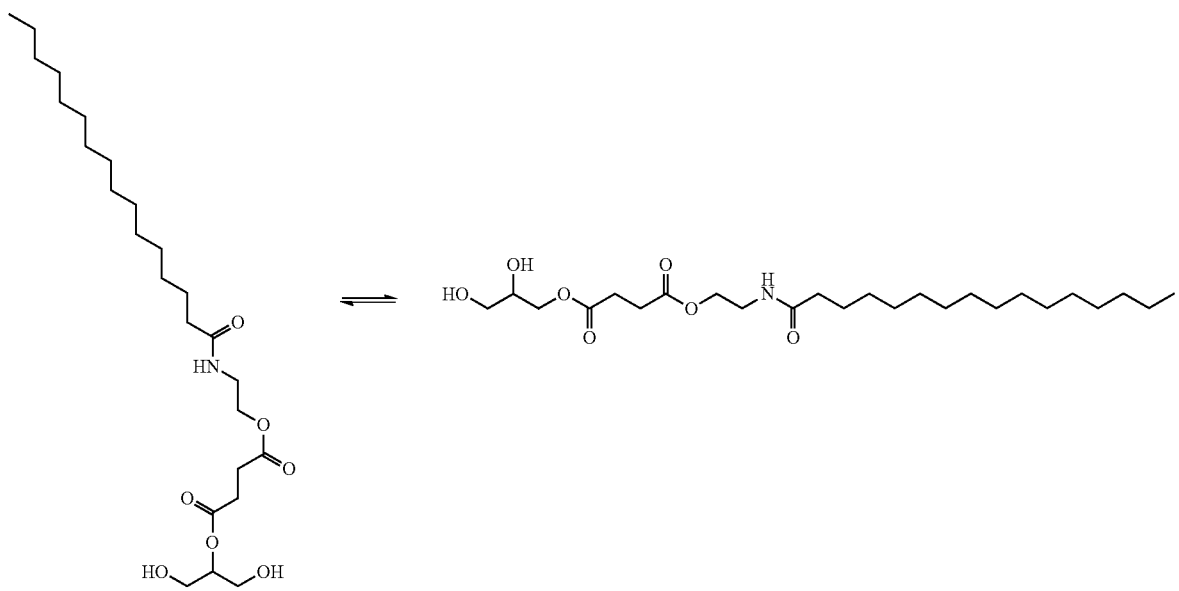 [SMILES: CCCCCCCCCCCCCCCC(=O)NCCOC(=O)CCC(=O)OC(CO)CO ; CCCCCCCCCCCCCCCC(=O)NCCOC(=O)CCC(=O)OCC(O)CO]

In some embodiments, isomerization occurs prior to administration. In some embodiments, isomerization occurs after administration.

In addition, the present disclosure provides the insight that, in some embodiments, a glycerol moiety that does not comprise a free alcohol will not isomerize. For example, in some embodiments, compound I-16 does not undergo positional isomerization.

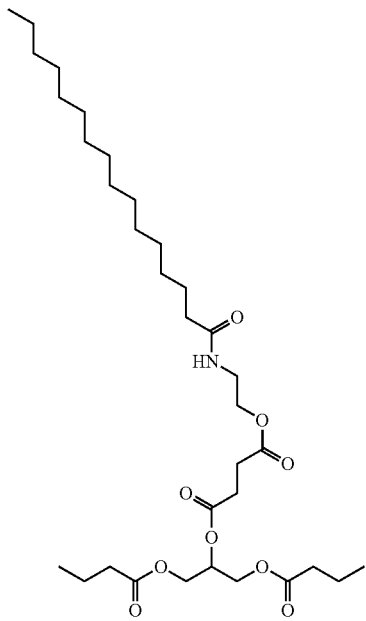 [SMILES: CCCCCCCCCCCCCCCC(=O)NCCOC(=O)CCC(=O)OC(COC(=O)CCC)COC(=O)CCC]

In some embodiments, the present disclosure provides compounds of formula II:

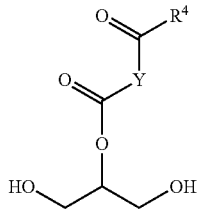

or a pharmaceutically acceptable salt thereof;
wherein Y and $R^4$ are as defined above.

In some embodiments, the present disclosure provides compounds of formula III:

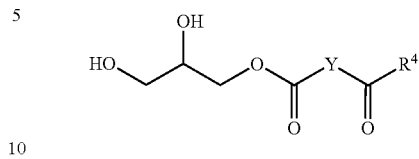

or a pharmaceutically acceptable salt thereof;
wherein Y and $R^4$ are as defined above.

In some embodiments, the present disclosure provides compounds of formulae III' or III"

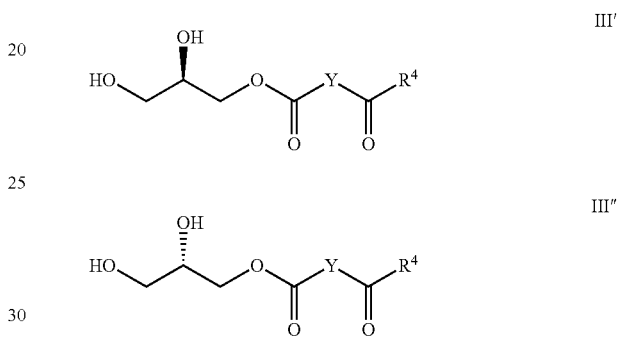

or a pharmaceutically acceptable salt thereof;
wherein Y and $R^4$ are as defined above.

In some embodiments, the present disclosure provides compounds of formula IV:

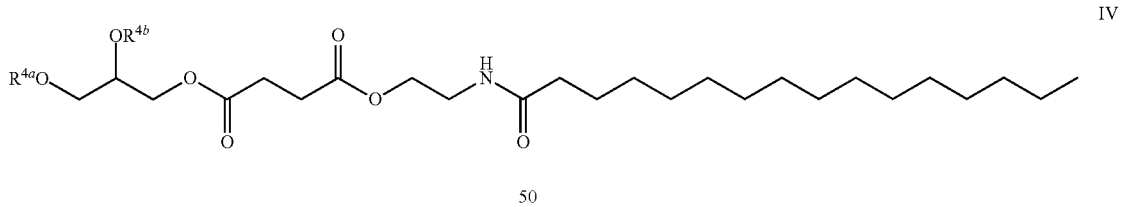

or a pharmaceutically acceptable salt thereof;
wherein:

$R^{4a}$ and $R^{4b}$ are independently hydrogen, —C(O)R', or —C(O)—Y—C(O)OR';
wherein
each R' is independently selected from the group consisting of hydrogen and an optionally substituted $C_{1-20}$ aliphatic; and
each Y is independently as defined above and described herein.

In some embodiments, the present disclosure provides compounds of formulae IV' or IV":

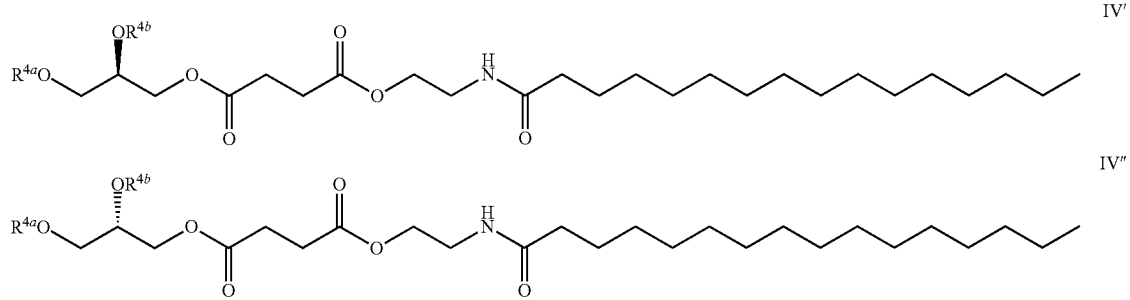

IV'

IV'' or a pharmaceutically acceptable salt thereof; wherein $R^{4a}$ and $R^{4b}$ are as defined above and herein.

In some embodiments, the present disclosure provides compounds of formula V:

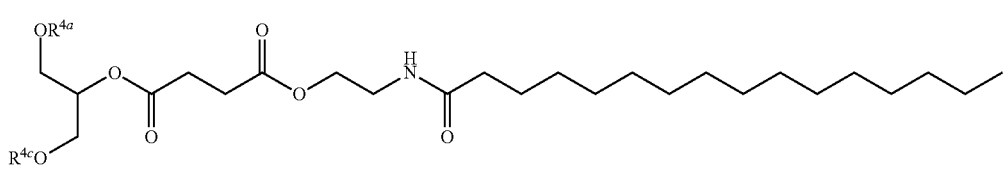

V wherein:
$R^{4a}$ and $R^{4c}$ are independently hydrogen, —C(O)R', or —C(O)—Y—C(O)OR';
wherein
each R' is independently selected from the group consisting of hydrogen and an optionally substituted $C_{1-20}$ aliphatic; and
each Y is independently as defined above and described herein.

In some embodiments, the present disclosure provides compounds of formulae V' or V''

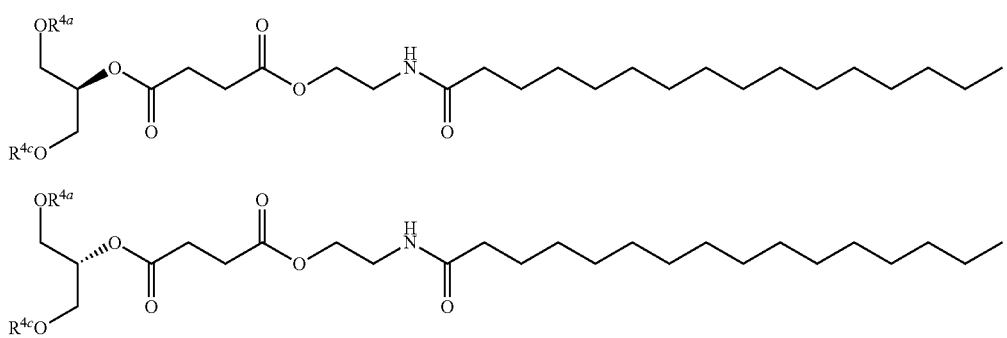

V'

V'' or a pharmaceutically acceptable salt thereof;

wherein $R^{4a}$ and $R^{4c}$ are as defined above and herein.

In some embodiments, $R^{4a}$ is hydrogen. In some embodiments, $R^{4a}$ is —C(O)R'. In some embodiments, $R^{4a}$ is —C(O)—Y—C(O)OR'. In some embodiments, $R^{4b}$ is hydrogen. In some embodiments, $R^{4b}$ is —C(O)R'. In some embodiments, $R^{4b}$ is —C(O)—Y—C(O)OR'. In some embodiments. $R^{4c}$ is hydrogen. In some embodiments, $R^{4c}$ is —C(O)R'. In some embodiments, $R^{4c}$ is is —C(O)—Y—C(O)OR'.

In some embodiments, R' is hydrogen. In some embodiments, R' is optionally substituted $C_{1-20}$ aliphatic. In some embodiments. R' is selected from the group consisting of: hydrogen,

,

-continued

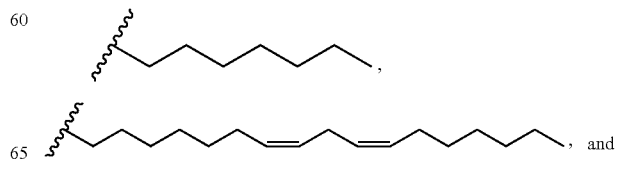

, and

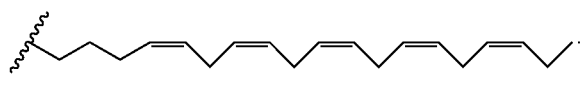

In some embodiments, R' is selected from the group consisting of:

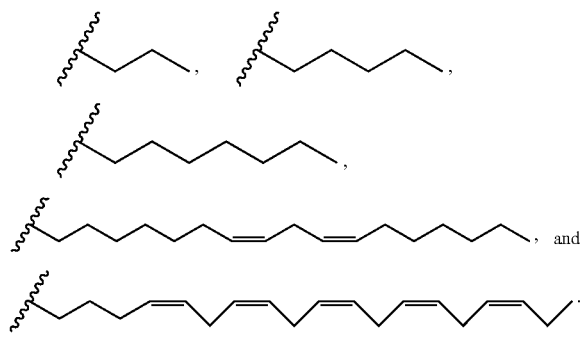

In some embodiments, R' is

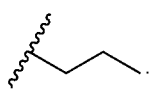

In some embodiments, R' is

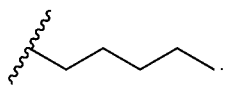 [SMILES: *CCCCC]

In some embodiments, R' is

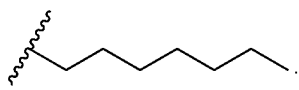 [SMILES: *CCCCCCC]

In some embodiments, R' is

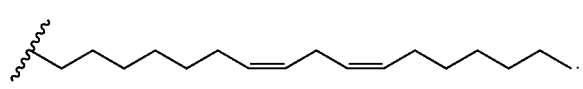

In some embodiments R' is

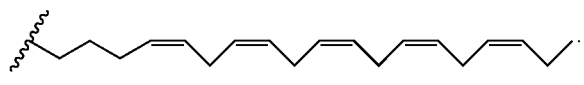

In some embodiments, $R^{4a}$ is —C(O)R'. In some embodiments, $R^{4a}$ is —C(O)R', wherein R' is optionally substituted $C_{1-20}$ aliphatic. In some embodiments, $R^{4a}$ is selected from the group consisting of:

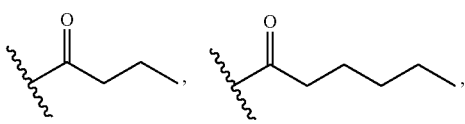

In some embodiments, $R^{4a}$ is selected from the group consisting of:

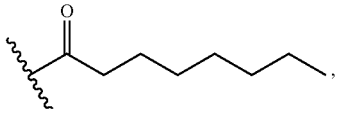

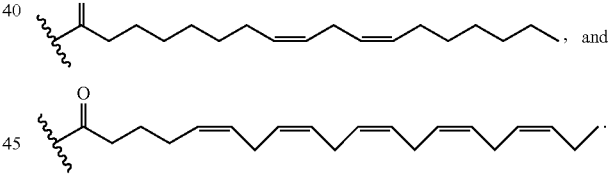

In some embodiments, $R^{4a}$ is

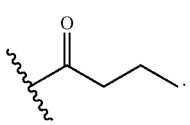

In some embodiments, $R^{4a}$ is

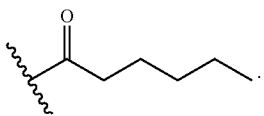 [SMILES: *C(=O)CCCCC]

In some embodiments, $R^{4a}$ is

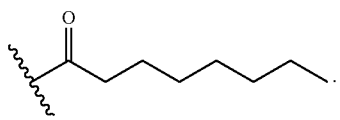 [SMILES: *C(=O)CCCCCCC]

In some embodiments, $R^{4a}$ is

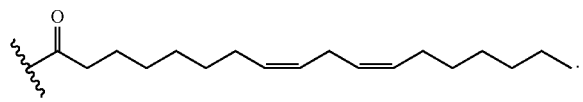 [SMILES: *C(=O)CCCCCC/C=C\C/C=C\CCCCCC]

In some embodiments, $R^{4a}$ is

In some embodiments, $R^{4a}$ is —C(O)—Y—C(O)OR". In some embodiments, $R^{4a}$ is —C(O)—Y—C(O)OR", wherein R' is optionally substituted $C_{1-20}$ aliphatic.

In some embodiments, $R^{4a}$ is —C(O)—Y—C(O)OR', wherein R' is selected from the group consisting of hydrogen,

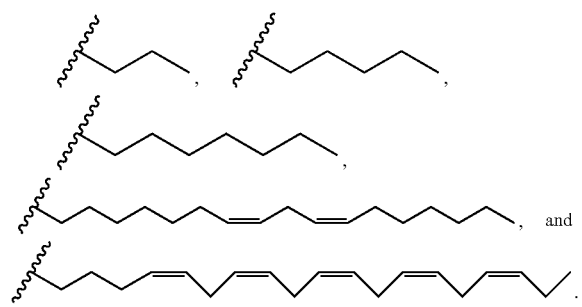

In some embodiments, $R^{4a}$ is —C(O)—Y—C(O)OR', wherein R' is hydrogen. In some embodiments, $R^{4a}$ is —C(O)—Y—C(O)OR', wherein R' is selected from the group consisting of

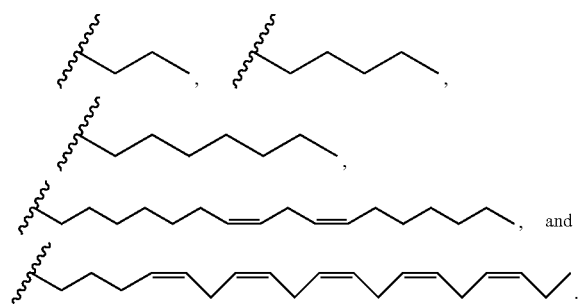

In some embodiments, $R^{4a}$ is —C(O)—Y—C(O)OR', wherein Y is a bivalent $C_{1-20}$ straight or branched hydrocarbon chain. In some embodiments, $R^{4a}$ is —C(O)—Y—C(O)OR', wherein Y is a bivalent $C_{1-15}$ straight or branched hydrocarbon chain. In some embodiments, $R^{4a}$ is —C(O)—Y—C(O)OR', wherein Y is a bivalent $C_{1-12}$ straight or branched hydrocarbon chain. In some embodiments, $R^{4a}$ is —C(O)—Y—C(O)OR', wherein Y is a bivalent $C_{1-10}$ straight or branched hydrocarbon chain. In some embodiments, $R^{4a}$ is —C(O)—Y—C(O)OR', wherein Y is a bivalent $C_{1-8}$ straight or branched hydrocarbon chain. In some embodiments, $R^{4a}$ is —C(O)—Y—C(O)OR', wherein Y is a bivalent $C_{1-6}$ straight or branched hydrocarbon chain. In some embodiments, $R^{4a}$ is —C(O)—Y—C(O)OR', wherein Y is a bivalent $C_{1-5}$ straight or branched hydrocarbon chain. In some embodiments, $R^{4a}$ is —C(O)—Y—C(O)OR', wherein Y is a bivalent $C_{1-4}$ straight or branched hydrocarbon chain. In some embodiments, $R^{4a}$ is —C(O)—Y—C(O)OR', wherein Y is a bivalent $C_{1-3}$ straight or branched hydrocarbon chain. In some embodiments, $R^{4a}$ is —C(O)—Y—C(O)OR', wherein Y is a bivalent $C_{1-2}$ straight or branched hydrocarbon chain.

In some embodiments, $R^{4a}$ is —C(O)—Y—C(O)OR, wherein Y is a bivalent $C_{1-20}$ straight hydrocarbon chain. In some embodiments, $R^{4a}$ is —C(O)—Y—C(O)OR', wherein Y is a bivalent $C_{1-15}$ straight hydrocarbon chain. In some embodiments, $R^{4a}$ is —C(O)—Y—C(O)OR', wherein Y is a bivalent $C_{1-12}$ straight hydrocarbon chain. In some embodiments, $R^{4a}$ is —C(O)—Y—C(O)OR', wherein Y is a bivalent $C_{1-10}$ straight hydrocarbon chain. In some embodiments, $R^{4a}$ is —C(O)—Y—C(O)OR', wherein Y is a bivalent $C_{1-8}$ straight hydrocarbon chain. In some embodiments, $R^{4a}$ is —C(O)—Y—C(O)OR', wherein Y is a bivalent $C_{1-6}$ straight hydrocarbon chain. In some embodiments, $R^{4a}$ is —C(O)—Y—C(O)OR', wherein Y is a bivalent $C_{1-5}$ straight hydrocarbon chain. In some embodiments, $R^{4a}$ is —C(O)—Y—C(O)OR', wherein Y is a bivalent $C_{1-4}$ straight hydrocarbon chain. In some embodiments, $R^{4a}$ is —C(O)—Y—C(O)OR' wherein Y is a bivalent $C_{1-3}$ straight hydrocarbon chain. In some embodiments, $R^{4a}$ is —C(O)—Y—C(O)OR', wherein Y is a bivalent $C_{1-2}$ straight hydrocarbon chain.

In some embodiments, $R^{4a}$ is —C(O)—Y—C(O)OR', wherein Y is a bivalent $C_1$ hydrocarbon chain. In some embodiments, $R^{4a}$ is —C(O)—Y—C(O)OR', wherein Y is a bivalent $C_2$ straight or branched hydrocarbon chain. In some embodiments, $R^{4a}$ is —C(O)—Y—C(O)OR', wherein Y is a bivalent $C_3$ straight or branched hydrocarbon chain. In some embodiments, $R^{4a}$ is —C(O)—Y—C(O)OR, wherein Y is a bivalent $C_4$ straight or branched hydrocarbon chain. In some embodiments, $R^{4a}$ is —C(O)—Y—C(O)OR', wherein Y is a bivalent $C_5$ straight or branched hydrocarbon chain. In some embodiments, $R^{4a}$ is —C(O)—Y—C(O)OR', wherein Y is a bivalent $C_6$ straight or branched hydrocarbon chain. In some embodiments, $R^{4a}$ is —C(O)—Y—C(O)OR', wherein Y is a bivalent $C_{10}$ straight or branched hydrocarbon chain.

In some embodiments, $R^{4a}$ is —C(O)—Y—C(O)OR', wherein, Y is propylene. In some embodiments, $R^{4a}$ is —C(O)—Y—C(O)OR', wherein Y is ethylene. In some embodiments, $R^{4a}$ is —C(O)—Y—C(O)OR', wherein Y is methylene.

In some embodiments, $R^{4a}$ is

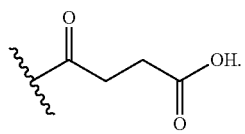 [SMILES: *C(=O)CCC(=O)O]

In some embodiments, $R^{4b}$ is —C(O)R' In some embodiments, $R^{4b}$ is —C(O)R', wherein R' is optionally substituted $C_{1-20}$ aliphatic. In some embodiments, $R^{4b}$ is selected from the group consisting of:

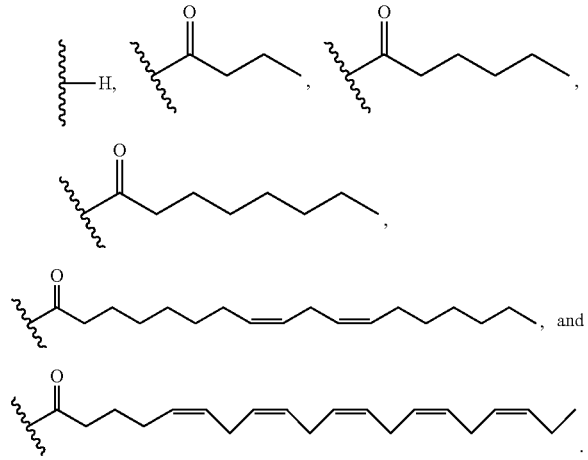

In some embodiments, $R^{4b}$ is selected from the group consisting of:

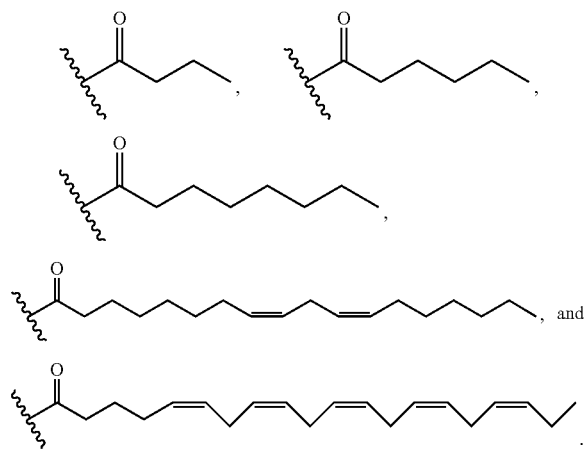

In some embodiments, $R^{4b}$ is

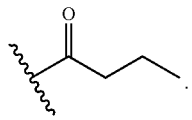 [SMILES: *C(=O)CCC]

In some embodiments, $R^{4b}$ is

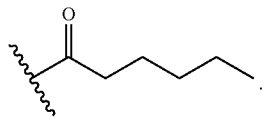 [SMILES: *C(=O)CCCCC]

In some embodiments, $R^{4b}$ is

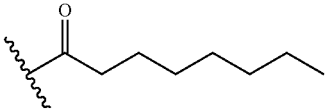

In some embodiments, $R^{4b}$ is

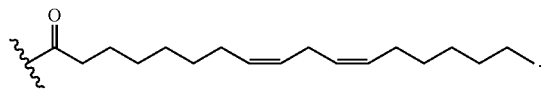 [SMILES: *C(=O)CCCCCC/C=C\C/C=C\CCCCCC]

In some embodiments, $R^{4b}$ is

In some embodiments, $R^{4b}$ is —C(O)—Y—C(O)OR'. In some embodiments, $R^{4b}$ is —C(O)—Y—C(O)OR', wherein R' is optionally substituted $C_{1-20}$ aliphatic.

In some embodiments, $R^{4b}$ is —C(O)—Y—C(O)OR', C(O)OR', wherein R' is selected from the group consisting of,

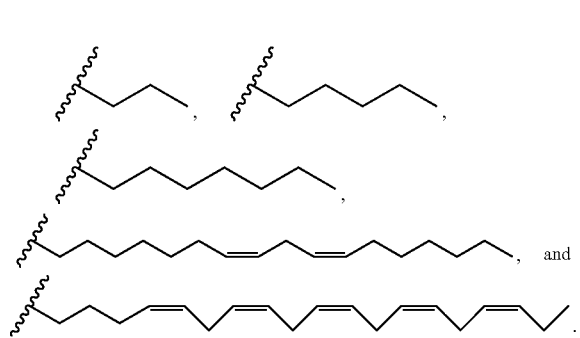

In some embodiments, $R^{4b}$ is —C(O)—Y—C(O)OR', wherein R' is hydrogen. In some embodiments, $R^{4b}$ is —C(O)—Y—C(O)OR', wherein R' is selected from the group consisting of

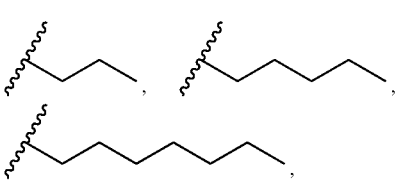

In some embodiments, $R^{4b}$ is —C(O)—Y—C(O)OR', wherein Y is a bivalent $C_{1-20}$ straight or branched hydrocarbon chain. In some embodiments, $R^{4b}$ is —C(O)—Y—C(O)OR', wherein Y is a bivalent $C_{1-15}$ straight or branched hydrocarbon chain. In some embodiments, $R^{4b}$ is —C(O)—

Y—C(O)OR', wherein Y is a bivalent $C_{1-12}$ straight or branched hydrocarbon chain. In some embodiments, R is —C(O)—Y—C(O)OR', wherein Y is a bivalent $C_{1-10}$ straight or branched hydrocarbon chain. In some embodiments, $R^{4b}$ is —C(O)—Y—C(O)OR', wherein Y is a bivalent $C_{1-8}$ straight or branched hydrocarbon chain. In some embodiments, $R^{4b}$ is —C(O)—Y—C(O)OR', wherein Y is a bivalent $C_{1-6}$ straight or branched hydrocarbon chain. In some embodiments, $R^{4b}$ is —C(O)—Y—C(O)OR', wherein Y is a bivalent $C_{1-5}$ straight or branched hydrocarbon chain. In some embodiments, $R^{4b}$ is —C(O)—Y—C(O)OR', wherein Y is a bivalent $C_{1-4}$ straight or branched hydrocarbon chain. In some embodiments, $R^{4b}$ is —C(O)—Y—C(O)OR', wherein Y is a bivalent $C_{1-3}$ straight or branched hydrocarbon chain. In some embodiments, $R^{4b}$ is —C(O)—Y—C(O)OR', wherein Y is a bivalent $C_{1-2}$ straight or branched hydrocarbon chain.

In some embodiments, $R^{4b}$ is —C(O)—Y—C(O)OR', wherein Y is a bivalent $C_{1-20}$ straight hydrocarbon chain. In some embodiments, $R^{4b}$ is —C(O)—Y—C(O)OR', wherein Y is a bivalent $C_{1-15}$ straight hydrocarbon chain. In some embodiments, $R^{4b}$ is —C(O)—Y—C(O)OR', wherein Y is a bivalent $C_{1-12}$ straight hydrocarbon chain. In some embodiments, $R^{4b}$ is —C(O)—Y—C(O)OR', wherein Y is a bivalent $C_{1-10}$ straight hydrocarbon chain. In some embodiments, $R^{4b}$ is —C(O)—Y—C(O)OR', wherein Y is a bivalent $C_{1-8}$ straight hydrocarbon chain. In some embodiments, $R^{4b}$ is —C(O)—Y—C(O)OR', wherein Y is a bivalent $C_{1-6}$ straight hydrocarbon chain. In some embodiments, $R^{4b}$ is —C(O)—Y—C(O)OR', wherein Y is a bivalent $C_{1-5}$ straight hydrocarbon chain. In some embodiments, $R^{4b}$ is —C(O)—Y—C(O)OR', wherein Y is a bivalent $C_{1-4}$ straight hydrocarbon chain. In some embodiments, $R^{4b}$ is —C(O)—Y—C(O)OR, wherein Y is a bivalent $C_{1-3}$ straight hydrocarbon chain. In some embodiments. $R^{4b}$ is —C(O)—Y—C(O)OR, wherein Y is a bivalent $C_{1-2}$ straight hydrocarbon chain.

In some embodiments, $R^{4b}$ is —C(O)—Y—C(O)OR', wherein Y is a bivalent $C_1$ hydrocarbon chain. In some embodiments, $R^{4b}$ is —C(O)—Y—C(O)OR', wherein Y is a bivalent $C_2$ straight or branched hydrocarbon chain. In some embodiments, $R^{4b}$ is —C(O)—Y—C(O)OR', wherein Y is a bivalent $C_3$ straight or branched hydrocarbon chain. In some embodiments, $R^{4b}$ is —C(O)—Y—C(O)OR', wherein Y is a bivalent $C_4$ straight or branched hydrocarbon chain. In some embodiments, $R^{4b}$ is —C(O)—Y—C(O)OR', wherein Y is a bivalent $C_5$ straight or branched hydrocarbon chain. In some embodiments, $R^{4b}$ is —C(O)—Y—C(O)OR', wherein Y is a bivalent $C_6$ straight or branched hydrocarbon chain. In some embodiments, $R^{4b}$ is —C(O)—Y—C(O)OR', wherein Y is a bivalent $C_{10}$ straight or branched hydrocarbon chain.

In some embodiments, $R^{4b}$ is —C(O)—Y—C(O)OR', wherein, Y is propylene. In some embodiments, $R^{4b}$ is —C(O)—Y—C(O)OR', wherein Y is ethylene. In some embodiments, $R^{4b}$ is —C(O)—Y—C(O)OR', wherein Y is methylene.

In some embodiments, $R^{4b}$ is

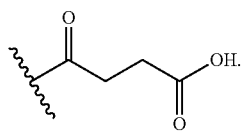 [SMILES: *C(=O)CCC(=O)O]

In some embodiments, $R^{4c}$ is —C(O)R'. In some embodiments, $R^{4c}$ is —C(O)R', wherein R' is optionally substituted $C_{1-20}$ aliphatic. In some embodiments, $R^{4c}$ is selected from the group consisting of:

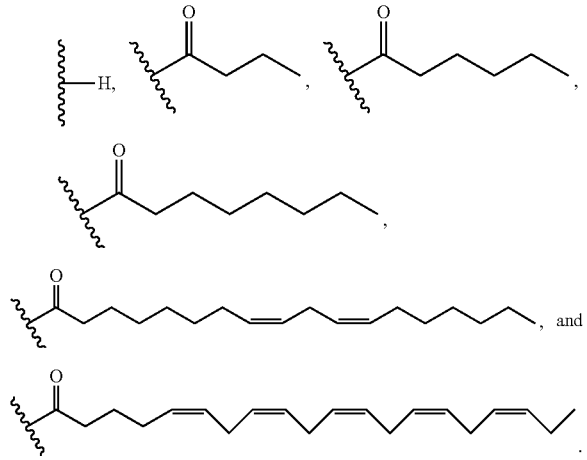

In some embodiments, $R^{4c}$ is selected from the group consisting of:

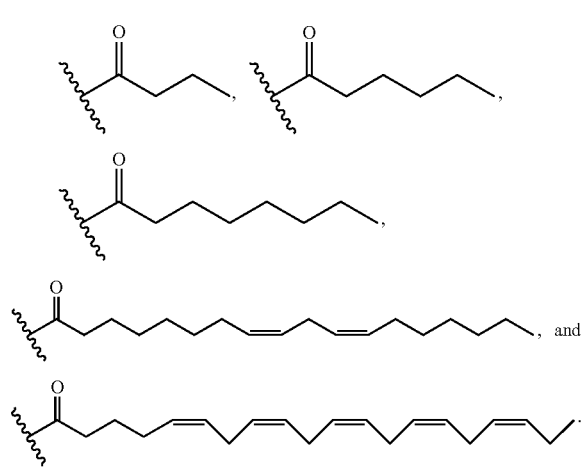

In some embodiments $R^{4c}$ is

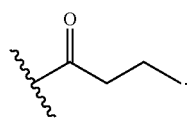

In some embodiments $R^{4c}$ is

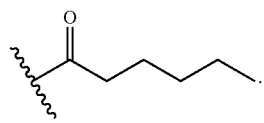 [SMILES: *C(=O)CCCCC]

In some embodiments $R^{4c}$ is

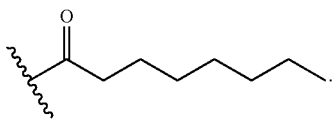 [SMILES: *C(=O)CCCCCCC]

In some embodiments $R^{4c}$ is

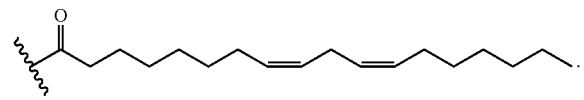 [SMILES: *C(=O)CCCCCC/C=C\C/C=C\CCCCCC]

In some embodiments $R^{4c}$ is

In some embodiments, $R^{4c}$ is —C(O)—Y—C(O)OR'. In some embodiments, $R^{4c}$ is —C(O)—Y—C(O)OR', wherein R' is optionally substituted $C_{1-20}$ aliphatic.

In some embodiments, $R^{4c}$ is —C(O)—Y—C(O)OR', wherein R' is selected from the group consisting of hydrogen,

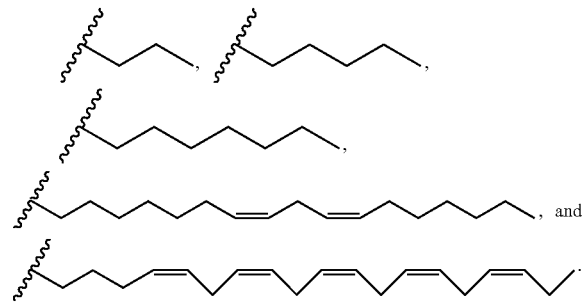

In some embodiments, $R^{4c}$ is —C(O)—Y—C(O)OR', wherein R' is hydrogen. In some embodiments, $R^{4c}$ is —C(O)—Y—C(O)OR', wherein R' is selected from the group consisting of

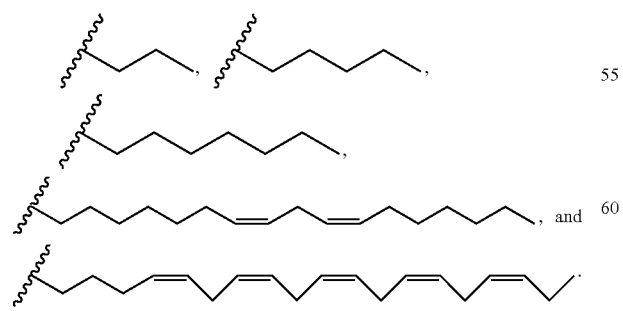

In some embodiments, $R^{4c}$ is —C(O)—Y—C(O)OR', wherein Y is a bivalent $C_{1-20}$ straight or branched hydrocarbon chain. In some embodiments, $R^{4c}$ is —C(O)—Y—C(O)OR', wherein Y is a bivalent $C_{1-15}$ straight or branched hydrocarbon chain. In some embodiments, $R^{4c}$ is —C(O)—Y—C(O)OR', wherein Y is a bivalent $C_{1-12}$ straight or branched hydrocarbon chain. In some embodiments, $R^{4c}$ is —C(O)—Y—C(O)OR', wherein Y is a bivalent $C_{1-10}$ straight or branched hydrocarbon chain. In some embodiments, $R^{4c}$ is —C(O)—Y—C(O)OR', wherein Y is a bivalent $C_{1-8}$ straight or branched hydrocarbon chain. In some embodiments, $R^{4c}$ is —C(O)—Y—C(O)OR', is —C(O)—Y—C(O)OR', wherein Y is a bivalent $C_{1-5}$ straight or branched hydrocarbon chain. In some embodiments, $R^{4c}$ is —C(O)—Y—C(O)OR', wherein Y is a bivalent $C_{1-4}$ straight or branched hydrocarbon chain. In some embodiments, $R^{4c}$ is —C(O)—Y—C(O)OR', wherein Y is a bivalent $C_{1-3}$ straight or branched hydrocarbon chain. In some embodiments, $R^{4c}$ is —C(O)—Y—C(O)OR', wherein Y is a bivalent $C_{1-2}$ straight or branched hydrocarbon chain.

In some embodiments, $R^{4c}$ is —C(O)—Y—C(O)OR', wherein Y is a bivalent $C_{1-20}$ straight hydrocarbon chain. In some embodiments, $R^{4c}$ is —C(O)—Y—C(O)OR', wherein Y is a bivalent $C_{1-15}$ straight hydrocarbon chain. In some embodiments, $R^{4c}$ is —C(O)—Y—C(O)OR', wherein Y is a bivalent $C_{1-12}$ straight hydrocarbon chain. In some embodiments, $R^{4c}$ is —C(O)—Y—C(O)OR', wherein Y is a bivalent $C_{1-10}$ straight hydrocarbon chain. In some embodiments, $R^{4c}$ is —C(O)—Y—C(O)OR', wherein Y is a bivalent $C_{1-8}$ straight hydrocarbon chain. In some embodiments, $R^{4c}$ is —C(O)—Y—C(O)OR', wherein Y is a bivalent $C_{1-6}$ straight hydrocarbon chain. In some embodiments, $R^4$ is —C(O)—Y—C(O)OR', wherein Y is a bivalent $C_{1-5}$ straight hydrocarbon chain. In some embodiments, $R^{4c}$ is —C(O)—Y—C(O)O—R', wherein Y is a bivalent $C_{1-4}$ straight hydrocarbon chain. In some embodiments, $R^{4c}$ is —C(O)—Y—C(O)OR', wherein Y is a bivalent $C_{1-3}$ straight hydrocarbon chain. In some embodiments, $R^{4c}$ is —C(O)—Y—C(O)OR', wherein Y is a bivalent $C_{1-2}$ straight hydrocarbon chain.

In some embodiments, $R^{4c}$ is —C(O)—Y—C(O)OR', wherein Y is a bivalent $C_1$ hydrocarbon chain. In some embodiments, $R^{4c}$ is —C(O)—Y—C(O)OR', wherein Y is a bivalent $C_2$ straight or branched hydrocarbon chain. In some embodiments, $R^{4c}$ is —C(O)—Y—C(O)OR', wherein Y is a bivalent $C_3$ straight or branched hydrocarbon chain. In some embodiments, $R^{4c}$ is —C(O)—Y—C(O)OR', wherein Y is a bivalent $C_4$ straight or branched hydrocarbon chain. In some embodiments, $R^{4c}$ is —C(O)—Y—C(O)OR', wherein Y is a bivalent $C_5$ straight or branched hydrocarbon chain. In some embodiments, $R^{4c}$ is —C(O)—Y—C(O)OR', wherein Y is a bivalent $C_6$ straight or branched hydrocarbon chain. In some embodiments, $R^{4c}$ is —C(O)—Y—C(O)OR', wherein Y is a bivalent $C_{10}$ straight or branched hydrocarbon chain.

In some embodiments, $R^{4c}$ is —C(O)—Y—C(O)OR', wherein, Y is propylene. In some embodiments, $R^{4c}$ is —C(O)—Y—C(O)OR', wherein Y is ethylene. In some embodiments, $R^{4c}$ is —C(O)—Y—C(O)OR', wherein Y is methylene.

In some embodiments, $R^{4c}$ is

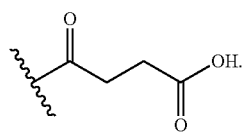 [SMILES: *C(=O)CCC(=O)O]

In some embodiments, each of $R^{4a}$, $R^{4b}$, and $R^{4c}$ is hydrogen. In some embodiments, each of $R^{4a}$, $R^{4b}$, and $R^{4c}$ is independently selected from the group consisting of:

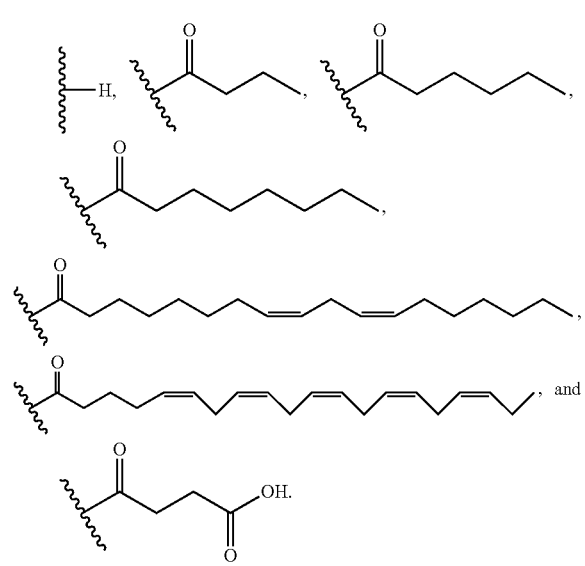

In some embodiments, each of $R^{4a}$, $R^{4b}$, and $R^{4c}$ is independently selected from the group consisting of:

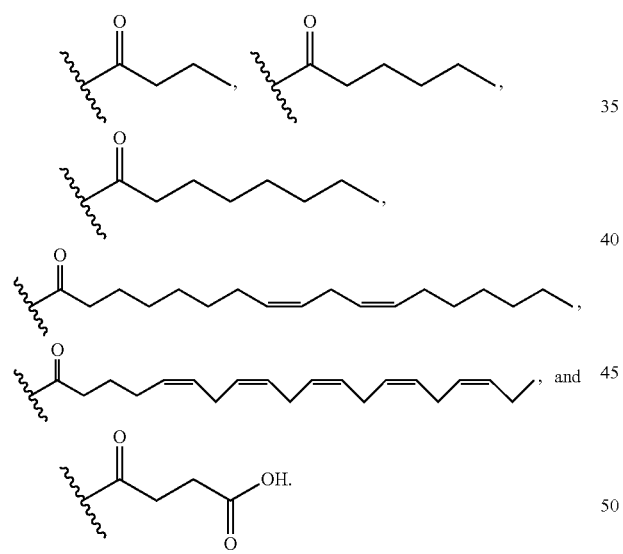

In some embodiments, each of $R^{4a}$, $R^{4b}$, and $R^{4c}$ is independently selected from the group consisting of:

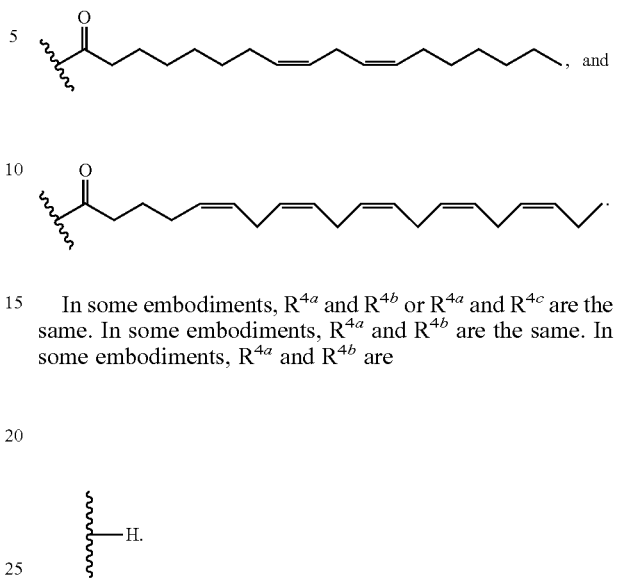

In some embodiments, $R^{4a}$ and $R^{4b}$ or $R^{4a}$ and $R^{4c}$ are the same. In some embodiments, $R^{4a}$ and $R^{4b}$ are the same. In some embodiments, $R^{4a}$ and $R^{4b}$ are

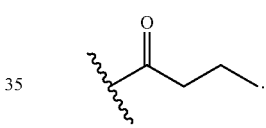

In some embodiments, $R^{4a}$ and $R^{4b}$ are

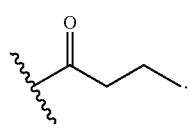 [SMILES: *C(=O)CCC]

In some embodiments, $R^{4a}$ and $R^{4b}$ are

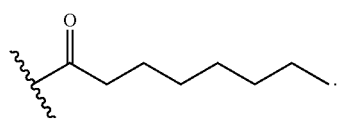 [SMILES: *C(=O)CCCCCCC]

In some embodiments, $R^{4a}$ and $R^{4b}$ are

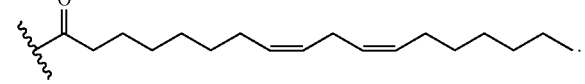

In some embodiments, $R^{4a}$ and $R^{4b}$ are

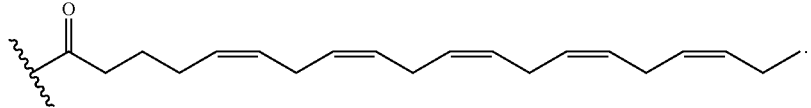 [SMILES: *C(=O)CCC/C=C\C/C=C\C/C=C\C/C=C\C/C=C\CC]

In some embodiments, $R^{4a}$ and $R^{4b}$ are

In some embodiments, $R^{4a}$ and $R^{4c}$ are the same. In some embodiments, $R^{4a}$ and $R^{4c}$ are

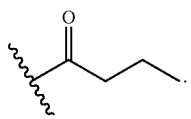 [SMILES: *C(=O)CCC]

In some embodiments, $R^{4a}$ and $R^{4c}$ are

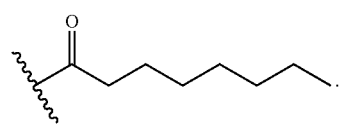

In some embodiments, $R^{4a}$ and $R^{4c}$ are

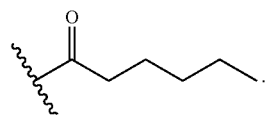 [SMILES: *C(=O)CCCCC]

In some embodiments, $R^{4a}$ and $R^{4c}$ are some embodiments, and $R^{4c}$ are

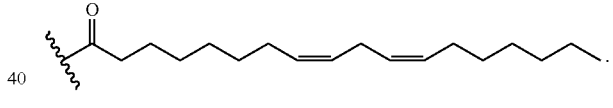

In some embodiments, $R^{4a}$ and $R^{4c}$ are

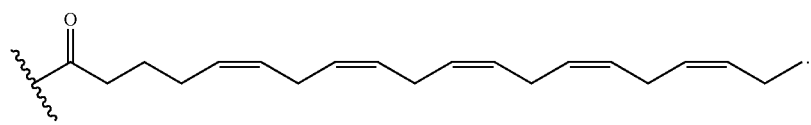 [SMILES: *C(=O)CCC/C=C\C/C=C\C/C=C\C/C=C\C/C=C\CC]

In some embodiments, $R^{4a}$ and $R^{4c}$ are

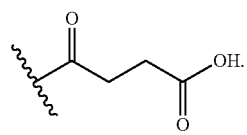 [SMILES: *C(=O)CCC(=O)O]

In some embodiments, the present disclosure provides N-acylethanolamide derivatives selected from those in Table 1.

TABLE 1
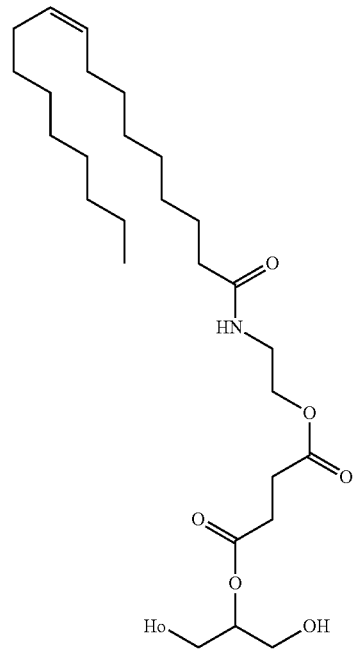
I-a-2
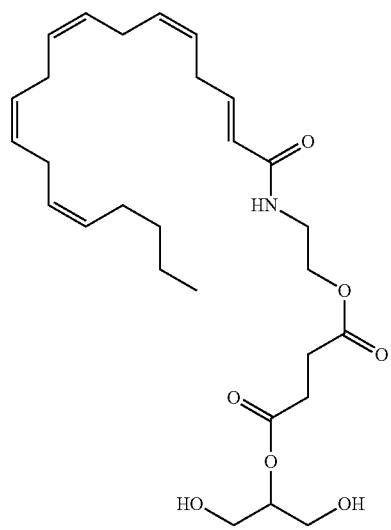 [SMILES: CCCC/C=C\C/C=C\C/C=C\C/C=C\C/C=C/C(=O)NCCOC(=O)CCC(=O)OC(CO)CO]
I-a-3
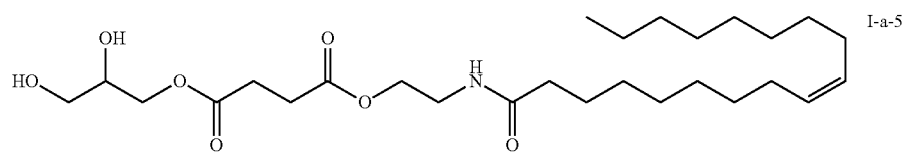
I-a-5
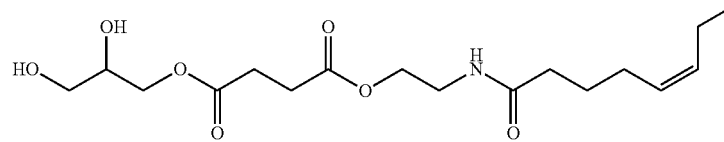
I-a-6

TABLE 1-continued
I-1
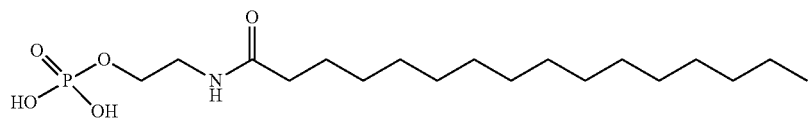 [SMILES: CCCCCCCCCCCCCCCC(=O)NCCOP(=O)(O)O]
I-2
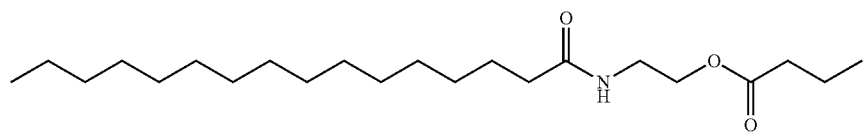 [SMILES: CCCCCCCCCCCCCCCC(=O)NCCOC(=O)CCC]
I-3
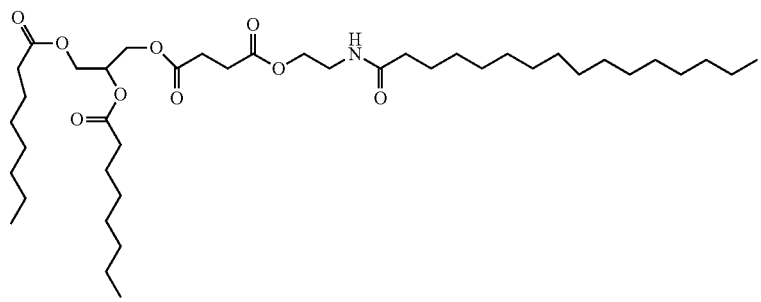 [SMILES: CCCCCCCCCCCCCCCC(=O)NCCOC(=O)CCC(=O)OCC(COC(=O)CCCCCCC)OC(=O)CCCCCCC]
I-4
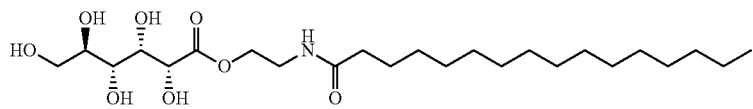 [SMILES: CCCCCCCCCCCCCCCC(=O)NCCOC(=O)[C@H](O)[C@@H](O)[C@H](O)[C@H](O)CO]
I-5
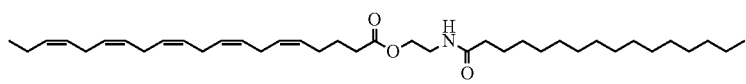 [SMILES: CC/C=C\C/C=C\C/C=C\C/C=C\C/C=C\CCCC(=O)OCCNC(=O)CCCCCCCCCCCCCCC]
I-6
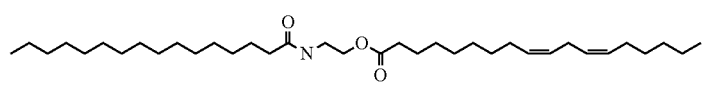 [SMILES: CCCCC/C=C\C/C=C\CCCCCCCC(=O)OCCNC(=O)CCCCCCCCCCCCCCC]
I-7
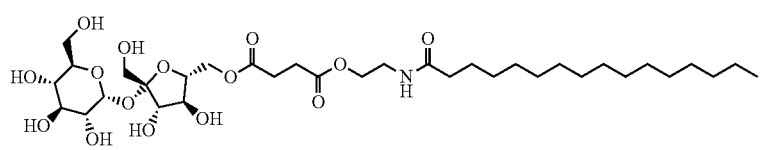

TABLE 1-continued
I-8
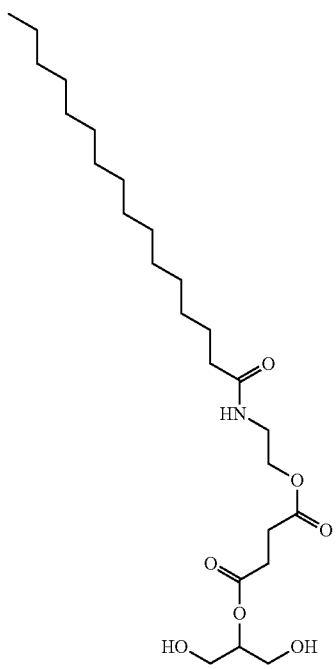 [SMILES: CCCCCCCCCCCCCCCC(=O)NCCOC(=O)CCC(=O)OC(CO)CO]
I-9
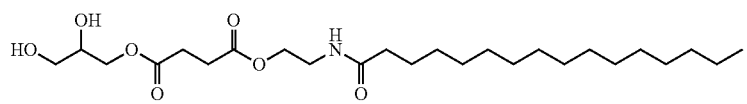 [SMILES: CCCCCCCCCCCCCCCC(=O)NCCOC(=O)CCC(=O)OCC(O)CO]
In some embodiments, the present disclosure provides compounds selected from those in Table 1-a.
TABLE 1-a
I-10
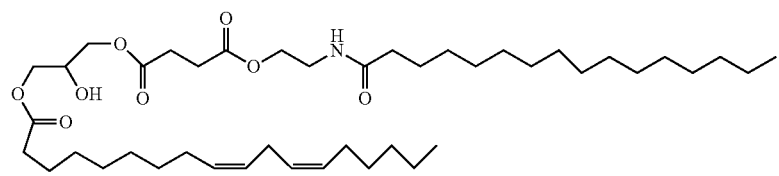 [SMILES: CCCCC/C=C\C/C=C\CCCCCCCC(=O)OCC(O)COC(=O)CCC(=O)OCCNC(=O)CCCCCCCCCCCCCCC]
I-11
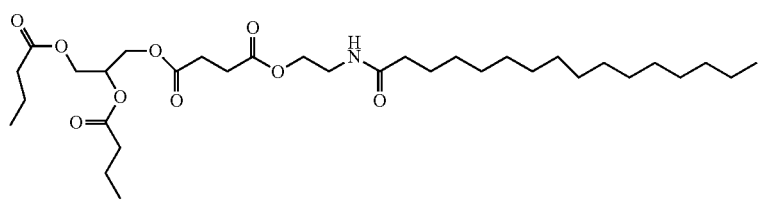 [SMILES: CCCCCCCCCCCCCCCC(=O)NCCOC(=O)CCC(=O)OCC(COC(=O)CCC)OC(=O)CCC]

TABLE 1-a-continued
I-12
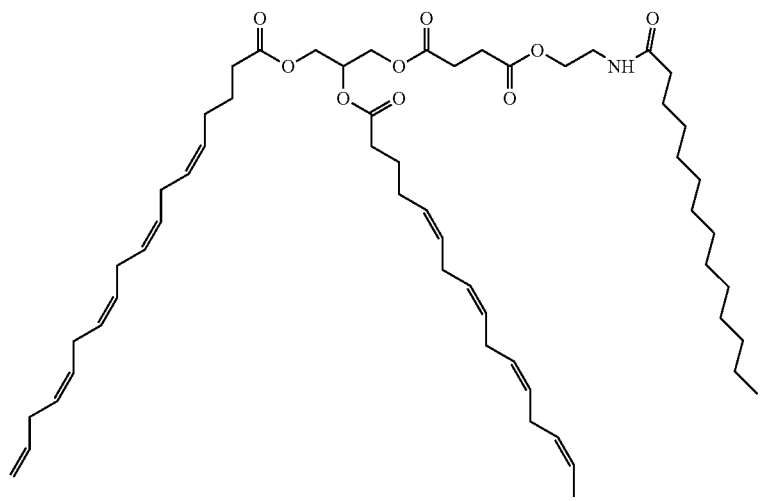 [SMILES: C=CC/C=C\C/C=C\C/C=C\C/C=C\CCCC(=O)OCC(COC(=O)CCC(=O)OCCNC(=O)CCCCCCCCCCCCC)OC(=O)CCC/C=C\C/C=C\C/C=C\C/C=C\C]
I-13
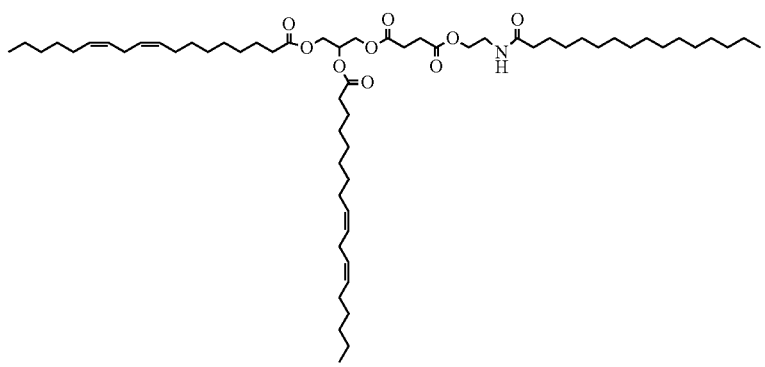 [SMILES: CCCCC/C=C\C/C=C\CCCCCCCC(=O)OCC(COC(=O)CCC(=O)OCCNC(=O)CCCCCCCCCCCCCCC)OC(=O)CCCCCCC/C=C\C/C=C\CCCCC]
I-14
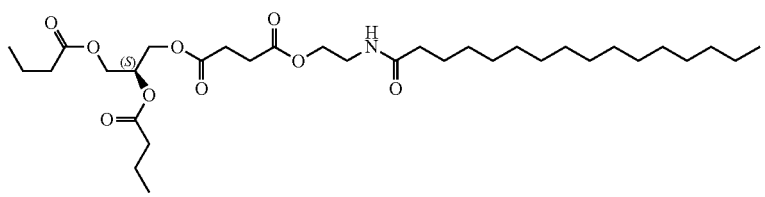
I-15
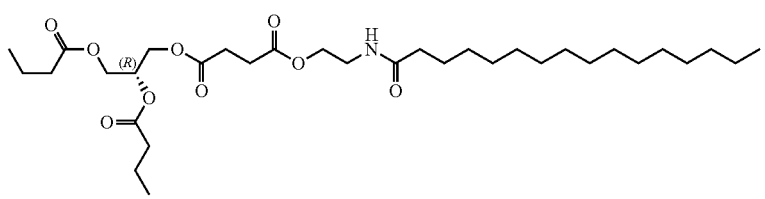

TABLE 1-a-continued

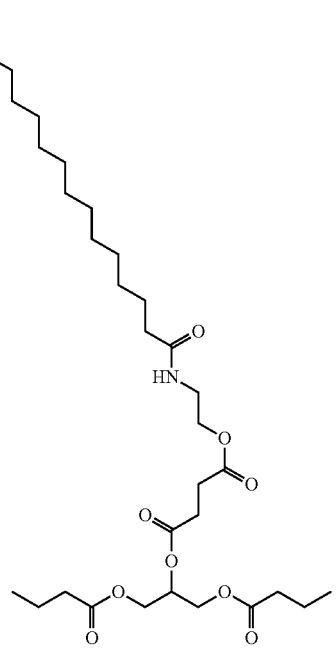

I-16

In some embodiments, one or more hydrogen atoms are replaced with a deuterium atom(s). In some embodiments, one or more of $R^1$, $R^2$, or $R^3$ is or contains deuterium.

In some embodiments, provided N-acylethanolamide derivative compounds display one or more activities that is/are comparable to that of a reference compound (e.g., a parent N-acylethanolamide compound). In some embodiments, provided N-acylethanolamide derivative compounds display one or more activities that is/are improved as compared to a reference compound (e.g., a parent N-acylethanolamide compound).

In some embodiments, provided N-acylethanolamide derivative compounds are characterized in that the compound may show improved solubility in an aqueous system as compared to a reference compound (e.g., a parent N-acylethanolamide compound). In some particular embodiments, aqueous solubility may be assessed according to an appropriate assay. In some embodiments, an appropriate assay is known in the art and/or described herein.

In some embodiments, provided N-acylethanolamide derivative compounds are characterized in that the compound may show improved stability as compared to a reference compound (e.g., a parent N-acylethanolamide compound) In some particular embodiments, stability may be assessed, for example, using an appropriate assay. In some embodiments, an appropriate assay is known in the art and/or described herein.

In some embodiments, provided N-acylethanolamide derivative compounds are characterized in that the compound is metabolized differently as compared to a reference compound (e.g., a parent N-acylethanolamide compound). In some embodiments, provided N-acylethanolamide derivative compounds are characterized in that the compound is metabolized at a different rate as compared to a reference compound (e.g., a parent N-acylethanolamide compound). In some embodiments, provided N-acylethanolamide derivative compounds are characterized in that the compound is metabolized at a faster rate as compared to a reference compound (e.g., a parent N-acylethanolamide compound). In some embodiments, provided N-acylethanolamide derivative compounds are characterized in that the compound is metabolized at a slower rate as compared to a reference compound (e.g., a parent N-acylethanolamide compound). In some particular embodiments, metabolized rate may be assessed, for example, using an appropriate assay. In some embodiments, an appropriate assay is known in the art and/or described herein.

In some embodiments, provided N-acylethanolamide derivative compounds are characterized in that when administered, the compound delivers a parent N-acylethanolamide compound or an active metabolite thereof.

In some embodiments, provided N-acylethanolamide derivative compounds are characterized in that when administered, the compound exhibits an improved oral bioavailability as compared to a reference compound (e.g., a parent N-acylethanolamide compound). In some particular embodiments, oral bioavailability may be assessed, for example, using an appropriate assay. In some embodiments, an appropriate assay is known in the art and/or described herein.

In some embodiments, a reference compound is or comprises a parent N-acylethanolamide compound. In some embodiments, a reference compound is or comprises palmitoylethanolamide.

In some embodiments, provided N-acylethanolamide derivative compounds display one or more activities that is/are comparable to that of palmitoylethanolamide. In some embodiments, provided N-acylethanolamide derivative compounds display one or more activities that is/are improved as compared to palmitoylethanolamide.

In some embodiments, provided N-acylethanolamide derivative compounds display increased solubility as compared to that of palmitoylethanolamide. In some particular embodiments, aqueous solubility may be assessed, for example, using an appropriate assay. In some embodiments, an appropriate assay is known in the art and or described herein.

In some embodiments, provided N-acylethanolamide derivative compounds display increased stability that is comparable to that of palmitoylethanolamide.

In some embodiments, provided N-acylethanolamide derivative compounds are metabolized differently as compared to that of palmitoylethanolamide. In some embodiments, provided N-acylethanolamide derivative compounds are metabolized at a faster rate as compared to that of palmitoylethanolamide. In some embodiments, provided N-acylethanolamide derivative compounds are metabolized at a slower rate as compared to that of palmitoylethanolamide.

In some embodiments, provided N-acylethanolamide derivative compounds when administered deliver palmitoylethanolamide or an active metabolite thereof. In some embodiments, provided N-acylethanolamide derivative compounds when administered display improved oral bioavailability as compared to the administration of palmitoylethanolamide.

In some embodiments, a reference compound is or comprises oleoylethanolamide.

In some embodiments, provided N-acylethanolamide derivative compounds display one or more activities that is/are comparable to that of oleoylethanolamide. In some embodiments, provided N-acylethanolamide derivative compounds display one or more activities that is/are improved as compared to oleoylethanolamide.

In some embodiments, provided N-acylethanolamide derivative compounds display increased solubility that is comparable to that of oleoylethanolamide. In some particular embodiments, aqueous solubility may be assessed, for example, using an appropriate assay. In some embodiments, an appropriate assay is known in the art and or described herein.

In some embodiments, provided N-acylethanolamide derivative compounds display increased stability that is comparable to that of oleoylethanolamide.

In some embodiments, provided N-acylethanolamide derivative compounds are metabolized differently as compared to that of oleoylethanolamide. In some embodiments, provided N-acylethanolamide derivative compounds are metabolized at a faster rate as compared to that of oleoylethanolamide. In some embodiments, provided N-acylethanolamide derivative compounds are metabolized at a slower rate as compared to that of oleoylethanolamide.

In some embodiments, provided N-acylethanolamide derivative compounds when administered deliver oleoylethanolamide or an active metabolite thereof. In some embodiments, provided N-acylethanolamide derivative compounds when administered display improved oral bioavailability as compared to the administration of oleoylethanolamide.

In some embodiments, a reference compound is or comprises arachidonylethanolamide.

In some embodiments, provided N-acylethanolamide derivative compounds display one or more activities that is/are comparable to that of arachidonylethanolamide. In some embodiments, provided N-acylethanolamide derivative compounds display one or more activities that is/are improved as compared to arachidonylethanolamide.

In some embodiments, provided N-acylethanolamide derivative compounds display increased solubility that is comparable to that of arachidonylethanolamide. In some particular embodiments, aqueous solubility may be assessed, for example, using an appropriate assay. In some embodiments, an appropriate assay is known in the art and/or described herein.

In some embodiments, provided N-acylethanolamide derivative compounds display increased stability that is comparable to that of arachidonylethanolamide.

In some embodiments, provided N-acylethanolamide derivative compounds are metabolized differently as compared to that of arachidonylethanolamide. In some embodiments, provided N-acylethanolamide derivative compounds are metabolized at a faster rate as compared to that of arachidonylethanolamide. In some embodiments, provided N-acylethanolamide derivative compounds are metabolized at a slower rate as compared to that of arachidonylethanolamide.

In some embodiments, provided N-acylethanolamide derivative compounds when administered deliver arachidonylethanolamide or an active metabolite thereof. In some embodiments, provided N-acylethanolamide derivative compounds when administered display improved oral bioavailability as compared to the administration of arachidonylethanolamide.

Uses

In some embodiments, the present disclosure provides methods of identifying and/or characterizing derivatives of an N-acylethanolamide compound (e.g., a parent N-acylethanolamide compound), which method comprising the steps of:
  providing a derivative compound comprising a moiety modifying or otherwise linked to an N-acylethanolamide; and
  determining that the derivative compound has one or more improved pharmacologic properties relative to the N-acylethanolamide compound.

In some embodiments, the present disclosure provides technologies for identifying, assessing, and/or characterizing one or more activities or attributes of one or more provided N-acylethanolamide derivative compounds.

In some embodiments, the present disclosure provides methods of treating a subject suffering from or susceptible to a disease, disorder, or condition, which method comprises a step of:
  administering an N-acylethanolamide derivative or composition disclosed herein to a subject in need thereof.

In some embodiments, an N-acylethanolamide derivative or composition disclosed herein is administered in combination with one or more other agents that treat the relevant disease, disorders, or conditions (or one or more symptoms thereof) from which a relevant subject is suffering.

Various diseases, disorders, and/or conditions may be affected by an N-acylethanolamide. In some embodiments, the present disclosure provides methods comprising administering to a subject suffering from or susceptible to a disease, disorder, or condition a pharmaceutically effective amount of a provided compound or composition.

Figure 1:
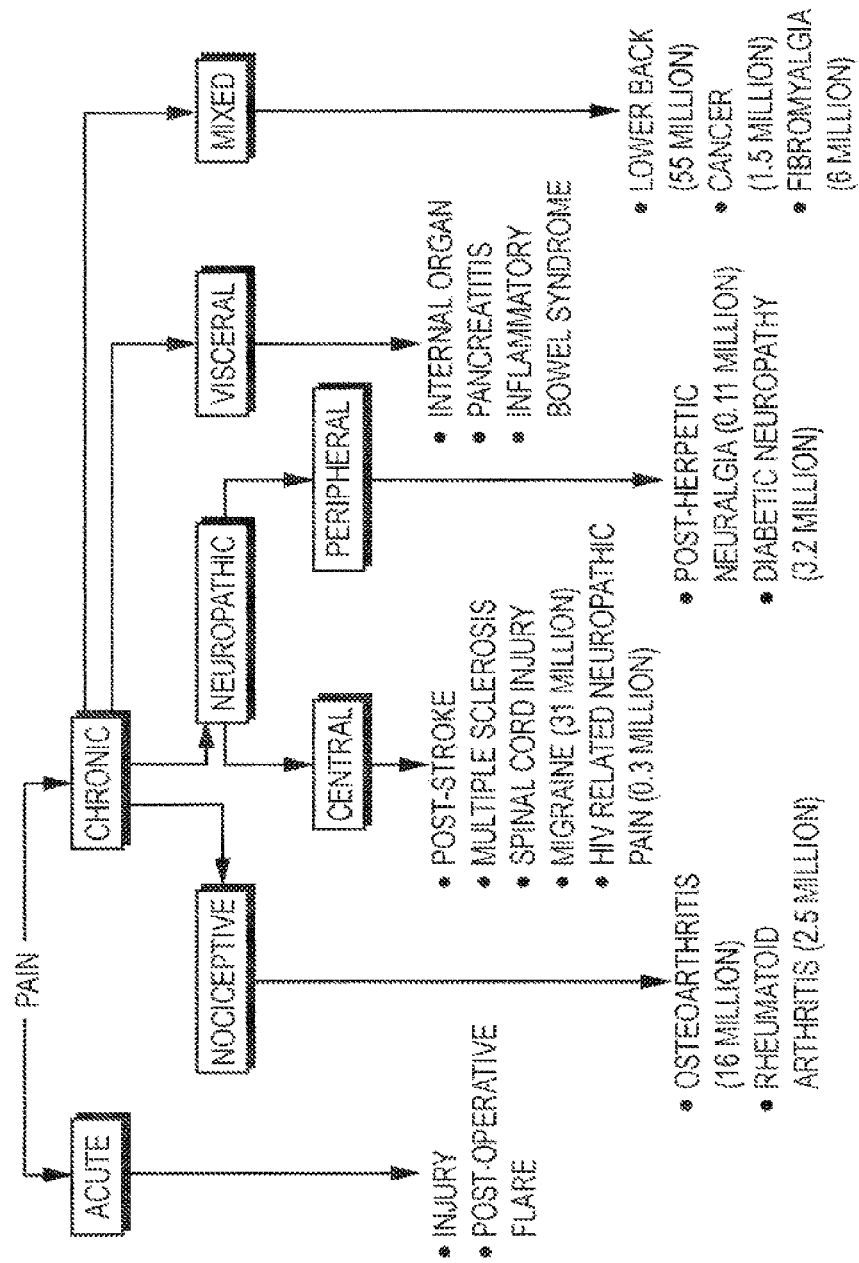
FIG. 1 is a flow chart indicating pain classification and representative indications. Distinguishing between different types of pain is critical for proper treatment. Pain can be classified by its duration into acute and chronic pain. Chronic pain is further classified by the source of pain production: nociceptive pain, which is transmitted by nociceptors from the site of injury or tissue damage (for example, inflamed joints in arthritis); neuropathic pain, which is initiated or caused by a primary lesion or dysfunction in the nervous system (further subdivided into central and peripheral, involving the central and peripheral nervous systems, respectively); visceral pain, which involves the internal organs; mixed pain, which is of mixed origin.

In some embodiments, a disease, disorder, or condition is or comprises pain. In some embodiments, pain may be chronic pain. In some embodiments, pain may be or include lower back pain. In some embodiments, a disease, disorder, or condition is or comprises chronic lower back pain. In some embodiments, a disease, disorder, or condition is or comprises sciatica. In some embodiments, a disease, disorder, or condition is or comprises radiculopathy. In some embodiments, a disease, disorder, or condition is or comprises radiating pain. Certain pain classification and representative indications are depicted in FIG. 1.

In some embodiments, a disease, disorder, or condition is or comprises anxiety. In some embodiments, a disease, disorder, or condition is or comprises depression. In some embodiments, a disease, disorder, or condition is characterized by one or more symptoms of schizophrenia.

In some embodiments, a disease, disorder, or condition is or comprises a neurologic, disease, disorder, or condition. In some embodiments, a disease, disorder or condition is or comprises Huntington's disease. In some embodiments, a disease, disorder or condition is or comprises Parkinson's disease. In some embodiments, a disease, disorder or condition is or comprises Alzheimer's disease. In some embodiments, a disease, disorder, or condition is or comprises Amyotrophic Lateral Sclerosis (ALS, also known as Lou Gehrig's disease). In some embodiments, a disease, disorder, or condition is or comprises multiple sclerosis. In some embodiments, a disease, disorder, or condition is or comprises neuropathic pain. In some embodiments, a disease, disorder, or condition is or comprises cerebral ischemia. In some embodiments, a disease, disorder, or condition is or comprises epilepsy.

In some embodiments, a disease, disorder, or condition is or comprises appetite loss. In some embodiments, a disease, disorder, or condition is or comprises dental pain. In some embodiments, a disease, disorder, or condition is or comprises osteoarthritis. In some embodiments, a disease, disorder, or condition is or comprises reduced gastrointestinal motility.

In some embodiments, a disease, disorder, or condition is or comprises cancer.

In some embodiments, a disease, disorder, or condition is or comprises an ophthalmic condition. In some embodiments, a disease, disorder, or condition is or comprises glaucoma.

In some embodiments, a disease, disorder, or condition is or comprises atopic dermatitis. In some embodiments, a disease, disorder, or condition is or comprises respiratory infection. In some embodiments, a disease, disorder, or condition is or comprises post-traumatic stress disorder. In some embodiments, a disease, disorder, or condition is or comprises obesity. In some embodiments, a disease, disorder, or condition is or comprises insomnia. In some embodiments, a disease, disorder, or condition is or comprises sleepiness.

In some embodiments, the present disclosure provides methods of reducing gastrointestinal motility in a patient, which method comprising the step of administering a compound or composition disclosed herein to a subject in need thereof.

In some embodiments, the present disclosure provides methods of reducing cancer cell proliferation in a patient or in a biological sample, which method comprising the step of administering to said patient or contacting said biological sample with a compound or composition disclosed herein.

In some embodiments, the present disclosure provides methods of inducing lipolysis in a patient or in a biological sample, which method comprising the step of administering to said patient or contacting said biological sample with a compound or composition disclosed herein.

In some particular embodiments, provided compounds including a butyric acid moiety is useful in the treatment of IBS-D and/or for the treatment of pain. Butyric acid (BA) is a critical component of gut heath and has been shown to decrease pain, reduce frequency and increased consistency of bowel movements for IBS-D patients.

In some embodiments, provided treatments that utilize one or more compounds as described herein (e.g., treatment of pain) may deliver PEA at a level corresponding to a dose greater than or equal to 1200 mg/day PEA. In some embodiments, provided treatments may involve administration once or twice daily.

In some embodiments, provided treatments that utilize one or more compounds as described herein (e.g., treatment of IBS-D) may deliver PEA at a level corresponding to a dose of about 3 g/day PEA.

In some embodiments, provided treatments with butyric-acid-moiety-containing compounds as described herein (e.g., treatment of pain and/or IBS-D) may deliver PEA at a level corresponding to a dose of about 3 g/day PEA and/or may deliver BA at a level corresponding to a dose of about 1 g/day BA.

In some embodiments, one or more particular compounds provided herein may be useful in the treatment of a plurality of different diseases, disorders or conditions; om some such embodiments, the compound may be differently formulated when utilized for different diseases, disorders or conditions.

Compositions

In some embodiments, compounds as provided herein are prepared and/or utilized in compositions, such as pharmaceutical compositions. In some embodiments, a provided pharmaceutical composition comprises a therapeutically effective amount of a provided compound, and at least one pharmaceutically acceptable inactive ingredient selected from pharmaceutically acceptable diluents, pharmaceutically acceptable excipients, and pharmaceutically acceptable carriers. In some embodiments, the pharmaceutical composition is formulated for intravenous injection, oral administration, buccal administration, inhalation, nasal administration, topical administration, ophthalmic administration or optic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising a provided compound or composition, in a mixture with a pharmaceutically acceptable excipient.

In therapeutic and/or diagnostic applications, provide compounds can be formulated for a variety of modes of administration, including systemic and topical or localized administration. Techniques and formulations generally may be found in Remington, The Science and Practice of Pharmacy, (20th ed. 2000).

Provided compounds and compositions thereof are effective over a wide dosage range. For example, in the treatment of adult humans, dosages from about 0.01 to about 10000 mg, from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, provided agents may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate provided compounds or compositions into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds can be formulated readily using pharmaceutically acceptable carriers well known in the art into dosages suitable for oral administration. Such carriers enable provided compounds and compositions to be formulated as tablets, pills, capsules, liquids, gels, syrups, slurries, suspensions and the like, for oral ingestion by a subject (e.g., patient) to be treated.

For nasal or inhalation delivery, provided compounds or compositions may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, provided compounds and compositions are delivered to the CNS. In certain embodiments, provided compounds and compositions are delivered to the cerebrospinal fluid. In certain embodiments, provided compounds and compositions are administered to the brain parenchyma. In certain embodiments, provided compounds and compositions are delivered to an animal/subject by intrathecal administration, or intracerebroventricular administration. Broad distribution of provided compounds and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, gels, syrups, suspensions, powders, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

In some embodiments, cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in a mixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with provided compounds or compositions. For example, chemotherapeutic agents or other anti-proliferative agents may be combined with provided compounds or compositions to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Methods of Making

In some embodiments, the present disclosure provides methods of manufacturing a provided N-acylethanolamide derivative compound, which method comprising steps of:
- conjugating, or otherwise linking, a N-acylethanolamide compound (e.g., a parent N-acylethanolamide compound) to a linker moiety;
- conjugating, or otherwise linking, a moiety to the linker-N-acylethanolamide moiety.

In some embodiments, the present disclosure provides methods of manufacturing a provided N-acylethanolamide derivative compound, which method comprising steps of:
- conjugating, or otherwise linking, a moiety to a linker moiety:
- conjugating, or otherwise linking, a N-acylethanolamide compound (e.g., a parent N-acylethanolamide compound) to the linker moiety.

In some embodiments, a moiety is selected from the group consisting of phosphate, butyric acid, glycerol, succinate, caprylic acid, gluconoic acid, eicosapentaeonoic acid, linoleic acid, succinate, and sucrose moieties, and combinations thereof.

In some embodiments, the present disclosure provides method of manufacturing a provided pharmaceutical composition, which method comprising a step of:
- formulating a provided N-acylethanolamide derivative compound together with at least one pharmaceutically acceptable carrier.

EXEMPLIFICATION

Example 1: (N-Palmiloylethanolamide) PEA in Pain

This Example provides a meta-analysis of 12 PEA pain studies and shows, among other things, that 67% of treated patients versus 21% of placebo achieved a VAS scores <=3. See FIGS. 2A-2F, and the table below, quoted from Guida et al., Dolor 2010; Paladini et al., Pain Physician Jounrla, February 2016; and Cobellis et al., Eur. J. Ob. and Gyn, July 2010.

|  | Etiopathogenesis | | | |
| --- | --- | --- | --- | --- |
|  | Degenerative | Neuropathic | Mixed | Miscellaneous |
| Patient number | 1174 (79.1%) | 170 (11.5%) | 82 (5.5%) | 58 (3.9%) |

Example 2: Treating IBS-D

The present Example illustrates treatment of IBS-D according to some embodiments of the present disclosure.

The present disclosure provides a strong rationale to combine butyric acid (BA) and PEA into a single dual active prodrug that will be metabolized in the gut to the two active constituents that will alleviate pain and improve fecal consistency In some embodiments, IBS-D treatment success comprises simultaneous improvement in (i) daily worst abdominal pain score by >30% as compared to baseline weekly average; and (ii) reduction in the Bristol Stool Scale (BSS) to <5 on at least 50% of the days within a 12-week time interval. Alternatively or additionally, treatment success may be or comprise improvement in daily worst abdominal pain in the absence of a concurrent bowel movement. See FIGS. 2G-2Q, and the tables below, quoted from Scarpellini et al., Digestive Liver Disease, 2007; Banasiewicz et al., Colorectal Disease. 2012; Scheppach et al., Gastroenterology, 1992; Capasso et al., Br. J. of Pharm, 2014; and Borrelli et al., Br. J. of Pharm, 2015. For example, short-chain fatly acid irrigation has been shown to ameliorate inflammation in diversion colitis. In the study by Scheppach, et al., the effect of butyrate enemas was tested in 10 patients with distal ulcerative colitis who had been unresponsive to or intolerant of standard therapy for 8 weeks. They were treated for 2 weeks with sodium butyrate (100 mmol/L) and 2 weeks with placebo in random order (single-blind trial). Before and after treatment, clinical symptoms were noted and the degree of inflammation was graded endoscopically and histologically. Rectal proliferation was assessed by autoradiography. After butyrate irrigation, stool frequency (n/day) decreased from 4.7±0.5 to 2.1±0.4 (P<0.01) and discharge of blood ceased in 9 of 10 patients. The endoscopic score fell from 6.5±0.4 to 3.8±0.8 (P<0.01). The histological degree of inflammation decreased from 2.4±0.3 to 1.5±0.3 (P<0.02). Overall crypt proliferation was unchanged, but the upper crypt-labeling index fell from 0.086±0.019 to 0.032±0.003 (P<0.03). On placebo, all of these parameters were unchanged. These data support the view that butyrate deficiency may play a role in the pathogenesis of distal ulcerative colitis and that butyrate irrigation ameliorates this condition. Scheppach, et al. "Effect of Butyrate Enemas on the Colonic Mucosa in Distal Ulcerative Colitis," Gastroenterology, 103:51-56 (1992).

Demographic Characteristics of Patients Included

|  | IBS-CP (n = 28) | IBS-CP (n = 22) | P |
| --- | --- | --- | --- |
| Gender (male/female) | 8/20 | 8/14 | ns |
| Age [mean (SD)] | 32 ± 5 | 34 ± 5 | ns |
| BMI (body mass index) | 21 ± 8 | 22 ± 7 | ns |

Effects of Therapy on Severity of Symptoms

|  | IBS-DP | | IBS-CP | |
| --- | --- | --- | --- | --- |
| Symptom | at inclusion | after treatment | at inclusion | after treatment |
| Abdominal pain | 9.5 (1)[a] | 6.1 (1)* | 9.2 (1) | 9.4 (1) |
| Meteorism | 9.6 (1) | 4.7 (1)* | 9.3 (1) | 9.0 (1) |
| Flatulence | 5.5 (1) | 4.0 (1)* | 5.1 (1) | 5.1 (1) |

[a]figure in brackets = SD
*Statistically significant (p < 0.005).

|  | MSB (N = 34) | | Placebo (N = 32) | | |
| --- | --- | --- | --- | --- | --- |
|  | Number of patients | Percentage of study group | Number of patients | Percentage of study group | P |
| After 4 weeks of study Patients reporting subjective relief in IBS symptoms YES | 11 | 32 | 2 | 6.25 | <0.01 |
| After 12 weeks of study Patients reporting subjective relief in IBS symptoms YES | 18 | 53 | 5 | 15.6 | <0.01 |

|  | MSB (N = 34) | | | Placebo (N = 32) | | | |
| --- | --- | --- | --- | --- | --- | --- | --- |
|  | Mean | SD | Median | Mean | SD | Median | P |
| Baseline | | | | | | | |
| Spontaneous abdominal pain | 0.53 | 0.51 | 1 | 0.53 | 0.51 | 1 | ns |
| Postprandial abdominal pain | 0.44 | 0.50 | 0 | 0.44 | 0.50 | 0 | ns |
| Abdominal pain during defaecation | 0.35 | 0.49 | 0 | 0.56 | 0.50 | 1 | ns |
| Urge sensation after the defaection | 0.26 | 0.45 | 0 | 0.38 | 0.49 | 0 | ns |
| Mucus in stool | 0.15 | 0.36 | 0 | 0.13 | 0.34 | 0 | ns |
| Changes in stool consistency | 0.44 | 0.50 | 0 | 0.38 | 0.49 | 0 | ns |
| Constipation | 0.38 | 0.49 | 0 | 0.47 | 0.51 | 0 | ns |
| After 4 weeks of study | | | | | | | |
| Spontaneous abdominal pain | 0.382 | 0.493 | 0 | 0.50 | 0.51 | 0.5 | ns |
| Postprandial abdominal pain | 0.324 | 0.475 | 0 | 0.56 | 0.50 | 1 | 0.0968 |
| Abdominal pain during defaecation | 0.176 | 0.387 | 0 | 0.59 | 0.50 | 1 | 0.0032 |
| Urge sensation after defaecation | 0.235 | 0.431 | 0 | 0.41 | 0.50 | 0 | ns |
| Mucus in stool | 0.088 | 0.288 | 0 | 0.13 | 0.34 | 0 | ns |
| Changes in stool consistency | 0.382 | 0.493 | 0 | 0.41 | 0.50 | 0 | ns |
| Constipation | 0.353 | 0.485 |  | 0.47 | 0.51 | 0 | ns |
| After 12 weeks of study | | | | | | | |
| Spontaneous abdominal pain | 0.21 | 0.41 | 0 | 0.50 | 0.51 | 0.5 | 0.0132 |
| Postprandial abdominal pain | 0.21 | 0.41 | 0 | 0.56 | 0.50 | 1 | 0.0031 |
| Abdominal pain during defaecation | 0.15 | 0.36 | 0 | 0.59 | 0.50 | 1 | 0.0002 |
| Urge sensation after defaecation | 0.15 | 0.36 | 0 | 0.44 | 0.50 | 0 | 0.0100 |
| Mucus in stool | 0.12 | 0.33 | 0 | 0.22 | 0.42 | 0 | ns |
| Changes in stool consistency | 0.18 | 0.39 | 0 | 0.41 | 0.50 | 0 | 0.0417 |
| Constipation | 0.24 | 0.43 | 0 | 0.47 | 0.51 | 0 | 0.0493 | ns, not significant

There were no adverse effects in either arm o the study. Values are shown on proportions.

Example 3: Method Development, Plasma Stability, and Method Qualification for PEA and Prodrugs The present example describes an LC-MS/MS method to determine PEA levels in Sprague-Dawley rat plasma and to determine the stability of compounds(s) provided here.

An LC-MS/MS method for the determination of PEA and PEA-prodrug I-9 in Sprague-Dawley rat plasma was developed. Each test article was infused onto an ABSciex API4000 mass spectrometer to determine optimized parameters. Next, liquid chromatography conditions were developed to obtain suitable specificity and to resolve the PEA and PEA-prodrug peaks.

The stability of the PEA-prodrug I-9 was assessed in Sprague-Dawley rat plasma containing sodium heparin as the anticoagulant, and in acidified rat plasma containing citric acid and formic acid. The acidified plasma was prepared by collecting Sprague-Dawley rat plasma over sodium heparin and adding 100 µL of 0.5 M citric acid per mL of blood. The blood was centrifuged to generate plasma, and then 100 µL of 10% formic acid was added per mL of plasma.

PEA-prodrug was added to each matrix to a final concentration of 1 µg/mL. Triplicate aliquots (50 µL) were immediately collected and added to 150 µL of acetonitrile containing internal standard. The remaining plasma aliquots were split equally. One aliquot was allowed to stand at room temperature while the second was placed on ice. After ninety minutes, triplicate aliquots of each sample were collected and added to acetonitrile. The samples were centrifuged at 13000 rpm for ten minutes, and the resulting supernatant was analyzed using the developed LC-MS/MS method. The peak area response ratios (PARR) of the analyte and internal standard from the incubated samples were then compared to the initial sample to determine the percent PEA prodrug remaining.

Following their initial analysis, the supernatant samples from the acidified plasma experiment were reinjected after storage on the autosampler (~8° C.) for two hours in order to assess the stability of the PEA-prodrug in the post-extract matrix.

Results of the stability experiments are shown in Tables 3a, 3b, and 3c.

TABLE 3a

Plasma Stability for PEA-Prodrug I-9 in Sprague Dawley Rat Plasma

| | Peak Area Response Ratio | Average Peak Area Response Ratio | % Remaining |
| --- | --- | --- | --- |
| Intial (t = 0) | 2.78E-01<br>2.75E-01<br>2.81E-01 | 2.78E-01 | ND |
| 90 minutes, ice | 2.02E-01<br>2.03E-01<br>2.07E-01 | 2.04E-01 | 73.4% |
| 90 minutes, RT | 8.38E-04<br>4.97E-04<br>3.60E-04 | 5.65E-04 | 0.203% |

ND: not determined

TABLE 3b

Plasma Stability for PEA-Prodrug I-9 in Acidified Sprague-Daley Rat Plasma

| | Peak Area Response Ratio | Average Peak Area Response Ratio | % Remaining |
| --- | --- | --- | --- |
| Intial (t = 0) | 1.31E+00<br>1.40E+00<br>1.31E+00 | 1.34E+00 | ND |
| 90 minutes, ice | 1.39E+00<br>1.46E+00<br>1.44E+00 | 1.43E+00 | 107% |

TABLE 3b-continued

Plasma Stability for PEA-Prodrug I-9
in Acidified Sprague-Daley Rat Plasma

| | Peak Area Response Ratio | Average Peak Area Response Ratio | % Remaining |
|---|---|---|---|
| 90 minutes, RT | 1.23E+00<br>1.30E+00<br>1.33E+00 | 1.29E+00 | 96.0% |

ND: not determined

TABLE 3c

Post-Extract Stability for PEA-Prodrug I-9 Extracted
from Acidified Sprague-Dawley Rat Plasma

| | Peak Area Response Ratio | Average Peak Area Response Ratio | % Remaining |
|---|---|---|---|
| Intial (t = 0) | 1.31E+00<br>1.40E+00<br>1.31E+00 | 1.34E+00 | ND |
| 2 Hour Storage on Autosampler (~8° C.) | 1.38E+00<br>1.46E+00<br>1.42E+00 | 1.42E+00 | 106% |

ND: not determined

Results of the stability of in each matrix are presented in Tables 3a and 3b. The prodrug was found to be unstable when stored at room temperature (0.203% remaining) and on ice (73.4% remaining) for 90 minutes. When the PEA-prodrug I-9 was fortified into rat plasma acidified with citric and formic acids, it was found to be stable at room temperature (107% remaining) and on ice (96.0% remaining) for 90 minutes. In addition, it was demonstrated that the PEA-prodrug I-9 was stable in the post-extract matrix following storage on the autosampler (~8° C.) for two hours (Table 3c).

The specificity, accuracy, and precision of the method for PEA and the PEA-prodrug I-9 in acidified Sprague-Dawley rat plasma were evaluated via a single-day pre-study qualification. A single eight-point standard curve and quality control samples at three levels with six replicates each were extracted and analyzed for PEA or PEA-prodrug I-9. In addition, a dilution QC of a high concentration sample was prepared to demonstrate parallelism of the method. Standards and quality control samples were prepared from independently prepared stock solutions of each test compound. Results of the plasma qualification are presented in Tables 3d and 3e.

TABLE 3d

Method Qualification Results for PEA in Acidified Rat Plasma

| Nominal Conc. (ng/mL) | 12.5 | 100 | 500 | 10000 |
|---|---|---|---|---|
| Measured Concentration (ng/mL) | 10.3 | 105 | 509 | 10800 |
| | 12.6 | 107 | 477 | 11800 |
| | 11.6 | 110 | 451 | 10100 |
| | 12.2 | 96.8 | 496 | 13100 |
| | 11.0 | 101 | 441 | 10900 |
| | 14.0 | 109 | 448 | 10800 |
| Average (ng/mL) | 12.0 | 105 | 470 | 11250 |
| Accuracy (%) | 95.6 | 105 | 94.1 | 113 |
| CV (%) | 10.9 | 4.83 | 5.96 | 9.39 |
| n | 6 | 6 | 6 | 6 |

TABLE 3e

Method Qualification Results for PEA-Prodrug
I-9 in Acidified Rat Plasma

| Nominal Conc. (ng/mL) | 2.50 | 50.0 | 500 | 10000 |
|---|---|---|---|---|
| Measured Concentration (ng/mL) | 2.62 | 48.2 | 537 | 10600 |
| | 2.12 | 50.2 | 517 | 10700 |
| | 2.35 | 48.7 | 522 | 10300 |
| | 2.39 | 49.5 | 536 | 10600 |
| | 2.23 | 51.2 | 567 | 10900 |
| | 2.15 | 48.2 | 547 | 10900 |
| Average (ng/mL) | 2.31 | 49.3 | 538 | 10667 |
| Accuracy (%) | 92.4 | 98.7 | 108 | 107 |
| CV (%) | 8.03 | 2.44 | 3.35 | 2.11 |
| n | 6 | 6 | 6 | 6 |

Plasma samples were extracted using the methods described below.

Analytical stock solutions (1.00 mg/mL of the free drug) were prepared in DMSO.

Sprague-Dawley rat blood was collected over sodium heparin and 0.5 M citric acid was added at a rate of 100 μL per mL of blood. Blood was centrifuged to collect plasma. A 100 μL aliquot of 10% formic acid was added to each mL of plasma.

Standards were prepared in acidified rat plasma. Standards and quality control samples were prepared from independently prepared stock solutions of each analyte. Working solutions were prepared in 50:50 acetonitrile: water and then added to plasma to make calibration standards to final concentrations of 1000, 500, 100, 50, 10, 5, 1, and 0.5 ng/mL and quality control samples to final concentrations of 2.50, 50.0, and 500 ng/mL for PEA-prodrug I-9. For PEA, calibration standards were prepared to final concentrations of 1000, 500, 100, 50, 25, 10, 5, and 2.5 ng/mL and quality control samples to final concentrations of 12.50, 100, and 500 ng/mL. A high concentration dilution QC was prepared at 10,000 ng/mL for each analyte. This sample was diluted 20-fold into the range of the assay prior to extraction.

Plasma samples were extracted via acetonitrile precipitation. Standards and QCs: Add 10 μL of appropriate working solution to 50 μL of blank matrix in a 96-well plate. Blanks: Add 10 μL 50:50 acetonitrile: water to 50 μL of blank matrix in a 96-well plate. Samples: Add 10 μL 50:50 acetonitrile: water to 50 μL of study sample in a 96-well plate. Cap and mix. Add 150 μL of acetonitrile (containing 100 ng/mL ritonavir as an internal standard) to each well. Cap and mix at 1000 rpm for five minutes. Centrifuge the plate at 3000 rpm for ten minutes. Transfer a 150 μL aliquot of the resulting supernatant into a clean 96-well plate. Cap for analysis. HPLC and Mass spectrometry conditions are described in Table 3f. Chromatograms are exemplified in FIGS. 3A, 3B, 3C, 3D, 3E, 3F, 3G, and 3H.

TABLE 3f

HPLC and Mass Spectrometry Conditions

HPLC Conditions

| | |
|---|---|
| Instrument: | Waters ACQUITY UPLC |
| Column: | Waters HSS $C_{18}$, 30 × 2.1 mm id, 1.8 μm |
| Mobile Phase Buffer: | 40 mM ammonium formate, pH 3.5 |
| Aqueous Reservoir (A): | 10% buffer, 90% water |
| Organic Reservoir (B): | 10% buffer, 90% acetonitrile |
| Gradient Program | |

TABLE 3-1

HPLC Gradient Program

| Time (mm) | Grad. Curve | % A | % B |
|---|---|---|---|
| 0.0 | 6 | 20 | 80 |
| 0.75 | 6 | 0 | 100 |
| 0.80 | 6 | 50 | 50 |
| 1.0 | 6 | 50 | 50 |

| | |
|---|---|
| Flow Rate: | 800 μL/min |
| Injection Volume: | 5 μL |
| Run Time: | 1.0 min |
| Column Temperature: | 40° C. |
| Sample Temperature: | 8° C. |
| Strong Autosampler Wash: | 1:1:1 (v:v:v) water:methanol:isopropanol with 0.2% formic acid |
| Weak Autosampler Wash: | 4 mM ammonium formate |
| Mass Spectrometer Conditions | |
| Instrument: | PE Sciex API4000 |
| Interface: | Electrospray ("Turbo Ion Spray" |
| Mode: | Multiple reactions monitoring (MRM) |
| Gases: | Cur 30, CAD 10, GS1 50, GS2 50 |
| Source Temperature: | 500° C. |
| Voltages and Ions Monitored* | |

TABLE 3-2

Mass Spectrometer Voltages and Ions Monitored

| Analyte | Polarity | Precursor Ion | Product Ion | IS | DP | EP | CE | CXP |
|---|---|---|---|---|---|---|---|---|
| PEA | Positive | 300.2 | 62.1 | 5500 | 106 | 10 | 30 | 6 |
| PEA-prodrug | Positive | 474.5 | 282.4 | 5500 | 80 | 10 | 24 | 7 |
| Ritonavir (Internal STD) | Positive | 721.3 | 296.1 | 5500 | 65 | 10 | 25 | 18 |

IS: Ion Spray Voltage;
DP: Declustering Potential;
EP: Entrance Potential;
CE: Collision Energy;
CXP: Collision Cell Exit Potential;
*All settings are in volts

Example 4: PEA Stability in Human and Rat Liver Microsomes, Human and Rat Intestinal S9 Fractions, and Simulated Gastric Fluid The present Example describes PEA stability observed in Human and Rat Liver Microsomes, Human and Rat Intestinal S9 Fractions, and Simulated Gastric fluid.

Liver Microsomal Stability

Mixed-gender human liver microsomes (Lot #1210347) and male Sprague-Dawley rat liver microsomes (Lot #1310030) were provided. The reaction mixture, minus cofactors, was prepared as described below. The test article was added into the reaction mixture at a final concentration of 1 μM. The control compound, testosterone, was run simultaneously with the test article in a separate reaction. An aliquot of the reaction mixture (without cofactor) was equilibrated in a shaking water bath at 37° C. for 3 minutes. The reaction was initiated by the addition of cofactor, and the mixture was incubated in a shaking water bath at 37° C. Aliquots (100 μL) were withdrawn at 0, 10, 20, 30, and 60 minutes. All samples were immediately combined with 400 μL of ice-cold 50/50 acetonitrile/H$_2$O containing 0.1% formic acid and internal standard to terminate the reaction. The samples were then mixed and centrifuged to precipitate proteins. Calibration standards were prepared in matched matrix. All samples and standards were assayed by LC-MS/MS using electrospray ionization for both the dosed prodrug I-9 and the expected drug (PEA). Analytical conditions are outlined in Appendix 4-1. The test article concentration at each time point was compared to the test article concentration at time 0 to determine the percent remaining at each time point. Half-lives were calculated using GraphPad software, fitting to a single-phase exponential decay equation. Results are shown in Tables 4a and 4b.

Reaction Composition
Liver Microsomes 0.5 mg/mL
NADPH (cofactor) 1 mM
UDPGA (cofactor) 1 mM
Potassium Phosphate, pH 7.4 100 mM
Magnesium Chloride 5 mM
Test Article 1 μM

TABLE 4a

PEA stability observed in Human and Rat Liver Microsomes

| Test Article | Species | 0 min | 10 min | 20 min | 30 min | 60 min | Half-Life$^a$ (min) | CL$_{int}^b$ (mL/min/mg protein) |
|---|---|---|---|---|---|---|---|---|
| | | | % Remaining of Initial (n = 1) | | | | | |
| I-9 | Human | 100 | 1.2 | <1.0 | <1.0 | <1.0 | <10(1.6) | >0.139 (0.888) |
| | Rat | 100 | 4.0 | <1.0 | <1.0 | <1.0 | <10(2.2) | >0.139 (0.642) |

$^a$When the calculated half-life is longer than the duration of the experiment, the half-life is expressed as > the longest incubation time. Similarly, if the calculated half-life is less than the shortest time point, the half-life is expressed as < that time point and the calculated half-life is also listed in parentheses.

$^b$Intrinsic clearance (CL$_{int}$) was calculated based on CL$_{int}$ = k/P, where k is the elimination rate constant and P is the protein concentration in the incubation.

| Control Compound | Species | Half-life (min) | Cl$_{int}$ (ml/min/mg protein) | Acceptable Range (t$_{1/2}$, min) |
|---|---|---|---|---|
| Testosterone | Human | 17 | 0.0792 | ≤41 |
|  | Rat | 1.4 | 1.03 | ≤15 |

Reaction Composition

Intestinal S9 Fraction 1.0 mg/mL

NADPH (cofactor) 1 mM

UDPGA (cofactor) 1 mM

PAPS (cofactor) 1 mM

GSH (cofactor) 1 mM

Potassium Phosphate, pH 7.4 100 mM

Magnesium Chloride 5 mM

Test Article 1 μM

TABLE 4c

PEA stability observed in Human and Rat Intestinal S9 Fraction

| Test Article | Species | % Remaining of Initial (n = 1) | | | | | Half-Life$^a$ (min) | CL$_{int}^b$ (mL/min/mg protein) |
|---|---|---|---|---|---|---|---|---|
| | | 0 min | 10 min | 20 min | 30 min | 60 min | | |
| I-9 | Human | 100 | 59 | 16 | 47 | <1.0 | <10(9.2) | >0.0693 (0.0753) |
|  | Rat | 100 | 119 | 88 | 75 | 49 | 55 | 0.125 |

$^a$When the calculated half-life is longer than the duration of the experiment, the half-life is expressed as > the longest incubation time. Similarly, if the calculated half-life is less than the shortest time point, the half-life is expressed as < that time point and the calculated half-life is also listed in parentheses.
$^b$Intrinsic clearance (CLint) was calculated based on CL$_{int}$ = k/P, where k is the elimination rate constant and P is the protein concentration in the incubation.

TABLE 4b

Measured concentrations of Prodrug and Drug

| Dosed Test Article | Species | Analyte | Concentration (μM) | | | | |
|---|---|---|---|---|---|---|---|
| | | | 0 min | 10 min | 20 min | 30 min | 60 min |
| I-9 | Human | I-9 | 0.18 | 0.0021 | 0 | 0 | 0 |
|  |  | PEA | 0.83 | 0.60 | 0.51 | 0.41 | 0.20 |
|  | Rat | I-9 | 0.21 | 0.0085 | 0 | 0 | 0 |
|  |  | PEA | 0.35 | 0.16 | 0.076 | 0.027 | 0.0030 |

Intestinal S9 Fraction Stability

Mixed-gender human intestinal S9 fraction (Lot #0710351) and male Sprague-Dawley rat intestinal S9 fraction (Lot #0510116) were provided. The reaction mixture, minus cofactors, was prepared as described below. The test article was added into the reaction mixture at a final concentration of 1 μM. The control compounds, testosterone and 7-hydroxycoumarin, were run simultaneously with the test article in a separate reaction. An aliquot of the reaction mixture (without cofactor cocktail) was equilibrated in a shaking water bath at 37° C. for 3 minutes. The reaction was initiated by the addition of cofactor cocktail, and the mixture was incubated in a shaking water bath at 37° C. Aliquots (100 μL) were withdrawn at 0, 10, 20, 30, and 60 minutes. All samples were immediately combined with 400 uL of icecold 50/50 acetonitrile/H$_2$O containing 0.1% formic acid and internal standard to terminate the reaction. The samples were then mixed and centrifuged to precipitate proteins. Calibration standards were prepared in matched matrix. All samples and standards were assayed by LC-MS/MS using electrospray ionization for both the dosed prodrug I-9 and the expected drug (PEA). Analytical conditions are outlined in Appendix 4-1. The test article concentration at each time point was compared to the test article concentration at time 0 to determine the percent remaining at each time point. Half-lives were calculated using GraphPad software, fitting to single-phase exponential decay equation. Results are shown in Tables 4c and 4d.

| Control Compound | Species | Half-life (mm) | Cl$_{int}$ (ml/min/mg protein) |
|---|---|---|---|
| Testosterone | Human | 26 | 0.0269 |
|  | Rat | 116 | 0.00597 |
| 7-HC | Human | 7.3 | 0.943 |
|  | Rat | 34 | 0.0201 |

TABLE 4d

Measured Concentrations of Prodrug and Drug

| Dosed Test Article | Species | Analyte | Concentration (μM) | | | | |
|---|---|---|---|---|---|---|---|
| | | | 0 min | 10 min | 20 min | 30 min | 60 min |
| I-9 | Human | I-9 | 0.61 | 0.36 | 0.099 | 0.029 | 0.0043 |
|  |  | PEA | 0.21 | 0.50 | 0.69 | 0.65 | 0.66 |
|  | Rat | I-9 | 0.77 | 0.91 | 0.68 | 0.58 | 0.38 |
|  |  | PEA | 0.031 | 0.088 | 0.13 | 0.16 | 0.24 |

Simulated Gastric Fluid Stability

Studies were carried out in simulated gastric fluid (SGF). SGF was prepared by dissolving 2.0 g of NaCl and 3.2 g of purified pepsin (derived from porcine stomach mucosa) in 7 mL of 10 N HCl and sufficient water to make 1000 mL. The pH was adjusted to pH 1.2. Control experiments were also run without the addition of pepsin to the matrix. The test article was added into the SGF at 37° C. at a final concentration of 2 μM, and incubated in a shaking water bath at 37° C. Individual tubes were dosed for each time point (0, 15, 30, 60, and 120 minutes). At the appropriate time, 500 μL of ice-cold acetonitrile containing 0.1% formic acid and internal standard was added to a single tube. The starting time of each tube was staggered so that all timepoints finished simultaneously. The samples were then mixed and centrifuged. Calibration standards were prepared in matched matrix. All samples and standards were assayed by LCMS/

MS using electrospray ionization for both the dosed prodrug I-9 and the expected drug (PEA). Analytical conditions are outlined in Appendix 4-1. The test article concentration at each time point was compared to the test article concentration at time 0 to determine the percent remaining at each time point. Half-lives were calculated using GraphPad software, fitting to a single-phase exponential decay equation. Results are shown in Tables 4e and 4f.

TABLE 4e

PEA stability observed in Simulated Gastric Fluid

| Test Article | Species | % Remaining of Initial (n = 1) | | | | | Half-Life[a] (min) |
|---|---|---|---|---|---|---|---|
| | | 0 min | 15 min | 30 min | 60 min | 120 min | |
| I-9 | SGF w/pepsin | 100 | 95 | 80 | 92 | 86 | >120 |
| | SGF w/o pepsin | 100 | 93 | 84 | 72 | 71 | >120 |

[a]When the calculated half-life is longer than the duration of the experiment, the half-life is expressed as > the longest incubation time.

TABLE 4f

Measured Concentrations of Prodrug and Drug

| Dosed Test Article | Matrix | Analyte | Concentration (µM) | | | | |
|---|---|---|---|---|---|---|---|
| | | | 0 min | 10 min | 20 min | 30 min | 60 min |
| I-9 | Human | I-9 | 1.52 | 1.45 | 1.21 | 1.40 | 1.31 |
| | | PEA | 0.0046 | 0.0078 | 0.0083 | 0.011 | 0.017 |
| | Rat | I-9 | 2.07 | 1.93 | 1.74 | 1.49 | 1.48 |
| | | PEA | 0.0046 | 0.0066 | 0.0067 | 0.0079 | 0.017 |

Microsome/S9 Fraction Control

As a control for the liver microsome and intestinal S9 fraction studies, additional experiments were run in reaction mixture, with the exclusion of microsomal proteins. The reaction mixture was prepared as described below. The test article was added into the reaction mixture at a final concentration of 2 µM, and then incubated in a shaking water bath at 37° C. Individual tubes were dosed for each time point (0, 10, 20, 30, and 60 minutes). At the appropriate time, 500 µL of ice-cold acetonitrile containing 0.1% formic acid and internal standard was added to a single tube. The starting time of each tube was staggered so that all timepoints finished simultaneously. The samples were then mixed and centrifuged to precipitate proteins. Calibration standards were prepared in matched matrix. All samples and standards were assayed by LC-MS/MS using electrospray ionization for both the dosed prodrug I-9 and the expected drug (PEA). Analytical conditions are outlined in Appendix 4-1. The test article concentration at each timepoint was compared to the test article concentration at time 0 to determine the percent remaining at each time point. Half-lives were calculated using GraphPad software, fitting to a single-phase exponential decay equation. Results are shown in Table 4g and 4h.

Reaction Composition
NADPH (cofactor) 1 mM
UDPGA (cofactor) 1 mM
PAPS (cofactor) 1 mM
GSH (cofactor) 1 mM
Potassium Phosphate, pH 7.4 100 mM
Magnesium Chloride 5 mM
Test Article 2 µM TABLE 4g Microsome/S9 Fraction Control

| Test Article | Matrix | % Remaining of Initial (n = 1) | | | | | Half-Life[a] (min) |
|---|---|---|---|---|---|---|---|
| | | 0 min | 10 min | 20 min | 30 min | 60 min | |
| I-9 | Control | 100 | 66 | 77 | 67 | 62 | >60 |

[a]When the calculated half-life is longer than the duration of the experiment, the half-life is expressed as > the longest incubation time.

TABLE 4h

Measured Concentration of Prodrug and Drug

| Dosed Test Article | Species | Analyte | Concentration (µM) | | | | |
|---|---|---|---|---|---|---|---|
| | | | 0 min | 10 min | 20 min | 30 min | 60 min |
| I-9 | Control | I-9 | 2.24 | 1.47 | 1.72 | 1.5 | 1.38 |
| | | PEA | 0 | 0 | 0 | 0 | 0 |

Appendix 4-1

Liquid Chromatography

Column: Waters ACQUITY UPLC BEH C18 30×2.1 mm 1.7 µm

M.P. Buffer: 25 mM ammonium formate buffer, pH 3.5

Aqueous Reservoir (A): 90% water, 10% buffer

Organic Reservoir (B): 90% acetonitrile, 10% buffer

Flow Rate: 0.8 mL/minute

Gradient Program

TABLE 4-1

Liquid Chromatography Gradient Program

| Time (mm) | % A | % B |
|---|---|---|
| 0.00 | 20 | 80 |
| 0.75 | 0 | 100 |
| 0.80 | 50 | 50 |
| 1.00 | 50 | 50 |

Total Run Time: 1.0 minutes
Autosampler: 10 µL Injection Volume
Wash 1: water/methanol/2-propanol: 1/1/1; with 0.2% formic acid
Wash 2: 0.1% formic acid in water
Mass Spectrometer Instrument: PE SCIEX API 4000
Interface: Turbo Ionspray
Mode: Multiple reaction monitoring
Method: 1.0 minute duration
Settings:

TABLE 4-2

Mass Spectrometer Settings

| Test Article | Q1/Q3 | DP | EP | CE | CXP | IS | TEM | CAD | CUR | GS1 | GS2 |
|---|---|---|---|---|---|---|---|---|---|---|---|
| I-9 | +474.5/282.4 | 80 | 10 | 24 | 7 | 5500 | 500 | 7 | 30 | 50 | 50 |
| PEA | +300.2/62.1 | 106 | 10 | 30 | 6 | 5500 | 500 | 7 | 30 | 50 | 50 |
| Warfarin(IS) | +309.2/251.1 | 80 | 10 | 30 | 5 | 5500 | 500 | 7 | 30 | 50 | 50 |

Example 5: Determination of the Oral Bioavailability of PEA Following Administration of PEA and PEA-Prodrug in Male Sprague-Dawley Rats The present Example describes PEA levels observed in Sprague-Dawley rats samples after oral administration of compound(s) provided herein.

The oral bioavailability of palmitoylethanolamide (PEA) was evaluated following oral dosing of PEA, a marketed PEA product, Normast, or a PEA-prodrug I-9. PEA was also dosed intravenously at 1 mg/kg. Blood samples were collected up to 8 hours post-dose, and PEA and PEA-prodrug plasma concentrations were determined with a qualified LC-MS/MS method. Pharmacokinetic analysis was conducted by a non-compartmental model using Phoenix Win-Nonlin v.6.4 software.

Preparation of Dosing Formulations

PEA for IV and PO dosing (St. Louis, Mo.). PEA-prodrug (lot 261-SB-85) and Normast (Epitech Group, lot D106C6) were provided. The IV dosing solution was prepared fresh on the day of dosing at 0.5 mg/mL in a vehicle comprised of 10% solutol HS15, 10% n-methylpyrrolidone (NMP), 10% polyethylene glycol 400 (PEG400), and 70% water. For PO dosing, torpac capsules were loaded with an appropriate amount of PEA, PEA-prodrug, or normast powder. Doses in groups 2, 3, and 4 were prepared to deliver a similar amount of active drug per rat. The PEA-prodrug is 63.2% (w/w) active and Normast contains 72.7% active (w/w). The prodrug dose in group 5 was the maximum amount of powder that would fit into a single capsule.

The pharmacokinetics of PEA and the PEA-prodrug were evaluated in fasted male Sprague-Dawley rats. Rats were housed one per cage. Each rat was fitted with a jugular vein cannula (JVC) for blood collection. Rats intended for IV dosing were fitted with an additional JVC for dosing. Each study group was dosing in triplicate. Rats were fasted for a minimum of twelve hours prior to dosing. Food was returned at four hours post dosing. Animals had free access to water throughout the study.

Animal Dosing

Blood samples (~300 µL) were collected from the rats via a JVC and placed into chilled polypropylene tubes containing sodium heparin as an anticoagulant, and 30 µL of 0.5 M citric acid. Samples were maintained chilled throughout processing. Blood samples were centrifuged at 4° C. and 3,000 g for 5 minutes. Plasma (~150 µL) was then transferred to a chilled, labeled polypropylene tube containing 15 µL of 10% formic acid, placed on dry ice, and stored in a freezer maintained at −60° C. to −80° C. Blood sampling times are shown in Table 5a.

TABLE 5a

Study Design

| Dose Group | Test Article | No. of Animals | Dosing Route | Dose (mg/kg) | Dosing Formulation Conc. (mg/mL) | Dosing Volume (mL/kg) | Vehicle | Blood Sampling Time Points |
|---|---|---|---|---|---|---|---|---|
| 1 | PEA | 3 | IV | 1 | 0.5 | 2 | 10% Solutol HS15, 10% NMP, 10% PEG400, 70% water | Pre-dose, 5, 15, 30 min, 1, 2, 4 and 8 hours |
| 2 | PEA | 3 | PO | ~10 | NA | 1 capsule | Torpac capsule | Pre-dose, 15, 30 min, 1, 2, 4, and 8 hours |
| 3 | PEA-prodrug | 3 | PO | ~16* | NA | 1 capsule | Torpac capsule | |
| 4 | RLD (Normast) | 3 | PO | ~16* | NA | 1 capsule | Torpac capsule | |
| 5 | PEA-prodrug | 3 | PO | ~126* | NA | 1 capsule | Torpac capsule | |

NMP: n-methyl pyrrolidone;
*mg of actual pro-drug or drug product, not corrected for active content.

An LC-MS/MS method for the determination of PEA and PEA-prodrug is described above (see e.g., Example 3).

Pharmacokinetic parameters were calculated from the time course of the plasma concentration and are presented in Tables 3 through 9. Pharmacokinetic parameters were determined with Phoenix WinNonlin (v6.4) software using a non-compartmental model. Maximum plasma concentrations ($C_0$) after IV dosing were estimated by extrapolation of the first two time points back to t=0. Maximum plasma concentration ($C_{max}$) and the time to reach maximum plasma drug concentration ($T_{max}$) after oral dosing were observed from the data. Area under the time concentration curve (AUC) was calculated using the linear trapezoidal rule with calculation to the last quantifiable data point, and with extrapolation to infinity if applicable. At least three quantifiable data points were required to determine the AUC. Plasma half-life ($t_{1/2}$) was calculated from 0.693/slope of the terminal elimination phase. Mean residence time, MRT, was calculated by dividing the area under the moment curve (AUMC) by the AUC. Clearance (CL) was calculated from dose/AUC. Steady-state volume of distribution ($V_{ss}$) was calculated from CL*MRT (mean residence time). Bioavailability was determined by dividing the individual PO dose normalized $AUC_{last}$ values by the average IV $AUC_{last}$ value. Any samples below the limit of quantitation were treated as zero for pharmacokinetic data analysis.

The IV dosing solution was analyzed by LC-MS/MS. The measured dosing solution concentration is shown in Table 5b. The dosing solutions were diluted into rat plasma and analyzed in triplicate. All concentrations are expressed as mg/mL of the free base. Capsules were not analyzed. Nominal dosing concentrations were used in all calculations for these groups.

TABLE 5b

Measured Dosing Solution Concentrations (mg/mL).

| Test Article | Route of Administration | Vehicle | Nominal Dosing Conc. (mg/mL) | Measured Dosing Solution Conc. (mg/mL) | % of Nominal |
|---|---|---|---|---|---|
| PEA | IV | 10% Solutol HS15, 10% NMP, 10% PEG400, 70% water | 0.5 | 0.382 | 76.3 |

NMP: n-methyl pyrrolidone

Endogenous levels of PEA were found in all rats. Measured concentrations of PEA in plasma samples were corrected by subtracting the concentration of PEA measured in the pre-dose samples. These corrected values are reported in the tables below and were used to determine pharmacokinetic parameters. Any corrected values that were negative are reported as not determined (ND).

Following IV dosing at 1 mg/kg, PEA had an average half-life of 0.596±0.165 hours, an average clearance rate of 15.1±3.15 L/hr/kg and an average volume of distribution of 9.12±0.832 L/kg. Results are shown in Table 5c and FIGS. 4A and 4B.

TABLE 5c

Individual and Average Plasma Concentrations (ng/mL) and Pharmacokinetic Parameters for PEA after Intravenous Administration of PEA in Male Sprague-Dawley Rats at 1 mg/kg (Group 1).
Intravenous (1 mg/kg)

| | Rat # | | | | |
|---|---|---|---|---|---|
| Time (hr) | 907 | 908 | 909 | Mean | SD |
| 0 (pre-dose) | 10.3 | 6.96 | 6.50 | 7.92 | 2.07 |
| 0.083 | 122 | 137 | 174 | 144 | 26.6 |
| 0.25 | 47.2 | 49.6 | 47.7 | 48.2 | 1.29 |
| 0.50 | 27.5 | 30.7 | 35.5 | 31.2 | 4.02 |
| 1.0 | 9.60 | 7.94 | 16.1 | 11.2 | 4.31 |
| 2.0 | 5.20 | 5.64 | 9.90 | 6.91 | 2.60 |
| 4.0 | ND | ND | ND | ND | ND |
| 8.0 | ND | ND | ND | ND | ND |
| Animal Weight (kg) | 0.275 | 0.265 | 0.262 | 0.267 | 0.007 |
| Volume Dosed (mL) | 0.55 | 0.53 | 0.52 | 0.53 | 0.02 |
| $C_0$ (ng/mL)[1] | 196 | 227 | 331 | 251 | 70.9 |
| $t_{max}$ (hr)[1] | 0 | 0 | 0 | 0 | 0 |
| $t_{1/2}$ (hr) | 0.564 | 0.449 | 0.774 | 0.596 | 0.165 |
| $MRT_{last}$ (hr) | 0.399 | 0.374 | 0.435 | 0.402 | 0.0306 |
| CL (L/hr/kg) | 17.4 | 16.4 | 11.5 | 15.1 | 3.15 |
| $V_{ss}$ (L/kg) | 10.0 | 8.39 | 8.94 | 9.12 | 0.832 |
| $AUC_{last}$ (hr ng/mL) | 53.3 | 57.2 | 75.8 | 62.1 | 012.0 |
| $AUC_\infty$ (hr ng/mL) | 57.6 | 60.8 | 86.8 | 68.4 | 16.0 |

$C_0$: maximum plasma concentration extrapolated to t = 0;
$t_{max}$: time of maximum plasma concentration;
$t_{1/2}$: half-life, data points used for half-life determination are in bold;
$MRT_{last}$: mean residence time, calculated to the last observable time point;
CL: clearance;
$V_{ss}$: steady state volume of distribution;
$AUC_{last}$: area under the curve, calculated to the last observable time point;
$AUC_\infty$: area under the curve, extrapolated to infinity;
ND: not determined;
[1]Extrapolated to t = 0.

Following oral dosing of PEA in group 2 (average dose of 11.7 mg/kg), nearly all plasma samples were below the endogenous levels measured in the predose samples. The highest concentration measured in one animal was 5.30 ng/mL at 2 hours post dose. No AUCs or bioavailability values could be determined for this group. Results are shown in Table 5d.

TABLE 5d

Individual and Average Plasma Concentrations (ng/mL) and Pharmacokinetic Parameters for PEA After Oral Administration of PEA in Male Sprague-Dawley Rats at ~10 mg/kg (Group 2).
Oral (~10 mg/kg, PEA after PEA Dose)

| | Rat # | | | | |
|---|---|---|---|---|---|
| Time (hr) | 910 | 911 | 912 | Mean | SD |
| 0 (pre-dose) | 8.04 | 8.30 | 6.00 | 7.45 | 1.26 |
| 0.25 | ND | ND | ND | ND | ND |
| 0.50 | ND | ND | ND | ND | ND |
| 1.0 | ND | ND | 2.34 | ND | ND |
| 2.0 | ND | ND | 5.30 | ND | ND |
| 4.0 | ND | ND | ND | ND | ND |
| 8.0 | ND | ND | ND | ND | ND |
| Animal Weight (kg) | 0.250 | 0.260 | 0.262 | 0.257 | 0.006 |
| Volume Dosed (mg) | 3.0 | 3.0 | 3.0 | 3.0 | 0.0 |
| Dose (mg/kg) | 12.0 | 11.5 | 11.5 | 11.7 | 0.295 |
| $C_{max}$ (ng/mL) | ND | ND | 5.30 | ND | ND |
| $t_{max}$ (hr) | N | ND | 2.0 | ND | ND |
| $t_{1/2}$ (hr) | ND | ND | ND | ND | ND |
| $MRT_{last}$ (hr) | ND | ND | ND | ND | ND |
| $AUC_{last}$ (hr ng/mL) | ND | ND | ND | ND | ND |
| $AUC_\infty$ (hr ng/mL) | ND | ND | ND | ND | ND |
| Dose-normalized Values | | | | | |
| $AUC_{last}$ (hr kg ng/mL/mg) | ND | ND | ND | ND | ND |
| $AUC_\infty$ (hr kg ng/mL/mg) | ND | ND | ND | ND | ND |
| Bioavailability (%) | ND | ND | ND | ND | ND |

$C_0$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined.

Following oral dosing of the PEA-prodrug in group 3 (average dose of 11.7 mg/kg active equivalents), nearly all plasma samples were below the endogenous levels measured in the predose samples. The highest concentration measured in one animal (rat 914) was 0.630 ng/ml at 0.25 hours post dose. The bioavailability in this animal was 0.108%. Results are shown in Table 5e and 5f.

TABLE 5e

Individual and Average Plasma Concentrations (ng/mL) and Pharmacokinetic Parameters for PEA-Prodrug After Oral Administration of PEA-Prodrug in Male Sprague-Dawley Rats at ~16 mg/kg (Group 3). Oral (~16 mg/kg, PEA-prodrug after PEA-prodrug Dose)

| | Rat # | | | | |
|---|---|---|---|---|---|
| Time (hr) | 913 | 914 | 915 | Mean | SD |
| 0 (pre-dose) | BLOQ | BLOQ | BLOQ | ND | ND |
| 0.25 | BLOQ | BLOQ | BLOQ | ND | ND |
| 0.50 | BLOQ | BLOQ | BLOQ | ND | ND |
| 1.0 | BLOQ | BLOQ | BLOQ | ND | ND |
| 2.0 | BLOQ | BLOQ | BLOQ | ND | ND |
| 4.0 | BLOQ | BLOQ | BLOQ | ND | ND |
| 8.0 | BLOQ | BLOQ | BLOQ | ND | ND |
| Animal Weight (kg) | 0.251 | 0.266 | 0.259 | 0.259 | 0.008 |
| Amount Dosed (mg) | 4.8 | 4.8 | 4.8 | 4.8 | 0 |
| Dose (mg/kg) | 19.1 | 18.0 | 18.5 | 18.6 | 0.540 |
| $C_{max}$ (ng/mL) | ND | ND | ND | ND | ND |
| $t_{max}$ (hr) | ND | ND | ND | ND | ND |
| $t_{1/2}$ (hr) | ND | ND | ND | ND | ND |
| $MRT_{last}$ (hr) | ND | ND | ND | ND | ND |
| $AUC_{last}$ (hr ng/mL) | ND | ND | ND | ND | ND |
| $AUC_{\infty}$ (hr ng/mL) | ND | ND | ND | ND | ND |
| Dose-normalized Values | | | | | |
| $AUC_{last}$ (hr kg ng/mL/mg) | ND | ND | ND | ND | ND |
| $AUC_{\infty}$ (hr kg ng/mL/mg) | ND | ND | ND | ND | ND |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined.
BLOQ: below the limit of quantitation (0.5 ng/mL).

TABLE 5f

Individual and Average Plasma Concentrations (ng/mL) and Pharmacokinetic Parameters for PEA After Oral Administration of PEA Prodrug in Male Sprague-Dawley Rats at ~16 mg/kg (Group 3). Oral (~16 mg/kg, PEA after PEA-prodrug Dose)

| | Rat # | | | | |
|---|---|---|---|---|---|
| Time (hr) | 913 | 914 | 915 | Mean | SD |
| 0 (pre-dose) | 6.23 | 3.80 | 5.17 | 5.07 | 1.22 |
| 0.25 | ND | 0.630 | ND | ND | ND |
| 0.50 | ND | ND | ND | ND | ND |
| 1.0 | ND | 0.500 | ND | ND | ND |
| 2.0 | ND | ND | ND | ND | ND |
| 4.0 | ND | 0.230 | ND | ND | ND |
| 8.0 | ND | ND | ND | ND | ND |
| $C_{max}$ (ng/mL) | ND | 0.630 | ND | ND | ND |
| $t_{max}$ (hr) | ND | 0.25 | ND | ND | ND |
| $t_{1/2}$ (hr) | ND | ND[3] | ND | ND | ND |
| $MRT_{last}$ (hr) | ND | 1.75 | ND | ND | ND |
| $AUC_{last}$ (hr ng/mL) | ND | 0.763 | ND | ND | ND |
| $AUC_{\infty}$ (hr ng/mL) | ND | ND[3] | ND | ND | ND |

TABLE 5f-continued

Individual and Average Plasma Concentrations (ng/mL) and Pharmacokinetic Parameters for PEA After Oral Administration of PEA Prodrug in Male Sprague-Dawley Rats at ~16 mg/kg (Group 3). Oral (~16 mg/kg, PEA after PEA-prodrug Dose)

| | Rat # | | | | |
|---|---|---|---|---|---|
| Time (hr) | 913 | 914 | 915 | Mean | SD |
| Dose-normalized Values[1] | | | | | |
| $AUC_{last}$ (hr kg ng/mL/mg) | ND | 0.0669 | ND | ND | ND |
| $AUC_{\infty}$ (hr kg ng/mL/mg) | ND | ND[3] | ND | ND | ND |
| Bioavailability (%)[2] | ND | 0.108 | ND | ND | ND |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined;
[1]dose normalized values determined by dividing the parameter by the dose in mg/kg;
[2]bioavailability determined by dividing the individual dose normalized $AUC_{last}$ value by the average IV $AUC_{last}$ value;
[3]not determined due to lack of quantifiable data points trailing the $C_{max}$.

Following oral dosing of Normast in group 4 (average dose of 18.5 mg/kg), many plasma samples were below the endogenous levels measured in the predose samples. Average maximum plasma concentration (n=3) was 3.38±2.17 ng/mL. Average bioavailability (n=2) was 0.561%. Results are shown in Table 5g.

TABLE 5g

Individual and Average Plasma Concentrations (ng/mL) and Pharmacokinetic Parameters for PEA After Oral Administration of Normast in Male Sprague-Dawley Rats at ~16 mg/kg (Group 4). Oral (~16 mg/kg, PEA after Normast Dose)

| | Rat # | | | | |
|---|---|---|---|---|---|
| Time (hr) | 916 | 917 | 918 | Mean | SD |
| 0 (pre-dose) | 4.43 | 2.36 | 4.05 | 3.61 | 1.10 |
| 0.25 | ND | 0.200 | ND | ND | ND |
| 0.50 | ND | ND | 2.19 | ND | ND |
| 1.0 | 1.11 | ND | 5.83 | 3.47 | ND |
| 2.0 | ND | 0.960 | 2.10 | 1.53 | ND |
| 4.0 | 2.62 | 1.69 | ND | 2.16 | ND |
| 8.0 | ND | ND | ND | ND | ND |
| Animal Weight (kg) | 0.264 | 0.25 | 0.263 | 0.259 | 0.008 |
| Amount Dosed (mg) | 4.8 | 4.8 | 4.8 | 4.8 | 0.0 |
| Dose (mg/kg) | 18.2 | 19.2 | 18.3 | 18.5 | 0.569 |
| $C_{max}$ (ng/mL) | 2.62 | 1.69 | 5.83 | 3.38 | 2.17 |
| $t_{max}$ (hr) | 4.0 | 4.0 | 1.0 | 3.0 | 1.7 |
| $t_{1/2}$ (hr) | ND | ND[3] | ND[3] | ND | ND |
| $MRT_{last}$ (hr) | ND | 3.04 | 1.10 | 2.07 | ND |
| $AUC_{last}$ (hr ng/mL) | ND | 3.18 | 6.24 | 4.71 | ND |
| $AUC_{\infty}$ (hr ng/mL) | ND | ND[3] | ND[3] | ND | ND |
| Dose-normalized Values[1] | | | | | |
| $AUC_{last}$ (hr kg ng/mL/mg) | ND | 0.227 | 0.469 | 0.348 | ND |
| $AUC_{\infty}$ (hr kg ng/mL/mg) | ND | ND[3] | ND[3] | ND | ND |
| Bioavailability (%)[2] | ND | 0.366 | 0.756 | 0.561 | ND |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined;
[1]dose normalized values determined by dividing the parameter by the dose in mg/kg;
[2]bioavailability determined by dividing the individual dose normalized $AUC_{last}$ value by the average IV $AUC_{last}$ value;
[3]not determined due to lack of quantifiable data points trailing the $C_{max}$.

Following oral dosing of the PEA-prodrug in group 5 (average dose of 90.6 mg/kg active equivalents), many plasma samples were below the endogenous levels measured in the predose samples. Average maximum plasma concentration (n=3) was 2.52±0.829 ng/mL. Bioavailability determined in one animal was 0.124%. Results are shown in Table 5h and 5j.

TABLE 5h

Individual and Average Plasma Concentrations (ng/mL) and Pharmacokinetic Parameters for PEA-Prodrug After Oral Administration of PEA-Prodrug in Male Sprague-Dawley Rats at ~126 mg/kg (Group 5) Oral (~126 mg/kg, PEA-prodrug after PEA-prodrug Dose)

| Time (hr) | Rat # 919 | 920 | 921 | Mean | SD |
|---|---|---|---|---|---|
| 0 (pre-dose) | BLOQ | BLOQ | BLOQ | ND | ND |
| 0.25 | BLOQ | BLOQ | BLOQ | ND | ND |
| 0.50 | BLOQ | BLOQ | BLOQ | ND | ND |
| 1.0 | BLOQ | BLOQ | BLOQ | ND | ND |
| 2.0 | BLOQ | BLOQ | BLOQ | ND | ND |
| 4.0 | BLOQ | BLOQ | BLOQ | ND | ND |
| 8.0 | BLOQ | BLOQ | BLOQ | ND | ND |
| Animal Weight (kg) | 0.263 | 0.269 | 0.263 | 0.265 | 0.003 |
| Amount Dosed (mg) | 38 | 38 | 38 | 38 | 0 |
| Dose (mg/kg) | 144 | 141 | 144 | 143 | 1.86 |
| $C_{max}$ (ng/mL) | ND | ND | ND | ND | ND |
| $t_{max}$ (hr) | ND | ND | ND | ND | ND |
| $t_{1/2}$ (hr) | ND | ND | ND | ND | ND |
| $MRT_{last}$ (hr) | ND | ND | ND | ND | ND |
| $AUC_{last}$ (hr ng/mL) | ND | ND | ND | ND | ND |
| $AUC_\infty$ (hr ng/mL) | ND | ND | ND | ND | ND |
| Dose-normalized Values | | | | | |
| $AUC_{last}$ (hr kg ng/mL/mg) | ND | ND | ND | ND | ND |
| $AUC_\infty$ (hr kg ng/mL/mg) | ND | ND | ND | ND | ND |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (0.5 ng/mL).

TABLE 5j

Individual and Average Plasma Concentrations (ng/mL) and Pharmacokinetic Parameters for PEA After Oral Administration of PEA Prodrug in Male Sprague-Dawley Rats at ~126 mg/kg (Group 5). Oral (~126 mg/kg, PEA after PEA-prodrug Dose)

| Time (hr) | Rat # 919 | 920 | 921 | Mean | SD |
|---|---|---|---|---|---|
| 0 (pre-dose) | 1.82 | 1.57 | 2.40 | 1.93 | 0.426 |
| 0.25 | ND | ND | ND | ND | ND |
| 0.50 | ND | ND | ND | ND | ND |
| 1.0 | ND | 3.47 | ND | ND | ND |
| 2.0 | 0.690 | 1.84 | 0.450 | 0.993 | 0.743 |
| 4.0 | 1.93 | 1.49 | 2.17 | 1.86 | 0.345 |
| 8.0 | ND | ND | ND | ND | ND |
| $C_{max}$ (ng/mL) | 1.93 | 3.47 | 2.17 | 2.52 | 0.829 |
| $t_{max}$ (hr) | 4.0 | 1.0 | 4.0 | 3.0 | 1.7 |
| $t_{1/2}$ (hr) | ND | ND | ND | ND | ND |
| $MRT_{last}$ (hr) | ND | 2.06 | ND | ND | ND |
| $AUC_{last}$ (hr ng/mL) | ND | 6.85 | ND | ND | ND |
| $AUC_\infty$ (hr ng/mL) | ND | ND | ND | ND | ND |
| Dose-normalized Values[1] | | | | | |
| $AUC_{last}$ (hr kg ng/mL/mg) | ND | 0.0767 | ND | ND | ND |

TABLE 5j-continued

Individual and Average Plasma Concentrations (ng/mL) and Pharmacokinetic Parameters for PEA After Oral Administration of PEA Prodrug in Male Sprague-Dawley Rats at ~126 mg/kg (Group 5). Oral (~126 mg/kg, PEA after PEA-prodrug Dose)

| Time (hr) | Rat # 919 | 920 | 921 | Mean | SD |
|---|---|---|---|---|---|
| $AUC_\infty$ (hr kg ng/mL/mg) | ND | ND | ND | ND | ND |
| Bioavailability (%)[2] | ND | 0.124 | ND | ND | ND |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
[1]dose normalized values determined by dividing the parameter by the dose in mg/kg;
[2]bioavailability determined by dividing the individual dose normalized $AUC_{last}$ value by the average IV $AUC_{last}$ value;
[3]not determined due to lack of quantifiable data points trailing the $C_{max}$.

The PEA-prodrug was not detectable in any plasma samples. No pharmacokinetic parameters were determined for the PEA-prodrug.

Example 6: PEA Levels in Rabbit Plasma Samples

The present Example describes PEA levels observed in rabbit plasma samples after oral administration of compound (s) provided herein. Blood samples were taken approximately five hours after the morning dosing.

Instability of the PEA-prodrug I-9 in untreated plasma samples has been demonstrated previously (see, e.g., Examples 3-5). Plasma samples from the current study were not treated to prolong the post-collection stability of the prodrug. Instead, all samples were allowed to stand, thawed and untreated, at room temperature for four hours prior to extraction and analysis. This strategy allowed for any remaining prodrug in the sample to convert to PEA. All reported concentrations are total PEA in the sample.

Seventy-nine New Zealand White rabbit plasma samples were analyzed with a previously developed LC-MS/MS method for the detection of palmitoylethanolamide (PEA). A total of 79 plasma samples were received for analysis. All samples were received frozen in good condition. Samples were stored at −80° C. until analysis.

An LC-MS/MS method for the determination of PEA in plasma was used to quantify samples in this study. See, e.g., Example 3. Study samples were extracted using the methods described in Examples 3-5.

Results are shown in Tables 6a through 6d

TABLE 6a

Individual and Average PEA Concentrations (ng/ML) in Group 1 (Vehicle treated) Plasma Samples.

| Day | Animal ID R3145 | R2038 | R2769 | R3147 | R3154 | Average | SD |
|---|---|---|---|---|---|---|---|
| −5 | BLOQ | BLOQ | BLOQ | BLOQ | BLOQ | ND | ND |
| −3 | BLOQ | BLOQ | BLOQ | BLOQ | BLOQ | ND | ND |
| −3 | BLOQ | BLOQ | 2.77 | BLOQ | BLOQ | ND | ND |
| 7 | BLOQ | BLOQ | BLOQ | BLOQ | BLOQ | ND | ND |

BLOQ: below the limit of quantitation (2.5 ng/mL);
ND: not determined.

TABLE 6b

Individual and Average PEA Concentrations (ng/mL) in Group 2 (Normast treated at 32 mg/kg/day) Plasma Samples

| | Animal ID | | | | | | |
|---|---|---|---|---|---|---|---|
| Day | R2771 | R3152 | R3143 | R3138 | R3140 | Average | SD |
| −5 | BLOQ | BLOQ | BLOQ | BLOQ | BLOQ | ND | ND |
| −3 | BLOQ | BLOQ | BLOQ | BLOQ | BLOQ | ND | ND |
| −3 | BLOQ | 2.97 | 4.52 | BLOQ | BLOQ | 3.75 | ND |
| 7 | BLOQ | BLOQ | BLOQ | 5.29 | BLOQ | ND | ND |

BLOQ: below the limit of quantitation (2.5 ng/mL);
ND: not determined.

TABLE 6c

Individual and Average PEA Concentrations (ng/mL) in Group 3 (PEA-prodrug treated at 32 mg/kg/day) Plasma Samples

| | Animal ID | | | | | | |
|---|---|---|---|---|---|---|---|
| Day | R3156 | R2050 | R2833 | R2037 | R2770 | Average | SD |
| −5 | BLOQ | BLOQ | BLOQ | BLOQ | BLOQ | ND | ND |
| −3 | BLOQ | BLOQ | BLOQ | BLOQ | BLOQ | ND | ND |
| 3 | 6.64 | 8.70 | 10.8 | 4.14 | 6.63 | ND | ND |
| 7 | 5.62 | 6.09 | 4.47 | BLOQ | 5.57 | ND | ND |

BLOQ: below the limit of quantitation (2.5 ng/mL);
ND: not determined.

TABLE 6d

Individual and Average PEA Concentrations (ng/mL) in Group 4 (PEA-prodrug at 160 mg/kg/day) Plasma Samples

| | Animal ID | | | | | | |
|---|---|---|---|---|---|---|---|
| Day | R3141 | R3139 | R3153 | R3157 | R3151 | Average | SD |
| −5 | BLOQ | BLOQ | BLOQ | BLOQ | BLOQ | ND | ND |
| −3 | BLOQ | BLOQ | BLOQ | BLOQ | BLOQ | ND | ND |
| 3 | 27.6 | 20.0 | 27.6 | 24.7 | 17.0 | 23.4 | 4.73 |
| 7 | 7.10 | 8.12 | 9.93 | 14.5 | 14.3 | 10.8 | 3.45 |

BLOQ: below the limit of quantitation (2.5 ng/mL);
ND: not determined.

One sample from the vehicle group (Group 1) is reported with a measureable PEA concentration (2.77 ng/mL, Day 3, Animal R2769). This positive result is likely due to the fact that PEA is an endogenous fatty acid. Several samples from the vehicle group and predose time points were near the LLOQ of the method (2.5 ng/mL), but this was the only such sample that exceeded the LLOQ.

Example 7: Determination of Bioavailability of PEA Following Oral (PO) Administration of PEA-Prodrugs in Male Sprague-Dawley Rats The present Example describes oral bioavailability of PEA following administration of PEA prodrugs I-2, I-3, I-5, I-6, I-7, I-9, and I-11 in male Sprague-Dawley rats.

Oral bioavailability of palmitoylethanolamide (PEA) was evaluated following oral dosing of seven different PEA-prodrugs. Prodrugs were dosed orally to deliver a total PEA dose of 10 mg/kg. Following oral administration of the PEA-prodrugs, PEA plasma concentrations were determined with a qualified LC-MS/MS method.

Preparation of Dosing Formulations

Pro-drugs were dosed so that a total dose of 10 mg/kg of PEA was administered. Each prodrug was formulated in a vehicle comprised of 10% Solutol, 10% n-methyl pyrrolidone (NMP), 10% polyethylene glycol 400 (PEG400) and 70% water. Formulations were prepared fresh on the day of dosing.

Animal Dosing

Pharmacokinetics of PEA were evaluated in fasted male Sprague-Dawley rats. Rats were housed one per cage. Each rat was fitted with a jugular vein cannula (JVC) for blood collection. Each study group was dosing in triplicate. Rats were fasted for a minimum of twelve hours prior to dosing. Food was returned at four hours post dosing. Animals had free access to water throughout the study.

Blood samples (~300 μL) were collected from the rats via a JVC and placed into chilled polypropylene tubes containing sodium heparin as an anticoagulant, and 30 μL of 0.5 M citric acid. Samples were maintained chilled throughout processing. Blood samples were centrifuged at 4° C. and 3,000 g for 5 minutes. Plasma (~150 μL) was then transferred to a chilled, labeled polypropylene tube containing 15 μL of 10% folinic acid, placed on dry ice, and stored in a freezer maintained at −60° C. to −80° C. Blood sampling times are shown in Table 7a.

TABLE 7a

Study Design

| Dose Group | Test Article | Number of Animals | Dosing Route | Dose (mg/kg of pro-drug)* | Dosing Solution Conc. (mg/mL) | Dosing Volume (mL/kg) | Vehicle | Blood Sampling Time Points |
|---|---|---|---|---|---|---|---|---|
| 1 | I-9 | 3 | PO | 16 | 3 | 5.3 | 10% Solutol, 10% NMP, 10% PEG400, 70% water | Pre-dose, 5, 15, 30 min, 1, 2, 4, and 8 hours |
| 2 | I-6 | 3 | PO | 19 | 3 | 6.3 | | |
| 3 | I-5 | 3 | PO | 19.7 | 3 | 6.6 | | |
| 4 | I-3 | 3 | PO | 24.5 | 3 | 8.2 | | |
| 5 | I-2 | 3 | PO | 12.5 | 3 | 4.2 | | |
| 6 | I-11 | 3 | PO | 20.7 | 3 | 6.9 | | |
| 7 | I-7 | 3 | PO | 24.5 | 3 | 8.2 | | |

NMP: n-methyl pyrrolidone;
*dose of actual pro-drug, all deliver 10 mg/kg of PEA.

An LC-MS/MS method for determination of PEA and PEA-prodrug is described above (see e.g., Example 3).

Pharmacokinetic parameters were calculated from the time course of the plasma concentration and are presented in Tables 7b-7h and FIGS. 7A-7N. Maximum plasma concentration ($C_{max}$) and time to reach maximum plasma drug concentration ($T_{max}$) after oral dosing were observed from the data. Area under the time concentration curve (AUC) was calculated using the linear trapezoidal rule with calculation to the last quantifiable data point, and with extrapolation to infinity if applicable. At least three quantifiable data points were required to determine AUC. Plasma half-life ($t_{1/2}$) was calculated from 0.693/slope of the terminal elimination phase. Mean residence time, MRT, was calculated by dividing area under the moment curve (AUMC) by AUC. Bioavailability was determined by dividing individual dose-normalized PO $AUC_{last}$ values by the average IV $AUC_{last}$ value (IV data Example 5). Samples below the limit of quantitation were treated as zero for pharmacokinetic data analysis.

Results

No adverse reactions were observed following the oral administration of PEA pro-drugs in male Sprague-Dawley Rats in this study.

The dosing solutions were not analyzed by LC-MS/MS. Concentrations are expressed as mg/ml of the free base. Nominal dosing level was used in all calculations.

Individual and average plasma concentrations and pharmacokinetic parameters for PEA and are shown in Tables 7b-7h. Data are expressed as ng/mL of the free drug. Samples that were below the limit of quantitation were not used in the calculation of averages. Plasma concentration versus time data are plotted in FIGS. 7A-7N. Endogenous levels of PEA were found in all rats. Measured concentrations of PEA in plasma samples were corrected by subtracting the concentration of PEA measured in the pre-dose samples. These corrected values are reported in the tables below and were used to determine pharmacokinetic parameters. Any corrected values that were negative are reported as not determined (ND).

Following PO dosing of I-9 (Group 1), maximum plasma concentrations (average of 10.4±2.29 ng/mL) were observed at 1 hour post dosing. Average half-life was not determined due to a lack of quantifiable data points trailing the $C_{max}$. Average exposure based on the dose-normalized $AUC_{last}$ was 1.61±0.692 hr*kg*ng/'mL/mg. Based on the IV data from study Example 5, the average oral bioavailability for I-9 was 2.60±1.11%. Results are shown in Table 7b and FIGS. 5A and 5B.

TABLE 7b

Individual and Average Plasma Concentrations (ng/ml) and Pharmacokinetic Parameters for PEA after Oral Administration of I-9 at 16/mg/kg in Male Sprague-Dawley Rats.
Oral (16 mg/kg I-9 equals 10 mg/kg PEA)

| | Rat # | | | | |
|---|---|---|---|---|---|
| Time (hr) | 161 | 162 | 163 | Mean | SD |
| 0 (pre-dose) | 2.74 | 3.83 | 3.30 | 3.29 | 0.545 |
| 0.083 | 1.83 | ND | 0.170 | 1.00 | ND |
| 0.25 | 7.56 | 2.41 | 5.50 | 5.16 | 2.59 |
| 0.50 | 7.36 | 7.07 | 11.4 | 8.61 | 2.42 |
| 1.0 | 9.36 | 8.77 | 13.0 | 10.4 | 2.29 |
| 2.0 | 3.93 | 1.84 | 5.33 | 3.70 | 1.76 |
| 4.0 | ND | ND | 0.640 | ND | ND |
| 8.0 | ND | ND | ND | ND | ND |
| Animal Weight (g) | 0.259 | 0.258 | 0.260 | 0.259 | 0.001 |
| Amount Dosed (m:) | 1.37 | 1.37 | 1.38 | 1.37 | 0.01 |
| $C_{max}$ (ng/mL) | 9.36 | 8.77 | 13.0 | 10.4 | 2.29 |
| $t_{max}$ (hr) | 1.00 | 1.00 | 1.00 | 1.00 | 0.00 |
| $t_{1/2}$ (hr) | ND³ | ND³ | ND³ | ND | ND |
| $MRT_{last}$ (hr) | 0.933 | 0.913 | 1.28 | 1.04 | 0.208 |
| $AUC_{last}$ (hr ng/mL) | 13.7 | 10.8 | 24.0 | 16.1 | 6.92 |
| $AUC_{\infty}$ (hr ng/mL) | ND³ | ND³ | ND³ | ND | ND |

TABLE 7b-continued

Individual and Average Plasma Concentrations (ng/ml) and Pharmacokinetic Parameters for PEA after Oral Administration of I-9 at 16/mg/kg in Male Sprague-Dawley Rats.
Oral (16 mg/kg I-9 equals 10 mg/kg PEA)

| | Rat # | | | | |
|---|---|---|---|---|---|
| Time (hr) | 161 | 162 | 163 | Mean | SD |
| Dose-normalized Values[1] | | | | | |
| $AUC_{last}$ (hr kg ng/mL/mg) | 1.37 | 1.08 | 2.40 | 1.61 | 0.692 |
| $AUC_{\infty}$ (hr kg ng/mL/mg) | ND³ | ND³ | ND³ | ND | ND |
| Bioavailability (%)[2] | 2.20 | 1.74 | 3.86 | 2.60 | 1.11 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined;
BLOQ: below the limit of quantitation (0.5 ng/mL);
[1]Dose normalized by dividing the parameter by the nominal dose in mg/kg;
[2]Bioavailability determined by dividing the individual dose normalized oral $AUC_{last}$ values by the average IV $AUC_{last}$ value 62.1 hr*ng/mL from Example 5;
[3]not determined due to lack of quantifiable data points trailing the $C_{max}$.

Following PO dosing of I-6 (Group 2), maximum plasma concentrations (average of 11.7±5.39 ng/mL) were observed at fifteen minutes post dosing. Average halflife after PO dosing was 1.96±2.04 hours. Average exposure based on the dose-normalized $AUC_{last}$ was 1.40±0.737 hr*kg*ng/mL/mg. Based on the IV data from Example 5, average oral bioavailability for I-6 was 2.25±1.19%. Results are shown in Tables 7c and FIGS. 5C and 5D.

TABLE 7c

Individual and Average Plasma Concentrations (ng/mL) and Pharmacokinetic Parameters for PEA after Oral Administration of I-6 at 19 mg/kg in Male Sprague-Dawley Rats (Group 21.
Oral (19 mg/kg I-6 equals 10 mg/kg PEA)

| | Rat # | | | | |
|---|---|---|---|---|---|
| Time (hr) | 164 | 165 | 166 | Mean | SD |
| 0 (pre-dose) | 3.27 | 4.06 | 4.26 | 3.86 | 0.523 |
| 0.083 | 2.13 | 1.27 | ND | 1.70 | ND |
| 0.25 | 17.3 | 11.3 | 6.54 | 11.7 | 5.41 |
| 0.50 | 16.5 | 7.24 | 5.73 | 9.83 | 5.85 |
| 1.0 | 5.17 | 3.40 | 5.04 | 4.54 | 0.987 |
| 2.0 | 5.43 | 2.31 | 4.46 | 4.07 | 1.60 |
| 4.0 | 0.220 | ND | ND | ND | ND |
| 8.0 | BLOQ | ND | ND | ND | ND |
| Animal Weight (g) | 0.250 | 0.256 | 0.249 | 0.252 | 0.004 |
| Volume Dosed (mL) | 1.58 | 1.61 | 1.57 | 1.59 | 0.02 |
| $C_{max}$ (ng/mL) | 17.3 | 11.3 | 6.54 | 11.7 | 5.39 |
| $t_{max}$ (hr) | 0.250 | 0.250 | 0.250 | 0.250 | 0.000 |
| $t_{1/2}$ (hr) | 0.600 | 0.979 | 4.31 | 1.96 | 2.04 |
| $MRT_{last}$ (hr) | 1.12 | 0.749 | 0.942 | 0.936 | 0.184 |
| $AUC_{last}$ (hr ng/mL) | 22.4 | 9.10 | 10.3 | 14.0 | 7.37 |
| $AUC_{\infty}$ (hr ng/mL) | 22.6 | 12.4 | ND³ | 17.5 | ND |
| Dose-normalized Values[1] | | | | | |
| $AUC_{last}$ (hr kg ng/mL/mg) | 2.24 | 0.910 | 1.03 | 1.40 | 0.737 |
| $AUC_{\infty}$ (hr kg ng/mL/mg) | 2.26 | 1.24 | ND³ | 1.75 | ND |
| Bioavailability (%)[2] | 3.61 | 1.47 | 1.66 | 2.25 | 1.19 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;

TABLE 7c-continued

Individual and Average Plasma Concentrations (ng/mL) and
Pharmacokinetic Parameters for PEA after Oral Administration
of I-6 at 19 mg/kg in Male Sprague-Dawley Rats (Group 21.
Oral (19 mg/kg I-6 equals 10 mg/kg PEA)

| Time (hr) | Rat # | | | | |
| --- | --- | --- | --- | --- | --- |
| | 164 | 165 | 166 | Mean | SD |

ND: not determined;
BLOQ: below the limit of quantitation (2.5 ng/mL);
[1]Dose normalized by dividing the parameter by the nominal dose in mg/kg;
[2]Bioavailability determined by dividing the individual dose-normalized oral $AUC_{last}$ values by the average IV $AUC_{last}$ value 62.1 hr*ng/mL from Example 5;
[3]not determined because the $AUC_\infty$ was a greater than 25% extrapolation above the $AUC_{last}$.

Following PO dosing of I-5 (Group 3), maximum plasma concentrations (average of 12.2±5.52 ng/mL) were observed between fifteen and thirty minutes post dosing. Average half-life after PO dosing was 3.15 hours. Average exposure based on the dose normalized $AUC_{last}$ was 2.38±1.47 hr*kg*ng/mL/mg. Based on the IV data from Example 5, average oral bioavailability for I-5 was 3.84±2.37%. Results are shown in Table 7d and FIGS. 5E and 5F.

TABLE 7d

Individual and Average Plasma Concentrations (ng/mL) and
Pharmacokinetic Parameters for PEA after Oral Administration
of I-5 at 19.7 mg/kg in Male Sprague-Dawley Rats (Group 3).
Oral (19 7 mg/kg I-5 equals 10 mg/kg PEA

| Time (hr) | Rat # | | | | |
| --- | --- | --- | --- | --- | --- |
| | 167 | 168 | 169 | Mean | SD |
| 0 (pre-dose) | 3.66 | BLOQ | BLOQ | ND | ND |
| 0.083 | ND | 3.92 | 6.53 | 5.23 | ND |
| 0.25 | 3.13 | 14.1 | 16.5 | 11.2 | 7.13 |
| 0.50 | 5.97 | 10.0 | 9.04 | 8.34 | 2.11 |
| 1.0 | 3.35 | 3.77 | 3.33 | 3.48 | 0.248 |
| 2.0 | 3.43 | 4.84 | 8.43 | 5.57 | 2.58 |
| 4.0 | ND | 2.94 | 3.03 | 2.99 | ND |
| 8.0 | BLOQ | 1.46 | 1.69 | 1.58 | ND |
| Animal Weight (g) | 0.255 | 0.256 | 0.251 | 0.254 | 0.003 |
| Volume Dosed (mL) | 1.68 | 1.69 | 1.66 | 1.68 | 0.02 |
| $C_{max}$ (ng/mL) | 5.97 | 14.1 | 16.5 | 12.2 | 5.52 |
| $t_{max}$ (hr) | 0.500 | 0.250 | 0.250 | 0.333 | 0.144 |
| $t_{1/2}$ (hr) | ND[3] | 3.53 | 2.77 | 3.15 | ND |
| $MRT_{last}$ (hr) | 0.994 | 2.71 | 2.66 | 2.12 | 0.977 |
| $AUC_{last}$ (hr ng/mL) | 7.27 | 29.0 | 35.3 | 23.8 | 14.7 |
| $AUC_\infty$ (hr ng/mL) | ND[3] | 36.4 | 42.0 | 39.2 | ND |
| Dose-normalized Values[1] | | | | | |
| $AUC_{last}$ (hr kg ng/mL/mg) | 0.727 | 2.90 | 3.53 | 2.38 | 1.47 |
| $AUC_\infty$ (hr kg ng/mL/mg) | ND[3] | 3.64 | 4.20 | 3.92 | ND |
| Bioavailability (%)[2] | 1.17 | 4.67 | 5.68 | 3.84 | 2.37 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized values determined by dividing the parameter by the nominal dose in mg/kg;
[2]Bioavailability determined by dividing the individual dose-normalized oral $AUC_{last}$ values by the average IV $AUC_{last}$ value 62.1 hr*ng/mL from Example 5;
[3]not determined due to lack of quantifiable data points trailing the $C_{max}$.

Following PO dosing of I-3 (Group 4), maximum plasma concentrations (average of 9.83±3.69 ng/mL) were observed between thirty minutes and 2 hours post dosing. Average half-life was not determined; however, the half-life of one rat was 0.779 hours. Average exposure based on the dose-normalized $AUC_{last}$ was 1.99±0.338 hr*kg*ng/mL/mg. Based on the IV data from Example 5, average oral bioavailability for I-3 was 3.20±0.544%. Results are shown in Table 7e and FIGS. 5G and 5H.

TABLE 7e

Individual and Plasma Concentrations (ng/mL) and
Pharmacokinetic Parameters for PEA after Oral
Administration of I-3 at 24.5 mg/kg in Male
Sprague-Dawley Rats (Group 4).
Oral (24.5 mg/kg I-3 equals 10 mg/kg PEA)

| Time (hr) | Rat # | | | | |
| --- | --- | --- | --- | --- | --- |
| | 170 | 171 | 172 | Mean | SD |
| 0 (pre-dose) | 2.81 | 3.07 | 2.22 | 2.70 | 0.436 |
| 0.083 | 0.640 | 1.02 | ND | 0.830 | ND |
| 0.25 | 3.90 | 7.43 | 6.20 | 5.84 | 1.79 |
| 0.50 | 3.52 | 10.4 | 13.2 | 9.04 | 4.98 |
| 1.0 | 3.45 | 8.03 | 12.9 | 8.12 | 4.72 |
| 2.0 | 5.89 | 6.61 | 10.7 | 7.73 | 2.58 |
| 4.0 | 2.27 | 0.640 | ND | 1.46 | ND |
| 8.0 | ND | BLOQ | ND | ND | ND |
| Animal Weight (g) | 0.254 | 0.259 | 0.260 | 0.258 | 0.003 |
| Volume Dosed (mL) | 2.08 | 2.12 | 2.13 | 2.11 | 0.03 |
| $C_{max}$ (ng/mL) | 5.89 | 10.4 | 13.2 | 9.83 | 3.69 |
| $t_{max}$ (hr) | 2.00 | 0.500 | 0.500 | 1.00 | 0.866 |
| $t_{1/2}$ (hr) | ND[3] | 0.779 | ND[3] | ND | ND |
| $MRT_{last}$ (hr) | 1.89 | 1.38 | 1.08 | 1.45 | 0.405 |
| $AUC_{last}$ (hr ng/mL) | 16.0 | 22.3 | 21.4 | 19.9 | 3.38 |
| $AUC_\infty$ (hr ng/mL) | ND[3] | 23.0 | ND[3] | ND | ND |
| Dose-normalized Values[1] | | | | | |
| $AUC_{last}$ (hr kg ng/mL/mg) | 1.60 | 2.23 | 2.14 | 1.99 | 0.338 |
| $AUC_\infty$ (hr kg ng/mL/mg) | ND[3] | 2.30 | ND[3] | ND | ND |
| Bioavailability (%)[2] | 2.58 | 3.59 | 3.44 | 3.20 | 0.544 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by the nominal dose in mg/kg;
[2]Bioavailability determined by dividing the individual dose-normalized oral $AUC_{last}$ values by the average IV $AUC_{last}$ value 62.1 hr*ng/mL from Example 5;
[3]not determined due to lack of quantifiable data points trailing the $C_{max}$.

Following PO dosing of I-2 (Group 5), maximum plasma concentrations (average of 8.83±1.23 ng/mL) were observed between fifteen and thirty minutes post dosing. Average half-life was not determined; however, the half-life of one rat was 0.797 hours. Average exposure based on the dose-normalized $AUC_{last}$ was 0.854±0.164 hr*kg*ng/mL/mg. Based on the IV data from Example 5, average oral bioavailability for I-2 was 1.38±0.264%. Results are shown in Table 7f and FIGS. 5I and 5J.

TABLE 7f

Individual and Average Plasma Concentrations (ng/mL) and
Pharmacokinetic Parameters for PEA after Oral Administration
of I-2 at 12.5 mg/kg in Male Sprague-Dawley Rats (Group 5).
Oral (12.5 mg/kg I-2 equals 10 mg/kg PEA)

| Time (hr) | Rat # | | | | |
| --- | --- | --- | --- | --- | --- |
| | 173 | 174 | 175 | Mean | SD |
| 0 (pre-dose) | 2.67 | 1.41 | 1.73 | 1.94 | 0.655 |
| 0.083 | 0.220 | 3.07 | 2.02 | 1.77 | 1.44 |
| 0.25 | 7.73 | 10.2 | 8.47 | 8.80 | 1.26 |
| 0.50 | 7.83 | 8.69 | 8.37 | 8.30 | 0.435 |
| 1.0 | 3.80 | 3.89 | 1.22 | 2.97 | 1.52 |
| 2.0 | 3.11 | 2.19 | 1.11 | 2.14 | 1.00 |

TABLE 7f-continued

Individual and Average Plasma Concentrations (ng/mL) and Pharmacokinetic Parameters for PEA after Oral Administration of I-2 at 12.5 mg/kg in Male Sprague-Dawley Rats (Group 5). Oral (12.5 mg/kg I-2 equals 10 mg/kg PEA)

| Time (hr) | Rat # 173 | 174 | 175 | Mean | SD |
|---|---|---|---|---|---|
| 4.0 | ND | BLOQ | BLOQ | ND | ND |
| 8.0 | ND | ND | BLOQ | ND | ND |
| Animal Weight (g) | 0.247 | 0.246 | 0.259 | 0.251 | 0.007 |
| Volume Dosed (mL) | 1.04 | 1.04 | 1.09 | 1.06 | 0.03 |
| $C_{max}$ (ng/mL) | 7.83 | 10.2 | 8.47 | 8.83 | 1.23 |
| $t_{max}$ (hr) | 0.500 | 0.250 | 0.250 | 0.333 | 0.144 |
| $t_{1/2}$ (hr) | $ND^3$ | 0.797 | $ND^5$ | ND | ND |
| $MRT_{last}$ (hr) | 0.862 | 0.742 | 0.606 | 0.736 | 0.128 |
| $AUC_{last}$ (hr ng/mL) | 9.09 | 9.84 | 6.70 | 8.54 | 1.64 |
| $AUC_{\infty}$ (hr ng/mL) | $ND^3$ | $ND^4$ | $ND^5$ | ND | ND |
| Dose-normalized Values[1] | | | | | |
| $AUC_{last}$ (hr kg ng/mL/mg) | 0.909 | 0.984 | 0.670 | 0.854 | 0.164 |
| $AUC_{\infty}$ (hr kg ng/mL/mg) | $ND^3$ | $ND^4$ | $ND^5$ | ND | ND |
| Bioavailability (%)[2] | 1.46 | 1.58 | 1.08 | 1.38 | 0.264 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined;
BLOQ: below the limit of quantitation (2.5 ng/mL);
[1]Dose-normalized by dividing the parameter by the nominal dose in mg/kg;
[2]Bioavailability determined by dividing the individual dose-normalized oral $AUC_{last}$ values by the average IV $AUC_{last}$ value 62.1 hr*ng/mL from Example 5;
[3]not determined due to lack of quantifiable data points trailing the $C_{max}$;
[4]not determined because the $AUC_{\infty}$ was a greater than 25% extrapolation above the $AUC_{last}$;
[5]not determined because the line defining the terminal elimination phase had an $r^2$ <0.85.

Following PO dosing of I-11 (Group 6), maximum plasma concentrations (average of 15.5±3.01 ng/mL) were observed between fifteen minutes and thirty minutes post dosing. Average half-life was not determined; however, the half-life of one rat was 0.685 hours. Average exposure based on the dose-normalized $AUC_{last}$ was 2.79±0.808 hr*kg*ng/mL/mg. Based on the IV data from Example 5, average oral bioavailability for I-11 was 4.49±1.30%. Results are shown in Table 7g and FIGS. 5K and 5L.

TABLE 7g

Individual Average Plasma Concentrations (ng/mL) and Pharmacokinetic Parameters for PEA after Oral Administration of I-11 at 20.7 mg/kg in Male Sprague-Dawley Rats (Group 6). Oral (20.7 mg/kg I-11 equals 10 mg/kg PEA)

| Time (hr) | Rat # 176 | 177 | 178 | Mean | SD |
|---|---|---|---|---|---|
| 0 (pre-dose) | 1.62 | 1.89 | BLOQ | 1.76 | ND |
| 0.083 | 3.26 | 1.41 | 4.33 | 3.00 | 1.48 |
| 0.25 | 12.7 | 11.1 | 15.2 | 13.0 | 2.06 |
| 0.50 | 12.6 | 18.7 | 14.9 | 15.4 | 3.10 |
| 1.0 | 6.74 | 10.6 | 13.1 | 10.2 | 3.20 |
| 2.0 | 4.414 | 5.73 | 5.80 | 5.22 | 0.939 |
| 4.0 | 0.340 | 0.510 | 0.828 | 0.559 | 0.248 |
| 8.0 | BLOQ | 0.520 | 2.62 | 1.57 | ND |
| Animal Weight (g) | 0.258 | 0.252 | 0.259 | 0.256 | 0.004 |
| Volume Dosed (mL) | 1.78 | 1.74 | 1.79 | 1.77 | 0.03 |
| $C_{max}$ (ng/mL) | 12.7 | 18.7 | 15.2 | 15.5 | 3.01 |
| $t_{max}$ (hr) | 0.250 | 0.500 | 0.250 | 0.333 | 0.144 |
| $t_{1/2}$ (hr) | 0.685 | $ND^3$ | $ND^3$ | ND | ND |
| $MRT_{last}$ (hr) | 1.13 | 1.52 | 2.33 | 1.66 | 0.612 |
| $AUC_{last}$ (hr ng/mL) | 19.5 | 28.7 | 35.5 | 27.9 | 8.08 |
| $AUC_{\infty}$ (hr ng/mL) | 19.8 | $ND^3$ | $ND^3$ | ND | ND |

TABLE 7g-continued

Individual Average Plasma Concentrations (ng/mL) and Pharmacokinetic Parameters for PEA after Oral Administration of I-11 at 20.7 mg/kg in Male Sprague-Dawley Rats (Group 6). Oral (20.7 mg/kg I-11 equals 10 mg/kg PEA)

| Time (hr) | Rat # 176 | 177 | 178 | Mean | SD |
|---|---|---|---|---|---|
| Dose-normalized Values[1] | | | | | |
| $AUC_{last}$ (hr kg ng/mL/mg) | 1.95 | 2.87 | 3.55 | 2.79 | 0.808 |
| $AUC_{\infty}$ (hr kg ng/mL/mg) | 1.98 | $ND^3$ | $ND^3$ | ND | ND |
| Bioavailability (%)[2] | 3.13 | 4.62 | 5.73 | 4.49 | 1.30 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined;
BLOQ: below the limit of quantitation (2.5 ng/mL);
[1]Dose-normalized by dividing the parameter by the nominal dose in mg/kg;
[2]Bioavailability determined by dividing the individual dose-normalized oral $AUC_{last}$ values by the average IV $AUC_{last}$ value 62.1 hr*ng/mL from Example 5;
[3]not determined because the line defining the terminal elimination phase had an $r^2$ < 0.85.

Following PO dosing of I-7 (Group 7), maximum plasma concentrations (average of 3.52 ng/mL) were observed between zero and fifteen minutes hour post dosing. Average half-life was not determined; however, the half-life of one rat was 0.736 hours. Average exposure based on the dose-normalized $AUC_{last}$ was 1.23 hr*kg*ng/mL/mg. Based on the IV data from Example 5, average oral bioavailability for I-7 was 1.98%. Results are shown in Table 7h and FIGS. 5M and 5N.

TABLE 7h

Individual and Average Plasma Concentrations (mg/mL) and Pharmacokinetic Parameters for PEA after Oral Administration of I-7 at 24.5 mg/kg in Male Sprague-Dawley Rats (Group 7). Oral (24.5 mg/kg I-7 equals 10 mg/kg PEA)

| Time (hr) | Rat # 179 | 180 | 181 | Mean | SD |
|---|---|---|---|---|---|
| 0 (pre-dose) | 3.15 | BLOQ | 3.85 | 3.50 | ND |
| 0.083 | ND | 2.88 | ND | ND | ND |
| 0.25 | 1.65 | 3.89 | ND | 2.77 | ND |
| 0.50 | 1.57 | 3.28 | ND | 2.43 | ND |
| 1.0 | 1.23 | 2.36 | ND | 1.80 | ND |
| 2.0 | 0.400 | 3.43 | ND | 1.92 | ND |
| 4.0 | ND | 2.46 | ND | ND | ND |
| 8.0 | ND | 2.85 | ND | ND | ND |
| Animal Weight (kg) | 0.254 | 0.249 | 0.263 | 0.255 | 0.007 |
| Volume Dosed (mL) | 2.08 | 2.04 | 2.16 | 2.09 | 0.06 |
| $C_{max}$ (ng/mL) | 3.15 | 3.89 | ND | 3.52 | ND |
| $t_{max}$ (hr) | 0.000 | 0.250 | ND | 0.125 | ND |
| $t_{1/2}$ (hr) | 0.736 | $ND^3$ | ND | ND | ND |
| $MRT_{last}$ (hr) | 0.779 | 3.93 | ND | 2.35 | ND |
| $AUC_{last}$ (hr ng/mL) | 2.19 | 22.4 | ND | 12.3 | ND |
| $AUC_{\infty}$ (hr ng/mL) | 2.61 | $ND^3$ | ND | ND | ND |
| Dose-normalized Values[1] | | | | | ND |
| $AUC_{last}$ (hr kg ng/mL/mg) | 0.219 | 2.24 | ND | 1.23 | ND |

TABLE 7h-continued

Individual and Average Plasma Concentrations (mg/mL) and Pharmacokinetic Parameters for PEA after Oral Administration of I-7 at 24.5 mg/kg in Male Sprague-Dawley Rats (Group 7). Oral (24.5 mg/kg I-7 equals 10 mg/kg PEA)

| Time (hr) | Rat # 179 | 180 | 181 | Mean | SD |
|---|---|---|---|---|---|
| $AUC_\infty$ (hr kg ng/mL/mg) | 0.261 | $ND^3$ | ND | ND | ND |
| Bioavailability (%)[2] | 0.352 | 3.61 | ND | 1.98 | ND |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by the nominal dose in mg/kg;
[2]Bioavailability determined by dividing the individual dose-normalized oral $AUC_{last}$ values by the average IV $AUC_{last}$ value 62.1 hr*ng/mL from Example 5;
[3]not determined because the line defining the terminal elimination phase had an $r^2$ <0.85.

Example 8: PEA Stability in Human, Rat Mouse and Dog Liver Microsomes, Human, Rat, Mouse and Dog Liver S9 Fraction, Human, Rat, Mouse and Dog Intestinal S9 Fraction, Human, Rat, Mouse and Dog Plasma, and Simulated Intestinal Fluid The present Example describes PEA stability observed in 1) human, rat, mouse, and dog liver microsomes; 2) human, rat, mouse, dog liver S9 fraction; human, rat, mouse, and dog intestinal S9 fraction; 4) human, rat, mouse, and dog plasma; and 5) simulated intestinal fluid containing various enzymes.

Liver Microsomal Stability

Mixed-gender human (Lot #1210347), male Sprague-Dawley rat (Lot #1310030), male CD-I mouse (Lot #1510043), and male Beagle dog (Lot #0810143) liver microsomes were provided. Reaction mixture, minus cofactors, was prepared as described below. Test article was added into the reaction mixture at a final concentration of 1 µM. Control compound, testosterone, was run simultaneously with the test article in a separate reaction. An aliquot of the reaction mixture (without cofactor) was equilibrated in a shaking water bath at 37° C. for 3 minutes. The reaction was initiated by the addition of cofactor, and the mixture was incubated in a shaking water bath at 37° C. Aliquots (100 µL) were withdrawn at 0, 10, 20, 30, and 60 minutes. Test article samples were immediately combined with 300 µL of ice-cold acetonitrile containing 1% formic acid. Control samples were immediately combined with 400 µL of ice-cold 50/50 acetonitrile (ACN)/dH₂O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodrug and expected drug (PEA). Analytical conditions are outlined in Appendix 8-1. Test article concentration at each time point was compared to test article concentration at time 0 to determine the percent remaining at each time point. Half-lives were calculated using GraphPad software, fitting to a single-phase exponential decay equation. Results are shown in Tables 8a and 8b.

Reaction Composition

| Liver Microsomes | 0.5 mg/mL |
|---|---|
| NADPH (cofactor) | 1 mM |
| Potassium Phosphate pH 7.4 | 100 mM |
| Magnesium Chloride | 5 mM |
| Test Article | 1 µL |

TABLE 8a

PEA stability observed in human, rat, mouse, and dog liver microsomes.

| Test Article | Species | % Remaining of Initial (n = 1) | | | | | Half-life[a] (min) | $CL_{int}^{b}$ (mL/min/mg protein) |
|---|---|---|---|---|---|---|---|---|
| | | 0 min | 10 min | 20 min | 30 min | 60 min | | |
| I-6 | Human | 100 | 82 | 58 | 66 | 68 | >60 (97) | <0.0231 (0.0143) |
| | Rat | 100 | 68 | 67 | 62 | 53 | >60 (63) | <0.0231 (0.0219) |
| | Mouse | 100 | 84 | 74 | 73 | 61 | >60 (84) | <0.0231 (0.0164) |
| | Dog | 100 | 103 | 100 | 91 | 77 | >60 | <0.0231 |
| I-2 | Human | 100 | 10 | 1.6 | <1.0 | <1.0 | 3.1 | 0.451 |
| | Rat | 100 | <1.0 | <1.0 | <1.0 | <1.0 | <1.0 | >1.38 |
| | Mouse | 100 | <1.0 | <1.0 | <1.0 | <1.0 | <1.0 | >1.38 |
| | Dog | 100 | 5.4 | <1.0 | <1.0 | <1.0 | 2.4 | 0.581 |
| I-9 | Human | 100 | <1.0 | <1.0 | <1.0 | <1.0 | <1.0 | >1.38 |
| | Rat | 100 | 1.9 | <1.0 | <1.0 | <1.0 | 1.8 | 0.791 |
| | Mouse | 100 | <1.0 | <1.0 | <1.0 | <1.0 | <1.0 | >1.38 |
| | Dog | 100 | <1.0 | <1.0 | <1.0 | <1.0 | <1.0 | >1.38 |
| I-3 | Human | 100 | 83 | 79 | 74 | 53 | >60 (69) | <0.0231 (0.0200) |
| | Rat | 100 | 81 | 88 | 72 | 68 | >60 (112) | <0.0231 (0.0124) |
| | Mouse | 100 | 82 | 83 | 60 | 70 | >60 (100) | <0.0231 (0.0138) |
| | Dog | 100 | 94 | 85 | 85 | 74 | >60 | <0.0231 |
| I-5 | Human | 100 | 90 | 82 | 79 | 62 | >60 (90) | <0.0231 (0.0154) |
| | Rat | 100 | 77 | 70 | 69 | 57 | >60 (75) | <0.0231 (0.0186) |
| | Mouse | 100 | 72 | 57 | 56 | 55 | 59 | 0.0236 |
| | Dog | 100 | 84 | 75 | 75 | 67 | >60 (104) | <0.0231 (0.0133) |

TABLE 8a-continued

PEA stability observed in human, rat, mouse, and dog liver microsomes.

| Test Article | Species | % Remaining of Initial (n = 1) | | | | | Half-life[a] (min) | $CL_{int}^{b}$ (mL/min/ mg protein) |
|---|---|---|---|---|---|---|---|---|
| | | 0 min | 10 min | 20 min | 30 min | 60 min | | |
| I-11 | Human | 100 | 3.1 | <1.0 | <1.0 | <1.0 | 2.0 | 0.696 |
| | Rat | 100 | 3.3 | <1.0 | <1.0 | <1.0 | 2.0 | 0.681 |
| | Mouse | 100 | 3.2 | <1.0 | <1.0 | <1.0 | 2.0 | 0.687 |
| | Dog | 100 | 3.6 | <1.0 | <1.0 | <1.0 | 2.1 | 0.665 |
| I-7 | Human | 100 | 4.6 | 1.3 | <1.0 | <1.0 | 2.3 | 0.612 |
| | Rat | 100 | 45 | 17 | 11 | 2.1 | 8.5 | 0.164 |
| | Mouse | 100 | 1.7 | 1.2 | <1.0 | <1.0 | 1.7 | 0.814 |
| | Dog | 100 | 1.6 | 1.4 | 1.3 | <1.0 | 1.7 | 0.823 |

[a]When the calculated half-life is longer than the duration of the experiment, the half-life is expressed as > the longest incubation time. Similarly, if the calculated half-life is less than the shortest time point, the half-life is expressed as < that time point and the calculated half-life is also listed in parentheses.
[b]Intrinsic clearance ($CL_{int}$) was calculated based on $CL_{int}$ = k/P, where k is the elimination rate constant and P is the protein concentration in the incubation.

| Control Compound | Species | Half-life (min) | $CL_{int}$ (ml/min/mg protein) | Acceptable Range ($t_{1/2}$, min) |
|---|---|---|---|---|
| Testosterone | Human | 27 | 0.0505 | ≤41 |
| | Rat | 1.8 | 0.760 | ≤15 |
| | Mouse | 4.9 | 0.285 | ≤15 |
| | Dog | 33 | 0.0415 | ≤40 |

TABLE 8b

Measured Concentrations of Drug.

| Dosed Test Article | Species | Analyte | Concentration (μM) | | | | |
|---|---|---|---|---|---|---|---|
| | | | 0 min | 10 min | 20 min | 30 min | 60 min |
| I-6 | Human | PEA | 0 | 0 | 0 | 0 | 0 |
| | Rat | | 0.14 | 0.064 | 0.017 | 0.0098 | 0.0012 |
| | Mouse | | 0.022 | 0.055 | 0.039 | 0.041 | 0.027 |
| | Dog | | 0.030 | 0.087 | 0.091 | 0.080 | 0.084 |
| I-2 | Human | | 0.15 | 0.23 | 0.19 | 0.15 | 0.071 |
| | Rat | | 0.40 | 0.11 | 0.028 | 0.0083 | 0 |
| | Mouse | | 0.48 | 0.34 | 0.19 | 0.12 | 0.023 |
| | Dog | | 0.23 | 0.48 | 0.38 | 0.29 | 0.17 |
| I-9 | Human | | 0.47 | 0.39 | 0.22 | 0.16 | 0.058 |
| | Rat | | 0.22 | 0.066 | 0.017 | 0 | 0 |
| | Mouse | | 0.52 | 0.29 | 0.18 | 0.11 | 0.036 |
| | Dog | | 0.39 | 0.42 | 0.32 | 0.26 | 0.18 |
| I-3 | Human | | 0 | 0.026 | 0.017 | 0.019 | 0.027 |
| | Rat | | 0.032 | 0.039 | 0.018 | 0.0067 | 0 |
| | Mouse | | 0.0079 | 0.025 | 0.025 | 0.042 | 0.025 |
| | Dog | | 0.00074 | 0.023 | 0.037 | 0.042 | 0.053 |
| I-5 | Human | | 0.014 | 0.020 | 0.025 | 0.022 | 0.016 |
| | Rat | | 0.034 | 0.033 | 0.015 | 0.015 | 0.0027 |
| | Mouse | | 0.048 | 0.080 | 0.052 | 0.048 | 0.024 |
| | Dog | | 0.025 | 0.081 | 0.090 | 0.087 | 0.063 |
| I-11 | Human | | 0.046 | 0.29 | 0.20 | 0.16 | 0.057 |
| | Rat | | 0.023 | 0.048 | 0.031 | 0.0086 | 0 |
| | Mouse | | 0.22 | 0.32 | 0.18 | 0.12 | 0.030 |
| | Dog | | 0.032 | 0.32 | 0.26 | 0.20 | 0.097 |
| I-7 | Human | | 0.22 | 0.39 | 0.28 | 0.22 | 0.080 |
| | Rat | | 0.054 | 0.14 | 0.087 | 0.045 | 0.0085 |
| | Mouse | | 0.28 | 0.29 | 0.18 | 0.11 | 0.034 |
| | Dog | | 0.59 | 0.50 | 0.47 | 0.38 | 0.20 |

Liver S9 Stability

Mixed gender human (Lot #1210091), male Sprague-Dawley rat (Lot #1410265), male CD-1 mouse (Lot #1510255), and male Beagle dog (Lot #1210278) liver S9 fraction were provided. Reaction mixture, minus cofactors, was prepared as described below. Test article was added into the reaction mixture at a final concentration of 1 μM. Control compounds, testosterone and 7-hydroxycoumarin (7-HC), were run simultaneously with the test article in a separate reaction. An aliquot of the reaction mixture (without cofactor cocktail) was equilibrated in a shaking water bath at 37° C. for 3 minutes. The reaction was initiated by the addition of cofactor cocktail (see below), and the mixture was then incubated in a shaking water bath at 37° C. Aliquots (100 μL) were withdrawn 0, 10, 20, 30 and 60 minutes. Test article samples were immediately combined with 300 μL of ice-cold acetonitrile containing 1% formic acid. Control samples were immediately combined with 400 μL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both the dosed prodrug and the expected drug (PEA). Analytical conditions are outlined in Appendix 8-1. Test article concentration at each time point was compared to the test article concentration at time 0 to determine the percent remaining at each time point. Half-lives were calculated using GraphPad software, fitting to a single-phase exponential decay equation. Results are shown in Tables 8c and 8d.

Reaction Composition

| Liver S9 Fraction | 1.0 mg/mL |
|---|---|
| NADPH (cofactor) | 1 mM |
| UDPGA (cofactor) | 1 mM |
| PAPS (cofactor) | 1 mM |
| GSH (cofactor) | 1 mM |
| Potassium Phosphate pH 7.4 | 100 mM |
| Magnesium Chloride | 5 mM |
| Test Article | 1 μM |

TABLE 8c

PEA stability observed in human, rat, mouse, and dog liver S9.

| Test Article | Species | \% Remaining of Initial (n = 1) | | | | | Half-life$^a$ (min) | $CL_{int}^b$ (mL/min/mg protein) |
|---|---|---|---|---|---|---|---|---|
| | | 0 min | 10 min | 20 min | 30 min | 60 min | | |
| I-6 | Human | 100 | 80 | 102 | 95 | 77 | >60 | <0.0116 |
| | Rat | 100 | 64 | 82 | 93 | 89 | >60 | <0.0116 |
| | Mouse | 100 | 87 | 87 | 99 | 75 | >60 | <0.0116 |
| | Dog | 100 | 101 | 106 | 102 | 110 | >60 | <0.0116 |
| I-2 | Human | 100 | 6.0 | 1.3 | <1.0 | <1.0 | 2.5 | 0.279 |
| | Rat | 100 | <1.0 | <1.0 | <1.0 | <1.0 | <1.0 | >0.691 |
| | Mouse | 100 | <1.0 | <1.0 | <1.0 | <1.0 | <1.0 | >0.691 |
| | Dog | 100 | 5.1 | 2.0 | <1.0 | <1.0 | 2.4 | 0.293 |
| I-9 | Human | 100 | <1.0 | <1.0 | <1.0 | <1.0 | <1.0 | >0.691 |
| | Rat | 100 | 13 | 2.1 | <1.0 | <1.0 | 3.4 | 0.207 |
| | Mouse | 100 | <1.0 | <1.0 | <1.0 | <1.0 | <1.0 | >0.691 |
| | Dog | 100 | <1.0 | <1.0 | <1.0 | <1.0 | <1.0 | >0.691 |
| I-3 | Human | 100 | 104 | 89 | 95 | 66 | >60 (104) | <0.0116 (0.00665) |
| | Rat | 100 | 66 | 69 | 71 | 52 | >60 (72) | <0.0116 (0.00967) |
| | Mouse | 100 | 82 | 61 | 78 | 61 | >60 (87) | <0.0116 (0.00797) |
| | Dog | 100 | 104 | 89 | 80 | 86 | >60 | <0.0116 |
| I-5 | Human | 100 | 80 | 81 | 70 | 72 | >60 | <0.0116 |
| | Rat | 100 | 98 | 82 | 75 | 67 | >60 (91) | <0.0116 (0.00764) |
| | Mouse | 100 | 66 | 50 | 59 | 50 | 53 | 0.0132 |
| | Dog | 100 | 72 | 79 | 74 | 85 | >60 | <0.0116 |
| I-11 | Human | 100 | 2.8 | <1.0 | <1.0 | <1.0 | 1.9 | 0.359 |
| | Rat | 100 | <1.0 | <1.0 | <1.0 | <1.0 | <1.0 | >0.691 |
| | Mouse | 100 | <1.0 | <1.0 | <1.0 | <1.0 | <1.0 | >0.691 |
| | Dog | 100 | 4.6 | 1.6 | <1.0 | <1.0 | 2.3 | 0.306 |
| I-7 | Human | 100 | 1.9 | <1.0 | <1.0 | <1.0 | 1.8 | 0.396 |
| | Rat | 100 | 43 | 22 | 11 | 1.4 | 8.8 | 0.0786 |
| | Mouse | 100 | 1.6 | <1.0 | <1.0 | <1.0 | 1.7 | 0.415 |
| | Dog | 100 | <1.0 | <1.0 | <1.0 | <1.0 | <1.0 | >0.691 |

$^a$When the calculated half-life is longer than the duration of the experiment, the half-life is expressed as > the longest incubation time. Similarly, if the calculated half-life is less than the shortest time point, the half-life is expressed as < that time point and the calculated half-life is also listed in parentheses.
$^b$Intrinsic clearance ($CL_{int}$) was calculated based on $CL_{int} = k/P$, where k is the elimination rate constant and P is the protein concentration in the incubation.

| Control Compound | Species | Half-life (min) | $CL_{int}$ (ml/min/mg protein) | Acceptable Range ($t_{1/2}$, min) |
|---|---|---|---|---|
| Testosterone | Human | 16 | 0.0447 | ≤34 |
| | Rat | 4.7 | 0.148 | ≤15 |
| | Mouse | 8.7 | 0.0800 | ≤37 |
| | Dog | 14 | 0.0485 | ≤42 |
| 7-hydroxycoumarin | Human | 10 | 0.0668 | ≤18 |
| | Rat | 4.6 | 0.152 | ≤15 |
| | Mouse | 4.1 | 0.171 | ≤15 |
| | Dog | 1.4 | 0.502 | ≤15 |

TABLE 8d

Measured Concentrations of Drug.

| Dosed Test Article | Species | Analyte | Concentration (µM) | | | | |
|---|---|---|---|---|---|---|---|
| | | | 0 min | 10 min | 20 min | 30 min | 60 min |
| I-6 | Human | PEA | 0.014 | 0.037 | 0.022 | 0.022 | 0.016 |
| | Rat | | 0.020 | 0.035 | 0.021 | 0.021 | 0.013 |
| | Mouse | | 0.030 | 0.041 | 0.033 | 0.031 | 0.015 |
| | Dog | | 0.016 | 0.044 | 0.041 | 0.049 | 0.037 |
| I-2 | Human | | 0.20 | 0.23 | 0.18 | 0.096 | 0.033 |
| | Rat | | 0.50 | 0.31 | 0.17 | 0.11 | 0.023 |
| | Mouse | | 0.51 | 0.26 | 0.19 | 0.12 | 0.022 |
| | Dog | | 0.23 | 0.38 | 0.35 | 0.21 | 0.11 |
| I-9 | Human | | 0.35 | 0.30 | 0.18 | 0.088 | 0.028 |
| | Rat | | 0.20 | 0.31 | 0.18 | 0.11 | 0.029 |
| | Mouse | | 0.52 | 0.23 | 0.13 | 0.077 | 0.022 |
| | Dog | | 0.32 | 0.29 | 0.21 | 0.18 | 0.078 |
| I-3 | Human | | 0.00032 | 0.0058 | 0.017 | 0.015 | 0.0096 |
| | Rat | | 0.015 | 0.045 | 0.033 | 0.017 | 0.013 |
| | Mouse | | 0.013 | 0.031 | 0.022 | 0.023 | 0.025 |
| | Dog | | 0.010 | 0.030 | 0.035 | 0.031 | 0.029 |
| I-5 | Human | | 0.024 | 0.036 | 0.036 | 0.025 | 0.018 |
| | Rat | | 0.020 | 0.025 | 0.037 | 0.026 | 0.013 |
| | Mouse | | 0.046 | 0.061 | 0.043 | 0.029 | 0.018 |
| | Dog | | 0.024 | 0.044 | 0.036 | 0.041 | 0.038 |
| I-11 | Human | | 0.047 | 0.25 | 0.18 | 0.14 | 0.033 |
| | Rat | | 0 | 0.14 | 0.091 | 0.059 | 0.0062 |
| | Mouse | | 0.18 | 0.24 | 0.13 | 0.083 | 0.015 |
| | Dog | | 0.069 | 0.51 | 0.34 | 0.29 | 0.13 |
| I-7 | Human | | 0.20 | 0.32 | 0.17 | 0.13 | 0.042 |
| | Rat | | 0.045 | 0.15 | 0.16 | 0.12 | 0.039 |
| | Mouse | | 0.22 | 0.22 | 0.14 | 0.084 | 0.020 |
| | Dog | | 0.21 | 0.16 | 0.15 | 0.12 | 0.049 |

Intestinal S9 Fraction Stability

Mixed-gender human (Lot #1410073), male Sprague-Dawley rat (Lot #1510303), male CD-1 mouse (Lot #1510194), and male Beagle dog (Lot #1510226) intestinal S9 fraction were provided. Reaction mixture, minus cofactors, was prepared as described below. Test article was added into the reaction mixture at a final concentration of 1 µM. Control compounds, testosterone and 7-hydroxycoumarin, were run simultaneously with the test article in a separate reaction. An aliquot of the reaction mixture (without cofactor cocktail) was equilibrated in a shaking water bath at 37° C. for 3 minutes. The reaction was initiated by the addition of cofactor cocktail, and the mixture was incubated in a shaking water bath at 37° C. Aliquots (100 μL) were withdrawn at 0, 10, 20, 30, and 60 minutes. Test article samples were immediately combined with 300 μL of ice-cold acetonitrile containing 1% formic acid. Control samples were immediately combined with 400 μL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both the dosed prodrug and the expected drug (PEA). Analytical conditions are outlined in Appendix 8-1. Test article concentration at each time point was compared to test article concentration at time 0 to determine the percent remaining at each time point. Half-lives were calculated using GraphPad software, fitting to a single-phase exponential decay equation. Results are shown in Tables 8e and 8f.

Reaction Composition

| | |
|---|---|
| Intestinal S9 Fraction | 1.0 mg/mL |
| NADPH (cofactor) | 1 mM |
| UDPGA (cofactor) | 1 mM |
| PAPS (cofactor) | 1 mM |
| GSH (cofactor) | 1 mM |
| Potassium Phosphate, pH 7.4 | 100 mM |
| Magnesium Chloride | 5 mM |
| Test Article | 1 μM |

TABLE 8e

PEA stability observed in human, rat, mouse, and dog intestinal S9 fraction.

| Test Article | Species | 0 min | 10 min | 20 min | 30 min | 60 min | Half-life$^a$ (min) | $CL_{int}^{b}$ (mL/min/mg protein) |
|---|---|---|---|---|---|---|---|---|
| I-6 | Human | 100 | 109 | 103 | 82 | 70 | >60 (102) | <0.0116 (0.00682) |
| | Rat | 100 | 78 | 92 | 79 | 59 | >60 (91) | <0.0116 (0.00765) |
| | Mouse | 100 | 62 | 69 | 61 | 53 | >60 (66) | <0.0116 (0.0105) |
| | Dog | 100 | 54 | 53 | 45 | 38 | 34 | 0.0201 |
| I-2 | Human | 100 | 73 | 41 | 28 | 9.6 | 17 | 0.0415 |
| | Rat | 100 | 35 | <1.0 | <1.0 | <1.0 | 5.6 | 0.123 |
| | Mouse | 100 | <1.0 | <1.0 | <1.0 | <1.0 | <1.0 | >0.691 |
| | Dog | 100 | 36 | 12 | 4.2 | <1.0 | 6.7 | 0.104 |
| I-9 | Human | 100 | 28 | 5.7 | 1.2 | <1.0 | 5.3 | 0.131 |
| | Rat | 100 | 45 | 26 | 15 | 3.6 | 10 | 0.0695 |
| | Mouse | 100 | 56 | 33 | 21 | 6.5 | 13 | 0.0537 |
| | Dog | 100 | <1.0 | <1.0 | <1.0 | <1.0 | <1.0 | >0.691 |
| I-3 | Human | 100 | 76 | 86 | 83 | 60 | >60 (98) | <0.0116 (0.00706) |
| | Rat | 100 | 53 | 46 | 42 | 31 | 26 | 0.0268 |
| | Mouse | 100 | 68 | 59 | 49 | 33 | 33 | 0.0211 |
| | Dog | 100 | 46 | 46 | 34 | 18 | 19 | 0.0368 |
| I-5 | Human | 100 | 82 | 49 | 38 | 45 | 32 | 0.0216 |
| | Rat | 100 | 57 | 48 | 46 | 44 | 38 | 0.0182 |
| | Mouse | 100 | 68 | 67 | 66 | 49 | 60 | 0.0116 |
| | Dog | 100 | 50 | 48 | 36 | 36 | 26 | 0.0263 |
| I-11 | Human | 100 | 4.1 | 1.2 | <1.0 | <1.0 | 2.2 | 0.318 |
| | Rat | 100 | 1.4 | <1.0 | <1.0 | <1.0 | 1.6 | 0.425 |
| | Mouse | 100 | <1.0 | <1.0 | <1.0 | <1.0 | <1.0 | >0.691 |
| | Dog | 100 | 1.8 | <1.0 | <1.0 | <1.0 | 1.7 | 0.404 |
| I-7 | Human | 100 | 46 | 22 | 9.8 | 3.8 | 9.0 | 0.0772 |
| | Rat | 100 | 60 | 37 | 31 | 13 | 16 | 0.0431 |
| | Mouse | 100 | 59 | 35 | 27 | 5.7 | 14 | 0.0485 |
| | Dog | 100 | 1.1 | <1.0 | <1.0 | <1.0 | 1.5 | 0.452 |

$^a$When the calculated half-life is longer than the duration of the experiment, the half-life is expressed as > the longest incubation time. Similarly, if the calculated half-life is less than the shortest time point, the half-life is expressed as < that time point and the calculated half-life is also listed in parentheses.

$^b$Intrinsic clearance ($CL_{int}$) was calculated based on $CL_{int} = k/P$, where k is the elimination rate constant and P is the protein concentration in the incubation.

| Control Compound | Species | Half-life (min) | $CL_{int}$ (ml/min/mg protein) |
|---|---|---|---|
| Testosterone | Human | 7.8 | 0.0889 |
| | Rat | >60 (106) | <0.0116 (0.00652) |
| | Mouse | >60 (75) | <0.0116 (0.00919) |
| | Dog | >60 (96) | <0.0116 (0.00722) |
| 7-hydroxycoumarin | Human | 13 | 0.0545 |
| | Rat | 27 | 0.0257 |
| | Mouse | 5.0 | 0.139 |
| | Dog | 8.6 | 0.0803 |

TABLE 8f

Measured Concentrations of Drug.

| Dosed Test Article | Species | Analyte | Concentration (μM) | | | | |
|---|---|---|---|---|---|---|---|
| | | | 0 min | 10 min | 20 min | 30 min | 60 min |
| I-6 | Human | PEA | 0.0089 | 0.023 | 0.043 | 0.056 | 0.072 |
| | Rat | | 0.069 | 0.088 | 0.094 | 0.10 | 0.11 |
| | Mouse | | 0.12 | 0.14 | 0.17 | 0.15 | 0.17 |
| | Dog | | 0.26 | 0.42 | 0.38 | 0.35 | 0.36 |
| I-2 | Human | | 0.011 | 0.057 | 0.075 | 0.067 | 0.11 |
| | Rat | | 0.69 | 0.63 | 0.60 | 0.52 | 0.52 |
| | Mouse | | 0.52 | 0.50 | 0.52 | 0.45 | 0.45 |
| | Dog | | 0.11 | 0.40 | 0.50 | 0.53 | 0.54 |
| I-9 | Human | | 0.048 | 0.18 | 0.23 | 0.22 | 0.18 |
| | Rat | | 0.034 | 0.22 | 0.31 | 0.36 | 0.39 |
| | Mouse | | 0.0024 | 0.12 | 0.15 | 0.19 | 0.23 |
| | Dog | | 0.26 | 0.48 | 0.47 | 0.46 | 0.45 |
| I-3 | Human | | 0 | 0.0027 | 0.025 | 0.034 | 0.048 |
| | Rat | | 0 | 0.024 | 0.037 | 0.047 | 0.073 |
| | Mouse | | 0 | 0.026 | 0.024 | 0.026 | 0.043 |
| | Dog | | 0.015 | 0.23 | 0.28 | 0.29 | 0.50 |
| I-5 | Human | | 0 | 0.050 | 0.063 | 0.074 | 0.10 |
| | Rat | | 0.029 | 0.062 | 0.099 | 0.11 | 0.18 |
| | Mouse | | 0.050 | 0.11 | 0.076 | 0.093 | 0.14 |
| | Dog | | 0.13 | 0.26 | 0.25 | 0.25 | 0.28 |
| I-11 | Human | | 0.018 | 0.13 | 0.20 | 0.21 | 0.18 |
| | Rat | | 0 | 0.13 | 0.24 | 0.35 | 0.38 |
| | Mouse | | 0 | 0.021 | 0.059 | 0.12 | 0.084 |
| | Dog | | 0.032 | 0.23 | 0.38 | 0.74 | 0.88 |
| I-7 | Human | | 0.090 | 0.46 | 0.62 | 0.63 | 0.48 |
| | Rat | | 0.042 | 0.24 | 0.35 | 0.47 | 0.60 |
| | Mouse | | 0.033 | 0.24 | 0.29 | 0.39 | 0.38 |
| | Dog | | 0.38 | 0.36 | 0.55 | 0.51 | 0.50 |

Plasma Stability

Studies were carried out in mixed-gender human plasma (Lot #GLP530-5), male Sprague-Dawley rat (Lot #RAT297944, RAT313140), male CD-1 mouse (Lot #MSE237700), and male Beagle dog (Lot #BGL87670, BGL82614), collected on sodium heparin. Plasma was adjusted to pH 7.4 prior to initiating the experiments. DMSO stocks were first prepared for the test articles. Aliquots of the DMSO solutions were dosed into 700 μL of plasma, which had been pre-warmed to 37° C., at a final test article concentration of 1 μM. Aliquots (100 μL) were taken at each time point (0, 15, 30, 60, and 120 minutes) and were immediately combined with 300 μL of ice-cold acetonitrile containing 1% formic acid. Samples were stored at 4° C. until the end of the experiment. After the final time point was sampled, the plate was mixed and then centrifuged at 3,000 rpm for 10 minutes. Calibration standards were prepared in matched matrix. Samples and standards were assayed by LC-MS/MS using electrospray ionization for both the dosed prodrug and the expected drug (PEA). Analytical conditions are outlined in Appendix 8-1. Test article concentration at each time point was compared to test article concentration at time 0 to determine the percent remaining at each time point. Half-lives were calculated using GraphPad software, fitting to a single-phase exponential decay equation. Results are shown in Tables 8g and 8h.

TABLE 8g

PEA Stability observed in human, rat, mouse, and dog plasma.

| Test Article | Species | 0 min | % Remaining of Initial (n = 1) | | | | Half-life$^a$ (min) |
|---|---|---|---|---|---|---|---|
| | | | 15 min | 30 min | 60 min | 120 min | |
| I-6 | Human | 100 | 79 | 102 | 74 | 53 | >120 (147) |
| | Rat | 100 | 93 | 119 | 100 | 29 | 110 |
| | Mouse | 100 | 83 | 89 | 39 | 23 | 56 |
| | Dog | 100 | 55 | 42 | 34 | 22 | 36 |
| I-2 | Human | 100 | 96 | 91 | 84 | 51 | >120 (135) |
| | Rat | 100 | 58 | 59 | 46 | 18 | 49 |
| | Mouse | 100 | 72 | 71 | 56 | 21 | 62 |
| | Dog | 100 | 95 | 71 | 54 | 24 | 61 |
| I-9 | Human | 100 | 6.4 | 1.4 | <1.0 | <1.0 | 3.8 |
| | Rat | 100 | 2.5 | <1.0 | <1.0 | <1.0 | 2.8 |
| | Mouse | 100 | 49 | 17 | 2.3 | <1.0 | 13 |
| | Dog | 100 | 8.7 | 12 | 1.2 | <1.0 | 4.7 |
| I-3 | Human | 100 | 109 | 84 | 65 | 77 | >120 (211) |
| | Rat | 100 | 94 | 79 | 76 | 79 | >120 |
| | Mouse | 100 | 23 | 24 | 9.1 | 4.7 | 9.4 |
| | Dog | 100 | 90 | 90 | 95 | 99 | >120 |
| I-5 | Human | 100 | 110 | 81 | 82 | 69 | >120 (195) |
| | Rat | 100 | 85 | 90 | 87 | 83 | >120 |
| | Mouse | 100 | 109 | 86 | 73 | 75 | >120 (213) |
| | Dog | 100 | 87 | 98 | 87 | 83 | >120 |
| I-11 | Human | 100 | 67 | 47 | 34 | 10 | 34 |
| | Rat | 100 | 9.0 | 23 | <1.0 | <1.0 | 5.6 |
| | Mouse | 100 | 2.9 | 2.1 | 1.9 | <1.0 | 3.0 |
| | Dog | 100 | 61 | 40 | 18 | 5.4 | 23 |
| I-7 | Human | 100 | <1.0 | <1.0 | <1.0 | <1.0 | <1.0 |
| | Rat | 100 | <1.0 | <1.0 | <1.0 | <1.0 | <1.0 |
| | Mouse | 100 | <1.0 | <1.0 | <1.0 | <1.0 | <1.0 |
| | Dog | 100 | <1.0 | <1.0 | <1.0 | <1.0 | <1.0 |

TABLE 8h

Measured Concentrations of Drug.

| Dosed Test Article | Species | Analyte | Concentration (μM) | | | | |
|---|---|---|---|---|---|---|---|
| | | | 0 min | 15 min | 30 min | 60 min | 120 min |
| I-6 | Human | PEA | 0 | 0 | 0 | 0 | 0 |
| | Rat | | 0 | 0 | 0.020 | 0.017 | 0.056 |
| | Mouse | | 0 | 0 | 0.015 | 0.059 | 0.11 |
| | Dog | | 0 | 0 | 0 | 0 | 0 |
| I-2 | Human | | 0.00043 | 0.035 | 0.064 | 0.10 | 0.21 |
| | Rat | | 0.052 | 0.22 | 0.28 | 0.28 | 0.38 |
| | Mouse | | 0.019 | 0.068 | 0.095 | 0.14 | 0.23 |
| | Dog | | 0.0061 | 0.12 | 0.18 | 0.21 | 0.26 |
| I-9 | Human | | 0.049 | 0.41 | 0.37 | 0.49 | 0.35 |
| | Rat | | 0.77 | 1.2 | 1.3 | 1.2 | 1.1 |
| | Mouse | | 0.51 | 0.60 | 0.62 | 0.64 | 0.89 |
| | Dog | | 0.13 | 0.58 | 0.61 | 0.62 | 0.55 |
| I-3 | Human | | 0 | 0 | 0 | 0 | 0.0071 |
| | Rat | | 0.0029 | 0.0043 | 0.013 | 0.020 | 0.033 |
| | Mouse | | 0.015 | 0.10 | 0.25 | 0.36 | 0.42 |
| | Dog | | 0 | 0 | 0 | 0 | 0 |
| I-5 | Human | | 0.0017 | 0.034 | 0.055 | 0.083 | 0.096 |
| | Rat | | 0.021 | 0.11 | 0.14 | 0.18 | 0.17 |
| | Mouse | | 0.074 | 0.19 | 0.19 | 0.18 | 0.29 |
| | Dog | | 0 | 0.040 | 0.047 | 0.070 | 0.072 |
| I-11 | Human | | 0.011 | 0.13 | 0.26 | 0.38 | 0.53 |
| | Rat | | 0.0022 | 0.016 | 0.017 | 0.025 | 0.025 |
| | Mouse | | 0.19 | 0.38 | 0.56 | 0.60 | 0.76 |
| | Dog | | 0.012 | 0.20 | 0.35 | 0.52 | 0.55 |

TABLE 8h-continued

Measured Concentrations of Drug.

| Dosed Test Article | Species | Analyte | Concentration (µM) | | | | |
|---|---|---|---|---|---|---|---|
| | | | 0 min | 15 min | 30 min | 60 min | 120 min |
| I-7 | Human | | 0.11 | 0.54 | 0.53 | 0.49 | 0.53 |
| | Rat | | 0.29 | 0.59 | 0.54 | 0.56 | 0.60 |
| | Mouse | | 0.87 | 0.75 | 0.81 | 0.81 | 0.91 |
| | Dog | | 0.17 | 0.52 | 0.55 | 0.53 | 0.51 |

Simulated Intestinal Fluid Stability

Studies were carried out in simulated intestinal fluid in the presence of various enzymes. Simulated intestinal fluid was prepared by dissolving 6.8 g of monobasic potassium phosphate in 1.0 L of water. Aliquots of this solution were taken and the pH was adjusted to 6.8. Individual enzymes were then spiked into aliquots for each experiment. A DMSO stock was first prepared for the test article. Aliquots of the DMSO solution were dosed into 700 µL of matrix, which had been pre-warmed to 37° C., at a final test article concentration of 1 µM. Aliquots (100 µL) were taken at each time point (0, 15, 30, 60, and 120 minutes) and were immediately combined with 300 µL of ice-cold acetonitrile containing 1% formic acid. Samples were stored at 4° C. until the end of the experiment. After the final time point was sampled, the plate was mixed and then centrifuged at 3,000 rpm for 10 minutes. Calibration standards were prepared in matched matrix. Samples and standards were assayed by LC-MS/MS using electrospray ionization for both the dosed prodrug and the expected drug (PEA). Analytical conditions are outlined in Appendix 8-1. Test article concentration at each time point was compared to test article concentration at time 0 to determine the percent remaining at each time point. Half-lives were calculated using GraphPad software, fitting to a single-phase exponential decay equation. Results are shown in Tables 8i and 8j.

TABLE 8i

PEA stability observed in simulated intestinal fluid (SIF).

| Test Article | Treatment | % Remaining of Initial (n = 1) | | | | | Half-life$^a$ (min) |
|---|---|---|---|---|---|---|---|
| | | 0 min | 15 min | 30 min | 60 min | 120 min | |
| I-6 | SIF + Pancreatin | 100 | 27 | 11 | 3.1 | 1.7 | 8.3 |
| | SIF + Elastase | 100 | 95 | 74 | 64 | 69 | >120 (185) |
| | SIF + Carboxypeptidase A | 100 | 77 | 46 | 60 | 56 | >120 (134) |
| | SIF + Carboxypeptidase B | 100 | 87 | 93 | 54 | 19 | 62 |
| | SIF + Chymotrypsin | 100 | 106 | 99 | 51 | 55 | 101 |
| | SIF + Trypsin | 100 | 116 | 87 | 83 | 123 | >120 |
| I-2 | SIF + Pancreatin | 100 | 93 | 91 | 98 | 60 | >120 (205) |
| | SIF + Elastase | 100 | 61 | 42 | 30 | 28 | 37 |
| | SIF + Carboxypeptidase A | 100 | 79 | 70 | 56 | 43 | 92 |
| | SIF + Carboxypeptidase B | 100 | 75 | 54 | 40 | 17 | 43 |
| | SIF + Chymotrypsin | 100 | 78 | 70 | 60 | 58 | >120 (144) |
| | SIF + Trypsin | 100 | 82 | 72 | 75 | 46 | >120 (121) |
| I-9 | SIF + Pancreatin | 100 | 35 | 34 | 20 | 13 | 17 |
| | SIF + Elastase | 100 | 49 | 22 | 10 | 6.3 | 15 |
| | SIF + Carboxypeptidase A | 100 | 43 | 15 | 10 | 5.5 | 12 |
| | SIF + Carboxypeptidase B | 100 | 44 | 14 | 6.1 | 4.7 | 12 |
| | SIF + Chymotrypsin | 100 | 45 | 24 | 11 | 7.2 | 14 |
| | SIF + Trypsin | 100 | 67 | 49 | 22 | 12 | 29 |
| I-3 | SIF + Pancreatin | 100 | <1.0 | <1.0 | <1.0 | <1.0 | <1.0 |
| | SIF + Elastase | 100 | 94 | 61 | 44 | 29 | 55 |
| | SIF + Carboxypeptidase A | 100 | 76 | 66 | 36 | 20 | 46 |
| | SIF + Carboxypeptidase B | 100 | 86 | 77 | 41 | 15 | 49 |
| | SIF + Chymotrypsin | 100 | 102 | 84 | 61 | 53 | 107 |
| | SIF + Trypsin | 100 | 67 | 60 | 55 | 43 | 93 |
| I-5 | SIF + Pancreatin | 100 | 13 | <1.0 | <1.0 | <1.0 | 5.1 |
| | SIF + Elastase | 100 | 103 | 70 | 48 | 35 | 65 |
| | SIF + Carboxypeptidase A | 100 | 84 | 63 | 39 | 15 | 44 |
| | SIF + Carboxypeptidase B | 100 | 94 | 62 | 43 | 14 | 45 |
| | SIF + Chymotrypsin | 100 | 75 | 59 | 37 | 23 | 47 |
| | SIF + Trypsin | 100 | 81 | 67 | 44 | 26 | 56 |
| I-11 | SIF + Pancreatin | 100 | <1.0 | <1.0 | <1.0 | <1.0 | <1.0 |
| | SIF + Elastase | 100 | 70 | 50 | 33 | 17 | 37 |
| | SIF + Carboxypeptidase A | 100 | 73 | 78 | 42 | 18 | 53 |
| | SIF + Carboxypeptidase B | 100 | 68 | 50 | 33 | 9.6 | 34 |
| | SIF + Chymotrypsin | 100 | 84 | 63 | 42 | 21 | 50 |
| | SIF + Trypsin | 100 | 77 | 62 | 45 | 23 | 53 |
| I-7 | SIF + Pancreatin | 100 | 40 | 19 | 6.5 | 2.7 | 12 |
| | SIF + Elastase | 100 | 44 | 14 | 3.8 | 3.5 | 12 |
| | SIF + Carboxypeptidase A | 100 | 30 | 10 | 4.1 | 3.9 | 8.8 |
| | SIF + Carboxypeptidase B | 100 | 33 | 14 | 5.7 | 2.2 | 10 |
| | SIF + Chymotrypsin | 100 | 42 | 23 | 13 | 15 | 14 |
| | SIF + Trypsin | 100 | 66 | 44 | 38 | 33 | 50 |

TABLE 8j

Measured Concentrations of Drug.

| Test Article | Treatment | Analyte | Concentration (μM) | | | | |
|---|---|---|---|---|---|---|---|
| | | | 0 min | 15 min | 30 min | 60 min | 120 min |
| I-6 | SIF + Pancreatin | PEA | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |
| I-2 | SIF + Pancreatin | | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |
| I-9 | SIF + Pancreatin | | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |
| I-3 | SIF + Pancreatin | | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |
| I-5 | SIF + Pancreatin | | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |
| I-11 | SIF + Pancreatin | | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |
| I-7 | SIF + Pancreatin | | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |

PEA was found to be endogenous in pancreatin and thus was not quantified in the assay samples.

Appendix 8-1
Liquid Chromatography

| Column: | Waters ACQUITY UPLC BEH C18 30 × 2.1 mm, 1.7 μm |
|---|---|
| M.P. Buffer: | 25 mM ammonium formate buffer, pH 3.5 |
| Aqueous Reservoir (A): | 90% water, 10% buffer |
| Organic Reservoir (B): | 90% acetonitrile, 10% buffer |
| Flow Rate: | 0.8 mL/minute |
| Gradient Program: | |

TABLE 8-1

Liquid Chromatography Gradient Program

| Time (mm) | % A | % B |
|---|---|---|
| 0.00 | 50 | 50 |
| 0.75 | 1 | 99 |
| 1.25 | 1 | 99 |
| 1.30 | 50 | 50 |
| 1.50 | 50 | 50 |

| Total Run Time: | 1.5 minutes |
|---|---|
| Autosampler: | 5 μL injection volume |
| Wash1: | water/methanol/2-propanol: 1/1/1; with 0.2% formic acid |
| Wash2: | 0.1% formic acid in water |

Mass Spectrometer

| Instrument: | PE SCIEX API 4000 |
|---|---|
| Interface: | Turbo Ionspray |
| Mode: | Multiple reaction monitoring |
| Method: | 1.5 minute duration |
| Settings: | |

TABLE 8-2

Mass Spectrometer Settings

| Test Article | Q1/Q3 | DP | EP | CE | CXP | IS | TEM | CAD | CUR | GS1 | GS2 |
|---|---|---|---|---|---|---|---|---|---|---|---|
| I-6 | +562.6/282.4 | 133 | 10 | 29 | 19 | 5500 | 500 | 7 | 30 | 50 | 50 |
| I-2 | +370.3/282.4 | 107 | 10 | 21 | 18 | 5500 | 500 | 7 | 30 | 50 | 50 |
| I-3 | +726.6/282.4 | 129 | 10 | 38 | 18 | 5500 | 500 | 7 | 30 | 50 | 50 |
| I-5 | +584.5/282.4 | 135 | 10 | 24 | 20 | 5500 | 500 | 7 | 30 | 50 | 50 |
| I-11 | +614.6/282.4 | 123 | 10 | 35 | 20 | 5500 | 500 | 7 | 30 | 50 | 50 |
| I-7 | +724.5/282.4 | 120 | 10 | 40 | 19 | 5500 | 500 | 7 | 30 | 50 | 50 |
| PEA | +300.3/62.1 | 123 | 10 | 29 | 10 | 5500 | 500 | 7 | 30 | 50 | 50 |

| | |
|---|---|
| Column: | Thermo BDS Hypersil C18 30 × 2.0 mm, 3 µm, with guard column |
| M.P. Buffer: | 25 mM ammonium formate buffer,, pH 3.5 |
| Aqueous Reservoir (A): | 90% water, 10% buffer |
| Organic Reservoir (B): | 90% acetonitrile, 10% buffer |
| Flow Rate: | 350 µL/minute |
| Gradient Program: | |

TABLE 8-3

Liquid Chromatography Gradient Program

| Time (mm) | % A | % B |
|---|---|---|
| 0.00 | 50 | 50 |
| .080 | 25 | 75 |
| 1.50 | 0 | 100 |
| 2.00 | 0 | 100 |
| 2.10 | 50 | 50 |
| 3.00 | 50 | 50 |

| | |
|---|---|
| Total Run Time: | 3.0 minutes |
| Autosampler: | 10 µL injection volume |
| Autosampler Wash: | water/methanol/2-propanol: 1/1/1; with 0.2% formic acid |
| Mass Spectrometer | |
| Instrument: | PE SCIEX API 4000 |
| Interface: | Turbo Ionspray |
| Mode: | Multiple reaction monitoring |
| Method: | 3.0 minute duration |
| Settings: | |

TABLE 8-4

Mass Spectrometer Settings

| Test Article | Q1/Q3 | DP | EP | CE | CXP | IS | TEM | CAD | CUR | GS1 | GS2 |
|---|---|---|---|---|---|---|---|---|---|---|---|
| I-9 | +562.6/282.4 | 107 | 10 | 29 | 19 | 5500 | 500 | 7 | 20 | 20 | 30 |
| PEA | +370.3/282.4 | 123 | 10 | 29 | 10 | 5500 | 500 | 7 | 20 | 20 | 30 |

Example 9: Determination of the Bioavailability of Palmitoylethanolamide (PEA) Following Oral Administration of PEA-Prodrug in Male Sprague-Dawley Rats The present Example describes oral bioavailability of PEA following administration of PEA prodrugs in male Sprague-Dawley rats.

Oral bioavailability of palmitoylethanolamide (PEA) was evaluated in male Sprague-Dawley rats following oral dosing of a PEA pro-drug, I-13. I-13 was dosed orally (PO) at 24.3 mg/kg, which is equivalent to a 10 mg/kg dose of PEA. Blood samples were collected up to 8 hours post-dose, and plasma concentrations of PEA were determined by LC-MS/MS. Pharmacokinetic parameters, with the exception of $C_{max}$ and $t_{max}$ were not determined due to a lack of quantifiable data points. Following PO dosing of I-13 (in 20% (solutol HS15:NMP 1:1) 10% PEG400; 70% 120), nearly all rat plasma samples were below the limit of quantification. Maximum plasma concentrations (average of 2.70±0.0681 ng/mL) were observed between 2 and 8 hours post dosing. No ACUs or bioavailability values were determined.

Preparation for Dosing Formulations

Pro-drugs were dosed so that a total dose of 10 mg/kg of PEA was administered. Prodrugs were formulated in a vehicle comprised of 10% Solutol HS15, 10% n-methyl pyrrolidone (NMP), 10% polyethylene glycol 400 (PEG400) and 70% water. Formulations were prepared fresh on the day of dosing.

Animal Dosing

Pharmacokinetics of PEA were evaluated in fasted male Sprague-Dawley rats. Rats were housed one per cage. Each rat was fitted with a jugular vein cannula (JVC) for blood collection. Each study group was dosing in triplicate. Rats were fasted for a minimum of twelve hours prior to dosing. Food was returned at four hours post dosing. Animals had free access to water throughout the study.

Blood samples (~300 µL) were collected from the rats via a JVC and placed into chilled polypropylene tubes containing sodium heparin as an anticoagulant, and 30 µL of 0.5 M citric acid. Samples were maintained chilled throughout processing. Blood samples were centrifuged at 4° C. and 3,000 g for 5 minutes. Plasma (~150 µL) was then transferred to a chilled, labeled polypropylene tube containing 15 µL of 10% formic acid, placed on dry ice, and stored in a freezer maintained at −60° C. to −80° C. Blood sampling times are shown in Table 9a.

TABLE 9a

Study Design.

| Test Article | Dosing Route | Total Animals n = | Dose (mg/kg) of pro-drug)* | Dosing Solution Conc. (mg/mL) | Dosing Volume (mL/kg) | Vehicle | Blood Sample Time Points |
|---|---|---|---|---|---|---|---|
| I-13 | PO | 3 | 24.3 | 3 | 8.1 | 20% (Solutol HS15:NMP 1:1) 10% PEG400; 70% H$_2$O | Pre-dose, 5, 15, 30 min, 1, 2, 4, 8 hours |

*All doses are based on mg/kg of the pro-drugs, and deliver 10 mg/kg of active drug, PEA.

An LC-MS/MS method for the determination of PEA and PEA-prodrug is described above (see e.g., Example 3).

Pharmacokinetic parameters, with the exception of $C_{max}$ and $t_{max}$ were not determined due to a lack of quantifiable data points. Maximum plasma concentration ($C_{max}$) and time to reach maximum plasma drug concentration ($T_{max}$) after oral dosing were observed from the data. Samples below the limit of quantitation were treated as zero for pharmacokinetic data analysis.

Results

No adverse reactions were observed following oral administration of PEA pro-drug in male Sprague-Dawley rats in this study.

Dosing solutions were not analyzed by LC-MS/MS. Nominal dosing level was used in all calculations. Individual and average plasma concentrations for PEA are shown in Table 9b. Data are expressed as ng/mL of the free drug. Samples that were below the limit of quantitation were not used in the calculation of averages. Plasma concentrations versus time data are plotted in FIG. 6. Endogenous levels of PEA found in all rats were below limit of quantitation; and therefore, measured concentrations of PEA in plasma samples were not corrected.

TABLE 9b

Individual and Average Plasma Concentrations (ng/mL) and Pharmacokinetic Parameters for PEA after Oral Administration of I-13 (in 20% (Soluto HS15:NMP 1:1) 10% PEG400, 70% H$_2$O) at 24.3 mg/kg in Male Sprague-Dawley Rats. Oral (24.3 mg/kg I-13 equals 10 mg/kg PEA)

| | Rat # | | | | |
|---|---|---|---|---|---|
| Time (hr) | 61 | 62 | 63 | Mean | SD |
| 0(pre-dose) | BLOQ | BLOQ | BLOQ | ND | ND |
| 0.083 | BLOQ | BLOQ | BLOQ | ND | ND |
| 0.25 | BLOQ | BLOQ | BLOQ | ND | ND |
| 0.50 | BLOQ | BLOQ | BLOQ | ND | ND |
| 1.0 | BLOQ | BLOQ | BLOQ | ND | ND |
| 2.0 | BLOQ | 2.75 | 2.62 | 2.69 | ND |
| 4.0 | BLOQ | BLOQ | BLOQ | ND | ND |
| 8.0 | 2.72 | BLOQ | BLOQ | ND | ND |
| Animal Weight (kg) | 0.239 | 0.241 | 0.228 | 0.236 | 0.007 |
| Volume Dosed (mL) | 1.94 | 1.95 | 1.85 | 1.91 | 0.06 |
| $C_{max}$ (ng/mL) | 2.72 | 2.75 | 2.62 | 2.70 | 0.0681 |
| $t_{max}$ (hr) | 8.00 | 2.00 | 2.00 | 4.00 | 3.46 |
| $t_{1/2}$(hr) | ND[1] | ND[1] | ND[1] | ND | ND |
| MRT$_{last}$ (hr) | ND[1] | ND[1] | ND[1] | ND | ND |
| AUC$_{last}$ (hr ng/mL) | ND[1] | ND[1] | ND[1] | ND | ND |
| AUC$_\infty$ (hr ng/mL) | ND[1] | ND[1] | ND[1] | ND | ND |

$C_{max}$: maximum plasma concentration;
$t_{max}$: time of maximum plasma concentration;
$t_{1/2}$: half-life, data points used for half-life determination are in bold;
MRT$_{last}$: mean residence time, calculated to the last observable time point;
AUC$_{last}$: area under the curve, calculated to the last observable time point;
AUC$_\infty$: area under the curve, extrapolated to infinity;
ND: not determined;
BLOQ: below limit of quantitation (2.5 ng/mL);
[1]not determined due to a lack of quantifiable data points.

Example 10: PEA Stability in Human, Rat, Mouse and Dog Liver Microsomes, Human, Rat, Mouse and Dog Liver S9 Fraction, Human, Rat, Mouse and Dog Intestinal S9 Fraction, Human, Rat, Mouse and Dog Plasma, and Simulated Intestinal Fluid The present Example describes PEA stability observed in 1) human, rat, mouse, and dog liver microsomes; 2) human, rat, mouse, dog liver S9 fraction; human, rat, mouse, and dog intestinal S9 fraction; 4) human, rat, mouse, and dog plasma; and 5) simulated intestinal fluid containing various enzymes.

Liver Microsomal Stability

Mixed-gender human (Lot #1010420), male Sprague-Dawley rat (Lot #1510115), male CD-1 mouse (Lot #1510043), and male Beagle dog (Lot #0810143) liver microsomes were provided. Reaction mixture, minus cofactors, was prepared as described below. Test article was added into the reaction mixture at a final concentration of 1 µM. Control compound, testosterone, were run simultaneously with the test article in a separate reaction. An aliquot of the reaction mixture (without cofactor) was equilibrated in a shaking water bath at 37° C. for 5 minutes. Reaction was initiated by the addition of cofactor, and the mixture was incubated in a shaking water bath at 37° C. Aliquots (100 µL) were withdrawn at 0, 10, 20, 30, and 60 minutes. Test article samples were immediately combined with 300 µL of ice-cold acetonitrile containing 1% formic acid. Control samples were immediately combined with 400 µL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both the dosed prodrug and the expected drug (PEA). Analytical conditions are outlined in Appendix 10-1. Test article concentration at each time point was compared to the test article concentration at time 0 to determine the percent remaining at each time point. Half-lives were calculated using GraphPad software, fitting to a single-phase exponential decay equation. Results are shown in Tables 10a and 10b.

Reaction Composition

| | |
|---|---|
| Liver Microsomes | 0.5 mg/mL |
| NADPH (cofactor) | 1 mM |
| Potassium Phosphate pH 7.4 | 100 mM |
| Magnesium Chloride | 5 mM |
| Test Article | 1 µM |

TABLE 10a

PEA stability observed in human, rat, mouse, and dog liver microsomes.

| Test Article | Species | % Remaining of Initial (n = 1) | | | | | Half-life$^a$ (min) | $CL_{int}^b$ (mL/min/mg protein) |
|---|---|---|---|---|---|---|---|---|
| | | 0 min | 10 min | 20 min | 30 min | 60 min | | |
| I-13 | Human | 100 | 79 | 73 | 60 | 42 | 47 | 0.0296 |
| | Rat | 100 | 91 | 72 | 60 | 38 | 41 | 0.0336 |
| | Mouse | 100 | 69 | 75 | 54 | 44 | 48 | 0.0291 |
| | Dog | 100 | 78 | 76 | 56 | 32 | 38 | 0.0362 |

$^a$When the calculated half-life is longer than the duration of the experiment, half-life is expressed as > the longest incubation time. Similarly, if calculated half-life is less than the shortest time point, half-life is expressed as < that time point and calculated half-life is also listed in parentheses.
$^b$Intrinsic clearance ($CL_{int}$) was calculated based on $CL_{int}$ = k/P, where k is elimination rate constant and P is protein concentration in the incubation.

| Control Compound | Species | Half-life (min) | $CL_{int}$ (ml/min/mg protein) | Acceptable Range ($t_{1/2}$, min) |
|---|---|---|---|---|
| Testosterone | Human | 21 | 0.0667 | ≤41 |
| | Rat | 1.4 | 1.01 | ≤15 |
| | Mouse | 7.3 | 0.190 | ≤15 |
| | Dog | 33 | 0.0419 | ≤40 |

TABLE 10b

Measured Concentrations of Drug.

| Dosed Test Article | Species | Analyte | Concentration (µM) | | | | |
|---|---|---|---|---|---|---|---|
| | | | 0 min | 10 min | 20 min | 30 min | 60 min |
| I-13 | Human | PEA | 0 | 0 | 0 | 0 | 0 |
| | Rat | | 0 | 0 | 0.013 | 0.013 | 0 |
| | Mouse | | 0 | 0 | 0 | 0 | 0 |
| | Dog | | 0 | 0 | 0 | 0 | 0 |

Liver S9 Stability

Mixed gender human (Lot #1210091), male Sprague-Dawley rat (Lot #1410265), male CD-1 mouse (Lot #1510255), and male Beagle dog (Lot #1310285) liver S9 fraction were provided. Reaction mixture, minus cofactors, was prepared as described below. Test article was added into the reaction mixture at a final concentration of 1 µM. Control compounds, testosterone and 7-hydroxycoumarin (7-HC), were run simultaneously with the test article in a separate reaction. An aliquot of the reaction mixture (without cofactor cocktail) was equilibrated in a shaking water bath at 37° C. for 5 minutes. Reaction was initiated by the addition of cofactor cocktail (see below), and mixture was then incubated in a shaking water bath at 37° C. Aliquots (100 µL) were withdrawn at 0, 10, 20, 30, and 60 minutes. Test article samples were immediately combined with 300 µL of ice-cold acetonitrile containing 1% formic acid. Control samples were immediately combined with 400 µL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodrug and expected drug (PEA). Analytical conditions are outlined in Appendix 10-1. Test article concentration at each time point was compared to test article concentration at time 0 to determine the percent remaining at each time point. Half-lives were calculated using GraphPad software, fitting to a single-phase exponential decay equation. Results are shown in Tables 10c and 10d.

Reaction Composition

| | |
|---|---|
| Liver S9 Fraction | 1.0 mg/mL |
| NADPH (cofactor) | 1 mM |
| UDPGA (cofactor) | 1 mM |
| PAPS (cofactor) | 1 mM |
| GSH (cofactor) | 1 mM |
| Potassium Phosphate pH 7.4 | 100 mM |
| Magnesium Chloride | 5 mM |
| Test Article | 1 µM |

TABLE 10c

PEA Stability observed in human, rat, mouse, and dog liver S9.

| Test Article | Species | % Remaining of Initial (n = 1) | | | | | Half-life$^a$ (min) | $CL_{int}^b$ (mL/min/mg protein) |
|---|---|---|---|---|---|---|---|---|
| | | 0 min | 10 min | 20 min | 30 min | 60 min | | |
| I-13 | Human | 100 | 93 | 87 | 78 | 45 | 58 | 0.0119 |
| | Rat | 100 | 76 | 74 | 59 | 45 | 50 | 0.0138 |
| | Mouse | 100 | 89 | 90 | 79 | 78 | >60 | <0.0116 |
| | Dog | 100 | 70 | 61 | 61 | 37 | 41 | 0.0169 |

$^a$When calculated half-life is longer than the duration of the experiment, half-life is expressed as > the longest incubation time. Similarly, if calculated half-life is less than shortest time point, half-life is expressed as < that time point and calculated half-life is also listed in parentheses.
$^b$Intrinsic clearance ($CL_{int}$) was calculated based on $CL_{int}$ = k/P, where k is the elimination rate constant and P is the protein concentration in the incubation.

| Control Compound | Species | Half-life (min) | $CL_{int}$ (ml/min/mg protein) | Acceptable Range ($t_{1/2}$, min) |
|---|---|---|---|---|
| Testosterone | Human | 28 | 0.0247 | ≤34 |
| | Rat | 2.7 | 0.260 | ≤15 |
| | Mouse | 7.1 | 0.0976 | ≤37 |
| | Dog | 14 | 0.0493 | ≤42 |

-continued

| Control Compound | Species | Half-life (min) | $CL_{int}$ (ml/min/mg protein) | Acceptable Range ($t_{1/2}$, min) |
|---|---|---|---|---|
| 7-hydroxycourmarin | Human | 15 | 0.0472 | ≤18 |
| | Rat | 1.9 | 0.362 | ≤15 |
| | Mouse | 3.8 | 0.182 | ≤15 |
| | Dog | 1.4 | 0.512 | ≤15 |

TABLE 10d

Measured Concentrations of Drug.

| Dosed Test Article | Species | Analyte | Concentration (μM) | | | | |
|---|---|---|---|---|---|---|---|
| | | | 0 min | 10 min | 20 min | 30 min | 60 min |
| I-13 | Human | PEA | 0 | 0 | 0 | 0 | 0 |
| | Rat | | 0 | 0 | 0 | 0 | 0 |
| | Mouse | | 0 | 0 | 0 | 0 | 0 |
| | Dog | | 0.015 | 0.025 | 0.020 | 0.024 | 0.021 | for both dosed prodrug and expected drug (PEA). Analytical conditions are outlined in Appendix 10-1. Test article concentration at each time point was compared to test article concentration at time 0 to determine the percent remaining at each time point. Halflives were calculated using GraphPad software, fitting to a single-phase exponential decay equation. Results are shown in Tables 10e and 10f.

Reaction Composition

| Intestinal S9 Fraction | 1.0 mg/mL |
|---|---|
| NADPH (cofactor) | 1 mM |
| UDPGA (cofactor) | 1 mM |
| PAPS (cofactor) | 1 mM |
| GSH (cofactor) | 1 mM |
| Potassium Phosphate, pH 7.4 | 100 mM |
| Magnesium Chloride | 5 mM |
| Test Article | 1 μM |

TABLE 10e

PEA stability observed in human, rat, mouse, and dog intestinal S9 fraction.

| Test Article | Species | % Remaining of Initial (n = 1) | | | | | Half-life[a] (min) | $CL_{int}$[b] (mL/min/ mg protein) |
|---|---|---|---|---|---|---|---|---|
| | | 0 min | 10 min | 20 min | 30 min | 60 min | | |
| I-13 | Human | 100 | 86 | 86 | 86 | 59 | >60 (92) | <0.0116 (0.00757) |
| | Rat | 100 | 80 | 82 | 81 | 55 | >60 (81) | <0.0116 (0.00859) |
| | Mouse | 100 | 97 | 71 | 81 | 57 | >60 (73) | <0.0116 (0.00951) |
| | Dog | 100 | 67 | 63 | 46 | 49 | 45 | 0.0153 |

[a] When calculated half-life is longer than the duration of the experiment, half-life is expressed as > the longest incubation time. Similarly, if calculated half-life is less than shortest time point, half-life is expressed as < that time point and calculated half-life is also listed in parentheses.
[b] Intrinsic clearance ($CL_{int}$) was calculated based on $CL_{int}$ = k/P, where k is elimination rate constant and P is protein concentration in the incubation.

Intestinal S9 Fraction Stability

Mixed-gender human (Lot #1410073), male Sprague-Dawley rat (Lot #1010042), male CD-1 mouse (Lot #1510194), and male Beagle dog (Lot #1510226) intestinal S9 fraction were provided. Reaction mixture, minus cofactors, was prepared as described below. Test article was added into the reaction mixture at a final concentration of 1 μM. Control compounds, testosterone and 7-hydroxycoumarin, were run simultaneously with test article in a separate reaction. An aliquot of the reaction mixture (without cofactor cocktail) was equilibrated in a shaking water bath at 37° C. for 5 minutes. Reaction was initiated by the addition of cofactor cocktail, and mixture was incubated in a shaking water bath at 37° C. Aliquots (100 μL) were withdrawn at 0, 10, 20, 30, and 60 minutes. Test article samples were immediately combined with 300 μL of ice-cold acetonitrile containing 1% formic acid. Control samples were immediately combined with 400 μL of ice-cold 50/50 acetonitrile (ACN)/dH₂O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization

| Control Compound | Species | Half-life (min) | $CL_{int}$ (ml/min/mg protein) |
|---|---|---|---|
| Testosterone | Human | 14 | 0.0509 |
| | Rat | >60 | <0.0116 |
| | Mouse | >60 | <0.0116 |
| | Dog | >60 | <0.0116 |
| 7-hydroxycourmarin | Human | 9.9 | 0.0698 |
| | Rat | 22 | 0.0320 |
| | Mouse | 4.3 | 0.160 |
| | Dog | 8.7 | 0.0799 |

TABLE 10f

Measured Concentrations of Drug.

| Dosed Test Article | Species | Analyte | Concentration (μM) | | | | |
|---|---|---|---|---|---|---|---|
| | | | 0 min | 10 min | 20 min | 30 min | 60 min |
| I-13 | Human | PEA | 0 | 0.010 | 0.014 | 0.018 | 0.031 |
| | Rat | | 0 | 0.020 | 0.048 | 0.064 | 0.092 |
| | Mouse | | 0.012 | 0.050 | 0.073 | 0.096 | 0.089 |
| | Dog | | 0.058 | 0.095 | 0.10 | 0.089 | 0.17 |

Plasma Stability

Studies were carried out in mixed-gender human plasma (Lot #AS1650-2), male Sprague-Dawley rat (Lot #RAT297944), male CD-I mouse (Lot #MSE237700), and male Beagle dog (Lot #BGL91384), collected on sodium heparin. Plasma was adjusted to pH 7.4 prior to initiating the experiments. DMSO stocks were first prepared for the test articles. Aliquots of the DMSO solutions were dosed into 700 µL of plasma, which had been pre-warmed to 37° C., at a final test article concentration of 1 µM. Aliquots (100 µL) were taken at each time point (0, 15, 30, 60, and 120 minutes) and were immediately combined with 300 µL of ice-cold acetonitrile containing 1% formic acid. Samples were stored at 4° C. until the end of the experiment. After the final time point was sampled, the plate was mixed and then centrifuged at 3,000 rpm for 10 minutes. Calibration standards were prepared in matched matrix. Samples and standards were assayed by LC-MS/MS using electrospray ionization for both dosed prodrug and expected drug (PEA). Analytical conditions are outlined in Appendix 10-1. Test article concentration at each time point was compared to test article concentration at time 0 to determine the percent remaining at each time point. Half-lives were calculated using GraphPad software, fitting to a single-phase exponential decay equation. Results are shown in Tables 10g and 10h.

TABLE 10g

PEA stability observed in human, rat, mouse, and dog plasma.

| Test Article | Species | % Remaining of Initial (n = 1) | | | | | Half-life$^a$ (min) |
|---|---|---|---|---|---|---|---|
| | | 0 min | 15 min | 30 min | 60 min | 120 min | |
| I-13 | Human | 100 | 104 | 115 | 95 | 40 | 120 |
| | Rat | 100 | 69 | 76 | 36 | 5.1 | 42 |
| | Mouse | 100 | 82 | 71 | 49 | 35 | 70 |
| | Dog | 100 | 90 | 72 | 54 | 23 | 61 |

TABLE 10h

Measured Concentrations of Drug.

| Dosed Test Article | Species | Analyte | Concentration (µM) | | | | |
|---|---|---|---|---|---|---|---|
| | | | 0 min | 15 min | 30 min | 60 min | 120 min |
| I-13 | Human | PEA | 0 | 0 | 0 | 0 | 0 |
| | Rat | | 0 | 0 | 0 | 0.022 | 0.053 |
| | Mouse | | 0 | 0.016 | 0.037 | 0.068 | 0.090 |
| | Dog | | 0 | 0 | 0 | 0 | 0 |

Simulated Intestinal Fluid Stability

Studies were carried out in simulated intestinal fluid in the presence of various enzymes. Simulated intestinal fluid was prepared by dissolving 6.8 g of monobasic potassium phosphate in 1.0 L of water. Aliquots of this solution were taken and the pH was adjusted to 6.8. Individual enzymes were then spiked into aliquots for each experiment. A DMSO stock was first prepared for the test article. Aliquots of the DMSO solution were dosed into 700 µL of matrix, which had been pre-warmed to 37° C., at a final test article concentration of 1 µM. Aliquots (100 µL) were taken at each time point (0, 15, 30, 60, and 120 minutes) and were immediately combined with 300 µL of ice-cold acetonitrile containing 1% formic acid. Samples were stored at 4° C. until the end of the experiment. After the final time point was sampled, the plate was mixed and then centrifuged at 3,000 rpm for 10 minutes. Calibration standards were prepared in matched matrix. Samples and standards were assayed by LC-MS/MS using electrospray ionization for both dosed prodrug and expected drug (PEA). Analytical conditions are outlined in Appendix 10-1. Test article concentration at each time point was compared to test article concentration at time 0 to determine the percent remaining at each time point. Half-lives were calculated using GraphPad software, fitting to a single-phase exponential decay equation. Results are shown in Tables 10i and 10j.

TABLE 10i

PEA Stability observed in simulated intestinal fluid (SIF).

| Test Article | Treatment | % Remaining of Initial (n = 1) | | | | | Half-life$^a$ (min) |
|---|---|---|---|---|---|---|---|
| | | 0 min | 15 min | 30 min | 60 min | 120 min | |
| I-13 | SIF + Pancreatin | 100 | 1.3 | 3.7 | 3.4 | <1.0 | <15 (2.5) |
| | SIF + Elastase | 100 | 41 | 16 | 5.6 | 5.0 | 12 |
| | SIF + Carboxypeptidase A | 100 | 77 | 53 | 27 | 37 | 47 |
| | SIF + Carboxypeptidase B | 100 | 65 | 31 | 14 | 8.7 | 20 |
| | SIF + Chymotrypsin | 100 | 82 | 67 | 45 | 15 | 49 |
| | SIF + Trypsin | 100 | 78 | 70 | 55 | <1.0 | 47 |

TABLE 10j

Measured Concentrations of Drug.

| Test Article | Treatment | Analyte | Concentration (µM) | | | | |
|---|---|---|---|---|---|---|---|
| | | | 0 min | 15 min | 30 min | 60 min | 120 min |
| I-13 | SIF + Pancreatin | PEA | — | — | — | — | — |
| | SIF + Elastase | | 0 | 0 | 0 | 0 | 0 |
| | SIF + Carboxypeptidase A | | 0 | 0 | 0 | 0 | 0 |

TABLE 10j-continued

Measured Concentrations of Drug.

| Test Article | Treatment | Analyte | Concentration (μM) | | | | |
|---|---|---|---|---|---|---|---|
| | | | 0 min | 15 min | 30 min | 60 min | 120 min |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |

PEA was found to be endogenous in pancreatin and thus could not be quantified in the assay samples.

Appendix 10-1
Liquid Chromatography

| | |
|---|---|
| Column: | Waters ACQUITY UPLC BEH C18 30 × 2.1 mm, 1. |
| M.P. Buffer: | 25 mM ammonium formate buffer,, pH 3.5 |
| Aqueous Reservoir (A): | 90% water, 10% buffer |
| Organic Reservoir (B): | 90% acetonitrile, 10% buffer |
| Flow Rate: | 0.8 mL/minute |
| Gradient Program: | |

TABLE 10-1

Liquid Chromatography Gradient Program

| Time (min) | % A | % B |
|---|---|---|
| 0.00 | 50 | 50 |
| 0.75 | 1 | 99 |
| 1.50 | 1 | 99 |
| 1.55 | 50 | 50 |
| 2.00 | 50 | 50 |

| | |
|---|---|
| Total Run Time: | 2.0 minutes |
| Autosampler: | 10 μL injection volume |
| Wash1: | water/methanol/2-propanol: 1/1/1; with 0.2% formic acid |
| Wash2: | 0.1% formic acid in water |
| Mass Spectrometer | |
| Instrument: | PE SCIEX API 4000 |
| Interface: | Turbo Ionspray |
| Mode: | Multiple reaction monitoring |
| Method: | 2.0 minute duration |
| Settings: | |

Table 10-2: Mass Spectrometer Settings

TABLE 10-2

Mass Spectrometer Settings

| Test Article | Q1/Q3 | DP | EP | CE | CXP | IS | TEM | CAD | CUR | GS1 | GS2 |
|---|---|---|---|---|---|---|---|---|---|---|---|
| I-13 | +998.9/282.2 | 141 | 10 | 68 | 28 | 5500 | 500 | 7 | 30 | 50 | 50 |
| | +1015.9/282.2 | 42 | 10 | 53 | 7 | 5500 | 500 | 7 | 30 | 50 | 50 |
| | +1015.9/998.9 | 63 | 10 | 20 | 17 | 5500 | 500 | 7 | 30 | 50 | 50 |
| PEA | +300.3/62.1 | 123 | 10 | 29 | 10 | 5500 | 500 | 7 | 30 | 50 | 50 |

Example 11: PEA Stability in Simulated Intestinal Fluid

Simulated Intestinal Fluid Stability

Studies were carried out in simulated intestinal fluid containing pancreatin. Simulated intestinal fluid was prepared by dissolving 6.8 g of monobasic potassium phosphate in 1.0 L of water. Pancreatin was then added to the solution and the pH was adjusted to 6.8. A DMSO stock was first prepared for the test articles. Aliquots of the DMSO solution were dosed into 300 μL of matrix, which had been pre-warmed to 37° C., at a final test article concentration of 1 μM. An individual tube was dosed for each time point. At each time point (0, 15, 30, 60, and 120 minutes), 900 μL of ice-cold acetonitrile containing 1.0% formic acid was added to an individual tube. Starting time for each tube was staggered such that all timepoints would finish at the same time. After the conclusion of the experiment, tubes were mixed and then centrifuged at 3,000 rpm for 10 minutes. Calibration standards were prepared in matched matrix. Samples and standards were assayed by LC-MS/MS using electrospray ionization. Analytical conditions are outlined in Appendix 11-1. Test article concentration at each time point was compared to test article concentration at time 0 to determine the percent remaining at each time point. Half-lives were calculated using GraphPad software, fitting to a single-phase exponential decay equation. Results are shown in Tables 11a and 11b.

TABLE 11a

PEA stability observed in simulated intestinal fluid (SIF)

| Test Article | Treatment | % Remaining of Initial (n = 1) | | | | | Half-life$^a$ (min) |
|---|---|---|---|---|---|---|---|
| | | 0 min | 15 min | 30 min | 60 min | 120 min | |
| I-15 | SIF + Pancreatin | 100 | <2.2 | <2.2 | <2.2 | <2.2 | ND |
| I-14 | SIF + Pancreatin | 100 | 25 | <2.2 | <2.2 | <2.2 | 7.6 |

TABLE 11b

Measured Concentrations of Drug.

| Test Article | Treatment | Concentration (µM) | | | | |
|---|---|---|---|---|---|---|
| | | 0 min | 15 min | 30 min | 60 min | 120 min |
| I-15 | SIF + Pancreatin | 0.18 | 0 | 0 | 0 | 0 |
| I-14 | SIF + Pancreatin | 0.19 | 0.047 | 0 | 0 | 0 |

Appendix 11-1 Liquid Chromatography

| Column: | Waters ACQUITY UPLC BEH C18 × 2.1 mm, 1.7 µm |
|---|---|
| M.P. Buffer: | 25 mM ammonium formate buffer,, pH 3.5 |
| Aqueous Reservoir (A): | 90% water, 10% buffer |
| Organic Reservoir (B): | 90% acetonitrile, 10% buffer |
| Flow Rate: | 0.7 mL/minute |
| Gradient Program: | |

TABLE 11-1

Liquid Chromatography Gradient Program

| Time (min) | % A | % B |
|---|---|---|
| 0.00 | 50 | 50 |
| 0.75 | 1 | 99 |
| 1.00 | 1 | 99 |
| 1.05 | 50 | 50 |
| 1.50 | 50 | 50 |

| Total Run Time: | 1.5 minutes |
|---|---|
| Autosampler: | 1 µL injection volume |
| Wash1: | water/methanol/2-propanol: 1/1/1; with 0.2% formic acid |
| Wash2: | 0.1% formic acid in water |
| Mass Spectrometer | |
| Instrument: | PE SCIEX API 4000 |
| Interface: | Turbo Ionspray |
| Mode: | Multiple reaction monitoring |
| Method: | 1.5 minute duration |
| Settings: | |

TABLE 11-2

Mass Spectrometer Settings

| Test Article | Q1/Q3 | DP | EP | CE | CXP | IS | TEM | CAD | CUR | GS1 | GS1 |
|---|---|---|---|---|---|---|---|---|---|---|---|
| I-15 | +614.5/282.6 | 112 | 10 | 40 | 7 | 5500 | 500 | 7 | 30 | 50 | 50 |
| I-14 | +614.5/282.8 | 124 | 10 | 30 | 8 | 5500 | 500 | 7 | 30 | 50 | 50 |

Example 12: Determination of the Bioavailability of Palmitoylethanolamide (PEA) Following Oral Administration of PEA-Prodrug in Male Sprague-Dawley Rats The present Example describes oral bioavailability of PEA following administration of PEA prodrugs in male Sprague-Dawley rats.

Oral bioavailability of palmitoylethanolamide (PEA) was evaluated in male Sprague-Dawley rats following oral dosing of a PEA pro-drug, I-12. I-12 was dosed orally (PO) at 35.2 mg/kg in two different formulations, which is equivalent to a 10 mg/kg dose of PEA. Blood samples were collected up to 8 hours post-dose, and plasma concentrations of PEA were determined by LC-MS/MS. Following PO dosing of Group 1 of I-12 (in 20% (Solutol HS15:NMP 1:1) 10% PEG400; 70% H$_2$O) with analysis of PEA, maximum plasma concentrations (average of 12.8±1.68 ng/mL) were observed at 1 hour post dosing. Average half-life could not be determined due to a lack of quantifiable data points trailing the Cma*. Average exposure for PEA based on the dose-normalized AUC$_{last}$ was 2.23±1.08 hr*kg*ng/mL/mg. Based on the IV data from Example 5, average oral bioavailability for PEA (Group 1) was 3.60±1.73%. Following PO dosing of Group 2 of I-12 (in 0.5% methyl cellulose in 20% (Solutol HS15:NMP 1:1); 10% PEG400: 70% H20) with analysis of PEA, maximum plasma concentrations (average of 16.1±3.62 ng/mL) were observed at 1 hour post dosing. Average half-life after PO dosing could not be determined; however, half-life for one rat was 4.34 hours. Average exposure for PEA based on the dose-normalized AUC$_{last}$ was 3.43±1.03 hr*kg*ng/mL/mg. Based on the IV data from Example 5, average oral bioavailability for PEA (Group 2) was 5.52±1.66%.

Preparation of Dosing Formulations

Pro-drugs were dosed so that a total dose of 10 mg/kg of PEA was administered. Pro-drugs were formulated in a vehicle comprised of 10% Solutol HS15, 10% n-methyl pyrrolidone (NMP), 10% polyethylene glycol 400 (PEG400) and 70% water for Group 1 or in in a vehicle comprised of 0.5% methyl cellulose in 10% Solutol HS15, 10% NMP, 10% PEG400 and 70% water (Group 2). Formulations were prepared fresh on the day of dosing.

Animal Dosing

Pharmacokinetics of PEA were evaluated in fasted male Sprague-Dawley rats. Rats were housed one per cage. Each rat was fitted with a jugular vein cannula (JVC) for blood collection. Each study group was dosing in triplicate. Rats were fasted for a minimum of twelve hours prior to dosing. Food was returned at four hours post dosing. Animals had free access to water throughout the study. Blood samples (~300 µL) were collected from rats via a JVC and placed into chilled polypropylene tubes containing sodium heparin as an anticoagulant, and 30 µL of 0.5 M citric acid. Samples were maintained chilled throughout processing. Blood samples were centrifuged at 4° C. and 3,000 g for 5 minutes. Plasma (~150 µL) was then transferred to a chilled, labeled polypropylene tube containing 15 µL of 10% formic acid, placed on dry ice, and stored in a freezer maintained at −60° C. to −80° C. Blood sampling times are shown in Table 12a.

TABLE 12a

Study Design.

| Dose group | Test Article | Dosing Route | Total Animals n = | Dose (mg/kg of pro-drug)* | Dosing Solution Conc. (mg/mL) | Dosing Volume (mL/kg) | Vehicle | Blood Sample Time Points |
|---|---|---|---|---|---|---|---|---|
| 1 | I-12 | PO | 3 | 35.2 | 5.03 | 7 | 20% (Solutol HS15:NMP 1:1) 10% PEG400; 70% H$_2$O | Pre-dose, 5, 15, 30 min, 1, 2, 4, 8 hours |
| 2 |  | PO | 3 | 35.2 | 5.03 | 7 | 20% (Solutol HS15:NMP 1:1) 10% PEG400; 70% H$_2$O | Pre-dose, 5, 15, 30 min, 1, 2, 4, 8 hours |

*All doses are based on mg/kg of the pro-drugs, and deliver 10 mg/kg of active drug, PEA.

An LC-MS/MS method for the determination of PEA and PEA-prodrug is described above (see e.g., Example 3).

Pharmacokinetic parameters were calculated from the time course of the plasma concentration. Maximum plasma concentration ($C_{max}$) and time to reach maximum plasma drug concentration ($T_{max}$) after oral dosing were observed from the data. Area under the time concentration curve (AUC) was calculated using the linear trapezoidal rule with calculation to the last quantifiable data point, and with extrapolation to infinity if applicable. At least three quantifiable data points were required to determine the AUC. Plasma half-life ($t_{1/2}$) was calculated from 0.693/slope of the terminal elimination phase. Mean residence time, MRT, was calculated by dividing area under the moment curve (AUMC) by the AUC. Bioavailability was determined by dividing the individual dose-normalized PO AUC$_{last}$ values by the average IV AUC$_{last}$ value (IV data from Example 5). Samples below the limit of quantitation were treated as zero for pharmacokinetic data analysis.

Results

No adverse reactions were observed following the oral administration of PEA pro-drug in male Sprague-Dawley rats in this study.

Dosing solutions were not analyzed by LC-MS/MS. Nominal dosing level was used in all calculations. Individual and average plasma concentrations for PEA and are shown in Tables 12b and 12c. Data are expressed as ng/mL of the free drug. Samples that were below the limit of quantitation were not used in the calculation of averages. Plasma concentrations versus time data are plotted in FIGS. 7A through 7D. Endogenous levels of PEA found in all rats were below the limit of quantitation; and therefore, measured concentrations of PEA in plasma samples were not corrected.

TABLE 12b

Individual and Average Plasma Concentrations (ng/mL) and Pharmacokinetic Parameters for PEA after Oral Administration of I-12 (in 20% Solutol HS15:NMP (1:1), 10% PEG400, 70% H$_2$O) at 35.2 mg/kg in Male Sprague-Dawley Rats (Group 1) Oral (35.2 mg/kg I-12 equals 10 mg/kg PEA)

| | Rat # | | | | |
|---|---|---|---|---|---|
| Time (hr) | 13 | 14 | 15 | Mean | SD |
| 0 (pre-dose) | BLOQ | BLOQ | BLOQ | ND | ND |
| 0.083 | BLOQ | BLOQ | BLOQ | ND | ND |
| 0.25 | 3.84 | 5.64 | 3.69 | 4.39 | 1.09 |
| 0.50 | 7.08 | 10.2 | 9.06 | 8.78 | 1.58 |
| 1.0 | 11.9 | 11.7 | 14.7 | 12.8 | 1.68 |
| 2.0 | 6.14 | 6.11 | 10.1 | 7.45 | 2.30 |
| 4.0 | BLOQ | BLOQ | 4.40 | ND | ND |
| 8.0 | BLOQ | BLOQ | BLOQ | ND | ND |
| Animal Weight (kg) | 0.291 | 0.279 | 0.277 | 0.282 | 0.008 |
| Volume Dosed (mL) | 2.04 | 1.95 | 1.94 | 1.98 | 0.06 |
| $C_{max}$ (ng/mL) | 11.9 | 11.7 | 14.7 | 12.8 | 1.68 |
| $t_{max}$ (hr) | 1.00 | 1.00 | 1.00 | 1.00 | 0.00 |
| $t_{1/2}$(hr) | ND[3] | ND[3] | ND[3] | ND | ND |
| MRT$_{last}$ (hr) | 1.07 | 1.02 | 1.75 | 1.28 | 0.409 |
| AUC$_{last}$ (hr ng/mL) | 15.5 | 16.8 | 34.7 | 22.3 | 10.8 |
| AUC$_\infty$ (hr ng/mL) | ND[3] | ND[3] | ND[3] | ND | ND |
| Dose-normalized Values[1] | | | | | |
| AUC$_{last}$ (hr kg ng/mL/mg) | 1.55 | 1.68 | 3.47 | 2.23 | 1.08 |
| AUC$_\infty$ (hr kg ng/mL/mg) | ND[3] | ND[3] | ND[3] | ND | ND |
| Bioavailability (%)[2] | 2.49 | 2.71 | 5.60 | 3.60 | 1.73 |

$C_{max}$: maximum plasma concentration;
$t_{max}$: time of maximum plasma concentration;
$t_{1/2}$: half-life, data points used for half-life determination are in bold;
MRT$_{last}$: mean residence time, calculated to the last observable time point;
AUC$_{last}$: area under the curve, calculated to the observable time point;
AUC$_\infty$: area under the curve, extrapolated to infinity;
ND: not determined;
BLOQ: below the limit of quantitation (2.5 ng/mL);
[1]Dosenormalized by dividing the parameter by the nominal dose in mg/kg;
[2]Bioavailability determined by dividing the individual dose-normalized oral AUC$_{last}$ values by the average IV AUC$_{last}$ value 62.1 hr*ng/mL from Example 5;
[3]not determined due to lack of quantifiable data points trailing the $C_{max}$.

TABLE 12c

Individual and Average Plasma Concentrations (ng/mL) and Pharmacokinetic Parameters for PEA after Oral Administration of I-12 (in 0.5% Methyl Cellulose in 20% (Solutol HS15:NMP (1:1), 10% PEG400, 70% $H_2O$) at 35.2 mg/kg in Male Sprague-Dawley Rats (Group 2). Oral (35.2 mg/kg I-12 equals 10 mg/kg PEA)

| | Rat # | | | | |
|---|---|---|---|---|---|
| Time (hr) | 16 | 17 | 18 | Mean | SD |
| 0 (pre-dose) | BLOQ | BLOQ | BLOQ | ND | ND |
| 0.083 | BLOQ | BLOQ | BLOQ | ND | ND |
| 0.25 | 5.79 | 3.55 | 2.98 | 4.11 | 1.49 |
| 0.50 | 8.27 | 9.21 | 7.72 | 8.40 | 0.753 |
| 1.0 | 20.1 | 13.0 | 15.3 | 16.1 | 3.62 |
| 2.0 | 6.78 | 2.71 | 6.56 | 5.35 | 2.29 |
| 4.0 | 3.96 | BLOQ | 5.02 | 4.49 | ND |
| 8.0 | BLOQ | 3.17 | 2.54 | 2.86 | ND |
| Animal Weight (kg) | 0.283 | 0.282 | 0.275 | 0.280 | 0.004 |
| Volume Dosed (mL) | 1.98 | 1.97 | 1.93 | 1.96 | 0.03 |
| $C_{max}$ (ng/mL) | 20.1 | 13.0 | 15.3 | 16.1 | 3.62 |
| $t_{max}$ (hr) | 1.00 | 1.00 | 1.00 | 1.00 | 0.00 |
| $t_{1/2}$ (hr) | $ND^3$ | $ND^3$ | 4.34 | ND | ND |
| $MRT_{last}$ (hr) | 1.58 | 2.90 | 2.97 | 2.48 | 0.780 |
| $AUC_{last}$ (hr ng/mL) | 33.5 | 24.3 | 45.0 | 34.3 | 10.3 |
| $AUC_{\infty}$ (hr ng/mL) | $ND^3$ | $ND^3$ | $ND^4$ | ND | ND |
| Dose-normalized Values[1] | | | | | |
| $AUC_{last}$ (hr kg ng/mL/mg) | 3.35 | 2.43 | 4.50 | 3.43 | 1.03 |
| $AUC_{\infty}$ (hr kg ng/mL/mg) | $ND^3$ | $ND^3$ | $ND^4$ | ND | ND |
| Bioavailability (%)[2] | 5.40 | 3.92 | 7.24 | 5.52 | 1.66 |

$C_{max}$: maximum plasma concentration;
$t_{max}$: time of maximum plasma concentration;
$t_{1/2}$: half- life, data points used for half-life determination are in bold;
$MRT_{last}$: mean residence time, calculated to the last observable time point;
$AUC_{last}$: area under the curve, calculated to the last observable time point;
$AUC_{\infty}$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]not determined due to lack of quantifiable data points trailing the $C_{max}$;
[4]not determined because the $AUC_{\infty}$ was a greater than 25% extrapolation above the $AUC_{last}$.

Example 13: PEA Stability in Human, Rat Mouse and Dog Liver Microsomes, Human, Rat, Mouse and Dog Liver S9 Fraction, Human, Rat, Mouse and Dog Intestinal S9 Fraction, Human, Rat, Mouse and Dog Plasma, and Simulated Intestinal Fluid The present Example describes PEA stability observed in 1) human, rat, mouse, and dog liver microsomes; 2) human, rat, mouse, dog liver S9 fraction; human, rat, mouse, and dog intestinal S9 fraction; 4) human, rat, mouse, and dog plasma; and 5) simulated intestinal fluid containing various enzymes.

Liver Microsomal Stability

Mixed-gender human (Lot #1010420), male Sprague-Dawley rat (Lot #1510115), male CD-1 mouse (Lot #1610148), and male Beagle dog (Lot #0810143) liver microsomes were provided. Reaction mixture, minus cofactors, was prepared as described below. Test article was added into the reaction mixture at a final concentration of 1 µM. Control compound, testosterone, was run simultaneously with the test article in a separate reaction. An aliquot of the reaction mixture (without cofactor) was equilibrated in a shaking water bath at 37° C. for 3 minutes. Reaction was initiated by the addition of cofactor, and the mixture was incubated in a shaking water bath at 37° C. Aliquots (100 µL) were withdrawn at 0, 10, 20, 30, and 60 minutes. Test article samples were immediately combined with 300 µL, of ice-cold acetonitrile containing 1% formic acid. Control samples were immediately combined with 400 µL of ice-cold 50/50 acetonitrile (ACN)/$dH_2O$ containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodrug and expected drug (PEA). Analytical conditions are outlined in Appendix 13-1. Test article concentration at each time point was compared to test article concentration at time 0 to determine the percent remaining at each time point. Half-lives were calculated using GraphPad software, fitting to a single-phase exponential decay equation. Results are shown in Tables 13a and 13b.

Reaction Composition

| Liver Microsomes | 0.5 mg/mL |
|---|---|
| NADPH (cofactor) | 1 mM |
| Potassium Phosphate pH 7.4 | 100 mM |
| Magnesium Chloride | 5 mM |
| Test Article | 1 µL |

TABLE 13a

PEA stability observed in human, rat, mouse, and dog liver microsomes.

| | | % Remaining of Initial (n = 1) | | | | | Half-life[a] | $CL_{int}^{b}$ |
|---|---|---|---|---|---|---|---|---|
| Test Article | Species | 0 min | 10 min | 20 min | 30 min | 60 min | (min) | (mL/min/mg protein) |
| I-12 | Human | 100 | 105 | 96 | 91 | 73 | >60 | <0.0231 |
| | Rat | 100 | 85 | 77 | 62 | 52 | 58 | 0.0240 |
| | Mouse | 100 | 83 | 88 | 68 | 61 | >60 (82) | <0.0231 (0.0169) |
| | Dog | 100 | 93 | 79 | 78 | 60 | >60 (80) | <0.0231 (0.0173) |

[a]When the calculated half-life is longer than the duration of the experiment, half-life is expressed as > the longest incubation time. Similarly, if calculated half-life is less than the shortest time point, half-life is expressed as < that time point and calculated half-life is also listed in parentheses.
[b]Intrinsic clearance ($CL_{int}$) was calculated based on $CL_{int}$ = k/P, where k is elimination rate constant and P is protein concentration in the incubation.

| Control Compound | Species | Half-life (min) | $CL_{int}$ (ml/min/mg protein) | Acceptable Range ($t_{1/2}$, min) |
|---|---|---|---|---|
| Testosterone | Human | 21 | 0.0667 | ≤41 |
| | Rat | 1.4 | 1.01 | ≤15 |
| | Mouse | 3.1 | 0.444 | ≤15 |
| | Dog | 33 | 0.0419 | ≤40 |

TABLE 13b

Measured Concentrations of Drug.

| Dosed | | | Concentration (μM) | | | | |
|---|---|---|---|---|---|---|---|
| Test Article | Species | Analyte | 0 min | 10 min | 20 min | 30 min | 60 min |
| I-12 | Human | PEA | 0 | 0 | 0 | 0 | 0 |
| | Rat | | 0.022 | 0.022 | 0.015 | 0.011 | 0.0048 |
| | Mouse | | 0.037 | 0.038 | 0.030 | 0.022 | 0.011 |
| | Dog | | 0.019 | 0.032 | 0.036 | 0.035 | 0.033 |

Liver S9 Stability

Mixed gender human (Lot #1210091), male Sprague-Dawley rat (Lot #1410265), male CD-1 mouse (Lot #1510255), and male Beagle dog (Lott #1310285) liver S9 fraction were provided. The reaction mixture, minus cofactors, was prepared as described below. Test article was added into the reaction mixture at a final concentration of 1 μM. Control compounds, testosterone and 7-hydroxycoumarin (7-HC), were run simultaneously with the test article in a separate reaction. An aliquot of the reaction mixture (without cofactor cocktail) was equilibrated in a shaking water bath at 37° C. for 3 minutes. Reaction was initiated by the addition of cofactor cocktail (see below), and the mixture was then incubated in a shaking water bath at 37° C. Aliquots (100 μL) were withdrawn at 0, 10, 20, 30, and 60 minutes. Test article samples were immediately combined with 300 μL of ice-cold acetonitrile containing 1% formic acid. Control samples were immediately combined with 400 μL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodrug and expected drug (PEA). Analytical conditions are outlined in Appendix 13-1. Test article concentration at each time point was compared to the test article concentration at time 0 to determine the percent remaining at each time point. Half-lives were calculated using GraphPad software, fitting to a single-phase exponential decay equation. Results are shown in Tables 13c and 13d.

Reaction Composition

| Liver S9 Fraction | 1.0 mg/mL |
|---|---|
| NADPH (cofactor) | 1 mM |
| UDPGA (cofactor) | 1 mM |
| PAPS (cofactor) | 1 mM |
| GSH (cofactor) | 1 mM |
| Potassium Phosphate pH 7.4 | 100 mM |
| Magnesium Chloride | 5 mM |
| Test Article | 1 μM |

TABLE 13c

PEA stability observed in human, rat, mouse, and dog liver S9.

| | | % Remaining of Initial (n = 1) | | | | | Half-life$^a$ (min) | $CL_{int}^b$ (mL/min/mg protein) |
|---|---|---|---|---|---|---|---|---|
| Test Article | Species | 0 min | 10 min | 20 min | 30 min | 60 min | | |
| I-12 | Human | 100 | 89 | 73 | 68 | 43 | 49 | 0.0141 |
| | Rat | 100 | 82 | 85 | 75 | 61 | >60 (90) | <0.0116 (0.00769) |
| | Mouse | 100 | 75 | 66 | 58 | 50 | 53 | 0.0130 |
| | Dog | 100 | 69 | 53 | 51 | 47 | 43 | 0.0161 |

$^a$When calculated half-life is longer than the duration of the experiment, half-life is expressed as > the longest incubation time. Similarly, if calculated half-life is less than shortest time point, half-life is expressed as < that time point and calculated half-life is also listed in parentheses.
$^b$Intrinsic clearance ($CL_{int}$) was calculated based on $CL_{int}$ = k/P, where k is the elimination rate constant and P is the protein concentration in the incubation.

| Control Compound | Species | Half-life (min) | $CL_{int}$ (ml/min/mg protein) | Acceptable Range ($t_{1/2}$; min) |
|---|---|---|---|---|
| Testosterone | Human | 28 | 0.0247 | ≤34 |
| | Rat | 2.7 | 0.260 | ≤15 |
| | Mouse | 9.0 | 0.0770 | ≤37 |
| | Dog | 14 | 0.0493 | ≤42 |
| 7-hydroxycourmarin | Human | 15 | 0.0472 | ≤18 |
| | Rat | 1.9 | 0.362 | ≤15 |
| | Mouse | 2.2 | 0.313 | ≤15 |
| | Dog | 1.4 | 0.512 | ≤15 |

TABLE 13d

Measured Concentrations of Drug.

| Dosed | | | Concentration (μM) | | | | |
|---|---|---|---|---|---|---|---|
| Test Article | Species | Analyte | 0 min | 10 min | 20 min | 30 min | 60 min |
| I-12 | Human | PEA | 0.016 | 0.042 | 0.047 | 0.040 | 0.035 |
| | Rat | | 0 | 0.018 | 0.017 | 0.020 | 0 |
| | Mouse | | 0.037 | 0.049 | 0.041 | 0.033 | 0.021 |
| | Dog | | 0.026 | 0.047 | 0.053 | 0.051 | 0.033 |

Intestinal S9 Fraction Stability

Mixed-gender human (Lot #1410073), male Sprague-Dawley rat (Lot #1010042), male CD-1 mouse (Lot #1510194), and male Beagle dog (Lot #1510226) intestinal S9 fraction were provided. Reaction mixture, minus cofactors, was prepared as described below. Test article was added into the reaction mixture at a final concentration of 1 µM. Control compounds, testosterone and 7-hydroxycoumarin, were run simultaneously with the test article in a separate reaction. An aliquot of the reaction mixture (without cofactor cocktail) was equilibrated in a shaking water bath at 37° C. for 3 minutes. Reaction was initiated by the addition of cofactor cocktail, and the mixture was incubated in a shaking water bath at 37° C. Aliquots (100 µL) were withdrawn at 0, 10, 20, 30, and 60 minutes. Test article samples were immediately combined with 300 µL of ice-cold acetonitrile containing 1% formic acid. Control samples were immediately combined with 400 µL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodrug and expected drug (PEA). Analytical conditions are outlined in Appendix 13-1. Test article concentration at each time point was compared to test article concentration at time 0 to determine the percent remaining at each time point. Halflives were calculated using GraphPad software, fitting to a single-phase exponential decay equation. Results are shown in Tables 13e and 13f.

Reaction Composition

| | |
|---|---|
| Intestinal S9 Fraction | 1.0 mg/mL |
| NADPH (cofactor) | 1 mM |
| UDPGA (cofactor) | 1 mM |
| PAPS (cofactor) | 1 mM |
| GSH (cofactor) | 1 mM |
| Potassium Phosphate, pH 7.4 | 100 mM |
| Magnesium Chloride | 5 mM |
| Test Article | 1 µM |

TABLE 13e

PEA stability observed in human, rat, mouse, and dog intestinal S9 fraction.

| Test Article | Species | % Remaining of Initial (n = 1) | | | | | Half-life[a] (min) | $CL_{int}^{b}$ (mL/min/mg protein) |
|---|---|---|---|---|---|---|---|---|
| | | 0 min | 10 min | 20 min | 30 min | 60 min | | |
| I-12 | Human | 100 | 98 | 82 | 79 | 65 | >60 (89) | <0.0116 (0.00782) |
| | Rat | 100 | 92 | 88 | 74 | 53 | >60 (67) | <0.0116 (0.0103) |
| | Mouse | 100 | 80 | 58 | 64 | 43 | 46 | 0.0151 |
| | Dog | 100 | 61 | 44 | 48 | 47 | 41 | 0.0169 |

[a]When calculated half-life is longer than the duration of the experiment, half-life is expressed as > the longest incubation time. Similarly, if calculated half-life is less than shortest time point, half-life is expressed as < that time point and calculated half-life is also listed in parentheses.
[b]Intrinsic clearance ($CL_{int}$) was calculated based on $CL_{int}$ = k/P, where k is elimination rate constant and P is protein concentration in the incubation.

| Control Compound | Species | Half-life (min) | $CL_{int}$ (ml/min/mg protein) |
|---|---|---|---|
| Testosterone | Human | 14 | 0.0509 |
| | Rat | >60 | <0.0116 |
| | Mouse | >60 | <0.0116 |
| | Dog | >60 | <0.0116 |
| 7-hydroxycoumarin | Human | 9.9 | 0.0698 |
| | Rat | 22 | 0.0320 |
| | Mouse | 4.3 | 0.160 |
| | Dog | 8.7 | 0.0799 |

TABLE 13f

Measured Concentrations of Drug.

| Test Article | Species | Analyte | Concentration (µM) | | | | |
|---|---|---|---|---|---|---|---|
| | | | 0 min | 10 min | 20 min | 30 min | 60 min |
| I-12 | Human | PEA | 0.0089 | 0.023 | 0.024 | 0.032 | 0.043 |
| | Rat | | 0 | 0.039 | 0.056 | 0.074 | 0.10 |
| | Mouse | | 0.022 | 0.084 | 0.11 | 0.15 | 0.16 |
| | Dog | | 0.088 | 0.19 | 0.22 | 0.23 | 0.26 |

Plasma Stability

Studies were carried out in mixed-gender human plasma (Lot #AS1650-2), male Sprague-Dawley rat (Lot #RAT297944), male CD-1 mouse (Lot #MSE237700), and male Beagle dog (Lot #BGL91384), collected on sodium heparin. Plasma was adjusted to pH 7.4 prior to initiating the experiments. DMSO stocks were first prepared for test articles. Aliquots of the DMSO solutions were dosed into 700 µL of plasma, which had been pre-warmed to 37° C., at a final test article concentration of 1 µM, Aliquots (100 µL) were taken at each time point (0, 15, 30, 60, and 120 minutes) and were immediately combined with 300 µL of ice-cold acetonitrile containing 1% formic acid. Samples were stored at 4° C. until the end of experiment. After the final time point was sampled, the plate was mixed and then centrifuged at 3,000 rpm for 10 minutes. Calibration standards were prepared in matched matrix. Samples and standards were assayed by LC-MS/MS using electrospray ionization for both dosed prodrug and the expected drug (PEA). Analytical conditions are outlined in Appendix 13-1. Test article concentration at each time point was compared to test article concentration at time 0 to determine the percent remaining at each time point. Half-lives were calculated using GraphPad software, fitting to a single-phase exponential decay equation. Results are shown in Tables 13g and 13h.

TABLE 13g

PEA stability observed in human, rat mouse, and dog plasma.

| Test Article | Species | % Remaining of Initial (n = 1) | | | | | Half-life$^a$ (min) |
|---|---|---|---|---|---|---|---|
| | | 0 min | 15 min | 30 min | 60 min | 120 min | |
| I-12 | Human | 100 | 114 | 123 | 87 | 55 | >120 (137) |
| | Rat | 100 | 85 | 71 | 89 | 61 | >120 (216) |
| | Mouse | 100 | 104 | 107 | 74 | 42 | 102 |
| | Dog | 100 | 85 | 99 | 88 | 48 | >120 (146) |

TABLE 13h

Measured Concentrations of Drug.

| Dosed Test Article | Species | Analyte | Concentration (µM) | | | | |
|---|---|---|---|---|---|---|---|
| | | | 0 min | 15 min | 30 min | 60 min | 120 min |
| I-12 | Human | PEA | 0 | 0.016 | 0.026 | 0.025 | 0.042 |
| | Rat | | 0.031 | 0.059 | 0.073 | 0.099 | 0.13 |
| | Mouse | | 0.046 | 0.073 | 0.094 | 0.098 | 0.10 |
| | Dog | | 0 | 0.023 | 0.027 | 0.039 | 0.048 |

Simulated Intestinal Fluid Stability

Studies were carried out in simulated intestinal fluid in the presence of various enzymes. Simulated intestinal fluid was prepared by dissolving 6.8 g of monobasic potassium phosphate in 1.0 L of water. Aliquots of this solution were taken and the pH was adjusted to 6.8. Individual enzymes were then spiked into aliquots for each experiment. A DMSO stock was first prepared for test article. Aliquots of the DMSO solution were dosed into 700 µL of matrix, which had been pre-warmed to 37° C., at a final test article concentration of 1 µM. Aliquots (100 µL) were taken at each time point (0, 15, 30, 60, and 120 minutes) and were immediately combined with 300 µL of ice-cold acetonitrile containing 1% formic acid. Samples were stored at 4° C. until the end of experiment. After final time point was sampled, the plate was mixed and then centrifuged at 3,000 rpm for 10 minutes. Calibration standards were prepared in matched matrix. Samples and standards were assayed by LC-MS/MS using electrospray ionization for both dosed prodrug and expected drug (PEA). Analytical conditions are outlined in Appendix 13-1. Test article concentration at each time point was compared to test article concentration at time 0 to determine the percent remaining at each time point. Half-lives were calculated using GraphPad software, fitting to a single-phase exponential decay equation. Results were shown in Tables 13i and 13j.

TABLE 13i

PEA stability observed in simulated intestinal fluid (SIF).

| Test Article | Treatment | % Remaining of Initial (n = 1) | | | | | Half-life$^a$ (min) |
|---|---|---|---|---|---|---|---|
| | | 0 min | 15 min | 30 min | 60 min | 120 min | |
| I-12 | SIF + Pancreatin | 100 | 24 | 14 | 4.7 | <1.0 | <15 (8.2) |
| | SIF + Elastase | 100 | 101 | 88 | 63 | 33 | 79 |
| | SIF + Carboxypeptidase A | 100 | 74 | 71 | 25 | 12 | 38 |
| | SIF + Carboxypeptidase B | 100 | 71 | 48 | 24 | 3.4 | 28 |
| | SIF + Chymotrypsin | 100 | 86 | 64 | 31 | 4.1 | 37 |
| | SIF + Trypsin | 100 | 77 | 55 | 64 | 37 | 86 |

TABLE 13j

Measured Concentrations of Drug.

| Test Article | Treatment | Analyte | Concentration (µM) | | | | |
|---|---|---|---|---|---|---|---|
| | | | 0 min | 15 min | 30 min | 60 min | 120 min |
| I-12 | SIF + Pancreatin | PEA | — | — | — | — | — |
| | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |

PEA was found to be endogenous in pancreatin and thus could not be quantified in the assay samples.

Appendix 13-1

Liquid Chromatography

| Column: | Waters ACQUITY UPLC BEH C18 30 × 2.1 mm, 1.7 μm |
|---|---|
| M.P. Buffer: | 25 mM ammonium formate buffer,, pH 3.5 |
| Aqueous Reservoir (A): | 90% water, 10% buffer |
| Organic Reservoir (B): | 90% acetonitrile, 10% buffer |
| Flow Rate: | 0.8 mL/minute |
| Gradient Program: | |

TABLE 13-1

Liquid Chromatography Gradient Program

| Time (mm) | % A | % B |
|---|---|---|
| 0.00 | 50 | 50 |
| 0.75 | 1 | 99 |
| 1.50 | 1 | 99 |
| 1.55 | 50 | 50 |
| 1.75 | 50 | 50 |

| Total Run Time: | 1.75 minutes |
|---|---|
| Autosampler: | 10 μL injection volume |
| Wash1: | water/methanol/2-propanol: 1/1/1; with 0.2% formic acid |
| Wash2: | 0.1% formic acid in water |
| Mass Spectrometer | |
| Instrument: | PE SCIEX API 4000 |
| Interface: | Turbo Ionspray |
| Mode: | Multiple reaction monitoring |
| Method: | 1.75 minute duration |
| Settings: | |

TABLE 13-2

Mass Spectrometer Settings

| Test Article | Q1/Q3 | DP | EP | CE | CXP | IS | TEM | CAD | CUR | GS1 | GS2 |
|---|---|---|---|---|---|---|---|---|---|---|---|
| I-12 | +1042.9/282.4 | 175 | 10 | 49 | 18 | 5500 | 500 | 7 | 30 | 50 | 50 |
|  | +1059.9/282.4 | 60 | 10 | 62 | 18 | 5500 | 500 | 7 | 30 | 50 | 50 |
|  | +1059.9/1043.0 | 60 | 10 | 29 | 37 | 5500 | 500 | 7 | 30 | 50 | 50 |
| PEA | +300.3/62.1 | 123 | 10 | 29 | 10 | 5500 | 500 | 7 | 30 | 50 | 50 |

Example 14: PEA Stability in Simulated Intestinal Fluid

Simulated Intestinal Fluid Stability

Studies were carried out in simulated intestinal fluid containing pancreatin. Simulated intestinal fluid was prepared by dissolving 6.8 g of monobasic potassium phosphate in 1.0 L of water. Pancreatin was then added to the solution and the pH was adjusted to 6.8. A DMSO stock was first prepared for test articles. Aliquots of DMSO solution were dosed into 300 μL of matrix, which had been pre-warmed to 37° C., at a final test article concentration of 1 μM. An individual tube was dosed for each time point. At each time point (0, 15, 30, 60, and 120 minutes), 900 μL of ice-cold acetonitrile containing 1.0% formic acid was added to an individual tube. The starting time for each tube was staggered such that all time points would finish at the same time. After the conclusion of the experiment, tubes were mixed and then centrifuged at 3,000 rpm for 10 minutes. Calibration standards were prepared in matched matrix. Samples and standards were assayed by LC-MS/MS using electrospray ionization. Analytical conditions are outlined in Appendix 14-1. Test article concentration at each time point was compared to test article concentration at time 0 to determine the percent remaining at each time point. Halflives were calculated using GraphPad software, fitting to a single-phase exponential decay equation. Results are shown in Tables 14a and 14b.

TABLE 14a

PEA stability observed in simulated intestinal fluid (SIF).

| | | % Remaining of Initial (n = 1) | | | | | Half-life[a] (min) |
|---|---|---|---|---|---|---|---|
| Test Article | Treatment | 0 min | 15 min | 30 min | 60 min | 120 min | |
| I-8 | SIF + Pancreatin | 100 | 17 | 6.8 | <1.3 | <1.3 | 6.2 |
| I-16 | SIF + Pancreatin | 100 | <4.5 | <4.5 | <4.5 | <4.5 | ND |

TABLE 14b

Measured Concentrations of Drug.

| | | Concentration (μM) | | | | |
|---|---|---|---|---|---|---|
| Test Article | Treatment | 0 min | 15 min | 30 min | 60 min | 120 min |
| I-8 | SIF + Pancreatin | 0.94 | 0.16 | 0.064 | 0 | 0 |
| I-16 | SIF + Pancreatin | 0.088 | 0 | 0 | 0 | 0 |

Appendix 14-1

| Column: | Waters ACQUITY UPLC BEH C18 30 × 2.1 mm, 1.7 μm |
|---|---|
| M.P. Buffer: | 25 mM ammonium formate buffer,, pH 3.5 |
| Aqueous Reservoir (A): | 90% water, 10% buffer |
| Organic Reservoir (B): | 90% acetonitrile, 10% buffer |
| Flow Rate: | 0.7 mL/minute |
| Gradient Program: | |

| Time (mm) | % A | % B |
|---|---|---|
| 0.0 | 50 | 50 |
| .75 | 1 | 99 |
| 1.00 | 1 | 99 |

-continued

| | | |
|---|---|---|
| 1.05 | 50 | 50 |
| 1.50 | 50 | 50 |

| | |
|---|---|
| Total Run Time: | 1.5 minutes |
| Autosampler: | 1 µL injection volume |
| Wash1: | water/methanol/2-propanol: 1/1/1; with 0.2% formic acid |
| Wash2: | 0.1% formic acid in water |
| Mass Spectrometer | |
| Instrument: | PE SCIEX API 4000 |
| Interface: | Turbo Ionspray |
| Mode: | Multiple reaction monitoring |
| Method: | 1.5 minute duration |
| Settings: | |

TABLE 14-2

Mass Spectrometer Settings

| Test Article | Q1/Q3 | DP | EP | CE | CXP | IS | TEM | CAD | CUR | GS1 | GS2 |
|---|---|---|---|---|---|---|---|---|---|---|---|
| I-8 | +474.3/282.2 | 112 | 10 | 28 | 18 | 5500 | 500 | 7 | 30 | 50 | 50 |
| I-16 | +614.5/282.6 | 123 | 10 | 37 | 18 | 5500 | 500 | 7 | 30 | 50 | 50 |

Example 15: Determination of the Bioavailability of Palmitoylethanolamide (PEA) Following Oral Administration of PEA-Prodrug in Male Sprague-Dawley Rats The present Example describes oral bioavailability of PEA following administration of PEA prodrugs in male Sprague-Dawley rats.

Oral bioavailability of palmitoylethanolamide (PEA) was evaluated in male Sprague-Dawley rats following oral administration of PEA pro-drugs, I-15 and I-14. Each test article was dosed orally (PO) at 20.7 mg/kg, which was equivalent to a 10 mg/kg dose of PEA. Blood samples were collected up to 8 hours post-dose, and plasma concentrations of PEA were determined by LC-MS/MS. Following PO dosing of I-15 (in 20% (Solutol HS15:NMP 1:1) 10% PEG400; 70% H$_2$O), average C$_{max}$ of 11.7±2.34 ng/mL was observed between 15 minutes and 1 hour post dose. Average exposure for I-15 (Group 1) based on the dose-normalized AUC$_{last}$ was 2.13±1.05 hr*kg*ng/mL/mg. Based on the IV data from Example 5, average oral bioavailability for I-15 (Group 1) was 3.42±1.69%. Following PO dosing of I-14 (in 20% (Solutol HS15:NMP 1:1) 10% PEG400; 70% H$_2$O), average C$_{max}$ of 16.9±1.47 ng/mL was observed at 30 minutes post dose in all rats. Average exposure for I-14 (Group 2) based on dose-normalized AUC$_{last}$ was 2.72±0.854 hr*kg*ng/mL/mg. Based on the IV data from Example 5, average oral bioavailability for I-14 (Group 2) was 4.39±1.37%.

Preparation of Dosing Formulations

Pro-drugs were dosed so that a total dose of 10 mg/kg of PEA was administered. Prodrugs were formulated in a vehicle comprised of 10% Solutol HS15, 10% n-methyl pyrrolidone (NMP), 10% polyethylene glycol 400 (PEG400) and 70% water.

Animal Dosing

Pharmacokinetics of PEA was evaluated in fasted male Sprague-Dawley rats. Rats were housed one per cage. Each rat was fitted with a jugular vein cannula (JVC) for blood collection. Each study group was dosing in triplicate. Rats were fasted for a minimum of twelve hours prior to dosing. Food was returned at four hours post dosing. Animals had free access to water throughout the study. Blood samples (~300 µL) were collected from the rats via a JVC and placed into chilled polypropylene tubes containing sodium heparin as an anticoagulant, and 30 µL of 0.5 M citric acid. Samples were maintained chilled throughout processing. Blood samples were centrifuged at 4° C. and 3,000 g for 5 minutes. Plasma (~150 µL) was then transferred to a chilled, labeled polypropylene tube containing 15 µL of 10% formic acid, placed on dry ice, and stored in a freezer maintained at −60° C. to −80° C. Blood sampling times are shown in Table 15a.

TABLE 15a

Study Design.

| Dose group | Test Article | Dosing Route | Total Animals n = | Dose (mg/kg of pro-drug)* | Dosing Solution Conc. (mg/mL) | Dosing Volume (mL/kg) | Vehicle | Blood Sample Time Points |
|---|---|---|---|---|---|---|---|---|
| 1 | I-15 | PO | 3 | 20.7 | 3 | 6.9 | 20% (Solutol HS15:NMP 1:1) 10% PEG400; 70% H$_2$O | Pre-dose, 5, 15, 30 min, 1, 2, 4, 8 hours |
| 2 | I-14 | PO | 3 | 20.7 | 3 | 6.9 | 20% (Solutol HS15:NMP 1:1) 10% PEG400; 70% H$_2$O | Predose, 5, 15, 30 min, 1, 2, 4, 8 hours |

*All doses are based on mg/kg of the pro-drugs, and deliver 10 mg/kg of active drug, PEA.

An LC-MS/MS method for the determination of PEA and PEA-prodrug is described above (see e.g., Example 3).

Pharmacokinetic parameters were calculated from the time course of the plasma concentration. Maximum plasma concentration ($C_{max}$) and the time to reach maximum plasma drug concentration ($T_{max}$) after oral dosing were observed from data. Area under the time concentration curve (AUC) was calculated using the linear trapezoidal rule with calculation to the last quantifiable data point, and with extrapolation to infinity if applicable. At least three quantifiable data points were required to determine the AUC. Plasma half-life ($t_{1/2}$) was calculated from 0.693/slope of the terminal elimination phase. Mean residence time, MRT, was calculated by dividing area under the moment curve (AUMC) by AUC. Bioavailability was determined by dividing individual dose-normalized PO $AUC_{last}$ values by the average IV $AUC_{last}$ value (IV data from Example 5). Samples below the limit of quantitation were treated as zero for pharmacokinetic data analysis.

Results

No adverse reactions were observed following the oral administration of PEA pro-drug in male Sprague-Dawley rats in this study. Dosing solutions were not analyzed by LC-MS/MS. Nominal dosing level was used in all calculations. Individual and average plasma concentrations for PEA and are shown in Table 15b and Table 15c. Data are expressed as ng/mL of the free drug. Samples that were below the limit of quantitation were not used in the calculation of averages. Plasma concentrations versus time data are plotted in FIGS. 15A through 15D. Endogenous levels of PEA found in all rats were below the limit of quantitation; and therefore, measured concentrations of PEA in plasma samples were not corrected.

TABLE 15b

Individual and Average Plasma Concentrations (ng/mL) and Pharmacokinetic Parameters for PEA after Oral Administration of I-15 in 20% Solutol HS 15:NMP (1:1), 10% PEG400, 70% $H_2O$ at 20.7 mg/kg in Male Sprague-Dawley Rats (Group 1)
Oral (20.7 mg/kg I-15 equals 10 mg/kg PEA)

| | Rat # | | | | |
|---|---|---|---|---|---|
| Time (hr) | 305 | 306 | 307 | Mean | SD |
| 0 (pre-dose) | BLOQ | BLOQ | BLOQ | ND | ND |
| 0.083 | BLOQ | 3.92 | BLOQ | 3.92 | ND |
| 0.25 | 8.62 | 9.44 | 9.00 | 9.02 | 0.410 |
| 0.50 | 11.4 | 12.6 | 8.92 | 11.0 | 1.88 |
| 1.0 | 13.4 | 6.95 | 4.60 | 8.32 | 4.56 |
| 2.0 | 9.93 | 10.7 | 4.36 | 8.33 | 3.46 |
| 4.0 | BLOQ | 3.41 | BLOQ | ND | ND |
| 8.0 | BLOQ | BLOQ | BLOQ | ND | ND |
| Animal Weight (kg) | 0.250 | 0.235 | 0.247 | 0.244 | 0.008 |
| Volume Dosed (mL) | 1.73 | 1.62 | 1.70 | 1.68 | 0.06 |
| $C_{max}$ (ng/mL) | 13.4 | 12.6 | 9.00 | 11.7 | 2.34 |
| $t_{max}$ (hr) | 1.0 | 0.50 | 0.25 | 0.58 | 0.38 |
| $t_{1/2}$ (hr) | ND[3] | ND[4] | ND[4] | ND | ND |
| $MRT_{last}$ (hr) | 1.07 | 1.69 | 0.917 | 1.23 | 0.409 |
| $AUC_{last}$ (hr ng/mL) | 21.1 | 31.9 | 10.9 | 21.3 | 10.5 |
| $AUC_\infty$ (hr ng/mL) | ND[3] | ND[4] | ND[4] | ND | ND |
| Dose-normalized Values[1] | | | | | |
| $AUC_{last}$ (hr kg ng/mL/mg) | 2.11 | 3.19 | 1.09 | 2.13 | 1.05 |
| $AUC_\infty$ (hr kg ng/mL/mg) | ND[3] | ND[4] | ND[4] | ND | ND |
| Bioavailability (%)[2] | 3.40 | 5.13 | 1.75 | 3.42 | 1.69 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.
[4]Not determined because the line defining the terminal elimination phase had an $r^2 > 0.85$.

TABLE 15b

Individual and Average Plasma Concentrations (ng/mL) and Pharmacokinetic Parameters for PEA after Oral Administration of I-14 in 20% Solutol HS15:NMP (1:1), 10% PEG400, 70% $H_2O$ at 20.7 mg/kg in Male Sprague-Dawley Rats (Group 1)
Oral (20.7 mg/kg I-14 equals 10 mg/kg PEA)

| | Rat # | | | | |
|---|---|---|---|---|---|
| Time (hr) | 308 | 309 | 310 | Mean | SD |
| 0 (pre-dose) | BLOQ | BLOQ | BLOQ | ND | ND |
| 0.083 | 4.46 | BLOQ | 4.54 | 4.50 | ND |
| 0.25 | 11.3 | 4.91 | 14.1 | 10.1 | 4.71 |
| 0.50 | 15.8 | 16.4 | 18.6 | 16.9 | 1.47 |
| 1.0 | 14.8 | 13.7 | 11.0 | 13.2 | 1.96 |
| 2.0 | 9.02 | 5.99 | 9.41 | 8.14 | 1.87 |
| 4.0 | BLOQ | BLOQ | 3.97 | ND | ND |
| 8.0 | BLOQ | BLOQ | BLOQ | ND | ND |
| Animal Weight (kg) | 0.239 | 0.248 | 0.249 | 0.245 | 0.006 |
| Volume Dosed (mL) | 1.65 | 1.71 | 1.72 | 1.69 | 0.04 |
| $C_{max}$ (ng/mL) | 15.8 | 16.4 | 18.6 | 16.9 | 1.47 |
| $t_{max}$ (hr) | 0.50 | 0.50 | 0.50 | 0.50 | 0.00 |
| $t_{1/2}$ (hr) | ND[3] | ND[3] | 1.96 | ND | ND |
| $MRT_{last}$ (hr) | 0.970 | 0.959 | 1.54 | 1.16 | 0.331 |
| $AUC_{last}$ (hr ng/mL) | 24.4 | 20.4 | 36.8 | 27.2 | 8.54 |
| $AUC_\infty$ (hr ng/mL) | ND[3] | ND[3] | 48.1 | ND | ND |
| Dose-normalized Values[1] | | | | | |
| $AUC_{last}$ (hr kg ng/mL/mg) | 2.44 | 2.04 | 3.68 | 2.72 | 0.854 |
| $AUC_\infty$ (hr kg ng/mL/mg) | ND[3] | ND[3] | 4.81 | ND | ND |
| Bioavailability (%)[2] | 3.94 | 3.29 | 5.93 | 4.39 | 1.37 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.

Example 16: Determined of Bioavailability of Palmitoylethanolamide (PEA) Following Oral Administration of PEA-Prodrug in Male Sprague-Dawley Rats The present Example describes oral bioavailability of PEA following administration of PEA prodrugs I-8 and I-16 in male Sprague-Dawley rats according to the methods described in, e.g., Example 15. Individual and average plasma concentrations for PEA and are shown in Table 16a and Table 16b. Plasma concentrations versus time data are plotted in FIGS. 9A through 9D.

TABLE 16a

Individual and Average Plasma Concentrations (ng/mL) and Pharmacokinetic Parameters for PEA after Oral Administration of I-8 in 20% Solutol HS15:NMP (1:1). 10% PEG400, 70% H$_2$O) at 16 mg/kg in Male Sprague-Dawley Rats (Group 1).
Oral (16 mg/kg I-8 equals 10 mg/kg PEA)

| | Rat # | | | | |
|---|---|---|---|---|---|
| Time (hr) | 317 | 318 | 319 | Mean | SD |
| 0 | BLOQ | BLOQ | BLOQ | ND | ND |
| 0.083 | 3.06 | 3.99 | 4.73 | 3.93 | 0.837 |
| 0.25 | 11.2 | 8.54 | 11.4 | 10.4 | 1.60 |
| 0.50 | 52.5 | 33.1 | 42.9 | 42.8 | 9.70 |
| 1.0 | 65.1 | 41.4 | 65.0 | 57.2 | 13.7 |
| 2.0 | 29.2 | 26.9 | 21.8 | 26.0 | 3.79 |
| 4.0 | 8.08 | 6.40 | 7.22 | 7.23 | 0.840 |
| 8.0 | BLOQ | 2.50 | BLOQ | ND | ND |
| Animal Weight (kg) | 0.275 | 0.269 | 0.271 | 0.272 | 0.003 |
| Volume Dosed (mL) | 1.46 | 1.43 | 1.44 | 1.44 | 0.02 |
| C$_{max}$ (ng/mL) | 65.1 | 41.4 | 65.0 | 57.2 | 13.7 |
| t$_{max}$ (hr) | 1.0 | 1.0 | 1.0 | 1.0 | 0.0 |
| t$_{1/2}$(hr) | ND$^3$ | 1.86 | ND$^3$ | ND | ND |
| MRT$_{last}$ (hr) | 1.56 | 2.23 | 1.49 | 1.76 | 0.411 |
| AUC$_{last}$ (hr ng/mL) | 114 | 105 | 103 | 107 | 6.17 |
| AUC$_∞$ (hr ng/mL) | ND$^3$ | 112 | ND$^3$ | ND | ND |
| Dose-normalized Values$^1$ | | | | | |
| AUC$_{last}$ (hr kg ng/mL/mg) | 11.4 | 10.5 | 10.3 | 10.7 | 0.617 |
| AUC$_∞$ (hr kg ng/mL/mg) | ND$^3$ | 11.2 | ND$^3$ | ND | ND |
| Bioavailability (%)$^2$ | 18.4 | 16.9 | 16.5 | 17.3 | 0.994 |

C$_{max}$: maximum plasma concentration;
t$_{max}$: time of maximum plasma concentration;
t$_{1/2}$: half-life, data points used for half-life determination are in bold;
MRT$_{last}$: mean residence time, calculated to the last observable time point;
AUC$_{last}$: area under the curve, calculated to the last observable time point;
AUC$_∞$: area under the curve, extrapolated to infinity;
ND: not determined;
BLOQ: below the limit of quantitation (2.5 ng/mL);
$^1$Dose-normalized by dividing the parameter by nominal dose in mg/kg;
$^2$Bioavailability determined by dividing individual dose-normalized oral AUC$_{last}$ values by the average IV AUC$_{last}$ value 62.1 hr*ng/mL from Example 5;
$^3$Not determined due to lack of quantifiable data points trailing the C$_{max}$.

TABLE 16b

Individual and Average Plasma Concentrations (ng/mL) and Pharmacokinetic Parameters for PEA after Oral Administration of I-16 in 20% Solutol HS15:NMP (1:1), 10% PEG400. 70% H$_2$O) at 16 mg/kg in Male Sprague-Dawley Rats (Group 1).
Oral (16 mg/kg I-16 equals 10 mg/kg PEA)

| | Rat # | | | | |
|---|---|---|---|---|---|
| Time (hr) | 320 | 321 | 322 | Mean | SD |
| 0 | BLOQ | BLOQ | BLOQ | ND | ND |
| 0.083 | 2.79 | 2.93 | BLOQ | 2.86 | ND |
| 0.25 | 8.32 | 5.06 | 4.65 | 6.01 | 2.01 |
| 0.50 | 43.4 | 23.0 | 18.5 | 28.3 | 13.3 |
| 1.0 | 55.0 | 34.3 | 40.2 | 43.2 | 10.7 |
| 2.0 | 27.8 | 14.0 | 12.8 | 18.2 | 8.34 |
| 4.0 | 6.81 | 8.79 | 5.15 | 6.92 | 1.82 |
| 8.0 | BLOQ | BLOQ | BLOQ | ND | ND |
| Animal Weight (kg) | 0.279 | 0.269 | 0.278 | 0.275 | 0.006 |
| Volume Dosed (mL) | 1.93 | 1.86 | 1.92 | 1.90 | 0.04 |
| C$_{max}$ (ng/mL) | 55.0 | 34.3 | 40.2 | 43.2 | 10.7 |
| t$_{max}$ (hr) | 1.0 | 1.0 | 1.0 | 1.0 | 0.0 |
| t$_{1/2}$(hr) | ND$^3$ | ND$^3$ | ND$^3$ | ND | ND |
| MRT$_{last}$ (hr) | 1.58 | 1.72 | 1.54 | 1.62 | 0.0980 |

TABLE 16b-continued

Individual and Average Plasma Concentrations (ng/mL) and Pharmacokinetic Parameters for PEA after Oral Administration of I-16 in 20% Solutol HS15:NMP (1:1), 10% PEG400. 70% H$_2$O) at 16 mg/kg in Male Sprague-Dawley Rats (Group 1).
Oral (16 mg/kg I-16 equals 10 mg/kg PEA)

| | Rat # | | | | |
|---|---|---|---|---|---|
| Time (hr) | 320 | 321 | 322 | Mean | SD |
| AUC$_{last}$ (hr ng/mL) | 101 | 62.5 | 61.7 | 75.0 | 22.4 |
| AUC$_∞$ (hr ng/mL) | ND$^3$ | ND$^3$ | ND$^3$ | ND | ND |
| Dose-normalized Values$^1$ | | | | | |
| AUC$_{last}$ (hr kg ng/mL/mg) | 10.1 | 6.25 | 6.17 | 7.50 | 2.24 |
| AUC$_∞$ (hr kg ng/mL/mg) | ND$^3$ | ND$^3$ | ND$^3$ | ND | ND |
| Bioavailability (%)$^2$ | 16.2 | 10.1 | 9.93 | 12.1 | 3.60 |

C$_{max}$: maximum plasma concentration;
t$_{max}$: time of maximum plasma concentration;
t$_{1/2}$: half-life, data points used for half-life determination are in bold;
MRT$_{last}$: mean residence time, calculated to the last observable time point;
AUC$_{last}$: area under the curve, calculated to the last observable time point;
AUC$_∞$: area under the curve, extrapolated to infinity;
ND: not determined;
BLOQ: below the limit of quantitation (2.5 ng/mL);
$^1$Dose-normalized by dividing the parameter by nominal dose in mg/kg;
$^2$Bioavailability determined by dividing individual dose-normalized oral AUC$_{last}$ values by the average IV AUC$_{last}$ value 62.1 hr*ng/mL from Example 5;
$^3$Not determined due to lack of quantifiable data points trailing the C$_{max}$.

Example 17: PEA Stability in Human, Rat, Mouse and Dog Liver Microsomes, Human, Rat, Mouse and Dog Liver S9 Fraction, Human, Rate, Mouse and Dog Intestinal S9 Fraction, Human Rat, Mouse and Dog Plasma, and Simulated Intestinal Fluid The present Example describes PEA stability observed in 1) human, rat, mouse, and dog liver microsomes; 2) human, rat, mouse, dog liver S9 fraction; human, rat, mouse, and dog intestinal S9 fraction; 4) human, rat, mouse, and dog plasma; and 5) simulated intestinal fluid containing various enzymes.

Liver Microsomal Stability

Mixed-gender human (Lot #1010420), male Sprague-Dawley rat (Lot #1510115), male CD-1 mouse (Lot #1610148), and male Beagle dog (Lot #1110044) liver microsomes were provided. Reaction mixture, minus cofactors, was prepared as described below. Test article was added into the reaction mixture at a final concentration of 1 µM. Control compound, testosterone, was run simultaneously with the test article in a separate reaction. An aliquot of the reaction mixture (without cofactor) was equilibrated in a shaking water bath at 37° C. for 3 minutes. Reaction was initiated by the addition of cofactor, and the mixture was incubated in a shaking water bath at 37° C. Aliquots (100 µL) were withdrawn at 0, 10, 20, 30, and 60 minutes. Test article samples were immediately combined with 300 µL, of ice-cold acetonitrile containing 1% formic acid. Control samples were immediately combined with 400 µL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodnig and expected drug (PEA). Analytical conditions are outlined in Appendix 17-1. Test article concentration at each time point was compared to test article concentration at time 0 to determine the percent remaining at each time point. Half-lives were calculated using GraphPad software, fitting to a single-phase exponential decay equation. Results are shown in Tables 17a and 17b.

Reaction Composition

| | |
|---|---|
| Liver Microsomes | 0.5 mg/mL |
| NADPH (cofactor) | 1 mM |
| Potassium Phosphate pH 7.4 | 100 mM |
| Magnesium Chloride | 5 mM |
| Test Article | 1 μL |

TABLE 17a

PEA stability observed in human, rat, mouse, and dog liver microsomes.

| Test Article | Species | 0 min | 10 min | 20 min | 30 min | 60 min | Half-life$^a$ (min) | $CL_{int}^b$ (mL/min/mg protein) |
|---|---|---|---|---|---|---|---|---|
| I-8 | Human | 100 | 2.8 | <1.0 | <1.0 | <1.0 | <10 (2.0) | >0.139 (0.712) |
| | Rat | 100 | 4.3 | 1.2 | <1.0 | <1.0 | <10 (2.2) | >0.139 (0.624) |
| | Mouse | 100 | <1.0 | <1.0 | <1.0 | <1.0 | <1.0 | >1.38 |
| | Dog | 100 | <1.0 | <1.0 | <1.0 | <1.0 | <1.0 | >1.38 |
| I-16 | Human | 100 | 8.0 | 3.5 | 1.9 | <1.0 | <10 (2.8) | >0.139 (0.493) |
| | Rat | 100 | 9.7 | 4.2 | 3.1 | <1.0 | <10 (3.1) | >0.139 (0.452) |
| | Mouse | 100 | 7.6 | 3.0 | 2.1 | 1.8 | <10 (2.8) | >0.139 (0.503) |
| | Dog | 100 | 4.4 | 1.6 | 1.4 | 1.5 | <10 (2.2) | >0.139 (0.618) |

% Remaining of Initial (n = 1)

$^a$When the calculated half-life is longer than the duration of the experiment, half-life is expressed as > the longest incubation time. Similarly, if calculated half-life is less than the shortest time point, half-life is expressed as < that time point and calculated half-life is also listed in parentheses.
$^b$Intrinsic clearance ($CL_{int}$) was calculated based on $CL_{int}$ = k/P, where k is elimination rate constant and P is protein concentration in the incubation.

| Control Compound | Species | Half-life (min) | $CL_{int}$ (ml/min/mg protein) | Acceptable Range ($t_{1/2}$, min) |
|---|---|---|---|---|
| Testosterone | Human | 9.2 | 0.151 | ≤41 |
| | Rat | 1.5 | 0.911 | ≤15 |
| | Mouse | 2.1 | 0.674 | ≤15 |
| | Dog | 23 | 0.0593 | ≤40 |

TABLE 17b

Measured Concentrations of Drug.

| Dosed Test Article | Species | Analyte | 0 min | 10 min | 20 min | 30 min | 60 min |
|---|---|---|---|---|---|---|---|
| I-8 | Human | PEA | 0.063 | 0.34 | 0.25 | 0.21 | 0.070 |
| | Rat | | 0.033 | 0.041 | 0.019 | 0 | 0 |
| | Mouse | | 0.45 | 0.30 | 0.15 | 0.086 | 0 |
| | Dog | | 0.33 | 0.54 | 0.46 | 0.44 | 0.20 |
| I-16 | Human | | 0 | 0.22 | 0.15 | 0.14 | 0.069 |
| | Rat | | 0.025 | 0.033 | 0.015 | 0 | 0 |
| | Mouse | | 0.29 | 0.27 | 0.12 | 0.089 | 0.0093 |
| | Dog | | 0.053 | 0.59 | 0.48 | 0.43 | 0.20 |

Concentration (μM)

Liver S9 Stability

Mixed gender human (Lot #0910396), male Sprague-Dawley rat (Lot #1410265), male CD-1 mouse (Lot #1310026), and male Beagle dog (Lot #1310285) liver S9 fraction were provided. Reaction mixture, minus cofactors, was prepared as described below. Test article was added into the reaction mixture at a final concentration of 1 μM. Control compounds, testosterone and 7-hydroxycoumarin (7-HC), were run simultaneously with the test article in a separate reaction. An aliquot of the reaction mixture (without cofactor cocktail) was equilibrated in a shaking water bath at 37° C. for 3 minutes. Reaction was initiated by the addition of cofactor cocktail (see below), and the mixture was then incubated in a shaking water bath at 37° C. Aliquots (100 μL) were withdrawn at 0, 10, 20, 30, and 60 minutes. Test article samples were immediately combined with 300 μL of ice-cold acetonitrile containing 1% formic acid. Control samples were immediately combined with 400 μL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodrug and the expected drug (PEA). Analytical conditions are outlined in Appendix 17-1. Test article concentration at each time point was compared to test article concentration at time 0 to determine the percent remaining at each time point. Half-lives were calculated using GraphPad software, fitting to a single-phase exponential decay equation. Results are shown in Tables 17c and 17d.

Reset Composition

| | |
|---|---|
| Liver S9 Fraction | 1.0 mg/mL |
| NADPH (cofactor) | 1 mM |
| UDPGA (cofactor) | 1 mM |
| PAPS (cofactor) | 1 mM |
| GSH (cofactor) | 1 mM |
| Potassium Phosphate pH 7.4 | 100 mM |
| Magnesium Chloride | 5 mM |
| Test Article | 1 μM |

TABLE 17c

PEA stability observed in human, rat, mouse, and dog liver S9.

| Test Article | Species | 0 min | % Remaining of Initial (n = 1) 10 min | 20 min | 30 min | 60 min | Half-life$^a$ (min) | $CL_{int}^b$ (mL/min/ mg protein) |
|---|---|---|---|---|---|---|---|---|
| I-8 | Human | 100 | 1.4 | <1.0 | <1.0 | <1.0 | <10 (1.6) | >0.0693 (0.431) |
| | Rat | 100 | 17 | 2.8 | <1.0 | <1.0 | <10 (3.9) | >0.0693 (0.177) |
| | Mouse | 100 | 4.6 | 1.0 | <1.0 | <1.0 | <10 (2.3) | >0.0693 (0.305) |
| | Dog | 100 | 32 | 11 | 3.5 | <1.0 | <10 (6.1) | >0.0693 (0.113) |
| I-16 | Human | 100 | 4.9 | 2.1 | <1.0 | <1.0 | <10 (2.3) | >0.0693 (0.299) |
| | Rat | 100 | 3.0 | <1.0 | <1.0 | <1.0 | <10 (2.0) | >0.0693 (0.352) |
| | Mouse | 100 | 3.7 | <1.0 | <1.0 | <1.0 | <10 (2.1) | >0.0693 (0.330) |
| | Dog | 100 | 2.1 | <1.0 | <1.0 | <1.0 | <10 (1.8) | >0.0693 (0.385) |

$^a$When the calculated half-life is longer than the duration of the experiment, half-life is expressed as > the longest incubation time. Similarly, if calculated half-life is less than the shortest time point, half-life is expressed as < that time point and calculated half-life is also listed in parentheses.
$^b$Intrinsic clearance ($CL_{int}$) was calculated based on $CL_{int} = k/P$, where k is the elimination rate constant and P is the protein concentration in the incubation.

| Control Compound | Species | Half-life (min) | $CL_{int}$ (ml/min/mg protein) | Acceptable Range ($t_{1/2}$, min) |
|---|---|---|---|---|
| Testosterone | Human | 15 | 0.0463 | ≤34 |
| | Rat | 2.7 | 0.260 | ≤15 |
| | Mouse | 17 | 0.0417 | ≤37 |
| | Dog | 25 | 0.0272 | ≤42 |
| 7-hydroxycoumarin | Human | 11 | 0.0628 | ≤18 |
| | Rat | 2.5 | 0.283 | ≤15 |
| | Mouse | 4.3 | 0.162 | ≤15 |
| | Dog | 2.1 | 0.334 | ≤15 |

TABLE 17d

Measured Concentrations of Drug.

| Dosed Test Article | Species | Analyte | 0 min | Concentration (µM) 10 min | 20 min | 30 min | 60 min |
|---|---|---|---|---|---|---|---|
| I-8 | Human | PEA | 0.19 | 0.57 | 0.47 | 0.41 | 0.28 |
| | Rat | | 0.069 | 0.17 | 0.092 | 0.061 | 0.013 |
| | Mouse | | 0.29 | 0.50 | 0.44 | 0.38 | 0.37 |
| | Dog | | 0.13 | 0.33 | 0.34 | 0.33 | 0.20 |
| I-16 | Human | | 0.10 | 0.46 | 0.42 | 0.39 | 0.27 |
| | Rat | | 0.050 | 0.13 | 0.13 | 0.058 | 0.020 |
| | Mouse | | 0.33 | 0.78 | 0.68 | 0.59 | 0.43 |
| | Dog | | 0.053 | 0.26 | 0.33 | 0.29 | 0.23 |

Intestinal S9 Fraction Stability

Mixed-gender human (Lot #1410073), male Sprague-Dawley rat (Lot #1510303), male CD-1 mouse (Lot #1510194), and male Beagle dog (Lot #1510226) intestinal S9 fraction were provided. Reaction mixture, minus cofactors, was prepared as described below. Test article was added into the reaction mixture at a final concentration of 1 µM. Control compounds, testosterone and 7-hydroxycoumarin, were run simultaneously with the test article in a separate reaction. An aliquot of the reaction mixture (without cofactor cocktail) was equilibrated in a shaking water bath at 37° C. for 3 minutes. Reaction was initiated by the addition of cofactor cocktail, and the mixture was incubated in a shaking water bath at 37° C. Aliquots (100 µL) were withdrawn at 0, 10, 20, 30, and 60 minutes. Test article samples were immediately combined with 300 µL of ice-cold acetonitrile containing 1% formic acid. Control samples were immediately combined with 400 µL of ice-cold 50/50 acetonitrile (ACN)/dH$_2$O containing 0.1% formic acid and internal standard to terminate the reaction. Samples were then mixed and centrifuged to precipitate proteins. Calibration standards were prepared in matched matrix. Samples and standards were assayed by LC-MS/MS using electrospray ionization for both dosed prodrug and expected drug (PEA). Analytical conditions are outlined in Appendix 17-1. Test article concentration at each time point was compared to test article concentration at time 0 to determine the percent remaining at each time point. Halflives were calculated using GraphPad software, fitting to a single-phase exponential decay equation. Results are shown in Tables 17e and 17f.

Reaction Compostion

| Intestinal S9 Fraction | 1.0 mg/mL |
|---|---|
| NADPH (cofactor) | 1 mM |
| UDPGA (cofactor) | 1 mM |
| PAPS (cofactor) | 1 mM |
| GSH (cofactor) | 1 mM |
| Potassium Phosphate, pH 7.4 | 100 mM |
| Magnesium Chloride | 5 mM |
| Test Article | 1 µM |

TABLE 17e

PEA stability observed in human, rat, mouse, and dog intestinal S9 fraction.

| Test Article | Species | 0 min | % Remaining of Initial (n = 1) 10 mm | 20 min | 30 min | 60 min | Half-life$^a$ (min) | $CL_{int}^b$ (mL/min/ mg protein) |
|---|---|---|---|---|---|---|---|---|
| I-8 | Human | 100 | 31 | 7.0 | 1.8 | <1.0 | <10 (5.7) | >0.0693 (0.122) |
| | Rat | 100 | 58 | 37 | 22 | 6.2 | 14 | 0.0503 |

TABLE 17e-continued

PEA stability observed in human, rat, mouse, and dog intestinal S9 fraction.

| Test Article | Species | 0 min | % Remaining of Initial (n = 1) | | | | Half-life[a] (min) | $CL_{int}^{b}$ (mL/min/ mg protein) |
|---|---|---|---|---|---|---|---|---|
| | | | 10 min | 20 min | 30 min | 60 min | | |
| | Mouse | 100 | 65 | 45 | 31 | 12 | 18 | 0.0389 |
| | Dog | 100 | <1.0 | <1.0 | <1.0 | <1.0 | <10 (1.5) | >0.0693 (0.473) |
| I-16 | Human | 100 | 3.2 | <1.0 | <1.0 | <1.0 | <10 (2.0) | >0.0693 (0.344) |
| | Rat | 100 | <1.0 | <1.0 | <1.0 | <1.0 | <1.0 | >0.691 |
| | Mouse | 100 | 2.0 | <1.0 | <1.0 | <1.0 | <10 (1.8) | >0.0693 (0.389) |
| | Dog | 100 | 1.7 | <1.0 | <1.0 | <1.0 | <10 (1.7) | >0.0693 (0.409) |

[a]When calculated half-life is longer than the duration of the experiment, half-life is expressed as > the longest incubation time. Similarly, if calculated half-life is less than shortest time point, half-life is expressed as < that time point and calculated half-life is also listed in parentheses.
[b]Intrinsic clearance ($CL_{int}$) was calculated based on $CL_{int} = k/P$, where k is elimination rate constant and P is protein concentration in the incubation.

| Control Compound | Species | Half-life (min) | $CL_{in}$ (ml/min/mg protein) |
|---|---|---|---|
| Testosterone | Human | 4.8 | 0.144 |
| | Rat | >60 (102) | <0.0116 (0.00680) |
| | Mouse | >60 (90) | <0.0116 (0.00767) |
| | Dog | >60 | <0.0116 |
| 7-hydroxycourmarin | Human | 13 | 0.0522 |
| | Rat | 29 | 0.0242 |
| | Mouse | 5.0 | 0.138 |
| | Dog | 9.0 | 0.0770 |

TABLE 17f

Measured Concentrations of Drug.

| Dosed | | | Concentration (μM) | | | | |
|---|---|---|---|---|---|---|---|
| Test Article | Species | Analyte | 0 min | 10 min | 20 min | 30 min | 60 min |
| I-8 | Human | PEA | 0.021 | 0.32 | 0.39 | 0.38 | 0.38 |
| | Rat | | 0.022 | 0.22 | 0.34 | 0.42 | 0.45 |
| | Mouse | | 0.012 | 0.12 | 0.19 | 0.22 | 0.26 |
| | Dog | | 0.33 | 0.71 | 0.81 | 0.67 | 0.81 |
| I-16 | Human | | 0 | 0.17 | 0.29 | 0.33 | 0.32 |
| | Rat | | 0 | 0.20 | 0.28 | 0.34 | 0.38 |
| | Mouse | | 0 | 0.10 | 0.17 | 0.18 | 0.26 |
| | Dog | | 0.042 | 0.50 | 0.57 | 0.54 | 0.68 |

Plasma Stability

Studies were carried out in mixed-gender human plasma (Lot #AS 1650-2), male Sprague-Dawley rat (Lot #RAT320835), male CD-1 mouse (Lot #MSE260693), and 6 male Beagle dog (Lot #BGL91384), on sodium heparin. Plasma was adjusted to pH 7.4 prior to initiating the experiments. DMSO stocks were first prepared for the test articles. Aliquots of the DMSO solutions were dosed into 700 μL of plasma, which had been pre-warmed to 37° C., at a final test article concentration of 1 μM. Aliquots (100 μL) were taken at each time point (0, 15, 30, 60, and 120 minutes) and were immediately combined with 300 μL of ice-cold acetonitrile containing 1% formic acid. Samples were stored at 4° C. until the end of the experiment. After the final time point was sampled, the plate was mixed and then centrifuged at 3,000 rpm for 10 minutes. Calibration standards were prepared in matched matrix. Samples and standards were assayed by LC-MS/MS using electrospray ionization for both dosed prodrug and expected drug (PEA). Analytical conditions are outlined in Appendix 17-1. Test article concentration at each time point was compared to test article concentration at time 0 to determine the percent remaining at each time point. Half-lives were calculated using GraphPad software, fitting to a single-phase exponential decay equation. Results are shown in Tables 17g and 17h.

TABLE 17g

PEA stability observed in human, rat mouse, and dog plasma.

| Test Article | Species | 0 min | % Remaining of Initial (n = 1) | | | | Half-life[a] (min) |
|---|---|---|---|---|---|---|---|
| | | | 15 min | 30 min | 60 min | 120 min | |
| I-8 | Human | 100 | <1.0 | <1.0 | <1.0 | <1.0 | <1.0 |
| | Rat | 100 | <1.0 | <1.0 | <1.0 | <1.0 | <1.0 |
| | Mouse | 100 | <1.0 | <1.0 | <1.0 | <1.0 | <1.0 |
| | Dog | 100 | <1.0 | <1.0 | <1.0 | <1.0 | <1.0 |
| I-16 | Human | 100 | 78 | 51 | 24 | 5.8 | 31 |
| | Rat | 100 | 20 | 9.3 | 4.1 | 1.6 | <15 (6.9) |
| | Mouse | 100 | 10 | 4.0 | 1.1 | <1.0 | <15 (4.7) |
| | Dog | 100 | 91 | 65 | 39 | 13 | 44 |

TABLE 17h

Measured Concentrations of Drug.

| Dosed | | | Concentration (μM) | | | | |
|---|---|---|---|---|---|---|---|
| Test Article | Species | Analyte | 0 min | 15 min | 30 min | 60 min | 120 min |
| I-8 | Human | PEA | 0.27 | 1.25 | 1.30 | 1.16 | 1.50 |
| | Rat | | 0.21 | 0.62 | 0.64 | 0.55 | 0.59 |
| | Mouse | | 0.97 | 0.93 | 0.92 | 1.05 | 1.30 |
| | Dog | | 0.33 | 0.72 | 0.72 | 0.73 | 0.69 |
| I-16 | Human | | 0 | 0.19 | 0.38 | 0.53 | 0.67 |
| | Rat | | 0 | 0.23 | 0.24 | 0.24 | 0.30 |
| | Mouse | | 0.12 | 0.53 | 0.55 | 0.68 | 0.79 |
| | Dog | | 0 | 0.12 | 0.18 | 0.34 | 0.44 |

Simulated Intestinal Fluid Stability

Studies were carried out in simulated intestinal fluid in the presence of various enzymes. Simulated intestinal fluid was prepared by dissolving 6.8 g of monobasic potassium phosphate in 1.0 L of water. Aliquots of this solution were taken and the pH was adjusted to 6.8. Individual enzymes were then spiked into aliquots for each experiment. A DMSO stock was first prepared for the test article. Aliquots of the DMSO solution were dosed into 700 μL of matrix, which had been pre-warmed to 37° C., at a final test article concentration of 1 μM. Aliquots (100 μL) were taken at each time point (0, 15, 30, 60, and 120 minutes) and were immediately combined with 300 μL of ice-cold acetonitrile containing 1% formic acid. Samples were stored at 4° C. until the end of the experiment. After the final time point was sampled, the plate was mixed and then centrifuged at 3,000 rpm for 10 minutes. Calibration standards were prepared in matched matrix. Samples and standards were assayed by LC-MS/MS using electrospray ionization for both dosed prodrug and expected drug (PEA). Analytical conditions are outlined in Appendix 17-1. Test article concentration at each time point was compared to the test article concentration at time 0 to determine the percent remaining at each time point. Half-lives were calculated using GraphPad software, fitting to a single-phase exponential decay equation. Results are shown in Tables 17i and 17j.

TABLE 17i

PEA stability observed in simulated intestinal fluid (SIF).

| Test Article | Treatment | 0 min | % Remaining of Initial (n = 1) | | | | Half-life$^a$ (min) |
|---|---|---|---|---|---|---|---|
| | | | 15 min | 30 min | 60 min | 120 min | |
| I-8 | SIF + Elastase | 100 | 38 | 17 | 16 | 17 | <15 (12) |
| | SIF + Carboxypeptidase A | 100 | 33 | 8.7 | <1.0 | <1.0 | <15 (9.2) |
| | SIF + Carboxypeptidase B | 100 | 30 | 7.1 | <1.0 | <1.0 | <15 (8.5) |
| | SIF + Chymotrypsin | 100 | 36 | 8.7 | <1.0 | <1.0 | <15 (9.6) |
| | SIF + Trypsin | 100 | 52 | 31 | 28 | 25 | 25 |
| I-16 | SIF + Elastase | 100 | 72 | 50 | 27 | 7.1 | 31 |
| | SIF + Carboxypeptidase A | 100 | 88 | 74 | 60 | 32 | 75 |
| | SIF + Carboxypeptidase B | 100 | 94 | 87 | 68 | 37 | 89 |
| | SIF + Chymotrypsin | 100 | 103 | 90 | 68 | 35 | 84 |
| | SIF + Trypsin | 100 | 89 | 82 | 62 | 37 | 85 |

$^a$When the calculated half-life is longer than the duration of the experiment, half-life is expressed as > the longest incubation time. Similarly, if calculated half-life is less than the shortest time point, half-life is expressed as < that time point and calculated half-life is also listed in parentheses.

TABLE 17j

Measured Concentrations of Drug.

| Test Article | Treatment | Analyte | Concentration (μM) | | | | |
|---|---|---|---|---|---|---|---|
| | | | 0 min | 15 min | 30 min | 60 min | 120 min |
| I-8 | SIF + Elastase | PEA | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |
| I-16 | SIF + Elastase | | 0 | 0 | 0 | 0 | 0 |
| | SIF + Carboxypeptidase A | | 0 | 0 | 0 | 0 | 0 |
| | SIF + Carboxypeptidase B | | 0 | 0 | 0 | 0 | 0 |
| | SIF + Chymotrypsin | | 0 | 0 | 0 | 0 | 0 |
| | SIF + Trypsin | | 0 | 0 | 0 | 0 | 0 |

Appendix 17-1

Liquid Chromatography

| Column: | Waters ACQUITY UPLC BEH Phenyl 30 × 2.1 mm, 1.7 μm |
|---|---|
| M.P. Buffer: | 25 mM ammonium formate buffer,, pH 3.5 |
| Aqueous Reservoir (A): | 90% water, 10% buffer |
| Organic Reservoir (B): | 90% acetonitrile, 10% buffer |
| Flow Rate: | 0.7 mL/minute |
| Gradient Program: | |

TABLE 17-1

Liquid Chromatography Gradient Program

| Time (mm) | % A | % B |
|---|---|---|
| 0.0 | 50 | 50 |
| 2.00 | 15 | 85 |
| 2.05 | 50 | 50 |
| 2.50 | 50 | 50 |

| Total Run Time: | 2.5 minutes |
|---|---|
| Autosampler: | 3 μL injection volume |
| Wash1: | water/methanol/2-propanol: 1/1/1; with 0.2% formic acid |
| Wash2: | 0.1% formic acid in water |

TABLE 17-1-continued

Liquid Chromatography Gradient Program

Mass Spectrometer

| Instrument: | PE SCIEX API 4000 |
|---|---|
| Interface: | Turbo Ionspray |
| Mode: | Multiple reaction monitoring |
| Method: | 2.5 minute duration |
| Settings: | |

TABLE 17-2

Mass Spectrometer Settings

| Test Article | +/- | Q1 | Q3 | DP | EP | CE | CXP | IS |
|---|---|---|---|---|---|---|---|---|
| I-8 | + | 474.3 | 282.2 | 112 | 10 | 28 | 18 | 5500 |
| I-16 | + | 614.5 | 282.6 | 123 | 10 | 37 | 18 | 5500 |
| PEA | + | 300.3 | 62.0 | 100 | 10 | 32 | 10 | 5500 |

TABLE A

Summary of Half Life and Oral Bioavailability Data.

| Compound | Half life (mins) | Bioavailability |
|---|---|---|
| PEA | n/a | 0.56% |
| I-11 | <1 | 4.5% |
| I-15 | <1 | 3.42% |
| I-14 | 7.5 | 4.39% |
| I-16 | <1 | 12.1% |
| I-8 | 6.2 | 17.3% |

Example 18: Determination of the Bioavailability of Palmitoylethanolamide (PEA) Following Oral Administration of PEA-Prodrug in Male Sprague-Dawley Rats The present Example describes oral bioavailability of PEA following administration of PEA prodrugs in male Sprague-Dawley rats.

Or a the oral bioavailability of palmitoylethanolamide (PEA) was evaluated in male Sprague-Dawley rats following oral dosing of PEA pro-drugs, I-8 and I-16. I-8 was dosed orally (PO) at 4, 8 and 16 mg/kg, and I-16 was dosed orally (PO) at 5.2, 10.35 and 20.7 mg/kg in a formulation consisting of 20% (Solutol HS15:NMP 1:1), 10% PEG400, and 70% water. Each prodrug dosed was equivalent to 2.5, 5, or 10 mg/kg dose of PEA. Blood samples were collected up to 8 hours post-dose, and plasma concentrations of PEA were determined by LC-MS/MS. Bioavailability was calculated using IV data from Example 5.

Following PO dosing of I-8 at 4 mg/kg (2.5 mg/kg PEA equivalent) maximum plasma concentrations (average of 25.3±6.67 ng/mL) were observed at 1 hour post dosing. Halflife could not be determined due to a lack of quantifiable data points trailing the $C_{max}$. Average exposure for I-8 based on the dose-normalized $AUC_{last}$ was 13.5±4.65 hr*kg*ng/mL/mg. Average oral bioavailability for PEA in this group was 21.7±7.48%.

Following PO dosing of I-8 at 8 mg/kg (5 mg/kg PEA equivalent) maximum plasma concentrations (average of 46.9±13.6 ng/mL) were observed at 1 hour post dosing. Halflife could not be determined due to a lack of quantifiable data points trailing the $C_{max}$. Average exposure for I-8 based on the dose-normalized $AUC_{last}$ was 14.8±1.19 hr*kg*ng/mL/mg. Average oral bioavailability for PEA in this group was 23.9±1.92%.

Following PO dosing of I-8 at 16 mg/kg (10 mg/kg PEA equivalent) maximum plasma concentrations (average of 102±31.8 ng/mL) were observed at 1 hour post dosing. Half-life could not be determined due to a lack of quantifiable data points trailing the $C_{max}$. Average exposure for I-8 based on the dose-normalized $AUC_{last}$ was 16.8±3.80 hr*kg*ng/mL/mg. Average oral bioavailability for PEA in this group was 27.1±6.13%.

Following PO dosing of I-16 at 5.2 mg/kg (2.5 mg/kg PEA equivalent) maximum plasma concentrations (average of 25.3±23.6 ng/mL) were observed between 30 minutes and 1 hour post dosing. Half-life could not be determined due to a lack of quantifiable data points trailing the $C_{max}$. Average exposure for I-16 based on the dose-normalized $AUC_{last}$ was 9.08±6.08 hr*kg*ng/mL/mg. Average oral bioavailability for PEA in this group was 14.6±11.1%.

Following PO dosing of I-16 at 10.35 mg/kg (5 mg/kg PEA equivalent) maximum plasma concentrations (average of 43.9±7.33 ng/mL) were observed at 1 hour post dosing. Halflife could not be determined due to a lack of quantifiable data points trailing the $C_{max}$. Average exposure for I-16 based on the dose-normalized $AUC_{last}$ was 10.6±0.544 hr*kg*ng/mL/mg. Average oral bioavailability for PEA in this group was 17.0±0.876%.

Following PO dosing of I-16 at 20.7 mg/kg (10 mg/kg PEA equivalent) maximum plasma concentrations (average of 68.3±11.4 ng/mL) were observed at 1 hour post dosing. Halflife could not be determined due to a lack of quantifiable data points trailing the $C_{max}$ Average exposure for I-16 based on the dose-normalized $AUC_{last}$ was 11.2±1.01 hr*kg*ng/mL/mg. Average oral bioavailability for PEA in this group was 18.0±1.63%.

Following each dose of I-8, there was a dose proportional increase in $C_{max}$ for PEA. Average PEA Cmax values after I-8 dosing were 25.3, 46.9, and 102 ng/mL following the 4, 8, and 16 mg/kg doses, respectively. Average dose normalized $AUC_{last}$ values (13.5, 14.8, and 16.8 hr*kg*ng/mL/mg) and bioavailability (21.7, 23.9, and 27.1%) were also after similar the 4, 8, and 16 mg/kg 1-8 doses, respectively.

Following each dose of I-16, there was a dose proportional increase in $C_{max}$ for PEA. Average PEA $C_{max}$ values after I-16 dosing were 25.3, 43.9, 68.3 ng/mL following the 5.2, 10.35, and 20.7 mg/kg doses, respectively. Average dose normalized $AUC_{last}$ values (9.08, 10.6, 11.2 hr*kg*ng/mL/mg) and bioavailability (14.6, 17.0, 18.0%) were also similar after the 5.2, 10.35, and 20.7 mg/kg I-16 doses, respectively.

Preparation of Dosing Formulations

Pro-drugs were dosed so that a total dose of 2.5, 5, 10 mg/kg of PEA was administered. Each prodrug was formulated in a vehicle comprised of 10% Solutol HS15, 10% n-methyl pyrrolidone (NMP), 10% polyethylene glycol 400 (PEG400) and 70% water. Formulations were prepared fresh on the day of dosing.

Animal Dosing

Pharmacokinetics of PEA were evaluated in fasted male Sprague-Dawley rats. Rats were housed one per cage. Each rat was fitted with a jugular vein cannula (JVC) for blood collection. Each study group was dosing in triplicate. Rats were fasted for a minimum of twelve hours prior to dosing. Food was returned at four hours post dosing. Animals had free access to water throughout the study. Blood samples (~300 µL) were collected from the rats via a JVC and placed into chilled polypropylene tubes containing sodium heparin as an anticoagulant, and 30 µL of 0.5 M citric acid. Samples were maintained chilled throughout processing. Blood samples were centrifuged at 4° C. and 3,000 g for 5 minutes. Plasma (~150 µL) was then transferred to a chilled, labeled polypropylene tube containing 15 µL of 10% formic acid, placed on dry ice, and stored in a freezer maintained at −60° C. to −80° C. Blood sampling times are shown in Table 18a.

TABLE 18a

Study Design.

| Group # | Test Article | Dosing Route | Total Animals n = | Dose (mg/kg of pro-drug)* | Dosing Solution Conc. (mg/mL) | Dosing Volume (mL/kg) | Vehicle | Blood Sample Time Points |
|---|---|---|---|---|---|---|---|---|
| 1 | I-8 | PO | 3 | 4 | 2 | 2 | 20% | Pre-dose, |
| 2 | | PO | 3 | 8 | 2 | 4 | (Solutol | 5, 15, |
| 3 | | PO | 3 | 16 | 3 | 5.3 | HS15:NMP 1:1) 10% PEG400; 70% H$_2$O | 30 min, 1, 2, 4, 8 hours |
| 4 | I-16 | PO | 3 | 5.2 | 2 | 2.6 | 20% | Pre-dose, |
| 5 | | PO | 3 | 10.35 | 3 | 3.45 | (Solutol | 5, 15, |
| 6 | | PO | 3 | 20.7 | 3 | 6.9 | HS15:NMP 1:1) 10% PEG400; 70% H$_2$O | 30 min, 1, 2, 4, 8 hours |

*All doses are based on mg/kg of the pro-drugs, and deliver 10 mg/kg of active drug, PEA.

An LC-MS/MS method for the determination of PEA and PEA-prodrug is described above (see e.g., Example 3).

Pharmacokinetic parameters were calculated from the time course of the plasma concentration. Maximum plasma concentration ($C_{max}$) and the time to reach maximum plasma drug concentration ($T_{max}$) after oral dosing were observed from the data. Area under the time concentration curve (AUC) was calculated using the linear trapezoidal rule with calculation to the last quantifiable data point, and with extrapolation to infinity if applicable. At least three quantifiable data points were required to determine the AUC. Mean residence time (MRT) was calculated by dividing the area under the moment curve (AUMC) by the AUC. Bioavailability was determined by dividing the individual dose-normalized PO $AUC_{last}$ values by the average IV $AUC_{last}$ value (IV data from Example 5). Samples below the limit of quantitation were treated as zero for pharmacokinetic data analysis.

Results

No adverse reactions were observed following the oral administration of PEA pro-drugs in male Sprague-Dawley rats. Dosing solutions were not analyzed by LC-MS/MS. Nominal dosing level was used in calculations. Concentrations are expressed as mg/mL of the free base.

Individual and average plasma concentrations for PEA and are shown in Table 18b through Table 18g. Data are expressed as ng/mL of the free drug. Samples that were below the limit of quantitation were not used in the calculation of averages. Plasma concentration versus time data are plotted in FIGS. 10A through 10L. Endogenous levels of PEA were found in the majority of all the rats. Measured concentrations of PEA in plasma samples were corrected by subtracting the concentration of PEA measured in the pre-dose samples. Corrected values are reported in tables below and were used to determine pharmacokinetic parameters. Corrected values that were negative are reported as not determined (ND).

TABLE 18b

Individual and Average Plasma Concentrations (ng/mL) and Pharmacokinetic Parameters for PEA after Oral Administration of I-8 in 20% Solutol HS15:NMP (1:1), 10% PEG400, 70% H$_2$O) at 4 mg/kg in Male Sprague-Dawley Rats. Oral (4 mg/kg I-8 equals 2.5 mg/kg PEA)

| | Rat # | | | | |
|---|---|---|---|---|---|
| Time (hr) | 446 | 447 | 448 | Mean | SD |
| 0 (pre-dose) | BLOQ | BLOQ | BLOQ | ND | ND |
| 0.083 | 6.36 | BLOQ | BLOQ | ND | ND |
| 0.25 | 4.60 | 2.71 | BLOQ | 3.66 | ND |
| 0.50 | 9.80 | 16.9 | 14.3 | 13.7 | 3.59 |
| 1.0 | 18.1 | 31.3 | 26.4 | 25.3 | 6.67 |
| 2.0 | 6.19 | 6.38 | 10.4 | 7.66 | 2.38 |
| 4.0 | BLOQ | BLOQ | 4.57 | ND | ND |
| 8.0 | BLOQ | BLOQ | BLOQ | ND | ND |
| Animal Weight (kg) | 0.294 | 0.287 | 0.294 | 0.292 | 0.004 |
| Volume Dosed (mL) | 0.59 | 0.57 | 0.59 | 0.58 | 0.01 |
| $C_{max}$ (ng/mL) | 18.1 | 31.3 | 26.4 | 25.3 | 6.67 |
| $t_{max}$ (hr) | 1.0 | 1.0 | 1.0 | 1.0 | 0.0 |
| $t_{1/2}$ (hr) | ND[3] | ND[3] | ND[3] | ND | ND |
| $MRT_{last}$ (hr) | 0.991 | 0.988 | 1.59 | 1.19 | 0.345 |
| $AUC_{last}$ (hr ng/mL) | 22.1 | 33.6 | 45.3 | 33.7 | 11.6 |
| $AUC_\infty$ (hr ng/mL) | ND[3] | ND[3] | ND[3] | ND | ND |
| Dose-normalized Values[1] | | | | | |
| $AUC_{last}$ (hr kg ng/mL/mg) | 8.84 | 13.4 | 18.1 | 13.5 | 4.65 |
| $AUC_\infty$ (hr kg ng/mL/mg) | ND[3] | ND[3] | ND[3] | ND | ND |
| Bioavailability (%)[2] | 14.2 | 21.6 | 29.2 | 21.7 | 7.48 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.

TABLE 18c

Individual and Average Plasma Concentrations (ng/mL) and Pharmacokinetic Parameters for PEA after Oral Administration of I-8 in 20% Solutol HS15:NMP (1:1), 10% PEG400, 70% $H_2O$) at 8 mg/kg in Male Sprague-Dawley Rats.
Oral (8 mg/kg I-8 equals 5 mg/kg PEA)

| | Rat # | | | | |
|---|---|---|---|---|---|
| Time (hr) | 449 | 450 | 451 | Mean | SD |
| 0 (pre-dose) | ND | ND | ND | ND | ND |
| 0.083 | 3.16 | 1.41 | 0.920 | 1.83 | 1.18 |
| 0.25 | 9.62 | 1.31 | 2.86 | 4.60 | 4.42 |
| 0.50 | 46.2 | 30.0 | 13.7 | 30.0 | 16.3 |
| 1.0 | 61.8 | 43.7 | 35.1 | 46.9 | 13.7 |
| 2.0 | 9.52 | 18.4 | 22.0 | 16.6 | 6.41 |
| 4.0 | 0.0300 | 1.13 | 3.37 | 1.51 | 1.70 |
| 8.0 | BLOQ | BLOQ | BLOQ | ND | ND |
| Animal Weight (kg) | 0.302 | 0.301 | 0.287 | 0.297 | 0.008 |
| Volume Dosed (mL) | 1.12 | 1.20 | 1.15 | 1.19 | 0.03 |
| $C_{max}$ (ng/mL) | 61.8 | 43.7 | 35.1 | 46.9 | 13.6 |
| $t_{max}$ (hr) | 1.0 | 1.0 | 1.0 | 1.0 | 0.0 |
| $t_{1/2}$ (hr) | ND[3] | ND[3] | ND[3] | ND | ND |
| $MRT_{last}$ (hr) | 1.05 | 1.34 | 1.58 | 1.32 | 0.268 |
| $AUC_{last}$ (hr ng/mL) | 80.4 | 73.2 | 68.5 | 74.0 | 5.97 |
| $AUC_\infty$ (hr ng/mL) | ND[3] | ND[3] | ND[3] | ND | ND |
| Dose-normalized Values[1] | | | | | |
| $AUC_{last}$ (hr kg ng/mL/mg) | 16.1 | 14.6 | 13.7 | 14.8 | 1.19 |
| $AUC_\infty$ (hr kg ng/mL/mg) | ND[3] | ND[3] | ND[3] | ND | ND |
| Bioavailability (%)[2] | 25.9 | 23.6 | 22.1 | 23.9 | 1.92 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.

TABLE 18d

Individual and Average Plasma Concentrations (ng/mL) and Pharmacokinetic Parameters for PEA after Oral Administration of I-8 in 20% Solutol HS15:NMP (1:1), 10% PEG400, 70% $H_2O$) at 16 mg/kg in Male Sprague-Dawley Rats.
Oral (16 mg/kg I-8 equals 5 mg/kg PEA)

| | Rat # | | | | |
|---|---|---|---|---|---|
| Time (hr) | 452 | 453 | 454 | Mean | SD |
| 0 (pre-dose) | ND | ND | BLOQ | ND | ND |
| 0.083 | ND | 2.60 | 5.10 | 3.85 | ND |
| 0.25 | 5.75 | BLOQ | 13.4 | 9.58 | ND |
| 0.50 | 70.2 | 45.0 | 80.6 | 65.3 | 18.3 |
| 1.0 | 95.8 | 74.4 | 137 | 102 | 31.8 |
| 2.0 | 28.6 | 38.0 | 46.0 | 37.5 | 8.72 |
| 4.0 | 6.97 | 13.3 | 6.56 | 8.94 | 3.78 |
| 8.0 | BLOQ | BLOQ | BLOQ | ND | ND |
| Animal Weight (kg) | 0.288 | 0.289 | 0.292 | 0.290 | 0.002 |
| Volume Dosed (mL) | 1.53 | 1.53 | 1.55 | 1.54 | 0.01 |
| $C_{max}$ (ng/mL) | 95.8 | 74.4 | 137 | 102 | 31.8 |
| $t_{max}$ (hr) | 1.0 | 1.0 | 1.0 | 1.0 | 0.0 |
| $t_{1/2}$ (hr) | ND[3] | ND[3] | ND[3] | ND | ND |
| $MRT_{last}$ (hr) | 1.33 | 1.62 | 1.33 | 1.43 | 0.162 |
| $AUC_{last}$ (hr ng/mL) | 149 | 143 | 212 | 168 | 38.0 |
| $AUC_\infty$ (hr ng/mL) | ND[3] | ND[3] | ND[3] | ND | ND |
| Dose-normalized Values[1] | | | | | |
| $AUC_{last}$ (hr kg ng/mL/mg) | 14.9 | 14.3 | 21.2 | 16.8 | 3.80 |
| $AUC_\infty$ (hr kg ng/mL/mg) | ND[3] | ND[3] | ND[3] | ND | ND |
| Bioavailability (%)[2] | 24.0 | 23.1 | 34.1 | 27.1 | 6.13 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.

TABLE 18e

Individual and Average Plasma Concentrations (ng/mL) and Pharmacokinetic Parameters for PEA after Oral Administration of I-16 in 20% Solutol HS15:NMP (1:1), 10% PEG400, 70% $H_2O$) at 5.2 mg; kg in Male Sprague-Dawley Rats.
Oral (5.2 mg/kg I-16 equals 2.5 mg/kg PEA)

| | Rat # | | | | |
|---|---|---|---|---|---|
| Time (hr) | 455 | 456 | 457 | Mean | SD |
| 0 (pre-dose) | ND | ND | ND | ND | ND |
| 0.083 | ND | ND | ND | ND | ND |
| 0.25 | ND | ND | 2.57 | ND | ND |
| 0.50 | 2.83 | 6.02 | 52.2 | 20.3 | 27.6 |
| 1.0 | 15.1 | 8.52 | 25.5 | 16.4 | 8.53 |
| 2.0 | 5.93 | 3.51 | 6.25 | 5.23 | 1.50 |
| 4.0 | ND | ND | ND | ND | ND |
| 8.0 | BLOQ | BLOQ | BLOQ | ND | ND |
| Animal Weight (kg) | 0.284 | 0.283 | 0.285 | 0.284 | 0.001 |
| Volume Dosed (mL) | 0.74 | 0.74 | 0.74 | 0.74 | 0.00 |
| $C_{max}$ (ng/mL) | 15.1 | 8.52 | 52.2 | 25.3 | 23.6 |
| $t_{max}$ (hr) | 1.0 | 1.0 | 0.50 | 0.83 | 0.29 |
| $t_{1/2}$ (hr) | ND[3] | ND[3] | ND[3] | ND | ND |
| $MRT_{last}$ (hr) | 1.16 | 1.06 | 0.833 | 1.02 | 0.167 |
| $AUC_{last}$ (hr ng/mL) | 15.4 | 10.4 | 42.4 | 22.7 | 17.2 |
| $AUC_\infty$ (hr ng/mL) | ND[3] | ND[3] | ND[3] | ND | ND |
| Dose-normalized Values[1] | | | | | |
| $AUC_{last}$ (hr kg ng/mL/mg) | 6.14 | 4.16 | 16.9 | 9.08 | 6.88 |
| $AUC_\infty$ (hr kg ng/mL/mg) | ND[3] | ND[3] | ND[3] | ND | ND |
| Bioavailability (%)[2] | 9.89 | 6.70 | 27.3 | 14.6 | 11.1 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.

TABLE 18f

Individual and Average Plasma Concentrations (ng/mL) and Pharmacokinetic Parameters for PEA after Oral Administration of I-16 in 20% Solutol HS15:NMP (1:1). 10% PEG400, 70% $H_2O$) at 10.35 mg/kg in Male Sprague-Dawley Rats. Oral (10.35 mg/kg I-16 equals 2.5 mg/kg PEA)

| | Rat # | | | | |
|---|---|---|---|---|---|
| Time (hr) | 458 | 459 | 460 | Mean | SD |
| 0 (pre-dose) | ND | ND | ND | ND | ND |
| 0.083 | ND | ND | ND | ND | ND |
| 0.25 | 0.400 | ND | 0.960 | 0.680 | ND |
| 0.50 | 30.0 | 11.4 | 24.4 | 21.9 | 9.52 |
| 1.0 | 47.2 | 35.5 | 49.0 | 43.9 | 7.31 |
| 2.0 | 5.98 | 12.5 | 16.1 | 11.5 | 5.13 |
| 4.0 | ND | 5.02 | ND | ND | ND |
| 8.0 | BLOQ | BLOQ | BLOQ | ND | ND |
| Animal Weight (kg) | 0.288 | 0.298 | 0.284 | 0.290 | 0.007 |
| Volume Dosed (mL) | 0.99 | 1.03 | 0.98 | 1.00 | 0.03 |
| $C_{max}$ (ng/mL) | 47.2 | 35.5 | 49.0 | 43.9 | 7.33 |
| $t_{max}$ (hr) | 1.0 | 1.0 | 1.0 | 1.0 | 0.0 |
| $t_{1/2}$ (hr) | $ND^3$ | $ND^3$ | $ND^3$ | ND | ND |
| $MRT_{last}$ (hr) | 0.946 | 1.58 | 1.06 | 1.20 | 0.337 |
| $AUC_{last}$ (hr ng/mL) | 49.7 | 54.7 | 54.2 | 52.8 | 2.72 |
| $AUC_\infty$ (hr ng/mL) | $ND^3$ | $ND^3$ | $ND^3$ | ND | ND |
| Dose-normalized Value[1] | | | | | |
| $AUC_{last}$ (hr kg ng/mL/mg) | 9.94 | 10.9 | 10.8 | 10.6 | 0.544 |
| $AUC_\infty$ (hr kg ng/mL/mg) | $ND^3$ | $ND^3$ | $ND^3$ | ND | ND |
| Bioavailability (%)[2] | 16.0 | 17.6 | 17.4 | 17.0 | 0.876 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.

TABLE 18g

Individual and Average Plasma Concentrations (ng/mL) and Pharmacokinetic Parameters for PEA after Oral Administration of I-16 in 20% Solutol HS15:NMP (1:1). 10% PEG400, 70% $H_2O$) at 20.7 mg/kg in Male Sprague-Dawley Rats. Oral (20.7 mg/kg I-16 equals 2.5 mg/kg PEA)

| | Rat # | | | | |
|---|---|---|---|---|---|
| Time (hr) | 461 | 462 | 463 | Mean | SD |
| 0 (pre-dose) | ND | ND | ND | ND | ND |
| 0.083 | ND | 1.53 | 1.96 | 1.75 | ND |
| 0.25 | 4.19 | 10.8 | 9.44 | 8.14 | 3.49 |
| 0.50 | 31.1 | 30.7 | 30.8 | 30.9 | 0.225 |
| 1.0 | 64.0 | 81.2 | 59.6 | 68.3 | 11.4 |
| 2.0 | 33.4 | 20.5 | 24.5 | 26.2 | 6.62 |
| 4.0 | 12.6 | 2.68 | 8.74 | 8.02 | 5.02 |
| 8.0 | ND | BLOQ | BLOQ | ND | ND |
| Animal Weight (kg) | 0.280 | 0.284 | 0.285 | 0.283 | 0.003 |
| Volume Dosed (mL) | 1.93 | 1.96 | 1.97 | 1.95 | 0.02 |
| $C_{max}$ (ng/mL) | 64.0 | 8.2 | 59.6 | 68.3 | 11.4 |
| $t_{max}$ (hr) | 1.0 | 1.0 | 1.0 | 1.0 | 0.0 |
| $t_{1/2}$ (hr) | $ND^3$ | $ND^3$ | $ND^3$ | ND | ND |
| $MRT_{last}$ (hr) | 1.66 | 1.29 | 1.53 | 1.49 | 0.190 |
| $AUC_{last}$ (hr ng/mL) | 123 | 108 | 104 | 112 | 10.1 |
| $AUC_\infty$ (hr ng/mL) | $ND^3$ | $ND^3$ | $ND^3$ | ND | ND |
| Dose-normalized Values[1] | | | | | |
| $AUC_{last}$ (hr kg ng/mL/mg) | 12.3 | 10.8 | 10.4 | 11.2 | 1.01 |
| $AUC_\infty$ (hr kg ng/mL/mg) | $ND^3$ | $ND^3$ | $ND^3$ | ND | ND |
| Bioavailability (%)[2] | 19.8 | 17.4 | 16.7 | 18.0 | 1.63 |

$C_{max}$: maximum plasma concentration;
$t_{max}$: time of maximum plasma concentration;
$t_{1/2}$: half-life, data points used for half-life determination are in bold;
$MRT_{last}$: mean residence time, calculated to the last observable time point;
$AUC_{last}$: area under the curve, calculated to the last observable time point;
$AUC_\infty$: area under the curve, extrapolated to infinity;
ND: not determined;
BLOQ: below the limit of quantitation (2.5 ng/mL);
[1]Dose-normalized by dividing the parameter by nominal dose in mg/kg;
[2]Bioavailability determined by dividing individual dose-normalized oral $AUC_{last}$ values by the average IV $AUC_{last}$ value 62.1 hr*ng/mL from Example 5;
[3]Not determined due to lack of quantifiable data points trailing the $C_{max}$.

Example 19: Synthesis of Compound I-9

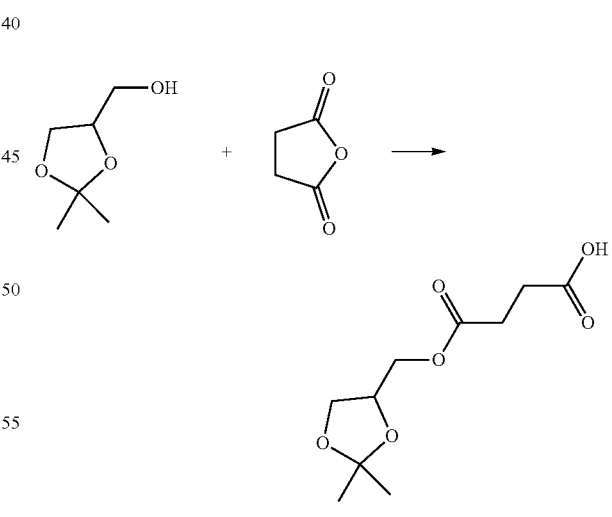

INT-19a

A mixture of solketal (21 gm, 0.16 mol), succinic anhydride (15.9 gm, 0.16 mol) and pyridine (500 mL) was heated to reflux for 16 hrs. Conversion was monitored by NMR. Pyridine was removed under high vacuum. Approximately 15-20% pyridine was still remaining. Mixture was taken to next step as is without further purification.

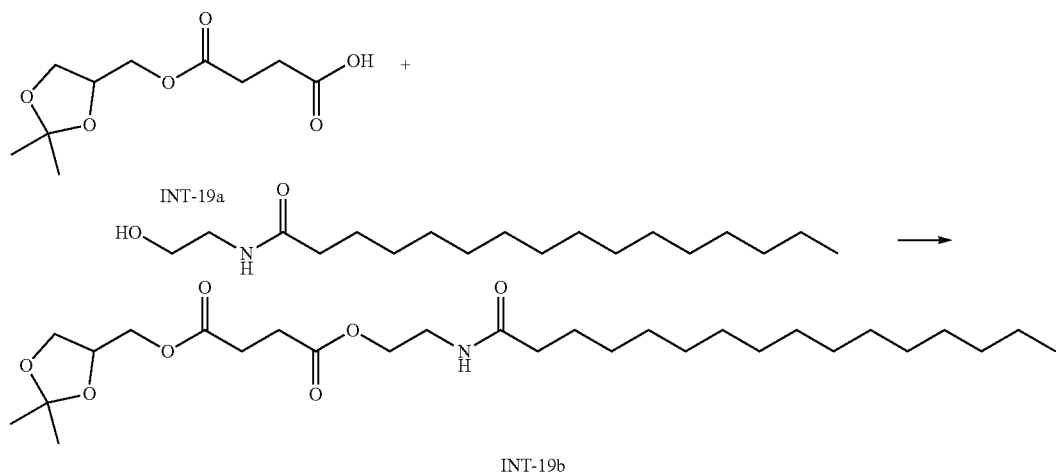

A solution of INT-19a (62.13 mg, 0.27 mol) and PEA (61.46 mg, 0.27 mol) in DCM (1 lire) was cooled to 0° C. To this solution was added 1-ethyl-3-(3-dimethylaminopropyl)carbodiimide (EDCI) (152.5 mg, 0.8 mol) followed by 4-dimethylaminopyridine (DMAP) (9.8 mg, 0.08 mol) in portions. Reaction mixture was warmed to room temperature and stirred for 24 hrs. Reaction mixture was washed with water and brine and extracted with DCM. Organic layers were separated and dried over anhydrous sodium sulfate, filtered and concentrated. Crude material was purified by column chromatography with hexanes and ethyl acetate to obtain 88 mg of pure INT-19b as white solid.

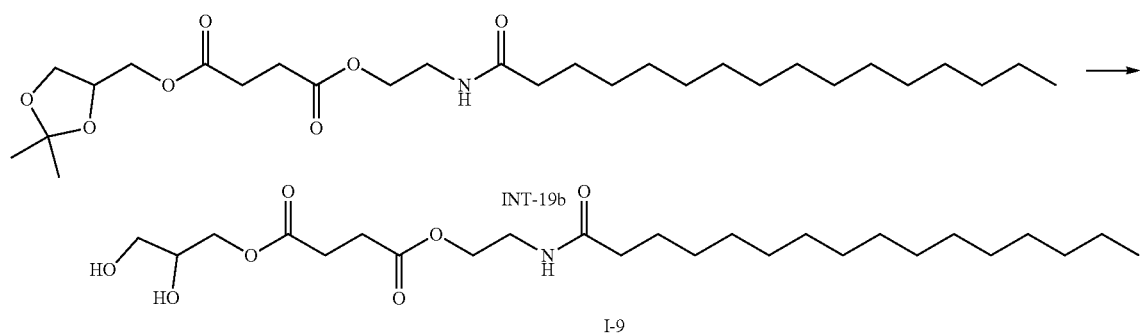

INT-19b (88 mg) was dissolved in methanol (4 Liter) and cooled to 5° C. To this solution was added Dowex H* resin (45 mg) and stirred at 5° C. for 8 hrs. Then resin was filtered off with a pad of celite. Filtrate was concentrated to obtain off white solid. Solids were recrystallized with ethyl acetate to give 73.6 mg of pure I-9.

Example 20: General Synthesis of Diester PEA Prodrugs

Compounds of the present invention may be synthesized according to Scheme 20.

Scheme 20.

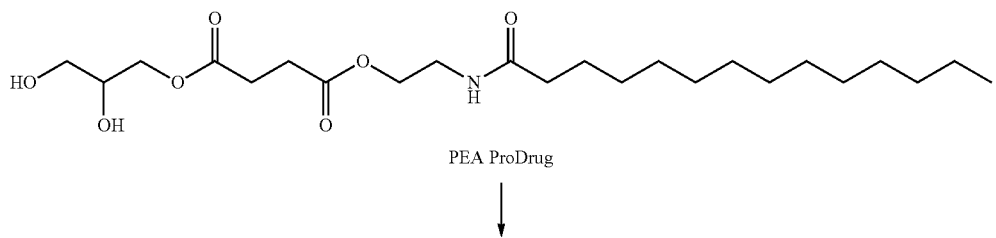

PEA ProDrug

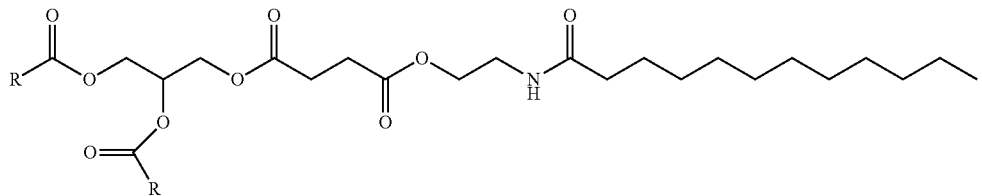

R = Any alkyl/alkenyl chain acid (RCOOH)

A solution of PEA prodrug (1 eq), RCOOH (2.2-3.0 eq) in DCM (10 vol) was cooled to 0° C. To this solution was added 1-ethyl-3-(3-dimethylaminopropyl)carbodiimide (EDCI) (3 eq) followed by addition of 4-dimethylaminopyridine (DMAP) (0.3 eq) in portions. Progress of the reaction was monitored by TLC/NMR. After conversion, the reaction mixture is diluted with DCM, washed with water, sat.aq sodium bicarbonate and brine and extracted with DCM. The organic layers were dried over anhydrous sodium sulfate, filtered and concentrated. The crude residue was purified by column chromatography with increasing gradient of ethylacetate in hexanes.

Example 21: Synthesis of Compounds I-8 and I-16

Compounds I-8 and I-16 may be synthesized according to Schemes 21a and 21h.

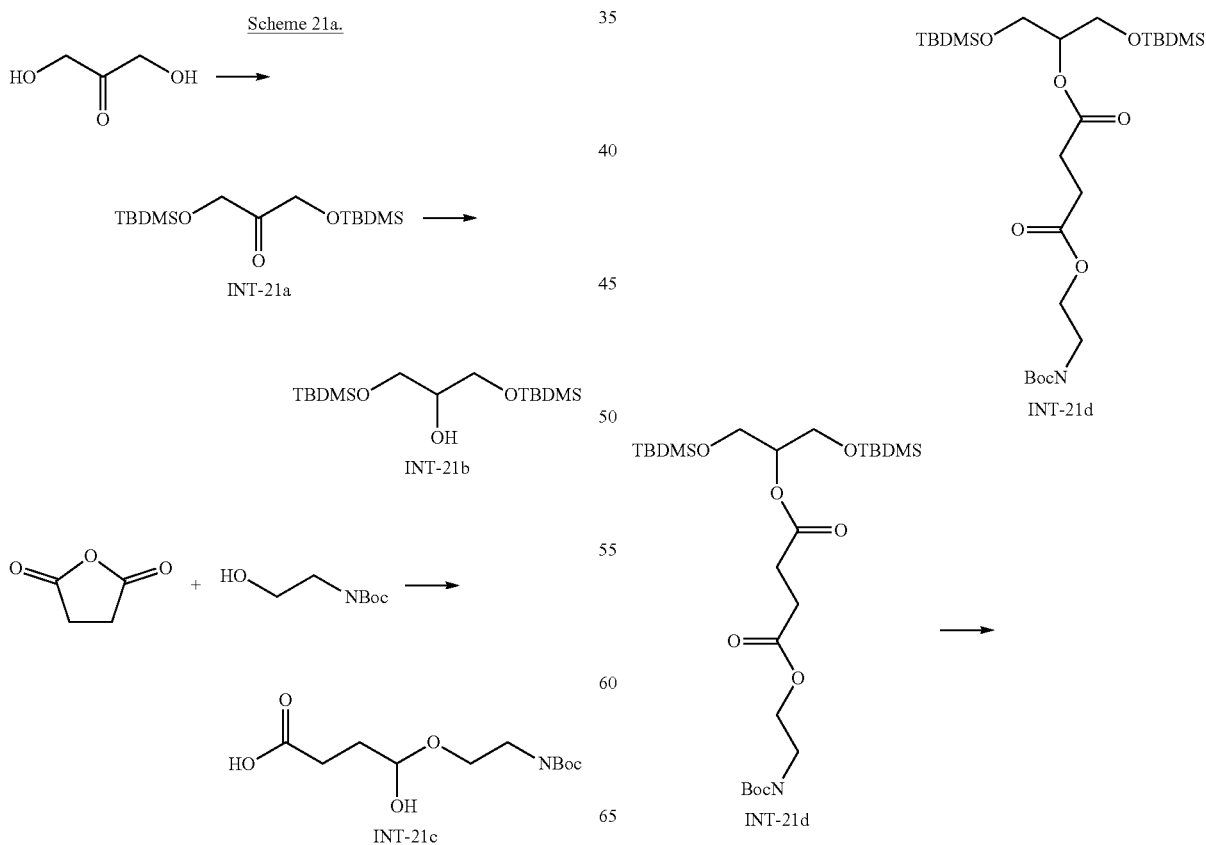

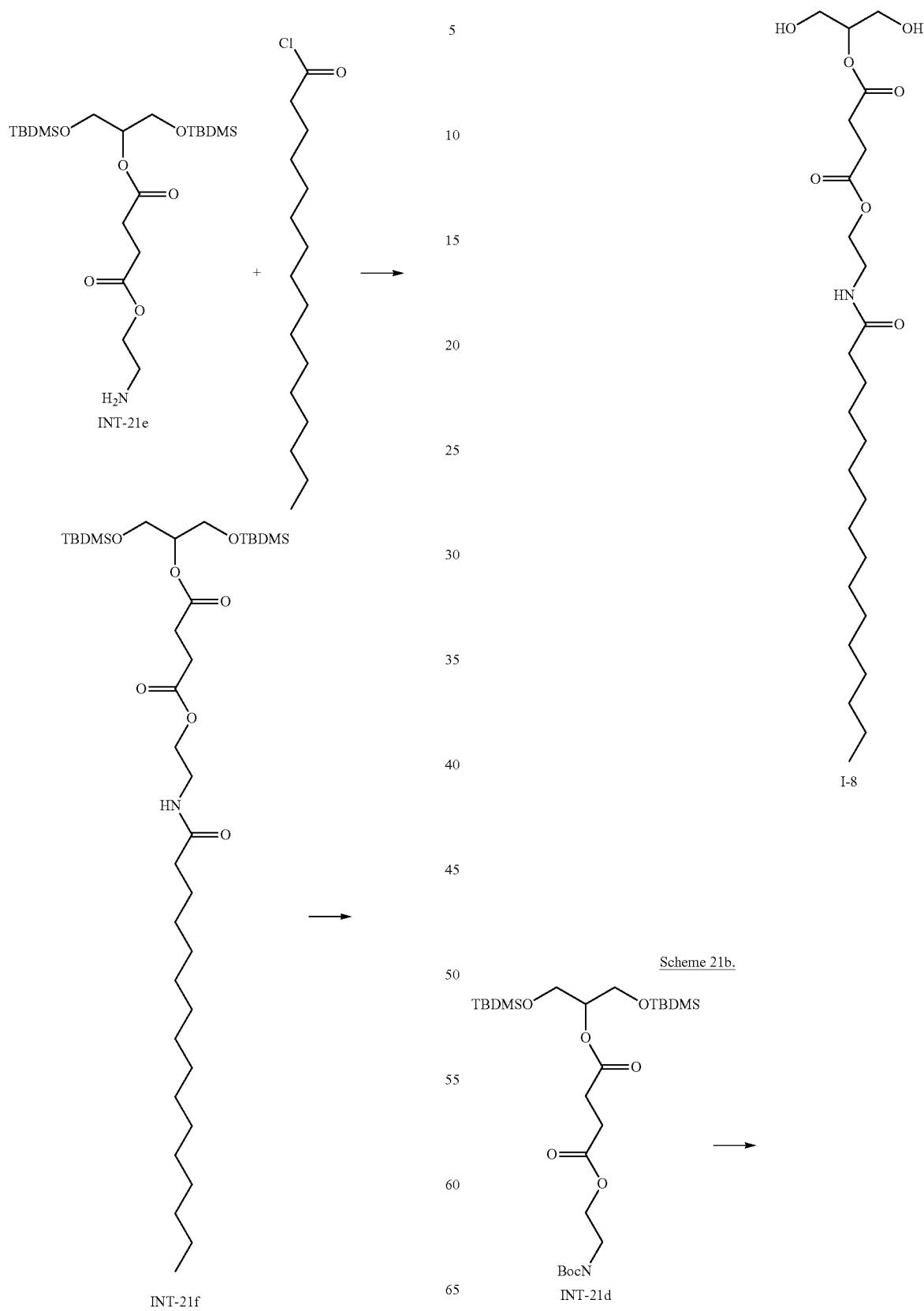

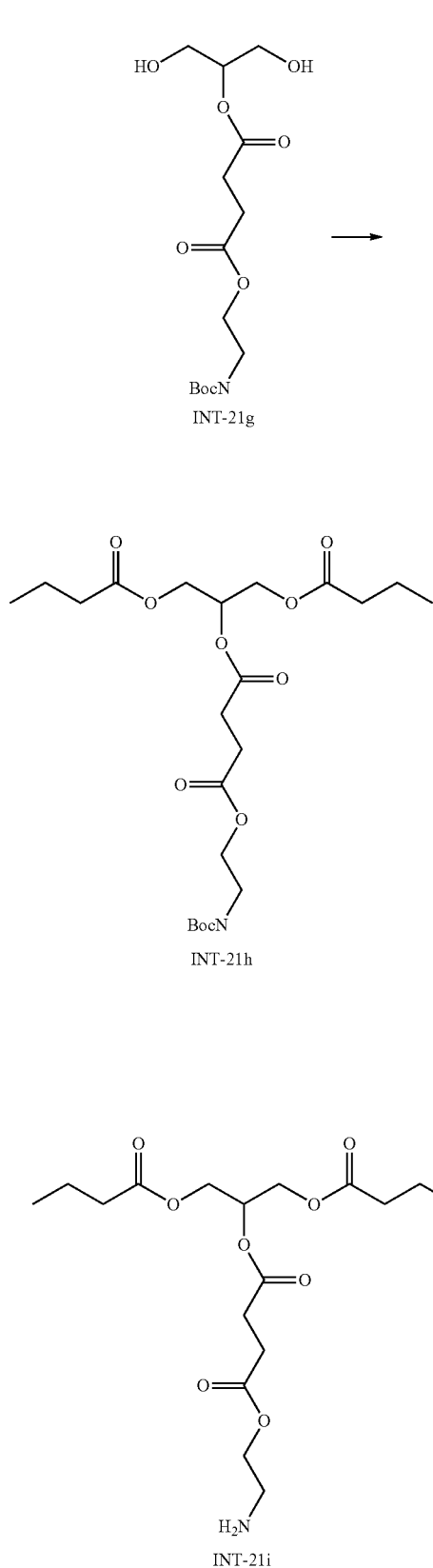
INT-21g
INT-21h
INT-21i
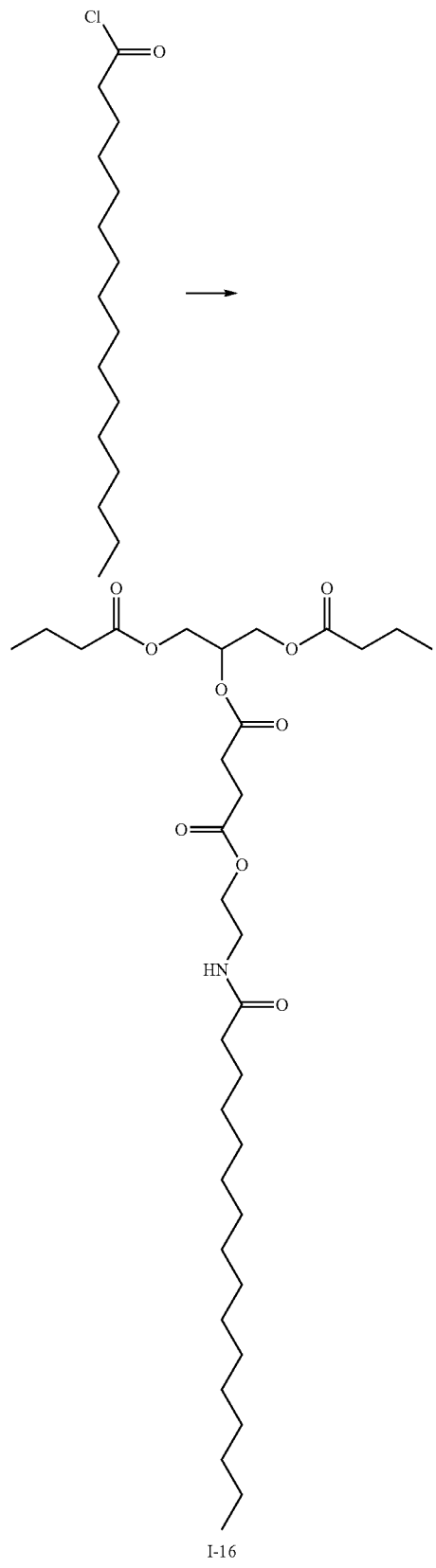
I-16

Example 22: Assessing the Analgesic Effects of I-16 in the Carrageenan-Induced Inflammatory Model Using Thermal Hyperalgesia Testing Sixty male Sprague Dawley rats were used in this study. Baseline thermal hyperalgesia thresholds were determined on day -1; animals were divided into 6 groups based on baseline thermal hyperalgesia thresholds. On day 0, animals received an oral dose of vehicle or I-16. Approximately 30 minutes after dosing the animals received an intra-plantar injection of 2% carrageenan solution. The animals were assessed for thermal hyperalgesia approximately 4 and approximately 24 hours after carrageenan injection.

Thermal hyperalgesia was assessed at baseline (prior to dosing with either vehicle or I-16), 4 hours, and 24 hours post-carrageenan injection. Oral administration of 10.25 mg/kg (equivalent to 5 mg/kg equivalents of PEA) I-16 did not significantly reduce the thermal hyperalgesia induced by carrageenan injection into the hind paw at any time point. Oral administration of 20.50 mg/kg (equivalent to 15 mg/kg of PEA) I-16 significantly reduced thermal hyperalgesia at the 4-hour time point, but did not significantly reduce thermal hyperalgesia at the 24-hour time point (FIG. 11).

Mean±SEM ipsilateral paw withdrawal latencies following carrageenan injection in vehicle and I-16 treated animals during the pharmacological assessment period (day 0). All animals received a mixture of 10% solutol, 10% n-methyl pyrrolidone, 10% PEG 400, and 70% water (10 mL/kg) or I-16 (10.25 or 20.50 mg/kg) via oral gavage (n=10).

These results indicate that administration of I-16 significantly reduces the degree of thermal hyperalgesia associated with inflammatory pain. Administration of I-16 produced a dose- and time-dependent reduction of thermal hyperalgesia with administration of 10.25 mg/kg I-16 producing no significant effect, and administration of 20.50 mg/kg I-16 significantly reducing thermal hyperalgesia at the 4-hour time point.

Example 23: Evaluation of Analgesic Effects in Rat Chronic Constriction Injury (CCI) Model Two test compounds (I-16 and Gabapentin) were formulated in 15% Solutol® HS15/15% Polyethylene glycol (PEG) 400/70% water for injection (WFI) for oral (PO) administrations for 17 consecutive days (qdx17). A dosing volume of 10 mL/kg was applied.

Methods:

Male Sprague Dawley rats weighing 180±20 g were used. Under pentobarbital (50 mg/kg, 5 ml/kg, IP) anesthesia, the left sciatic nerve was exposed at mid-thigh level. Four chromic gut ligatures, about 1 mm apart, were loosely tied around the nerve. The animals were then housed socially in cages with soft bedding for at least 10 days before testing for mechanical allodynia and thermal hyperalgesia.

Mechanical Allodynia

The rats were placed under inverted Plexiglas cages on a wire mesh rack and allowed to acclimate for 20 to 30 minutes. Allodynia was evaluated by the Chaplin up/down method using von Frey filaments to the plantar surface of the left hind paw. All rats were assessed for mechanical allodynia for pre-surgical allodynia threshold on Day -3 (pre-surgery baseline). For gabapentin group, the rats were pre-selected for experimentation only if the pain threshold on Day 13 after nerve ligation (pre-treatment) is reduced by 10 grams of force relative to the response of the individual paw before nerve ligation (pre-ligation), namely, with clear presence of allodynia. On Day 14, the mechanical allodynia test was performed at 1 hour after administrations of I-16, vehicle, or gabapentin.

Thermal Hyperalgesia

Thermal hyperalgesia was measured by the IITC Model-336G (IITC Inc., USA) apparatus. Each rat was placed within a plastic box atop a glass floor for 20 to 30 minutes. A light beam under the floor was aimed at the plantar surface of the left hind paw. The time was measured automatically when the paw was withdrawn away from the thermal stimulus. A cut-off latency of 23 sec was imposed. The latency to withdrawal is obtained for each rat and defined as the heat pain threshold. All rats were assessed for thermal hyperalgsia for pre-surgical threshold on Day -3 (pre-surgery baseline). For gabapentin group, the rats were pre-selected for experimentation only if the pain threshold on Day 13 after nerve ligation (pre-treatment) is reduced by 15 seconds. On Day 14, the thermal hyperalgesia test was performed at 1.5 hour after administrations of I-16, vehicle, or gabapentin.

Group differences were compared to the vehicle control group. Differences were considered significant at P<0.05.

The formulations and dosing protocols are provided in Table 23 and visualized in FIG. 12A:

TABLE 23

| Group | Test Article | Route | Conc. mg/mL | Dosage mL/kg | Dosage mg/kg | Rats (Male) |
|---|---|---|---|---|---|---|
| 1 | Vehicle[a] | PO | NA | 10 | NA, qd × 17 (Days -2~14) | 8[b] |
| 2 | Gabapentin | PO | 10 | 10 | 100, qd × 1 | 8[c] |
| 3 | I-16 | PO | 3.1 | 10 | 31, qd × 17 (Days -2~14) | 8[b] |

[a]Vehicle: 15% solutol ® HS15, 15% PEG400 & 70% WFI.

Dose preparation instructions: first mix the TA in solutol, then add PEG400 and vortex, then add water and vortex to ensure a clear solution.

[b]The rats were randomized on Day -3.

[c]The rats were randomized on Day 13. Each group was underwent mechanical allodynia and thermal hyperalgesia testing on Day 14.

The results of an assay measuring the mechanical allodynia at post treatment (1-hr) and (1.5-hr) is reported in FIG. 12B.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A compound which is:

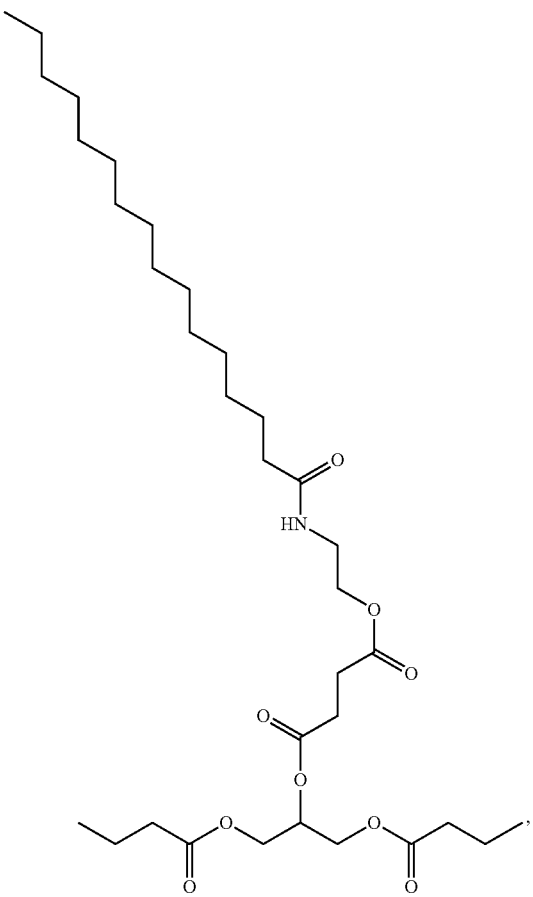 [SMILES: CCCCCCCCCCCCCCCC(=O)NCCOC(=O)CCC(=O)OC(COC(=O)CCC)COC(=O)CCC]

or a salt thereof.

2. The compound of claim 1, wherein the compound is a salt.

3. The compound of claim 2, wherein the salt is a pharmaceutically acceptable salt.

4. A pharmaceutical composition comprising the compound of claim 1 or a pharmaceutically acceptable salt thereof and a pharmaceutically acceptable excipient.

5. The pharmaceutical composition of claim 4, comprising one or more additional therapeutic agents.

6. The pharmaceutical composition of claim 4, which is formulated for oral delivery.

7. The pharmaceutical composition of claim 6, which is formulated as a solid formulation.

8. The pharmaceutical composition according to claim 7, wherein the solid formulation is a capsule.

9. The pharmaceutical composition according to claim 8, wherein the capsule encloses a liquid.

10. A method of treating pain comprising administering the compound according to claim 1 or a pharmaceutically acceptable salt thereof to a patient in need thereof.

11. A method of treating inflammatory pain comprising administering the compound according to claim 1 or a pharmaceutically acceptable salt thereof to a patient in need thereof.

12. A method of treating neuropathic pain comprising administering the compound according to claim 1 or a pharmaceutically acceptable salt thereof to a patient in need thereof.

13. A method of treating pain comprising administering the pharmaceutical composition according to claim 4 to a patient in need thereof.

14. A method of treating inflammatory pain comprising administering the pharmaceutical composition according to claim 4 to a patient in need thereof.

15. A method of treating neuropathic pain comprising administering the pharmaceutical composition according to claim 4 to a patient in need thereof.

* * * * *